US008129386B2

(12) United States Patent
Shimada et al.

(10) Patent No.: US 8,129,386 B2
(45) Date of Patent: Mar. 6, 2012

(54) FUSED AZOLE-PYRIMIDINE DERIVATIVES

(75) Inventors: Mitsuyuki Shimada, Nara (JP); Toshiki Murata, Nara (JP); Kinji Fuchikami, Kyoto (JP); Hideki Jishita, Kyoto (JP); Naoki Omori, Kyoto (JP); Issei Kato, Nara (JP); Mami Miura, Nara (JP); Klaus Urbahns, Hyogo (JP); Florian Gantner, Osaka (JP); Kevin Bacon, Hyogo (JP)

(73) Assignee: Bayer Pharma Aktiengesellschaft, Berlin (DE)

( * ) Notice: Subject to any disclaimer, the term of this patent is extended or adjusted under 35 U.S.C. 154(b) by 188 days.

(21) Appl. No.: 12/414,257

(22) Filed: Mar. 30, 2009

(65) Prior Publication Data
US 2009/0270388 A1  Oct. 29, 2009

Related U.S. Application Data

(63) Continuation of application No. 10/527,376, filed as application No. PCT/EP03/10377 on Sep. 18, 2003, now Pat. No. 7,511,041.

(30) Foreign Application Priority Data

Sep. 30, 2002 (EP) .................................... 02021861

(51) Int. Cl.
*A01N 43/58* (2006.01)
*A01N 43/60* (2006.01)
*A61K 31/50* (2006.01)
*A61K 31/495* (2006.01)

(52) U.S. Cl. ...................................... 514/250; 514/257
(58) Field of Classification Search .................... 514/267
See application file for complete search history.

(56) References Cited

U.S. PATENT DOCUMENTS 3,644,354 A   2/1972  Hardtmann
6,066,642 A * 5/2000  Jacobson et al. ............. 514/267

FOREIGN PATENT DOCUMENTS

WO   WO-96/04923 A1   2/1996
WO   WO-01/81346 A2   11/2001

OTHER PUBLICATIONS

Hirsch, et al., Resistance to Thromboembolism in PI3Kγ-deficient Mice, The FASEB J., 15, 2019-2021 (2001).*
Stein, et al., Waterfield MD: PI3-kinase inhibition: A Target for Drug Development?, Mol. Med. Today, 6, 347-357 (2000).*
Ui, M., et al., "Wortmannin as a unique probe for an intracellular signaling protein, phosphoinositide 3-kinase," TIBS, 20(8): 303-307 (Aug. 1995).
Vlahos, C. J. , et al., "a Specific Inhibitor of Phosphatidylinositol 3-Kinase, 2-(4-Morpholinyl)-8-phenyl-4H-1-benzopyran-4-ome (LY294002)," J. Biol. Chem, 269(7): 5241-5248 (Feb. 1994).
Barber, et al., PI3Ky Inhibition Blocks Glomerulonephritis and Extends Lifespan in a Mouse Model of Systemic Lupus, Nature Medicine, vol. 11, No. 9, 933-935 (2005).
Kihara, et al., Protective Effect of Dopamine D2 Agonists in Cortical Neurons Via the Phosphatidylinositol 3 Kinase Cascade, Journal of Neuroscience Research, 70, 274-282 (2002).

* cited by examiner

*Primary Examiner* — Andrew D Kosar
*Assistant Examiner* — Erich A Leeser

(57) ABSTRACT

The present invention relates to novel fused azolepyrimidine derivatives, processes for preparing them and pharmaceutical preparations containing them. The fused azolepyrimidine derivatives of the present invention exhibit enhanced potency for phosphotidylinositol-3-kinase (PI3K) inhibition, especially for PI3K-γ inhibition and can be used for the prophylaxis and treatment of diseases associated with PI3K and particularly with PI3K-γ activity.

More specifically, the azole derivatives of the present invention are useful for treatment and prophylaxis of diseases as follows: inflammatory and immunoregulatory disorders, such as asthma, atopic dermatitis, rhinitis, allergic diseases, chronic obstructive pulmonary disease (COPD), septic shock, joint diseases, autoimmune pathologies such as rheumatoid arthritis, and Graves' disease, cancer, myocardial contractility disorders, heart failure, thromboembolism, ischemia, and atherosclerosis.

The compounds of the present invention are also useful for pulmonary hypertension, renal failure, cardiac hypertrophy, as well as neurodegenerative disorders such as Parkinson's disease, Alzheimer's disease, diabetes and focal ischemia, since the diseases also relate to PI3K activity in a human or animal subject.

16 Claims, No Drawings

FUSED AZOLE-PYRIMIDINE DERIVATIVES

This application is a continuation of U.S. patent application Ser. No. 10/527,376, filed Oct. 14, 2005, which is a U.S. National Stage application under 35 U.S.C. §371 of International Patent Application Serial No. PCT/EP03/10377, filed on Sep. 18, 2003, which claims priority to European Patent application No. 02021861.6, filed on Sep. 30, 2002, the disclosures of each of which are expressly incorporated by reference in their entireties.

DETAILED DESCRIPTION OF INVENTION

1. Technical Field

The present invention relates to novel fused azolepyrimidine derivatives, processes for preparing them and pharmaceutical preparations containing them. The fused azolepyrimidine derivatives of the present invention exhibit enhanced potency for phosphotidylinositol-3-kinase (PI3K) inhibition, especially for PI3K-γ inhibition and can be used for the prophylaxis and treatment of diseases associated with PI3K and particularly with PI3K-γ activity.

More specifically, the fused azolepyrimidine derivatives of the present invention are useful for treatment and prophylaxis of diseases as follows: inflammatory and immunoregulatory disorders, such as asthma, atopic dermatitis, rhinitis, allergic diseases, chronic obstructive pulmonary disease (COPD), septic shock, joint diseases, autoimmune pathologies such as rheumatoid arthritis, and Graves' disease, cancer, myocardial contractility disorders, heart failure, thromboembolism, ischemia, and atherosclerosis.

The compounds of the present invention are also useful for pulmonary hypertension, renal failure, cardiac hypertrophy, as well as neurodegenerative disorders such as Parkinson's disease, Alzheimer's disease, diabetes and focal ischemia, since the diseases also relate to PI3K activity in a human or animal subject.

2. Background Art

Signal transduction pathways originating from chemoattractant receptors are considered to be important targets in controlling leukocyte motility in inflammatory diseases. Leukocyte trafficking is controlled by chemoattractant factors that activate heterotrimeric G-protein coupled receptors (GPCRs) and thereby trigger a complex variety of downstream intracellular events. Signal transduction at one of the pathways, that results in mobilization of intracellular free $Ca^{2+}$, cytoskeletal reorganisation, and directional movement depends on lipid-derived second messengers produced by phosphoinositide 3-kinase (PI3K) activity [1,2].

PI3K phosphorylates the D3-hydroxyl position of the membrane phospholipid phosphatidylinositol-4,5-bisphosphate (PtdIns(4,5)$P_2$) to yield phosphatidylinositol-3,4,5-trisphosphate (PtdIns(3,4,5)$P_3$). Based on substrate specificity and protein structure, the PI3K family comprises three classes [4-6]. Of particular interest in leukocyte migration are class I PI3Ks, which are all involved in receptor-induced inflammatory cellular responses and are further divided into the subclasses IA (p110α, β, δ) and IB (p110γ).

Class IA enzymes (p110α, β, δ) associate with a p85 adapter subunit, which contains two SH2 domains, to form a heterodimeric complex. This complex is able to recognize phosphotyrosine YxxM motifs, resulting in association with receptor tyrosine kinases and subsequent activation of the enzyme through receptor tyrosine kinases [1, 2]. The class IA subtypes are considered to be associated with cell proliferation and carcinogenesis. The IA subtypes bind to activated ras oncogene, which is found in many cancers, to express their enzyme activity. It has also found that both p110α and β play important roles in human cancer growth [3].

Class IB (p110γ) enzyme, whose expression is largely confined to leukocytes, is activated by the G protein βγ complex, and functions downstream of seven transmembrane chemoattractant receptors [7-9]. The p101 adapter protein, which bears no resemblance to any other known protein, is essential for the G protein βγ responsiveness of the p110γ (PI3Kγ). [10-12].

Recent studies in mice lacking functional PI3Kγ (PI3Kγ−/− mice), which were viable, fertile, and displayed a normal life span in a conventional mouse facility, have revealed that neutrophils are unable to produce PtdIns(3,4,5)$P_3$ when stimulated with GPCR agonists such as fMLP, C5a or IL-8. This demonstrates that PI3Kγ is the sole PI3K that is coupled to these GPCRs in these cells [13-16]. Moreover, PtdIns(3,4,5)$P_3$-dependent activation of protein kinase B (PKB) was also absent in those neutrophils, while PKB could still be activated by GM-CSF or IgG/C3b-coated zymosan via either p110α, β or δ. At the same time, G-protein-mediated responses such as PLCβ activation were intact. PI3Kγ−/− mice showed impaired thymocyte development and increases in neutrophil, monocyte, and eosinophil populations [14]. Furthermore, neutrophils and macrophages isolated from PI3Kγ−/− mice exhibited severe defects in migration and respiratory burst in response to GPCR agonists and chemotactic agents [14,16]. Expression of PI3Kγ was also examined in transgenic mice expressing green fluorescence protein (GFP) under the control of the endogenous PI3Kγ promoter. GFP was detected in spleen and bone marrow cells, and neutrophils, suggesting that the expression of PI3Kγ is restricted to hematopoietic cells [15]. Collectively, the class IB phosphoinositide 3-kinase PI3Kγ seems to be pivotal in the control of leukocyte trafficking and accordingly the development of isotype-selective inhibitors of PI3Kγ should be an attractive anti-inflammatory strategy.

Hypertrophic responses can be initiated by PI3K signaling pathways. Currently new research was published which identify a function for PTEN-PI3Kγ pathway in the modulation of heart muscle contractility. Whereas PI3Kα mediates the alteration in cell size seen during heart hypertrophy up to heart failure, PI3Kγ acts as a negative regulator of cardiac contractility.

PTEN is a dual-specificity protein phosphatase recently implicated as a phosphoinositide phosphatase in cellular growth signaling. The tumor suppressor PTEN is shown to dephosphorylate phosphatidylinositol 3,4,5-triphosphate (PIP3) which is an important second messenger generated specifically by the actions of PI3K. The PTEN reduces the levels of PIP3 within the cells and antagonizes PI3K mediated cellular signaling. It is also reported that expression of dominant-negative PTEN in rat cardiomyocytes in tissue culture results in hypertrophy.

PI3Kγ modulates baseline cAMP levels and controls contractility in cells. This study also indicates that alterations in baseline cAMP level contribute to the increased contractility in mutant mice [17].

Therefore, this research result shows that PI3Kγ is involved in myocardial contractility and therefore the inhibitors would be potential treatments of congestive heart failure, ischemia, pulmonary hypertension, renal failure, cardiac hypertrophy, atherosclerosis, thromboembolism, and diabetes.

A inhibitor of PI3K, which is expected to block signal transduction from GPCR and the activation of various immune cells, should have a broad anti-inflammatory profile with potential for the treatment of inflammatory and immunoregulatory disorders, [2] including asthma, atopic dermatitis, rhinitis, allergic diseases, chronic obstructive pulmonary disease (COPD), septic shock, joint diseases, autoimmune pathologies such as rheumatoid arthritis, and Graves' disease, diabetes, cancer, myocardial contractility disorders, thromboembolism [18], and atherosclerosis.

Some PI3-kinase inhibitors has been identified: wortmannin, originally isolated as a fungal toxin from *Penicllium wortmannii* [19], the closely related but less well characterized demethoxyviridin and LY294002, a morpholino derivative of the broad-spectrum kinase inhibitor quercetin [20].

U.S. Pat. No. 3,644,354 discloses 5-substituted 2,3, dihydroimidazo[1,2-c]quinazolines represented by the general formula:

wherein R and $R^0$ is independently, hydrogen, lower alkyl, lower alkenyl; R' and R" are independently, hydrogen, halogen, lower alkyl, lower alkoxy or as a hypotensive agents and coronary dilators However, none of the references discloses fused azolepyrimidine such as, but not limited to, azole-quinazoline, azole-pyridopyridazine, azole-pyrimidopyrimidine, azole-pyrimidopyridazine, azole-pyrimidotriazine, azole-pteridine, azole-pyrimidotetrazine and other derivatives having acylated amine or —$CR^5R^6$—C(O)— ($R^5$ is hydrogen or $C_{1-6}$ alkyl and $R^6$ is halogen, hydrogen, or $C_{1-6}$ alkyl) linker at the 5 or 6 position of the fused azolepyrimidine also having PI3K inhibitory activity.

The development of a compound which is useful for treatment and prophylaxis of inflammatory, cancer and/or myocardial contractility disorders associated with PI3K activity has been still desired.

SUMMARY OF THE INVENTION

As a result of extensive studies on chemical modification of the fused azolepyrimidine derivatives, the present inventors have found that the compounds of novel chemical structure related to the present invention have PI3K inhibitory activity and particularly have PI3K-γ inhibitory activity. The present invention has been accomplished based on these findings.

This invention is to provide novel fused azolepyrimidine derivatives of the formula (I) their tautomeric and stereoisomeric forms, and salts thereof.

wherein
X represents $CR^5R^6$ or NH;
$Y^1$ represents $CR^3$ or N;
Chemical bond between $Y^2$=$Y^3$ represents a single bond or double bond,
with the proviso that when the $Y^2$=$Y^3$ represents a double bond,
$Y^2$ and $Y^3$ independently represent $CR^4$ or N, and
when $Y^2$=$Y^3$ represents a single bond, $Y^2$ and $Y^3$ independently represent $CR^3R^4$ or $NR^4$;
$Z^1$, $Z^2$, $Z^3$ and $Z^4$ independently represent CH, $CR^2$ or N;
$R^1$ represents aryl optionally having 1 to 3 substituents selected from $R^{11}$, $C_{3-8}$ cycloalkyl optionally having 1 to 3 substituents selected from $R^{11}$,
$C_{1-6}$ alkyl optionally substituted by
aryl, heteroaryl, $C_{1-6}$ alkoxyaryl, aryloxy, heteroaryloxy or one or more halogen,
$C_{1-6}$ alkoxy optionally substituted by
carboxy, aryl, heteroaryl, $C_{1-6}$ alkoxyaryl, aryloxy, heteroaryloxy or one or more halogen,
or
a 3 to 15 membered mono- or bi-cyclic heterocyclic ring that is saturated or unsaturated, and contains 1 to 3 heteroatoms selected from the group consisting of N, O and S, and optionally having 1 to 3 substituents selected from $R^{11}$
wherein
$R^{11}$ represents
halogen, nitro, hydroxy, cyano, carboxy, amino, N—($C_{1-6}$ alkyl)amino, N-(hydroxy$C_{1-6}$alkyl)amino, N,N-di($C_{1-6}$ alkyl)amino, N—($C_{1-6}$acyl)amino, N-(formyl)-N—($C_{1-6}$alkyl)amino, N—($C_{1-6}$alkanesulfonyl)amino, N-(carboxy$C_{1-6}$-alkyl)-N—($C_{1-6}$alkyl)amino, N—($C_{1-6}$alkoxycarbonyl)amino, N—[N,N-di($C_{1-6}$alkyl)amino methylene]amino, N—[N,N-di($C_{1-6}$alkyl)amino ($C_{1-6}$ alkyl)methylene]amino, N—[N,N-di($C_{1-6}$alkyl) amino $C_{2-6}$alkenyl]amino, aminocarbonyl, N—($C_{1-6}$ alkyl)aminocarbonyl, N,N-di($C_{1-6}$alkyl)aminocarbonyl, $C_{3-8}$cycloalkyl, $C_{1-6}$ alkylthio, $C_{1-6}$alkanesulfonyl, sulfamoyl, $C_{1-6}$alkoxycarbonyl,
N-arylamino wherein said aryl moiety is optionally having 1 to 3 substituents selected from $R^{101}$, N-(aryl $C_{1-6}$alkyl) amino wherein said aryl moiety is optionally having 1 to 3 substituents selected from $R^{101}$, aryl $C_{1-6}$alkoxycarbonyl wherein said aryl moiety is optionally having 1 to 3 substituents selected from $R^{101}$,
$C_{1-6}$alkyl optionally substituted by
mono-, di- or tri-halogen, amino, N—($C_{1-6}$alkyl)amino or N,N-di($C_{1-6}$alkyl)amino,
$C_{1-6}$alkoxy optionally substituted by
mono-, di- or tri-halogen, N—($C_{1-6}$alkyl)sulfonamide, or N-(aryl)sulfonamide,
or
a 5 to 7 membered saturated or unsaturated ring having 1 to 3 heteroatoms selected from the group consisting of O, S and N, and optionally having 1 to 3 substituents selected from $R^{101}$ wherein
R$^{107}$ represents
halogen, carboxy, amino, N—(C$_{1-6}$ alkyl)amino, N,N-di(C$_{1-6}$alkyl)amino, aminocarbonyl, N—(C$_{1-6}$alkyl)aminocarbonyl, N,N-di(C$_{1-6}$alkyl)aminocarbonyl, pyridyl, C$_{1-6}$ alkyl optionally substituted by cyano or mono- di- or tri-halogen,
or
C$_{1-6}$alkoxy optionally substituted by cyano, carboxy, amino, N—(C$_{1-6}$ alkyl)amino, N,N-di(C$_{1-6}$alkyl)amino, aminocarbonyl, N—(C$_{1-6}$alkyl)aminocarbonyl, N,N-di(C$_{1-6}$alkyl)aminocarbonyl or mono-, di- or tri-halogen;
R$^2$ represents hydroxy, halogen, nitro, cyano, amino, N—(C$_{1-6}$alkyl)amino, N,N-di(C$_{1-6}$alkyl)amino, N-(hydroxyC$_{1-6}$alkyl)amino, N-(hydroxyC$_{1-6}$alkyl)-N—(C$_{1-6}$ alkyl)amino, C$_{1-6}$ acyloxy, aminoC$_{1-6}$ acyloxy, C$_{2-6}$-alkenyl, aryl, a 5-7 membered saturated or unsaturated heterocyclic ring having 1 to 3 heteroatoms selected from the group consisting O, S and N, and optionally substituted by hydroxy, C$_{1-6}$ alkyl, C$_{1-6}$ alkoxy, oxo, amino, amino C$_{1-6}$alkyl, N—(C$_{1-6}$(C$_{1-6}$alkyl)amino, N,N-di(C$_{1-6}$alkyl)amino, N—(C$_{1-6}$ acyl)amino, N—(C$_{1-6}$alkyl)carbonylamino, phenyl, phenyl C$_{1-6}$ alkyl, carboxy, Cl$_6$alkoxycarbonyl, aminocarbonyl, N—(C$_{1-6}$alkyl)aminocarbonyl, or N,N-di(C$_{1-6}$alkyl)amino,
—C(O)—R$^{20}$
wherein
R$^{20}$ represents C$_{1-6}$ alkyl, C$_{1-6}$ alkoxy, amino, N—(C$_{1-6}$ alkyl)amino, N,N-di(C$_{1-6}$alkyl)amino, N—(C$_{1-6}$ acyl)amino, or a 5-7 membered saturated or unsaturated heterocyclic ring having 1 to 3 heteroatoms selected from the group consisting O, S and N, and optionally substituted by C$_{1-6}$ alkyl, C$_{1-6}$ alkoxy, oxo, amino, N—(C$_{1-6}$ alkyl)amino, N,N-di(C$_{1-6}$alkyl)amino, N—(C$_{1-6}$ acyl)amino, phenyl, or benzyl,
C$_{1-6}$ alkyl optionally substituted by R$^{21}$
or
C$_{1-6}$ alkoxy optionally substituted by R$^{21}$
wherein
R$^{21}$ represents cyano, mono-, di or tri-halogen, hydroxy, amino, N—(C$_{1-6}$alkyl)amino, N,N-di(C$_{1-6}$alkyl)amino, N-(hydroxyC$_{1-6}$ alkyl) amino, N-(halophenylC$_{1-6}$ alkyl) amino, amino C$_{2-6}$ alkylenyl, CI, alkoxy, hydroxyC$_{1-6}$ alkoxy, —C(O)—R$^{201}$, —NHC(O)—R$^{201}$, C$_{3-8}$cycloalkyl, isoindolino, phthalimidyl, 2-oxo-1,3-oxazolidinyl, aryl or a 5 or 6 membered saturated or unsaturated heterocyclic ring having 1 to 4 heteroatoms selected from the group consisting O, S and N optionally substituted by
hydroxy, C$_{1-6}$ alkyl, C$_{1-6}$ alkoxy, C$_{1-6}$ alkoxycarbonyl, hydroxyC$_{1-6}$ alkoxy, oxo, amino, aminoC$_{1-6}$alkyl, N—(C$_{1-6}$alkyl)amino, N,N-di(C$_{1-6}$alkyl)amino, N—(C$_{1-6}$ acyl)amino, or benzyl,
wherein
R$^{201}$ represents hydroxy, amino, N—(C$_{1-6}$alkyl)amino, N,N-di(C$_{1-6}$alkyl)amino, N-(halophenylC$_{1-6}$ alkyl) amino, C$_{1-6}$alkyl, aminoC$_{1-6}$ alkyl, aminoC$_{2-6}$ alkylenyl, C$_{1-4}$ alkoxy, a 5 or 6 membered saturated or unsaturated heterocyclic ring having 1 to 4 heteroatoms selected from the group consisting O, S and N optionally substituted by
hydroxy, C$_{1-6}$ alkyl, C$_{1-6}$ alkoxy, C$_{1-6}$ alkoxycarbonyl, hydroxyC$_{1-6}$ alkoxy, oxo, amino, N—(C$_{1-6}$alkyl) amino, N,N-di(C$_{1-6}$alkyl)amino, N—(C$_{1-6}$ acyl) amino or benzyl;

R$^3$ represents hydrogen, halogen, aminocarbonyl, or C$_{1-6}$ alkyl optionally substituted by aryl C$_{1-6}$ alkoxy or mono-, di- or tri-halogen;
R$^4$ represents hydrogen or C$_{1-6}$ alkyl;
R$^5$ represents hydrogen or C$_{1-6}$ alkyl; and
R$^6$ represents halogen, hydrogen or C$_{1-6}$ alkyl.

The compounds of the present invention show PI3K inhibitory activity and PI3K-γ inhibitory activity. They are, therefore, suitable for the production of medicament or medical composition, which may be useful for treatment and prophylaxis of PI3K and/or PI3K-γ related diseases for example, inflammatory and immunoregulatory disorders, such as asthma, atopic dermatitis, rhinitis, allergic diseases, chronic obstructive pulmonary disease (COPD), septic shock, joint diseases, autoimmune pathologies such as rheumatoid arthritis, and Graves' disease, myocardial contractility disorders, heart failure, thromboembolism, ischemia, cardiac. hypertrophy, atherosclerosis and cancer such as skin cancer, bladder cancer, breast cancer, uterus cancer, ovary cancer, prostate cancer, lung cancer, colon cancer, pancreas cancer, renal cancer, gastric cancer, brain tumor, leukemia, etc.

The compounds of the present invention are also useful for treatment of pulmonary hypertension, renal failure, Huntington's chorea and cardiac hypertrophy, as well as neurodegenerative disorders such as Parkinson's disease, Alzheimer's disease, diabetes and focal ischemia, since the diseases also relate to PI3K activity in a human or animal subject.

This invention is also to provide a method for treating or preventing a disorder or disease associated with PI3K activity, especially with PI3K-γ activity, in a human or animal subject, comprising administering to said subject a therapeutically effective amount of the fused azolepyrimidine derivatives shown in the formula (I), its tautomeric or stereoisomeric form, or a physiologically acceptable salt thereof.

Further this invention is to provide a use of the fused azolepyrimidine derivatives shown in the formula (I), its tautomeric or stereoisomeric form, or a physiologically acceptable salt thereof in the preparation of a medicament.

In one embodiment, the present invention provides the fused azolepyrimidine derivative of the formula (I), its tautomeric or stereoisomeric form, or a salt thereof; wherein
X represents CR$^5$R$^6$ or NH;
Y$^1$ represents CR$^3$ or N;
Chemical bond between Y$^2$═Y$^3$ represents a single bond or double bond,
with the proviso that when the Y$^2$═Y$^3$ represents a double bond,
Y$^2$ and Y$^3$ independently represent CR$^4$ or N, and
when Y$^2$═Y$^3$ represents a single bond, Y$^2$ and Y$^3$ independently represent CR$^3$R$^4$ or NR$^4$;
Z$^1$, Z$^2$, Z$^3$ and Z$^4$ independently represent CH, CR$^2$ or N;
R$^1$ represents
C$_{1-6}$ alkyl optionally substituted by
mono-, di- or tri-halogen, phenyl, methoxyphenyl, phenoxy, or thienyl,
C$_{1-6}$ alkoxy optionally substituted by mono-, di- or tri-halogen, phenyl, methoxyphenyl, phenoxy, or thienyl,
or
one of the following carbocyclic and heterocyclic rings selected from the group consisting of cyclopropyl, cyclohexyl, piperidinyl, piperazinyl, pyrrolyl, pyrazolyl, furyl, thienyl, thiazolyl, isothiazolyl, oxazolyl, isoxazolyl, imidazolyl, isoimidazolyl, pyrazolyl, 1,2,3-thiadiazolyl, 1,2,4-thiadiazolyl, 1,2,5-thiadiazolyl, 1,3,4-thiadiazolyl, 1,2,3-oxadiazolyl, 1,2,4-oxadiazolyl, 1,2,5-oxadiazolyl, 1,3,4-oxadiazolyl, 1,2,3-triazole, 1,2,4-triazole, 1,2,5-triazole, 1,3,4-triazole, phenyl, pyridyl, pyrazinyl, pyrimidinyl, pyridazinyl, 1-benzothiophenyl, benzothiazolyl, benzimidazolyl, 3H-imidazo[4,5-b]pyridinyl, benzotriazolyl, indolyl, indazolyl, imidazo[1,2-a]pyridinyl, quinolinyl, and 1,8-naphthyridinyl, wherein said carbocyclic and heterocyclic rings optionally substituted with 1 to 3 substituents selected from the group consisting of hydroxy, halogen, nitro, cyano, carboxy, amino, N—($C_{1-6}$alkyl)amino, N,N-di($C_{1-6}$alkyl)amino, N—($C_{1-6}$acyl)amino, N—($C_{1-6}$alkoxycarbonyl)amino, N-(formyl)-N—($C_{1-6}$alkyl)amino, N[N,N-di($C_{1-6}$alkyl)amino methylene]amino, N[,N-di($C_{1-6}$alkyl)amino ($C_{1-6}$alkylene)methylene]amino, N—[N,N-di($C_{1-6}$alkyl)amino $C_{2-6}$alkenyl]amino, $C_{1-6}$ alkylthio, $C_{1-6}$alkanesulfonyl, sulfamoyl, $C_{1-6}$alkoxy, $C_{1-6}$alkoxycarbonyl, pyrrolyl, imidazolyl, pyrazolyl, pyrrolidinyl, pyridyl, phenyl $Cl_6$alkoxycarbonyl, thiazolyl optionally substituted by pyridyl, piperazinyl optionally substituted by $C_{1-6}$ alkyl or $C_{1-6}$alkoxy and $C_{1-6}$alkyl optionally substituted by mono-, di- or tri-halogen;

$R^2$ represents hydroxy, halogen, nitro, cyano, carboxy, amino, N—($C_{1-6}$alkyl)amino, N-(hydroxy $C_{1-6}$alkyl)amino, N,N-di($C_{1-6}$alkyl)amino, N-(hydroxy $C_{1-6}$alkyl)-N—($C_{1-6}$alkyl)amino, $C_{2-6}$alkenyl, $C_{1-6}$alkoxycarbonyl, aminocarbonyl, $C_{1-6}$acyloxy, amino$C_{1-6}$ acyloxy, furyl, morpholino, phenyl, piperidino, aryl, pyrrolidinyl optionally substituted by $C_{1-6}$acylamino, piperidino optionally substituted by hydroxy, $C_{1-6}$ alkyl, carboxy, aminocarbonyl, N—($C_{1-6}$alkyl)aminocarbonyl, or N,N-di($C_{1-6}$alkyl)aminocarbonyl, piperazinyl optionally substituted-by $C_{1-6}$ alkyl, $C_{1-6}$ alkyl optionally substituted by cyano, mono-, di- or tri-halogen, hydroxy, amino, N—($C_{1-6}$alkyl)amino, N-(hydroxy $C_{1-6}$alkyl)amino, N,N-di($C_{1-6}$alkyl)amino, $C_{3-6}$cycloalkyl, tetrazolyl, tetrahydropyranyl, morpholino, phthalimidyl, 2-oxo-1,3oxazolidinyl, phenyl, —C(O)—$R^{201}$, pyrrolidinyl optionally substituted by $C_{1-6}$acylamino, piperidino optionally substituted by hydroxy, $C_{1-6}$ alkyl, carboxy, aminocarbonyl, N—($C_{1-6}$alkyl)aminocarbonyl, or N,N-di($C_{1-6}$alkyl)aminocarbonyl, or piperazinyl optionally substituted by $C_{1-6}$ alkyl, wherein $R^{201}$ represents hydroxy, amino, N—($C_{1-6}$alkyl)amino, N,N-di($C_{1-6}$alkyl)amino, N-(halobenzyl)amino, $C_{1-6}$alkyl, $C_{1-6}$ alkoxy, tetrazolyl, tetrahydropyranyl, morpholino, pyrrolidinyl optionally substituted by $C_{1-6}$acylamino, piperidino optionally substituted by hydroxy, $C_{1-6}$ alkyl, carboxy, aminocarbonyl, N—($C_{1-6}$alkyl)aminocarbonyl, or N,N-di($C_{1-6}$alkyl)aminocarbonyl, or piperazinyl optionally substituted by $C_{1-6}$ alkyl, $C_{1-6}$ alkoxy optionally substituted by cyano, mono-, di- or tri-halogen, hydroxy, $C_{1-6}$alkoxy, hydroxy $C_{1-6}$ alkoxy, amino, N—($C_{1-6}$alkyl)amino, N,N-di($C_{1-6}$alkyl)amino, pyrrolyl, tetrazolyl, tetrahydropyranyl, morpholino, phthalimidyl, 2-oxo-1,3oxazolidinyl, phenyl, —C(O)—$R^{201}$, pyrrolidinyl optionally substituted by $C_{1-6}$acylamino, piperidino optionally substituted by hydroxy, $C_{1-6}$ alkyl, carboxy, aminocarbonyl, N—($C_{1-6}$-alkyl)aminocarbonyl, or N,N-di($C_{1-6}$-allyl)aminocarbonyl, or piperazinyl optionally substituted by $C_{1-6}$ alkyl, wherein $R^{201}$ represents hydroxy, amino, N—($C_{1-6}$alkyl)amino, N,N-di($C_{1-6}$alkyl)amino, N(halobenzyl)amino, $C_{1-6}$ alkyl, $C_{1-6}$ alkoxy, amino $C_{2-6}$ alkylenyl, tetrazolyl, tetrahydropyranyl, morpholino, pyrrolidinyl optionally substituted by $C_{1-6}$acylamino, piperidino optionally substituted by hydroxy, $C_{1-6}$ alkyl, carboxy, aminocarbonyl, N—($C_{1-6}$alkyl)aminocarbonyl, or N,N-di($C_{1-6}$alkyl)aminocarbonyl, or piperazinyl optionally substituted by $C_{1-6}$alkyl;

$R^3$ represents hydrogen, halogen, $C_{1-6}$ alkyl optionally substituted by aminocarbonyl, aryl$C_{1-6}$ alkoxy, or mono-, di- or tri-halogen;

$R^4$ represents hydrogen or $C_{1-6}$ alkyl;

$R^5$ represents hydrogen or $C_{1-6}$ alkyl; and $R^6$ represents hydrogen, halogen or $C_{1-6}$ alkyl.

In another embodiment, the present invention provides the fused azolepyrimidine derivative of the formula (I), its tautomeric or stereoisomeric form, or a salt thereof:

wherein

X represents $CR^5R^6$ or NH;

$Y^1$ represents N;

$Y^2$ and $Y^3$ represent $CR^3R^4$;

Chemical bond between $Y^2$=$Y^3$ represents a single bond $Z^4$ represents CH;

$Z^1$, $Z^2$ and $Z^3$ independently represent N, CH or $CR^2$;

$R^1$ represents cyclopropyl, cyclopentyl, cyclohexyl, 2-furyl, 3-furyl, imidazolyl, pyrimidinyl, pyridazinyl, piperazinyl, 1,2,3-thiadiazolyl, 1,3-benzothiazolyl, quinolyl, 3H-imidazo[4,5-b]pyridinyl, 1H-pyrrol-2-yl optionally substituted by $C_{1-6}$alkyl, 1H-pyrrol-3-yl optionally substituted by $C_{1-6}$alkyl, pyrazolyl optionally substituted by 1 or 2 $C_{1-6}$alkyl, isoxazolyl optionally substituted by 1 or 2 $C_{1-6}$alkyl, 2-thienyl optionally substituted by chloro, nitro, cyano, or $C_{1-6}$ alkyl, 3-thienyl optionally substituted by chloro, nitro, cyano, or $C_{1-6}$ alkyl, piperidinyl optionally substituted by $C_{1-6}$alkoxycarbonyl, or benzyloxycarbonyl, phenyl optionally substituted by 1 to 3 substituents selected from the group consisting of fluoro, chloro, hydroxy, nitro, cyano, carboxy, $C_{1-6}$ alkyl, $C_{1-6}$alkoxy, $C_{1-6}$alkoxycarbonyl, amino, N—($C_{1-6}$alkyl)amino, N—($C_{1-6}$acyl)amino, N—($C_{1-6}$alkoxycarbonyl)amino, N,N-di($C_{1-6}$alkyl)amino, N-(formyl)-N—$C_{1-6}$alkyl amino, $C_{1-6}$ alkylthio, $C_1$alkanesulfonyl, sulfamoyl, pyrrolyl, imidazolyl, pyrazolyl, and piperazinyl optionally substituted by $C_{1-6}$alkyl, pyridyl optionally substituted by 1 or 2 substituents selected from the group consisting of chloro, hydroxy, carboxy, $C_1$ alkoxy, $C_{1-6}$alkylthio, amino, N—($C_{1-6}$alkyl)amino, N-(hydroxy$C_{1-6}$alkyl)amino, N,N-di($C_{1-6}$alkyl)amino, N—($C_{1-6}$acyl)amino, N—($C_{1-6}$alkane)sulfonyl amino, N[N,N-di($C_{1-6}$alkyl)amino methylene] amino, and $C_{1-6}$alkyl optionally substituted by tri halogen, pyrazinyl optionally substituted by $C_{1-6}$alkyl, 1,3-thiazolyl optionally substituted by 1 or 2 substituents selected from the group consisting of $C_{1-6}$alkyl, pyridyl and N—($C_{1-6}$alkoxycarbonyl)amino, indolyl optionally substituted by $C_{1-6}$alkyl, benzimidazolyl optionally substituted by $C_{1-6}$alkyl or tri-halo $C_{1-6}$alkyl, 1,2,3-benzotriazolyl optionally substituted by $C_{1-6}$alkyl, 1,8-naphthyridinyl optionally substituted by $C_{1-6}$alkyl optionally substituted by tri halogen,
$C_{1-6}$ alkyl optionally substituted by tri-halogen, phenyl, phenoxy, or thienyl,
or
$C_{1-6}$alkoxy optionally substituted by phenyl, phenoxy, or thienyl;
$R^2$ represents fluoro, chloro, bromo, hydroxy, nitro, vinyl, cyano, amino, aminoacetoxy, N—($C_{1-6}$alkyl)amino, N,N-di($C_{1-6}$alkyl)amino, N-(hydroxy$C_{1-6}$alkyl)-N—($C_{1-6}$alkyl)amino, 2-furyl, piperidino, morpholino, phenyl,
pyrrolidinyl optionally substituted by acetamido,
piperidino optionally substituted by hydroxy,
piperazinyl optionally substituted by methyl, benzyl, $C_{1-6}$alkoxycarbonyl, or aminocarbonyl,
$C_{1-6}$ alkyl optionally substituted by cyano, tri-fluoro, carboxy, methoxycarbonyl, aminocarbonyl, tert-butoxycarbonyl, tetrahydropyranyl, or morpholino,
$C_{1-6}$ alkoxy optionally substituted by hydroxy, cyano, methoxy, methoxycarbonyl, tert-butoxycarbonyl, carboxy, aminoacetyl, dimethylamino, aminocarbonyl, methylaminocarbonyl, dimethylaminocarbonyl, isopropylaminocarbonyl, fluorobenzylaminocarbonyl, cyclopropyl, pyrrolidinyl, piperidino, tetrahydropyranyl, morpholino, morpholinocarbonyl, 2-oxo-1,3-oxazolidin-4-yl, phthalimid-N-yl, or hydroxy $C_{1-6}$ alkyleneoxy,
$R^3$ represents hydrogen;
$R^4$ represents hydrogen;
$R^5$ represents hydrogen; and
$R^6$ represents hydrogen.
In another embodiment, the present invention provides the fused azolepyrimidine derivative of the formula (I), its tautomeric or stereoisomeric form, or a salt thereof:
X represents $CR^5R^6$ or NH;
$Y^1$ represents N;
$Y^2$ and $Y^3$ represent $CR^3R^4$;
Chemical bond between $Y^2=Y^3$ represents a single bond
$Z^3$ and $Z^4$ represent CH;
$Z^1$ and $Z^2$ independently represent CH or $CR^2$;
$R^1$ represents 3H-imidazo[4,5-b]pyridinyl, benzimidazolyl pyridyl optionally substituted by hydroxy, amino, acetamido, methoxybenzyloxy or methylsulfonylamino,
or
1,3-thiazolyl optionally substituted by 1 or 2 methyl;
$R^2$ represents fluoro, chloro, bromo, morpholino, piperazinyl, methylpiperazinyl, methyl, tri-fluoro methyl, or
$C_{1-6}$ alkoxy optionally substituted by hydroxy, cyano, carboxy, dimethylaminocarbonyl, tetrahydropyranyl, morpholino, morpholinocarbonyl, tetrazolyl, or phthalimid-N-yl;
$R^3$ represents hydrogen;
$R^4$ represents hydrogen;
$R^5$ represents hydrogen; and
$R^6$ represents hydrogen.
In another embodiment, the present invention provides the fused azolepyrimidine derivative of the formula (I), its tautomeric or stereoisomeric form, or a salt thereof:
wherein
X represents $CR^5R^6$ or NH;
$Y^1$ represents N;
$Y^2$ and $Y^3$ represent $CR^3R^4$;
Chemical bond between $Y^2=Y^3$ represents a single bond.
$Z^3$ and $Z^4$ represent CH;
$Z^1$ and $Z^2$ independently represent CH or $CR^2$;

In another embodiment, the present invention provides the fused azolepyrimidine derivative of the formula (I), its tautomeric or stereoisomeric form, or a salt thereof:
X represents $CR^5R^6$ or NH;
$Y^1$ represents N;
$Y^2$ and $Y^3$ represent $CR^3R^4$;
Chemical bond between $Y^2=Y^3$ represents a single bond
$Z^1$ and $Z^4$ represent CH;
$Z^2$ and $Z^3$ independently represent CH or $CR^2$;
In another embodiment, the present invention provides the fused azolepyrimidine derivative of the formula (I), its tautomeric or stereoisomeric form, or a salt thereof:
X represents $CR^5R^6$ or NH;
$Y^1$ represents N;
$Y^2$ and $Y^3$ represent $CR^3R^4$;
Chemical bond between $Y^2=Y^3$ represents a single bond;
$Z^1$, $Z^3$ and $Z^4$ represent CH;
$Z^2$ represents $CR^2$;
The preferable compounds of the present invention are as follows:
N-(7,8-dimethoxy-2,3-dihydroimidazo[1,2-c]quinazolin-5-yl)nicotinamide;
2-(7,8-dimethoxy-2,3-dihydroimidazo[1,2-c]quinazolin-5-yl)-1-pyridin-3-yl-ethylenol;
N-(7,8-dimethoxy-2,3-dihydroimidazo[1,2-c]quinazolin-5-yl)-1H-benzimidazole-5-carboxamide;
6-(acetamido)-N-(7,8-dimethoxy-2,3-dihydroimidazo[1,2-c]quinazolin-5-yl)nicotinamide;
N-{5-[2-(7,8-dimethoxy-2,3-dihydroimidazo[1,2-c]quinazolin-5-yl)-1-hydroxyvinyl]pyridin-2-yl}acetamide;
2-({5-[2-hydroxy-2-pyridin-3-ylvinyl]-7-methoxy-2,3-dihydroimidazo[1,2-c]quinazolin-8-yl}oxy)-N,N-dimethylacetamide;
2-[7-methoxy-8-(tetrahydro-2H-pyran-2-ylmethoxy)-2,3-dihydroimidazo[1,2-c]quinazolin-5-yl]-1-pyridin-3-yl-ethylenol;
2-[8-(2-hydroxyethoxy)-7-methoxy-2,3-dihydroimidazo[1,2-c]quinazolin-5-yl]-1-pyridin-3-ylethylenol;
({5-[2-hydroxy-2-pyridin-3-ylvinyl]-7-methoxy-2,3-dihydroimidazo[1,2-c]quinazolin-8-yl}oxy)acetic acid;
4-({5-[2-hydroxy-2-pyridin-3-ylvinyl]-7-methoxy-2,3-dihydroimidazo[1,2-c]quinazolin-8-yl}oxy)butanoic acid;
({5-[2-hydroxy-2-pyridin-3-ylvinyl]-7-methoxy-2,3-dihydroimidazo[1,2-c]quinazolin-8-yl}oxy)acetonitrile;
2-[7-methoxy-8-(2H-tetrazol-5-ylmethoxy)-2,3-dihydroimidazo[1,2-c]quinazolin-5-yl]-1-pyridin-3-ylethylenol;
2-[7-methoxy-8-(4-morpholin-4-yl-4-oxobutoxy)-2,3-dihydroimidazo[1,2-c]quinazolin-5-yl]-1-pyridin-3-ylethylenol;
5-[1-hydroxy-2-(8-morpholin-4-yl-2,3-dihydroimidazo[1,2-c]quinazolin-5-yl)vinyl]pyridin-3-ol;
N-(2,3-dihydroimidazo[1,2-c]quinazolin-5-yl)-5-hydroxynicotinamide;
6-(acetamido)-N-(7,9-dimethoxy-8-methyl-2,3-dihydroimidazo[1,2-c]quinazolin-5-yl)nicotinamide;
N-(8,9-dimethoxy-2,3-dihydroimidazo[1,2-c]quinazolin-5-yl)-5-hydroxynicotinamide;
5-hydroxy-N-(7-methoxy-2,3-dihydroimidazo[1,2-c]quinazolin-5-yl)nicotinamide;
N-(7,8-dimethoxy-2,3-dihydroimidazo[1,2-c]quinazolin-5-yl)-5-[(4-methoxybenzyl)oxy]nicotinamide;
N-(7,8-dimethoxy-2,3-dihydroimidazo[1,2-c]quinazolin-5-yl)-5-hydroxynicotinamide;
5-hydroxy-N-[8-(trifluoromethyl)-2,3-dihydroimidazo[1,2-c]quinazolin-5-yl]nicotinamide;

N-{8-[3-(1,3-dioxo-1,3-dihydro-2H-isoindol-2-yl)propoxy]-2,3-dihydroimidazo[1,2-c]quinazolin-5-yl}nicotinamide;
N-(7-bromo-8-methoxy-2,3-dihydroimidazo[1,2-c]quinazolin-5-yl)nicotinamide;
6-amino-N-(8-methoxy-2,3-dihydroimidazo[1,2-c]quinazolin-5-yl)nicotinamide;
1-(1H-benzimidazol-5-yl)-2-(8,9-dimethoxy-2,3-dihydroimidazo[1,2-c]quinazolin-5-yl)ethylenol;
2-(8,9-dimethoxy-2,3-dihydroimidazo[1,2-c]quinazolin-5-yl)-1-(2,4-dimethyl-1,3-thiazol-5-yl)ethylenol;
N-(9-methoxy-2,3-dihydroimidazo[1,2-c]quinazolin-5-yl)-1H-benzimidazole-5-carboxamide;
N-(8-bromo-2,3-dihydroimidazo[1,2-c]quinazolin-5-yl)nicotinamide;
N-(8-bromo-2,3-dihydroimidazo[1,2-c]quinazolin-5-yl)-1H-benzimidazole-5-carboxamide;
N-(8-methoxy-2,3-dihydroimidazo[1,2-c]quinazolin-5-yl)-1H-benzimidazole-5-carboxamide;
N-(8-methyl-2,3-dihydroimidazo[1,2-c]quinazolin-5-yl)-1H-benzimidazole-5-carboxamide;
N-[8-(trifluoromethyl)-2,3-dihydroimidazo[1,2-c]quinazolin-5-yl]-1H-benzimidazole-5-carboxamide;
N-(7-fluoro-2,3-dihydroimidazo[1,2-c]quinazolin-5-yl)-1H-benzimidazole-5-carboxamide;
N-(7-methoxy-2,3-dihydroimidazo[1,2-c]quinazolin-5-yl)nicotinamide;
N-(8-chloro-2,3-dihydroimidazo[1,2-c]quinazolin-5-yl)-1H-benzimidazole-5-carboxamide;
6-(acetamido)-N-(8-morpholin-4-yl-2,3-dihydroimidazo[1,2-c]quinazolin-5-yl)nicotinamide;
1-(1H-benzimidazol-5-yl)-2-(8-morpholin-4-yl-2,3-dihydroimidazo[1,2-c]quinazolin-5-yl)ethylenol;
N-{5-[1-hydroxy-2-(8-morpholin-4-yl-2,3-dihydroimidazo[1,2-c]quinazolin-5-yl)vinyl]pyridin-2-yl}acetamide;
6-methyl-N-(8-morpholin-4-yl-2,3-dihydroimidazo[1,2-c]quinazolin-5-yl)nicotinamide;
1-(1H-benzimidazol-5-yl)-2-[8-(4-methylpiperazin-1-yl)-2,3-dihydroimidazo[1,2-c]quinazolin-5-yl]ethylenol;
N-(2,3-dihydroimidazo[1,2-c]quinazolin-5-yl)-3H-imidazo[4,5-b]pyridine-6-carboxamide;
N-(7,8-dimethoxy-2,3-dihydroimidazo[1,2-c]quinazolin-5-yl)-3H-imidazo[4,5-b]pyridine-6-carboxamide;
N-[7-(trifluoromethyl)-2,3-dihydroimidazo[1,2-c]quinazolin-5-yl]-1H-benzimidazole-5-carboxamide;
N-(7,9-dimethoxy-2,3-dihydroimidazo[1,2-c]quinazolin-5-yl)-1H-benzimidazole-5-carboxamide;
N-{5-[2-(7,9-dimethoxy-8-methyl-2,3-dihydroimidazo[1,2-c]quinazolin-5-yl)-1-hydroxyvinyl]pyridin-2-yl}acetamide;
N-{5-[2-(7-bromo-9-methyl-2,3-dihydroimidazo[1,2-c]quinazolin-5-yl)-1-hydroxyvinyl]pyridin-2-yl}acetamide; and
2-(8,9-dimethoxy-2,3-dihydroimidazo[1,2-c]quinazolin-5-yl)-1-pyridin-3-ylethylenol;
and its tautomeric or stereoisomeric form, pharmaceutically acceptable salts thereof.

Further, the present invention provides a medicament, which includes one of the compounds, described above and optionally pharmaceutically acceptable excipients.

Alkyl per se and "alk" and "alkyl" in alkane, alkoxy, alkanoyl, alkylamino, alkylaminocarbonyl, alkylaminosulphonyl, alkylsulphonylamino, alkoxycarbonyl, alkoxycarbonylamino and alkanoylamino represent a linear or branched alkyl radical having generally 1 to 6, preferably 1 to 4 and particularly preferably 1 to 3 carbon atoms, representing illustratively and preferably methyl, ethyl, propyl, isopropyl, isobutyl, tert-butyl, sec-butyl, pentyl, n-hexyl, and the like.

Alkylene represents the divalent linear or branched saturated hydrocarbon radical, consisting solely of carbon and hydrogen atoms, having generally 1 to 6 carbon preferably 1 to 4 and particularly preferably 1 to 3 carbon atoms, representing illustratively and preferably methylene, ethylene, 2-methyl-propylene, butylene, 2-ethylbutylene and the like.

Alkoxy illustratively and preferably represents methoxy, ethoxy, n-propoxy, isopropoxy, tert-butoxy, n-pentoxy, n-hexyl, and the like.

Alkylamino represents an alkylamino radical having one or two (independently selected) alkyl substituents, illustratively and preferably representing methylamino, ethylamino, n-propylamino, isopropylamino, tert-butylamino, n-pentylamino, n-hexyl-amino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino, N-n-hexyl-N-methylamino and the like.

Alkylaminocarbonyl represents an radical having one or two (independently selected) alkyl substituents, illustratively and preferably representing methylaminocarbonyl, ethylaminocarbonyl, n-propylaminocarbonyl, isopropylamino-carbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylamino-carbonyl, N-n-hexyl-N-methylaminocarbonyl and the like.

Alkylaminosulphonyl represents an alkylaminosulphonyl radical having one or two (independently selected) alkyl substituents, illustratively and preferably representing methylaminosulphonyl, ethylaminosulphonyl, n-propylaminosulphonyl, isopropylaminosulphonyl, tert-butylaminosulphonyl, n-pentylaminosulphonyl, n-hexyl-aminosulphonyl, N,N-dimethylaminosulphonyl, N,N-diethylaminosulphonyl, N-ethyl-N-methylamino-sulphonyl, N-methyl-N-n-propylaminosulphonyl, N-isopropyl-N-n-propylaminosulphonyl, N-t-butyl-N-methylaminosulphonyl, N-ethyl-N-n-pentylaminosulphonyl, N-n-hexyl-N-methylaminosulphonyl and the like.

Alkylsulphonyl illustratively and preferably represents methylsulphonyl, ethylsulphonyl, n-propylsulphonyl, isopropylsulphonyl, tert-butyl-sulphonyl, n-pentylsulphonyl, n-hexylsulphonyl and the like.

Alkoxycarbonyl illustratively and preferably represents methoxycarbonyl, ethoxycarbonyl, n-propoxycarbonyl, isopropoxycarbonyl, tert-butoxycarbonyl, n-pentoxycarbonyl, n-hexoxycarbonyl and the like.

Alkoxycarbonylamino illustratively and preferably represents methoxycarbonylamino, ethoxycarbonylamino, n-propoxycarbonylamino, isopropoxycarbonylamino, tert-butoxycarbonylamino, n-pentoxycarbonylamino, n-hexoxycarbonylamino and the like.

Alkanoylamino illustratively and preferably represents acetamido, ethylcarbonylamino and the like.

Cycloalkyl per se and in cycloalkylamino and in cycloalkylcarbonyl represents a cycloalkyl group having generally 3 to 8 and preferably 5 to 7 carbon atoms, illustratively and preferably representing cyclopropyl, cyclobutyl, cyclopentyl, cyclohexyl, cycloheptyl and the like.

Aryl per se and "aryl" in arylamino, arylcarbonyl, alkoxyaryl, represents a mono- to tricyclic aromatic carbocyclic radical having generally 6 to 14 carbon atoms, illustratively and preferably representing phenyl, naphthyl, phenanthrenyl and the like.

Arylamino represents an arylamino radical having one or two (independently selected) aryl substituents, illustratively and preferably representing phenylamino, diphenylamino, naphthylamino and the like.

Heteroaryl per se and "heteroaryl" in heteroarylamino and heteroarylcarbonyl represents an aromatic mono- or bicyclic radical having generally 5 to 15 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, thiazolyl, pyrazinyl, pyridinyl, pyrimidinyl, pyridazinyl, thiophenyl, indolyl, isoindolyl, indazolyl, benzofuranyl, benzothiophenyl, quinolinyl, isoquinolinyl, 1,3 benzodioxole, benzofuranyl, benzofuran-2,5-diyl, benzofuran-3,5-diyl, and the like.

Heterocyclic per se and heterocyclic ring per se represent a mono- or polycyclic, preferably mono- or bicyclic, nonaromatic heterocyclic radical having generally 4 to and preferably 5 to 8 ring atoms and up to 3 and preferably up to 2 hetero atoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two hetero atoms selected from the group consisting of O, N and S, such as illustratively and preferably tetrahydrofuran-2-yl, pyrrolidin-2-yl, pyrrolidin-3-yl, pyrrolinyl, piperidinyl, morpholino, perhydroazepinyl.

Heterocyclylcarbonyl illustratively and preferably represents tetrahydrofuran-2-carbonyl, pyrrolidine-2-carbonyl, pyrrolidine-3-carbonyl, pyrrolinecarbonyl, piperidinecarbonyl, morpholinecarbonyl, perhydroazepinecarbonyl.

Halogen and Halo represents fluoro, chloro, bromo and/or iodo.

Further, the present invention provides a medicament which include one of the compounds described above and optionally pharmaceutically acceptable excipients.

EMBODIMENT OF INVENTION

The compound of the formula (I) of the present invention can be, but not limited to be, prepared by reactions described below. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis ($3^{nd}$ Edition)" by Greene and Wuts.

The compound of the formula (I) of the present invention can be, but not limited to be prepared by the Method [A], and [B] below.

The compound of the formula (I-a):

(wherein $R^1$, $R^5$, $R^6$, $Y^1$, $Y^2$, $Y^3$, $Z^1$, $Z^2$, $Z^3$ and $Z^4$ are the same as defined above) can be, but not limited to be, prepared by the following Method A.

The compound of formula (I-a) can be prepared, for example, by the reaction of the compound of formula (II) (wherein $Y^1$, $Y^2$, $Y^3$, $Z^1$, $Z^2$, $Z^3$ and $Z^4$ are the same as defined above) with a compound of formula (III) (wherein $R^1$, $R^5$ and $R^6$ are the same as defined above, and L represents $C_{1-6}$ alkyl).

The reaction may be carried out without solvent, or in a solvent including, for instance, ethers such as diethyl ether, isopropyl ether, dioxane and tetrahydrofuran (THF) and 1,2-dimethoxyethane; aromatic hydrocarbons such as benzene, toluene and xylene; amides such as N,N-dimethylformamide (DMF), N,N-dimethylacetamide and N-methylpyrrolidone; sulfoxides such as dimethylsulfoxide (DMSO); alcohols such as methanol, ethanol, 1-propanol, isopropanol and tert-butanol; water, and others. Optionally, two or more of the solvents selected from the listed above can be mixed and used.

The reaction temperature can be optionally set depending on the compounds to be reacted. The reaction temperature is usually, but not limited to, about 10° C. to 200° C. and preferably about 50° C. to 160° C. The reaction may be conducted for, usually, 10 minutes to 48 hours and preferably 30 minutes to 24 hours.

Preparation of the Intermediates

The compound of formula (II') (wherein $Y^1$, $Z^1$, $Z^2$, $Z^3$ and $Z^4$ are the same as defined above, $Y^2$ and $Y^3$ independently represent $CR^3R^4$ or $NR^1$ and are connected by single bond) and the compound of formula (II') (wherein $Y^1$, $Z^1$, $Z^2$, $Z^3$ and $Z^4$ are the same as defined above, $Y^2$ and $Y^3$ independently represent CH or N and are connected by double bond) can be, but not limited to be, prepared by the following Method [A-i].

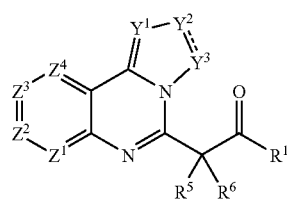

Method [A-i]

step 1

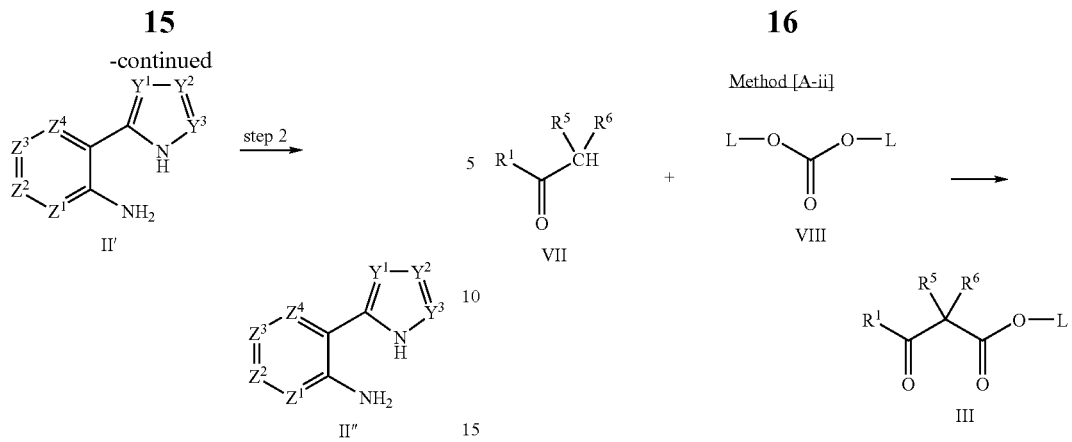

In the step 1, the compound of formula (II') (wherein $Y^1$, $Z^1$, $Z^2$, $Z^3$ and $Z^4$ are the same as defined above, $Y^2$ and $Y^3$ independently represent $CR^3R^4$ or $NR^4$ and are connected by single bond) can be prepared, for example, by the reaction of the compound of formula (VI) (wherein $Z^1$, $Z^2$, $Z^3$ and $Z^4$ are the same as defined above) with an diaminoalkane derivatives such as ethylenediamine.

The reaction can be advantageously carried out using appropriate dehydrating agents such as $SOCl_2$, $POCl_3$, $P_2O_5$, $P_2S_5$, $CS_2$ and others.

The reaction may be carried out without solvent, or in a solvent including for instance, ethers such as diethyl ether, isopropyl ether, dioxane and tetrahydrofuran (THF) and 1,2-dimethoxyethane; aromatic hydrocarbons such as benzene, toluene and xylene and others. Optionally, two or more of the solvents selected from the listed above can be mixed and used.

The reaction temperature is usually, but not limited to, about 10° C. to 200° C. and preferably about 50° C. to 200° C. The reaction may be conducted for, usually, 10 minutes to 48 hours and preferably 30 minutes to 24 hours.

In the step 2, the compound of formula (II") (wherein $Y^1$, $Z^1$, $Z^2$, $Z^3$ and $Z^4$ are the same as defined above, $Y^2$ and $Y^3$ independently represent CH or N and are connected by double bond) can be prepared, for example, from the compound of formula (II') (wherein $Y^1$, $Z^1$, $Z^2$, $Z^3$ and $Z^4$ are the same as defined above, $Y^2$ and $Y^3$ independently represent $CR^3R^4$ or $NR^4$ and are connected by single bond) by the oxidation reaction using an agent such as $MnO_2$, $KMnO_4$ and others, or by the dehydrogenation reaction using palladium on carbon.

The reaction can be carried out in a solvent including, for instance, ethers such as diethyl ether, isopropyl ether, dioxane and tetrahydrofuran (THF) and 1,2-dimethoxyethane; aromatic hydrocarbons such as benzene, toluene and xylene; dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NW), and others. Optionally, two or more of the solvents selected from the listed above can be mixed and used.

The reaction temperature is usually, but not limited to, about 0° C. to 200° C. and preferably about 50° C. to 200° C. The reaction may be conducted for, usually, 30 minutes to 48 hours and preferably 2 hours to 24 hours.

The compound of formula (VI) is commercially available or can be synthesized by conventional method.

The compound of formula (III) can be prepared, for example, by the following Method [A-ii].

The compound of formula (I) (wherein L, $R^1$, $R^5$ and $R^6$ are the same as defined above) can be prepared by the reaction of the compound of formula (VII) (wherein $R^1$, $R^5$ and $R^6$ are the same as defined above) with the compound of formula (VIII) (wherein L is the same as defined above) in the presence of a base such as potassium hydride, potassium hexamethyldisilazide, and others.

The reaction can be carried out in a solvent including, for instance, ethers such as diethyl ether, isopropyl ether, dioxane and tetrahydrofuran (THF) and 1,2-dimethoxyethane; aromatic hydrocarbons such as benzene, toluene and xylene, dimethylformamide (DMF), dimethylacetamide(DMAC), 1,3-dimethyl-3,4,5,6-tetrahydro-2(1H)-pyrimidinone (DMPU), 1,3-dimethyl-2-imidazolidinone (DCM, N-methylpyrrolidinone (NMP), and others. Optionally, two or more of the solvents selected from the listed above can be mixed and used.

The reaction temperature is usually, but not limited to, about −100° C. to 100° C. The reaction may be conducted for, usually, 30 minutes to 48 hours and preferably 2 hours to 12 hours.

Alternatively, the compound of formula (III) can be prepared, for example, by the following Method [A-iii].

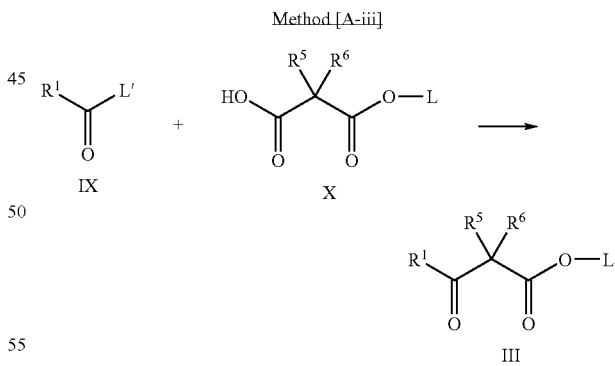

The compound of formula (III) (wherein L, $R^1$, $R^5$ and $R^6$ are the same as defined above) can be prepared by the reaction of the compound of formula (In) (wherein $R^1$ is the same as defined above and L' is a leaving group such as halogen atom e.g., chlorine or bromine atom, or imidazole) with the compound of formula (X) (wherein wherein L, $R^5$ and $R^6$ are the same as defined above) or its salts, for example, potassium salt.

The reaction can be carried out in the presence of Lewis acid including magnesium salts, such as magnesium bromide, magnesium chloride, magnesium. iodide, magnesium acetate, and others or a base such as n-butyl lithium, sec-butyl lithium, and others. The reaction can be carried out in a solvent including, for instance, ethers such as diethyl ether, isopropyl ether, dioxane and tetrahydrofuran (THF) and 1,2-dimethoxyethane; aromatic hydrocarbons such as benzene, toluene and xylene, and others. Optionally, two or more of the solvents selected from the listed above can be mixed and used.

The Preparation of the Compound Formula (I-b):

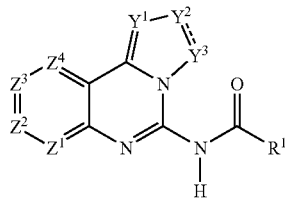

(wherein $R^1$, $Y^1Y^2$, $Y^3$, $Z^1$, $Z^2$, $Z^3$ and $Z^4$ are the same as defined above) can be, but not limited to be, prepared by the following Method B.

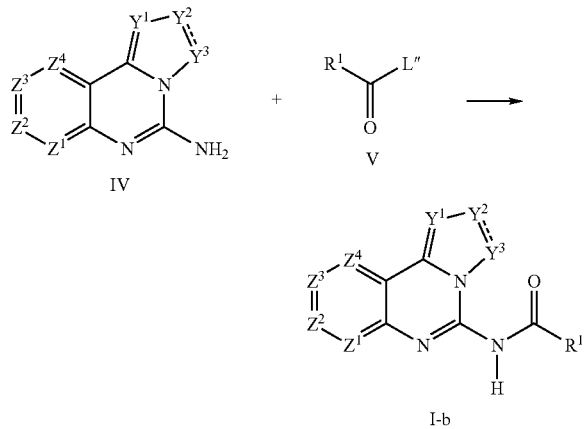

The compound of formula (I-b) can be prepared, for example, by the reaction of the compound of formula (IV) (wherein $Y^1$, $Y^2$, $Y^3$, $Z^1$, $Z^2$, $Z^3$ and $Z^4$ are the same as defined above) with a compound of formula (V) (wherein $R^1$ is the same as defined above and L" is a leaving group, such as hydroxy; halogen atom e.g., chlorine, bromine, or iodine atom; imidazole or,

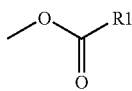

herein $R^1$ is the same as defined above). In the case L" is hydroxy, the reaction can be advantageously carried out by using a coupling agent such as benzotriazole-1-yl-oxy-tris-pyrrolidino-phosphonium hexafluorophosphate (PyBOP), 1,1'-carbonyldi(1,3-imiazole)(CDI), 1,1'-carbonyldi(1,2,4-triazole) (CDT) and others.

In the case L" is halogen atom, imidazole, or

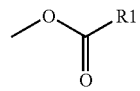

the reaction can be advantageously conducted in the presence of a base, including, for instance, such as pyridine, triethylamine and N,N-diisopropylethylamine, dimethylaniline, diethylaniline. and others.

The reaction may be carried out without solvent, or in a solvent including, for instance, ethers such as diethyl ether, isopropyl ether, dioxane and tetrahydrofuran (THF) and 1,2-dimethoxyethane; aromatic hydrocarbons such as benzene, toluene and xylene; nitrites such as acetonitrile; amides such as N,N-dimethylformamide (DMF), N,N-dimethylacetamide (DMAC) and N-methylpyrrolidone (NW); urea such as 1,3-dimethyl-2-imidazolidinone (DM); sulfoxides such as dimethylsulfoxide (DMSO); and others. Optionally, two or more of the solvents selected from the listed above can be mixed and used.

The reaction temperature is usually, but not limited to, about 40° C. to 200° C. and preferably about 20° C. to 180° C. The reaction may be conducted for, usually, 30 minutes to 48 hours and preferably 2 hours to 12 hours.

Preparation of Intermediates

The compound of formula (IV) can be, but not limited to be, prepared by the following Method [B-i]:

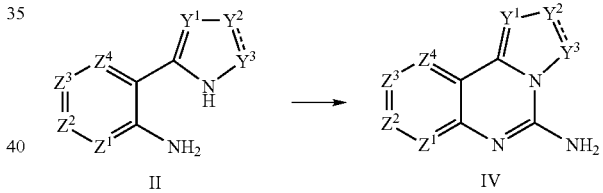

The compound of formula (IV) (wherein $Y^1$, $Y^2$, $Y^3$, $Z^1$, $Z^2$, $Z^3$ and $Z^4$ are the same as defied above) can be prepared by the reaction of compound of formula (II) (wherein $Y^1$, $Y^2$, $Y^3$, $Z^1$, $Z^2$, $Z^3$ and $Z^4$ are the same as defined above) with cyanogen halides such as cyanogen bromide.

The reaction may be carried out in a solvent including, for instance, ethers such as diethyl ether, isopropyl ether, dioxane and tetrahydrofuran (THF) and 1,2-dimethoxyethane; aromatic hydrocarbons such as benzene, toluene and xylene; amides such as N,N-dimethylformamide (DMF), N,N-dimethylacetamide and N-methylpyrrolidone; alcohols such as methanol, ethanol, 1-propanol, isopropanol and tert-butanol; and others. Optionally, two or more of the solvents selected from the listed above can be mixed and used.

The reaction temperature is usually, but not limited to, about −10° C. to 200° C. The reaction may be conducted for, usually, 30 minutes to 48 hours and preferably 1 hour to 24 hours.

The compound of formula (II) (wherein $Y^1$, $Y^2$, $Y^3$ Z, $Z^2$, $Z^3$ and $Z^4$ are the same as defined above) can be obtained in the same manner described in Method [A-i].

The compound of formula (VII), (VIII), (IX) and (X) are commercially available or can be synthesized by conventional method.

When the compound shown by the formula (I) or a salt thereof has an asymmetric carbon(s) in the structure, their optically active compounds and racemic mixtures are also included in the scope of the present invention.

Typical salts of the compound shown by the formula (I) include salts prepared by the reaction of the compound of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydroiodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tri(hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or a salts thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills, powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely. divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and a sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described in detail below in the form of examples, but they should by no means be construed as defining the metes and bounds of the present invention.

In the examples below, all quantitative data, if not stated otherwise, relate to percentages by weight.

$^1$H NMR spectra were recorded using either Bruker DR-X-300 (300 MHz for 1H) spectrometer or Brucker 500 UltraShieled™ (500 MHz for 1H). Chemical shifts are reported in parts per million (ppm) with tetramethylsilane (TMS) as an internal standard at zero ppm. Coupling constant (J) are given in hertz and the abbreviations s, d, t, q, m, and br refer to singlet, doublet, triplet, quartet, multiplet, and broad, respectively. The mass determinations were carried out by MAT95 (Finnigan MAT).

Liquid Chromatography-Mass spectroscopy (LC-MS) data were recorded on a Micromass Platform LC with Shimadzu Phenomenex ODS column (4.6 mm φ×30 mm) flushing a mixture of acetonitrile-water (9:1 to 1:9) at 1 ml/min of the flow rate. Mass spectra were obtained -using electrospray (ES) ionization techniques (Micromass Platform LC). TLC was performed on a precoated silica gel plate (Merck silica gel 60 F-254). Silica gel (WAKO-gel C-200 (75-150 μM)) was used for all column chromatography separations. All chemicals were reagent grade and were purchased from Sigma-Aldrich, Wako pure chemical industries, Ltd., Tokyo kasei kogyo Co., Ltd., Nacalai tesque, Inc., Watanabe Chemical Ind. Ltd., Maybridge plc, Lancaster Synthesis Ltd., Merck KgaA, Kanto Chemical Co., Ltd.

The effects of the compounds of the present invention were examined by the following assays.

[Determination of IC50 Values of Compounds in Kinase Assay of PI3Kγ]

Chemicals and Assay Materials

Phosphatidylinositol (PtdIns) and phosphatidylserine (PtdSer) were purchased from DOOSAN SERDARY RESEARCH LABORATORIES (Toronto, Canada). Recombinant human PI3Kγ (full length human PI3K p110γ fused with a His$_6$-tag (SEQ ID NO: 1) at the C-terminus expressed in S. frugiperda 9 insect cells) was obtained from ALEXIS BIOCHEMICALS (#201-055-C010; San Diego, Calif.). [γ$^{33}$P]ATP and unlabeled ATP were purchased from AMERSHAM PHARMACIA BIOTECH (Buckinghamshire, UK) and ROCHE DIAGNOSTICS (Mannheim, Germany), respectively. Scintillation cocktails and MicroScint PS™ were purchased from PACKARD (Meriden, Conn.). Maxisorp™ plates were purchased from NALGE NUNC INTERNATIONAL K.K. (Tokyo, Japan). All other chemicals not further specified were from WAKO PURE CHEMICAL (Osaka, Japan).

Solid-Phase Lipid Kinase Assay

To assess inhibition of PI3Kγ by compounds, the Maxisorp™ plates were coated with 50 μl/well of a solution containing 50 μg/ml PtdIns and 50 μg/ml PtdSer dissolved in chloroform:ethanol (3:7). The plates were subsequently air-dried by incubation for at least 2 hours in a fume hood. The reaction was set up by mixing 25 μl/well of assay buffer 2×(100 mM MOPSO/NaOH, 0.2 M NaCl, pH 7.0, 8 mM MgCl$_2$, 2 mg/ml BSA (fatty acid-free)) and 50 ng/well PI3Kγ in the lipid pre-coated plate and 10× test compounds were added in 2% DMSO. The reaction was started by adding 20 μl/well of ATP mix (final 10 μM ATP; 0.05 μCi/well [γ$^{33}$P]ATP). After incubation at RT for 2 hours, the reaction was terminated by adding 50 μl/well stop solution (50 mM EDTA, pH 8.0). The plate was then washed twice with Tris-buffered saline (TBS, pH 7.4). MicroScint PS™ (PACKARD) scintillation mix was added at 100 μl/well, and radioactivity was counted by using a TopCount™ (PACKARD) scintillation counter.

The inhibition percent at each concentration of compound was calculated, and IC50 values were determined from the inhibition of curve.

[Isozyme Selectivity Test in PI3K]

{Determination of IC50 Values of Compounds in Kinase Assay of PI3Kβ}

Recombinant baculovirus of PI3Kβ p110β and GST-p85α were obtained from Dr. Katada (University of Tokyo). Recombinant PI3K heterocomplex of p110β and GST-p85α were co-expressed in insect cells according to manufacture's instruction (Pharmingen, San Diego, Calif.), and purified with glutathione affinity column. Kinase assay of PI3Kβ was prepared in a similar manner as described in the part of [Determination of IC50 values of compounds in kinase assay of PI3Kγ].

[Selectivity Test with Other Kinases]

Kinase selectivity of the compounds was assessed by using a few kinase assaies such as kinase assay of Syk.

{Syk Tyrosine Kinase Inhibitory Assay for Selectivity}

(1) Preparation of Syk Protein

A cDNA fragment encoding human Syk open reading frame was cloned from total RNA of human Burkitt's lymphoma B. cell lines, Raji (American Type Culture Collection), with the use of RT-PCR method. The cDNA fragment was inserted into pAcG2T (Pharmingen, San Diego, Calif.) to construct a baculovirus transfer vector. Then the vector, together with the linearized baculovirus (BaculoGold™, Pharmingen), was used to transfect Sf21 cells (Invitrogen, San Diego, Calif.).

Generated recombinant baculovirus was cloned and amplified in Sf21 cells. Sf21 cells were infected with this amplified high titer virus to produce a chimeric protein of Syk kinase fused by glutathione-5-transferase (GST).

The resulting GST-Syk was purified with the use of glutathione column (Amersham Pharmacia Biotech AB, Uppsala, Sweden) according to the manufacturer's instruction. The purity of the protein was confirmed to be more than 90% by SDS-PAGE.

(2) Synthesize of a Peptide

Next, a peptide fragment of 30 residues including two tyrosine residues, KISDFGLSKALRADENYYKAQTHGKWPVKW SEQ ID NO: 2), was synthesized by a peptide synthesizer. The N-terminal of the fragment was then biotinylated to obtain biotinylated activation loop peptide (AL).

(3) The Measurement of Syk Tyrosine Kinase Activity

All reagents were diluted with the Syk kinase assay buffer (50 mM Tris-HCl (pH 8.0), 10 mM MgCl$_2$, 0.1 mM Na$_3$VO$_4$, 0.1% BSA, 1 mM DTT). First, a mixture (35 μl) including 3.2 μg of GST-Syk and 0.5 μg of AL was put in each well in 96-well plates. Then 5 μl of a test compound in the presence of 2.5% dimethyl sulfoxide (DMSO) was added to each well. To this mixture was added 300 μM ATP (10 μl) to initiate the kinase reaction. The final reaction mixture (50 pd) consists of 0.65 nM GST-Syk, 3 μM AL, 30 μM ATP, a test compound, 0.25% DMSO, and a Syk kinase assay buffer.

The mixture was incubated for 1 hour at room temperature (RT), and the reaction was terminated by the addition of 120 μl of termination buffer (50 mM Tris-HCl (pH 8.0), 10 mM EDTA, 500 mM NaCl, 0.1% BSA). The mixture was transferred to streptavidin-coated plates and incubated for 30 minutes. at room temperature to combine biotin-AL to the plates. After washing the plates with Tris-buffered saline (TBS) (50 mM Tris-HCl (pH 8.0), 138 mM NaCl, 2.7 mM KCl) containing 0.05% Tween-20 for 3 times, 100 0 of antibody solution consisting of 50 mM Tris-HCl (pH 8.0), 138 mM NaCl, 2.7 mM KCl, 1% BSA, 60 ng/ml anti-phosphotyrosine monoclonal antibody, 4G10 (Upstate Biotechnology), which was labeled with europium by Amersham Pharmacia's kit in advance, was added and incubated at room temperature for 60 minutes. After washing, 100 p of enhancement solution (Amersham Pharmacia Biotech) was added and then time-resolved fluorescence was measured by multi-label counter ARVO (Wallac Oy, Finland) at 340 nm for excitation and 615 run for emission with 400 msec of delay and 400 msec of window.

[Determination of IC50 Values of Compounds in Superoxide Generation from Human Peripheral Mononuclear Cells]

Blood (100 ml/donor) was taken from healthy human volunteers by venepuncture with 50 ml syringes containing 50 units heparin. Red blood cells were removed by incubation with 1% (w/v) dextran and 0.45% (w/v) glucose for 30 minutes at room temperature. After centrifugation at 350×g for 10 minutes, the cell pellet was resuspended in 10 ml PBS. The cell suspension was gently layered on 20 ml of 60% and 20 ml of 80% Percoll (Amersham Pharmacia Biotech, Sweden) gradient in PBS in 50 ml tube (#2335-050, Iwaki, Japan). After centrifugation at 400×g for 30 minutes at room temperature, peripheral polymorphonuclear leukocytes (PMNs) were obtained from the interference between 60% and 80% Percoll phases. After twice washing in PBS, PMNs were suspended at a density of $10^7$ cells/ml in Hank's Balanced Salt Solution (HBSS: Nissui, Japan) supplemented by 10 mM Na-Hepes (pH 7.6), 0.1% BSA and kept on ice until further use.

To test inhibition of formyl-methionyl-4-leucyl-phenylalanine (fMLP)-induced superoxide generation by compounds, PMNs ($2\times10^5$ cells/well) were seeded in HBSS, 10 mM Na-Hepes (pH 7.6), 0.1% BSA in 96-well clear bottom black plate (Cat. #3904, Costar) and pretreated with luminol (1 µg/well; Sigma) and test compounds for 10 minutes at 37° C. fMLP peptide (Cat. #4066; Peptide Institute Inc, Japan) was prepared in 10 p in the same buffer and prepared in a polypropylene plate (Cat. #3365, Coster). Chemiluminescence (CL) was measured by FDSS-6000 (Hamamatsu Photonics) over 15 minutes after stimulation with 1 µM fMLP. The percentage of inhibition at each concentration of compound was calculated based on the first peak of CL at approximately 1 minute after addition of stimulus and IC50 values were determined from the inhibition curve.

For opsonized zymosan (OZ) and phorbol 12-myristate 13-acetate (PMA) stimulation, Zymosan A (Sigma) was suspended in HBSS at a concentration of 1 mg/ml and incubated with human pooled serum at a final concentration range of 9 to 80% at 37° C. for 30 minutes to opsonize the zymosan, followed by centrifugation at 500×g for 10 minutes at 4° C. Then the sediments were washed twice in HBSS and finally resuspended in HBSS to a concentration between 1 and 10 mg/ml. Opsonized zymosan (OZ) was used at 5 mg/ml for stimulation. Phorbol 12-myristate 13-acetate (PMA) was initially dissolved at a concentration of 0.1 mg/ml in DMSO as a stock solution and stored frozen at −20° C. PMA solution was prepared from the stock solution by further dilution in HBSS to the concentration of 100 ng/ml. PMNs ($2\times10^5$ cells/well) were seeded in HBSS, 10 mM Na-Hepes (pH 7.6), 0.1% BSA in 96-well white plate (Packard) and pretreated with luminol (1 µg/well; Sigma) and test compounds for 10 minutes at 37° C. CL was measured by Arvo counter (Wallac)) at 30 minutes after the stimulation with OZ or PMA. The percentage of inhibition at each concentration of compound was calculated and IC50 values were determined from the inhibition curve.

[Determination of IC50 Values of Compounds in Elastase Release from Human Peripheral Mononuclear Cells]

To test inhibition of elastase release by compounds, PMNs ($5\times10^5$ cells/well) were seeded in HBSS supplemented with 10 mM Na-Hepes (pH 7.6), 0.1% BSA in 96-well plate. Cells were pretreated with cytochalasine B (0.1 µg/well; Nakarai, Japan) and test compounds in 90 µl/well for 10 minutes at 37° C. Cells were stimulated with 1 µM fMLP for 15 minutes at 37° C. Supernatants (40 µL/well) were collected into 384 well black plate (Packard) to measure elastase activity. Fluorescent-based elastase reaction was started by the addition of 10 µl of 0.5 mM Suc-Ala-Ala-Ala-MCA (Cat. #3133v; Peptide Institute Inc, Japan) into the 384 well plate at room temperature. The fluorescence emission was measured at 460 nm ($\lambda$ex, 360 nm) by using a Wallac-Arvo counter (PerkinElmer, Boston, Mass.) fluorescence plate leader for 120 minutes. IC50 values of compounds were determined at the initial velocity of the reaction.

[Determination of IC50 Values of Compounds in Chemotaxis Assay with the Use of Human PMNs]

Freshly prepared PMNs ($1.1\times10^7$ cells/ml) were incubated with compounds in a polypropylene 96 well plate (Cat. #3365, Coster) for 10 minutes in HBSS supplemented with 10 mM Na-Hepes (pH 7.6), 0.1% BSA. Cells (100 µl) were incubated with test compounds or vehicle for 30 minutes and were transferred into an Multiwell insert (Cat. # 351183; Falcon) 24w plate. FMLP (10 nM, 0.5 ml) was added into the lower chamber of the plate, and chemotaxis was measured in $CO_2$ incubator at 37° C. for 1 hour. Migrated cells were counted using FACScan (Becton Dickinson, Franklin Lakes, N.J.). The percentage of inhibition at the each concentration of compound was calculated, and the IC50 values were determined from the inhibition curve.

[Determination of IC50 Values of Compounds in Chemotaxis Assay with the Use of Transfectants]

(1) Cell

Human CCR3-transformed L1.2 cells were used. Human CCR3-expressing L1.2 stable transformant was established by electroporation, referring to the methods described in J. Exp. Med. 183:2437-2448, 1996. The human CCR3-transformed L1.2 cells were maintained in RPMI-1640 supplemented with 10% FCS, 100 units/ml of penicillin G and 100 µg/ml of streptomycin, and 0.4 mg/ml of Geneticin. One day before the chemotaxis assay, cells were pretreated with 5 mM sodium butyrate-containing culture medium ($5\times10^5$ cells/ml) for 20-24 hours to increase the expression of CCR3.

(2) Chemotaxis Assay

Butyrate-pretreated cells were suspended in chemotaxis buffer (Hanks' solution Cat. #05906 Nissui, 20 mM HEPES pH 7.6, 0.1% human serum albumin Cat. #A-1887 Sigma) at a cell density of $1.1\times10^7$ cells /ml. A mixture of 90 µl of cell suspension and 10 µl of compound solution diluted with chemotaxis buffer (10-times concentration of the final concentration) were preincubated for 10 minutes at 37° C. The mixture of cells and compounds was added into the upper chamber of the 24-well chemotaxis chamber (Transwell™, Cat. #3421, Costar, pore size; 5 µm). 0.5 ml of 10 nM of human recombinant eotaxin (Cat. #23209, Genzyme Techne) solution, diluted with chemotaxis buffer, was added into the lower chamber of the chemotaxis plate. Then, chemotaxis was performed in $CO_2$ incubator at 37° C. for 4 hours. After 4 hours incubation, migrated cells were counted using FACScan (Becton Dickinson). The percentage of inhibition at the each concentration of compound was calculated, and IC50 values were determined from the inhibition curve.

[Mouse fMLP-Induced Pleurisy Model]

Seven weeks old BALB/c female mice were divided into 3 groups, a nontreatment group, a vehicle group and a treatment group. Mice in the treated group were first injected intravenously with compounds of the present invention at varied doses. Mice in the vehicle group were injected with vehicle containing 10% Cremophor EL (Nacalai Tesque) in saline. Three minutes after the treatment, a solution containing 1 mg/mouse of fMLP in 3.3% DMSO in PBS was administrated intrapleuraly into a vehicle group and a treated group mice. Four hours after fMLP-injection, mice were sacrificed and pleural fluid was collected by washing the pleural cavity twice with 2 ml PBS. Total cells per milliliter of pleural fluid were counted using a hemacytometer. Cell differentiation of pleural fluid was determined by counting a minimum of 200 cells from a Giemsa's-stained cytospin slide preparation. Statistical analysis was performed by means of Student's t-test for paired data or analysis of variance with Dunnett's Post test , using GraphPadPRISM for Windows, version 2.01.

For practical reasons, the compounds are grouped in some classes of activity as follows:

In vitro $IC_{50}=A(= \text{ or } <)0.1 \text{ μM}<B(= \text{ or } <)0.5 \text{ μM}<C(= \text{ or } <)2 \text{ μM}<D$ The compounds of the present invention also show strong activity in vivo assays.

(dec.) in the following tables represents decomposition.

Example 1-1

Z)-2-(8,9-Dimethoxy-2,3-dihydroimidazo[1,2-c]quinazolin-5-yl)-1-(3-pyridinyl)ethenol (1) Methyl 3-oxo-3-(3-pyridinyl)propanoate

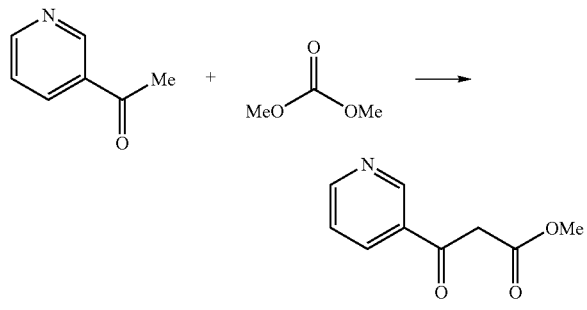

A 0.5 M solution of potassium hexamethyldisilazide in toluene (22 ml, 11 mmol) was mixed with tetrahydrofuran (5 ml), and the mixture was cooled at −78° C. To the cold (−78° C.) mixture was added dropwise a solution of 3-acetylpyridine (1.0 g, 8.26 mmol) in tetrahydrofuran (5 ml). The mixture was warmed to room temperature and stirred for 3 hours. The mixture was cold at −78° C., and then dimethyl carbonate (1.2 ml, 14.3 mmol) was added dropwise. The resulting solution was allowed to warm to room temperature and stirred overnight. The reaction solution was quenched by adding aqueous 1N HCl solution, and extracted three times with ethyl acetate. The combined organic layers were washed with water and brine, dried over magnesium sulfate, filtrated, and concentrated under reduced pressure. The residue was purified by column chromatography on silica-gel (hexane/ ethyl acetate, 1/1) to give methyl 3-oxo-3-(3-pyridinyl)propanoate (1.0 g, 68% yield) as an oil.

(2) 2-(4,5-Dihydro-1H-imidazol-2-yl)-4,5-dimethoxyaniline

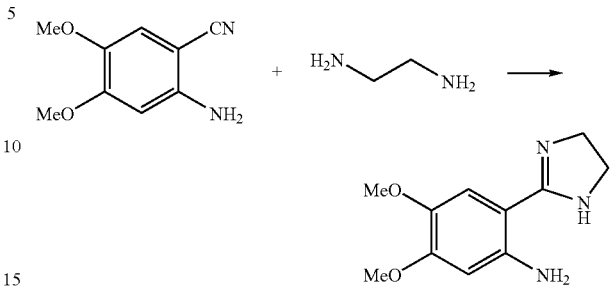

2-Amino-4,5-dimethoxybenzonitrile (5.0 g, 28 mmol) was added to ethylenediamine (7.9 g, 131 mmol) at room temperature. The resulting solution was warmed to 40., and a catalytic amount of diphosphorus pentasulfide (50 mg) was added. The mixture was heated to 80-90, and the stirring was continued overnight. The reaction mixture was diluted with water, and the resulting precipitate was collected by filtration to give 2-(4,5-dihydro-1H-imidazol-2-yl)-4,5-dimethoxyaniline (5.1 g, 82%) as a solid.

(3) (Z)-2-(8,9-Dimethoxy-2,3-dihydroimidazo[1,2-c]quinazolin-5-yl)-1-(3-pyridinyl)ethenol

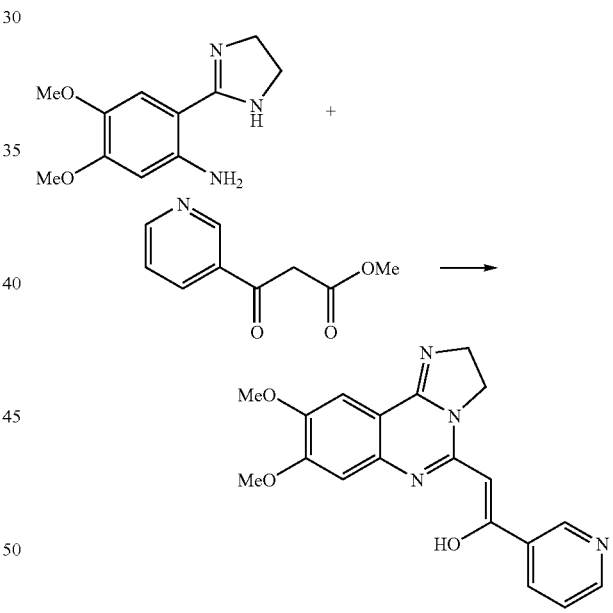

A mixture of 2-(4,5-dihydro-1H-imidazol-2-yl)-4,5-dimethoxyaniline (0.15 g, 0.68 mmol) and methyl-3-oxo-3 (3-pyridinyl)propanoate (0.20 g, 1.12 mmol) was stirred at 155 for 1 hour. The reaction mixture was purified by column chromatography on silica-gel (dichloromethane/ methanol, 25/1) to give (Z)-2-(8,9-dimethoxy-2,3-dihydroimidazo[1,2-c]quinazolin-5-yl)-1-(3-pyridinyl)ethenol (66.9 mg, 28%) as a yellow solid.

Melting point: 275° C.
Mass spectrometry: 351
In vitro PI3K-β inhibitory activity: C
In vitro PI3K-γ inhibitory activity: A
$^1$H-NMR (500. MHz, DMSO-d$_6$): δ 3.79 (3H, s), 3.88 (3H, s), 3.98-4.08 (4H, m), 5.63 (1H, s), 7.13 (1H, s), 7.24 (1H, s), 7.50 (1H, dd, J=4.7, 7.8 Hz), 8.27 (1H, dt, J=1.6, 7.8 Hz), 8.67 (1H, dd, J=1.6, 4.7 Hz), 9.13 (1H, d, J=1.6 Hz), 13.9 (1H, bs).

Example 1-2

(Z)-2-(8,9-Dimethoxy-2,3-dihydroimidazo[1,2-c]quinazolin-5-yl)-1-(3-pyridinyl)ethenol hydrochloride

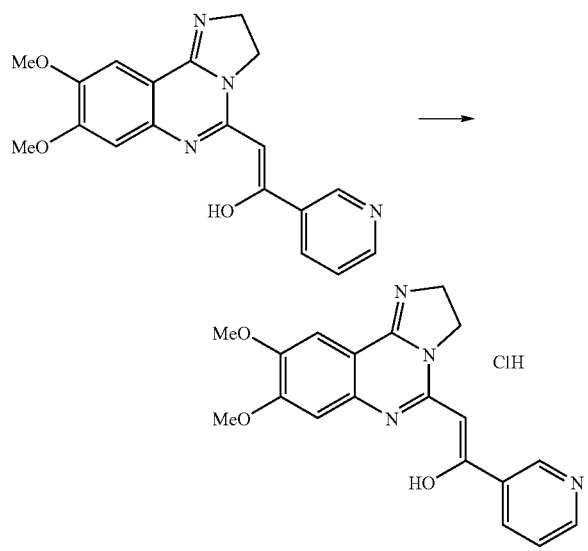

To a solution of (Z)-2-(8,9-dimethoxy-2,3-dihydroimidazo[1,2-c]quinazolin-5-yl)-1-(3-pyridinyl)ethenol (16.8 mg, 0.05 mmol)) in dioxane (15 ml) at room temperature was added aqueous 6N HCl solution (0.05 ml). After being stirred for 30 minutes, the mixture was dried under reduced pressure to give (Z)-2-(8,9-dimethoxy-2,3-dihydroimidazo[1,2-c]quinazolin-5-yl)-1-(3-pyridinyl)ethenol hydrochloride (18.5 mg, quantitative) as a yellow solid.
Melting point: >300° C.
Mass spectrometry: 351
In vitro PI3K-β inhibitory activity: C
In vitro PI3K-γ inhibitory activity: A
$^1$H-NMR (500 MHz, DMSO-d$_6$): δ 3.88 (3H, s), 4.00 (3H, s), 4.22 (2H, t, J=9.1 Hz), 4.55 (2H, t, J=9.1 Hz), 6.21 (1H, s), 7.60 (1H, s), 7.66 (1H, dd, J=4.7, 8.2 Hz), 7.90 (1H, s), 8.47 (1H, d, J=8.2 Hz), 8.79 (1H, d, J=4.7 Hz), 9.28 (1H, s), 14.9 (1H, bs).

Example 1-3

2-[7-Methoxy-8-(methoxymethoxy)-2,3-dihydroimidazo[1,2-c]quinazolin-5-yl]-1-pyridin-3-ylethylenol (1) 4-Formyl-2-methoxy-3-nitrophenyl acetate

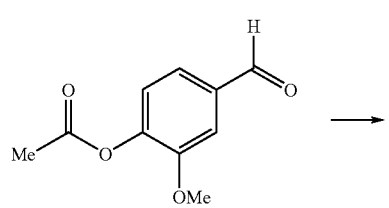

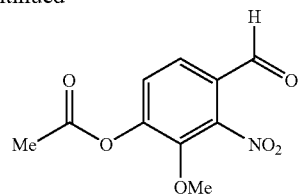

By the procedure described in U.S. Pat. No. 4,287,341 or J. Chem. Soc. 376 (1948), vanillin acetate 5.00 g afforded the title compound 4.54 g as yellow solid. Yield 73.6%.
H-NMR (500 MHz, DMSO-d$_6$) δ: 2.40 (s 3H), 3.87 (s 3H), 7.75 (d 1H J=8.4 Hz), 7.94 (d 1H J=8.4 Hz), 9.90 (s 1H)

(2) 4Hydroxy-3-methoxy-2-nitrobenzaldehyde

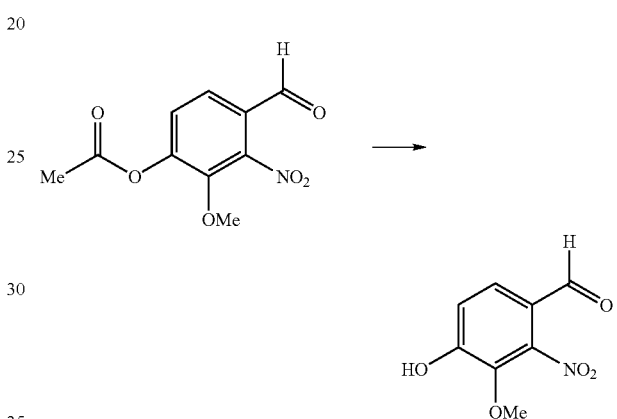

A mixture of 4-formyl-2-methoxy-3-nitrophenyl acetate 4.54 g (19.0 mmol) and potassium carbonate 5.24 g (37.9 mmol) in methanol 40m was stirred at room temperature for 2 hours. The reaction mixture was poured into water, acidified by 1N HCl solution and extracted into AcOEt. The organic layer was washed with brine, dried over MgSO$_4$, filtrated and the solvent was evaporated. The residue was washed with n-hexane to give the title compound 3.60 g as white solid. Yield 96.3%.

(3) 4-Hydroxy-3-methoxy-2-nitrobenzonitrile

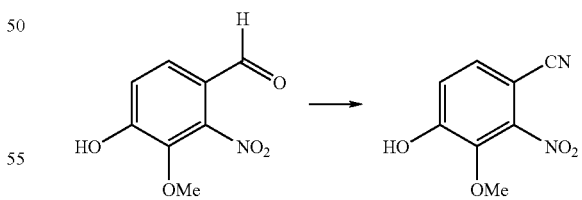

To a mixture of 4-hydroxy-3-methoxy-2-nitrobenzaldehyde 14.5 g (73.5 mmol) in 28% ammonia solution 150 mL and tetrahydrofuran 15 mL was added iodine 22.4 g (88.2 mmol) and stirred at room temperature for overnight. The reaction mixture was concentrated in vacuo. The residue was acidified with 2H HCl solution and extracted into diethyl ether. The organic layer was washed with brine, dried over MgSO$_4$, filtrated and the solvent was evaporated. The residue was washed with diisopropyl ether to give the title compound 12.1 g as brown solid. Yield 84.5%

(4)
3-Methoxy-4-(methoxymethoxy)-2-nitrobenzonitrile

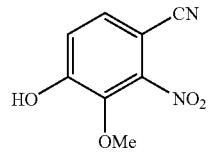

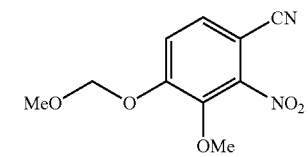

A mixture of 4-hydroxy-3-methoxy-2-nitrobenzonitrile 1.00 g, chloromethyl methyl ether 0.47 mL (6.18 mmol) and potassium carbonate 3.56 g (25.8 mmol) in N,N-dimethylformamide 10 mL was stirred at 50° C. for 2 hours. The reaction mixture was poured into water and extracted into diethyl ether. The organic layer was washed with brine, dried over MgSO$_4$, filtrated and the solvent was evaporated. Silica gel chromatography (n-hexane/AcOEt=4/1) afforded the title compound 1.03 g as colorless solid. Yield 83.5%.

(5)
2-Amino-3-methoxy-4(methoxymethoxy)benzonitrile

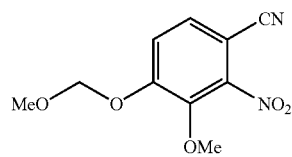

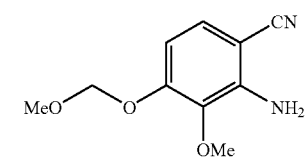

To 5% palladium on activated carbon 6.00 g under argon atmosphere was added a solution of 3-methoxy-4-(methoxymethoxy)-2-nitrobenzonitrile 6.00 g (25.2 mmol) in ethanol 50 mL and stirred under hydrogen atmosphere at room temperature for 8 hours. The reaction mixture was filtrated and the filtrate was concentrated in vacuo. Silica gel chromatography (n-hexane/AcOEt=4/1) afforded the title compound 2.83 g as white solid. Yield 53.9%.

(6) [6-(4,5-Dihydro-1H-imidazol-2-yl)-2-methoxy-3-(methoxymethoxy)phenyl]amine

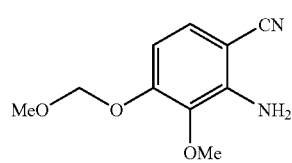

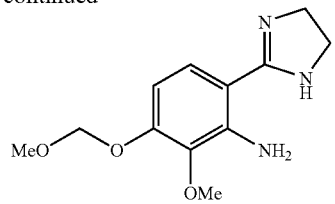

A solution of 2-amino-3-methoxy-4-(methoxymethoxy) benzonitrile 475 mg (2.28 mmol) and phosphorus pentasulfide 25.4 mg (0.11 mmol) in ethylenediamine 2.75 g was stirred at 120° C. for overnight. The reaction mixture was cooled to room temperature and poured into water. The precipitate was collected and washed with water to give the title compound 293 mg as white solid. Yield 51.1%.

(7) Ethyl 3-oxo-3-(pyridin-3-yl)propanoate

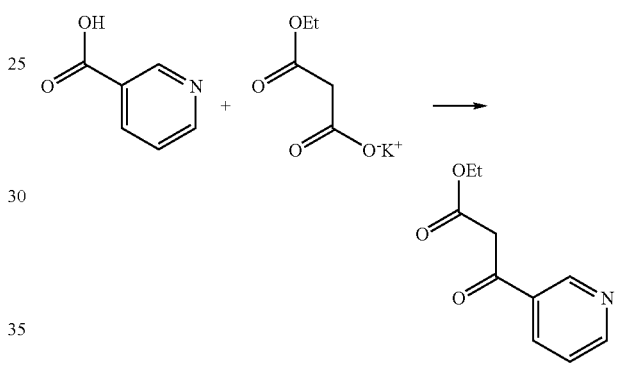

To a suspension of nicotinic acid 5.00 g (40.6 mmol) in tetrahydrofuran 50 mL was added carbonyl diimidazole 9.76 g (60.9 mmol) at 5° C. and stirred at room temperature for 1 hour. In a separate flask, a suspension of MgCl$_2$ 4.64 g (48.7 mmol) and ethyl malonate potassium salt 10.37 g (60.92 mmol) in tetrahydrofuran 50 mL was stirred at 50° C. for 4 hours. To this suspension was added the aforementioned imidazolide solution at room temperature and stirred for 12 hours. The reaction was quenched by the addition of water and extracted into ethyl acetate. The organic layer was washed by brine, dried over MgSO$_4$, filtrated and the solvent was evaporated. Silica gel chromatography (n-hexane/AcOEt=2/1) afforded the title compound 3.89 g as pale yellow oil. Yield 49.5%.

(8) 2-[7-Methoxy-8-(methoxymethoxy)-2-3-dihydroimidazo[1,2-c]quinazolin-5-yl]-1-pyridin-3-ylethylenol

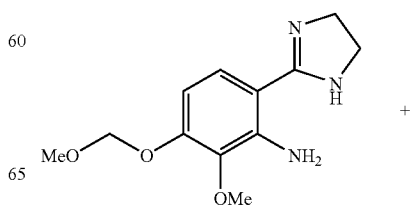 +

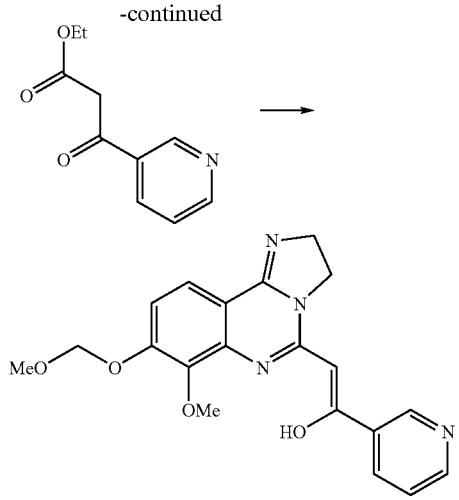

A solution of [6-(4,5-dihydro-1H-imidazol-2-yl)-2-methoxy-3-(methoxymethoxy)phenyl] amine 1.31 g (5.20 mmol) and ethyl 3-oxo-3-(pyridin-3-yl)propanoate 1.00 g (5.20 mmol) in toluene 30mL was refluxed for overnight. The precipitate was collected and washed with diethyl ether to give the title compound 1.52 g as a yellow solid. Yield 76.9%.
Melting point: 215-216° C.
Mass spectrometry: 381
In vitro PI3K-β inhibitory activity:
In vitro PI3K-γ inhibitory activity: B
H-NMR (500 MHz, CDCl$_3$) δ: 3.54 (s 3H), 3.95 (t 2H J=9.5 Hz), 4.08 (s 3H), 4.22 (t 2H J=9.5 Hz), 5.30 (s 2H), 5.38 (s 1H), 6.98 (d 1H J=8.8 Hz), 7.37 (dd 1H J=8.0 Hz, 4.9 Hz), 7.64 (d 1H J=8.8 Hz), 8.21 (dt 1H J=8.0 Hz, 1.7 Hz), 8.67 (dd 1H J=4.9 Hz, 1.7 Hz), 9.09 (d 1H J=1.7 Hz), 13.75 (s 1H)

Example 1-4

5-(2-Hydroxy-2-pyridin-3-ylvinyl)-7-methoxy-2,3-dihydroimidazo[1,2-c]quinazolin-8-ol hydrochloride

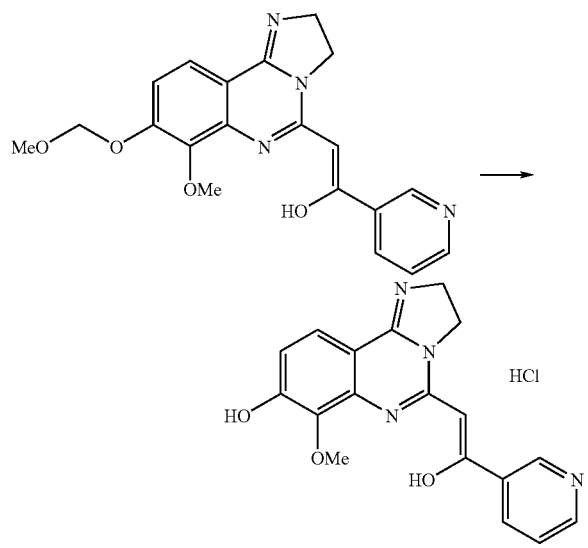

A suspension of 2-[7-methoxy-8-(methoxymethoxy)-2,3-dihydroimidazo[1,2-c]quinazolin-5-yl]-1-pyridin-3-ylethyl-enol (Example 1-3) 1.52 g (4.00 mmol) in 4N HCl in 1,4-dioxane 30 mL and water 0.3 mL was stirred at room temperature for overnight. The reaction mixture was diluted with diethyl ether. The precipitate was collected and washed with diethyl ether to give the title compound 1.23 g as a yellow solid. Yield 82.4%
Melting point: 245° C.
Mass spectrometry: 337
In vitro PI3K-β inhibitory activity: C
In vitro PI3K-γ inhibitory activity: A
H-NMR (500 MHz, DMSO-d$_6$) δ: 3.97 (s 3H), 4.22 (dd 2H J=12.3 Hz, 9.0 Hz), 4.43 (dd 2H J=12.3 Hz, J=9.0 Hz), 6.17 (s 1H), 7.10 (d 1H J=9.0 Hz), 7.71 (dd 1H J=7.7 Hz, 4.7 Hz), 7.98 (d 1H J=9.0 Hz), 8.57 (br d 1H J=7.7 Hz), 8.82 (dd 1H J=4.7 Hz, 1.4 Hz), 9.34 (d 1H J=1.4 Hz), 11.79 (s 1H), 14.60 (s 1H)

Example 1-5

Methyl 4-{[5-(2-hydroxy-2-pyridin-3-ylvinyl)-7-methoxy-2,3-dihydroimidazo[1,2-c]quinazolin-8-yl]oxy}butanoate

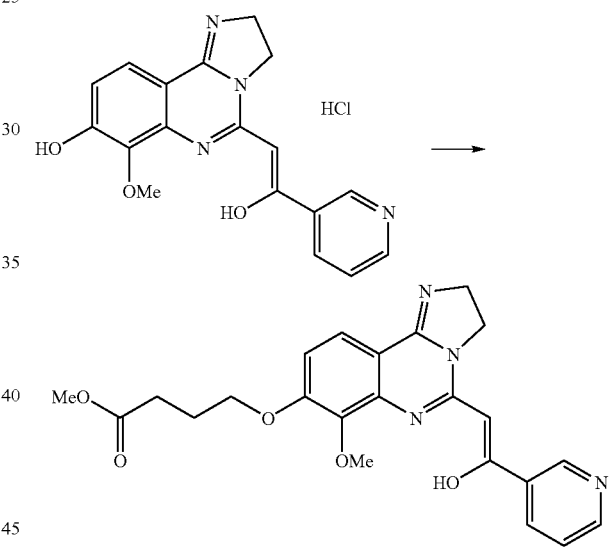

A mixture of 5-(2-hydroxy-2-pyridin-3-ylvinyl)-7-methoxy-2,3-dihydroimidazo[1,2-c]quinazolin-8-ol hydrochloride (Example 1-4) 50.4 mg (0.14 mmol), methyl chlorobutyrate 22.2 mg (0.16 mmol) and potassium carbonate 186.9 mg (1.35 mmol) in N,N-dimethylformamide 1 mL was stirred at 120° C. for 4 hours. The reaction mixture was poured into water and extracted into dichloromethane. The organic layer was washed with brine, dried over MgSO$_4$, filtrated and the solvent was evaporated. The residue was washed by diethyl ether to give the title compound 35.0 mg as yellow solid. Yield 59.3%.
Melting point: 199-200° C.
Mass spectrometry: 437
In vitro PI3K-β inhibitory activity: C
In vitro PI3K-γ inhibitory activity: A
H-NMR (500 MHz, CDCl$_3$) δ: 2.20 (quint 2H J=7.1 Hz), 2.58 (t 2H J=7.09 Hz), 3.71 (s 3H), 3.94 (t 2H J=9.5 Hz), 4.06 (s 3H), 4.15 (t 2H J=7.1 Hz), 4.21 (t 2H J=9.5 Hz), 5.38 (s 1H), 6.76 (d 1H J=8.8 Hz), 7.37 (dd 1H J=8.2 Hz, 5.2 Hz), 7.65 (d 1H J=8.8 Hz), 8.21 (dt J=8.2 Hz, 2.1 Hz), 8.67 (d 1H J=5.2 Hz), 9.09 (s 1H), 13.70 (s 1H)

Example 1-6

Example 3-4

4-{[5-(2-Hydroxy-2-pyridin-3-ylvinyl)-7-methoxy-2,3-dihydroimidazo[1,2-c]quinazolin-8-yl]oxy}butanoic acid

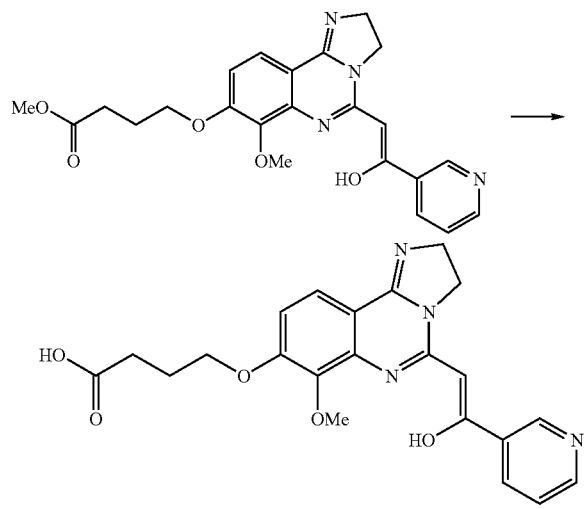

A solution of methyl 4-{[5-(2-hydroxy-2-pyridin-3-ylvinyl)-7-methoxy-2,3-dihydroimidazo[1,2-c]quinazolin-8-yl]oxy}butanoate (example 1-5) 20.0 mg (0.05 mmol) in 1N LiOH solution 0.1 mL and ethanol 1.0mL was stirred at room temperature for overnight. The reaction mixture was neutralized with 1N HCl solution and concentrated in vacuo. The residue was triturated in water. The precipitate was collected to give the title compound 10.0 mg as white solid. Yield 51.7%.

Melting point: 257-258° C.
Mass spectrometry: 423
In vitro PI3K-β inhibitory activity: B
In vitro PI3K-γ inhibitory activity: A
H-NMR (500 MHz, DMSO-$d_6$) δ: 2.02 (quint 2H J=6.2 Hz), 2.45 (t 2H J=6.2 Hz), 3.94 (s 3H), 3.98 (br t 2H J=8.5 Hz), 4.06 (br t 2H J=8.5 Hz), 4.14 (t 2H J=6.2 Hz), 5.67 (s 1H), 6.97 (d 1H J=8.7 Hz), 7.49 (dd 1H J=8.2 Hz, 4.4 Hz), 7.57 (d 1H 1=8.7 Hz), 8.29 (d 1H J=8.2 Hz), 8.67 (d 1H J=4.4 Hz), 9.14 (s 1H), 12.15 (s 1H), 13.76 (s 1H)

Example 1-7

4-{[5-(2-Hydroxy-2-pyridin-3-ylvinyl)-7-methoxy-2,3-dihydroimidazo[1,2-c]quinazolin-8-yl]oxy}butanoic acid hydrochloride

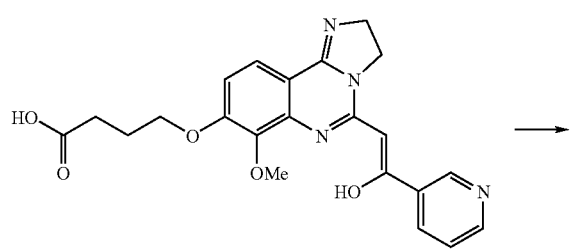

-continued

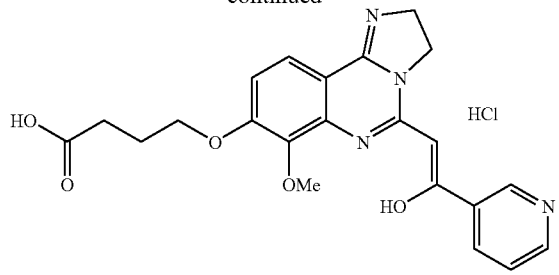

A mixture of 4-{[5-(2-hydroxy-2-pyridin-3-ylvinyl)-7-methoxy-2,3-dihydroimidazo[1,2-c]quinazolin-8-yl]oxy}butanoic acid (Example 1-6) 4.0 mg (9.5 micromol) in 4N HCl in 1,4-dioxane 2.0 mL was stirred at room temperature for 2 hours. The reaction mixture was diluted with diethyl ether. The precipitate was collected to give the title compound 4.00 mg as a yellow solid. Yield 92.0%.

Melting point: 249-251° C.
Mass spectrometry: 423
In vitro PI3K-β inhibitory activity: B
In vitro PI3K-γ inhibitory activity: A
H-NMR (500 MHz, DMSO-$d_6$) δ: 2.06 (quint 2H J=7.3 Hz), 2.46 (t 2H J=7.3 Hz), 4.01 (s 3H), 4.24 (t 2H J=9.0 Hz), 4.29 (t 2H J=7.3 Hz), 4.45 (t 2H J=9.0 Hz), 6.18 (s 1H), 7.36 (d 1H J=9.1 Hz), 7.70 (dd 1H J=7.9 Hz, 5.0 Hz), 8.14 (d 1H J=9.1 Hz), 8.56 (br d 1H J=7.9 Hz), 8.82 (br d 1H J=5.0 Hz), 9.34 (s 1H), 12.34 (s 1H), 14.57 (s 1H)

Example 1-8

2-[7-Methoxy-8-(4-morpholin-4-yl-4-oxobutoxy)-2,3-dihydroimidazo[1,2-c]quinazolin-5-yl]-1-pyridin-3-ylethylenol

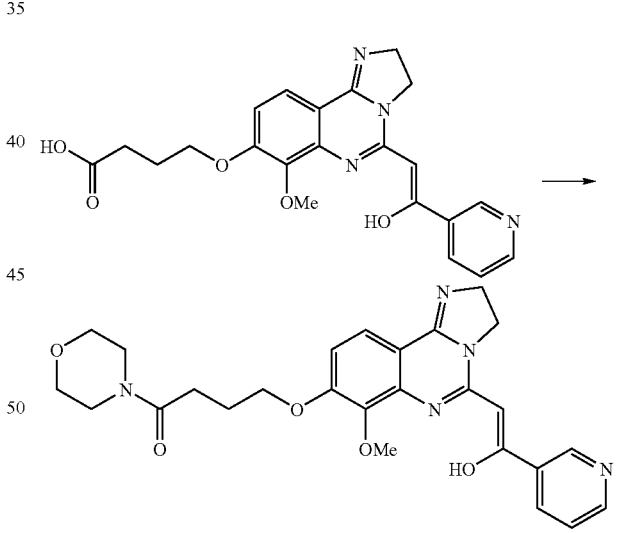

To a solution of 4-{[5-(2-hydroxy-2-pyridin-3-ylvinyl)-7-methoxy-2,3-dihydroimidazo[1,2-c]quinazolin-8-yl]oxy}butanoic acid (Example 1-6) 20.0 mg (0.044 mmol), morpholine 19.0 mg (0.22 mmol) and N,N-diisopropylethylamine 0.038 mL (0.22 mmol) in N,N-dimethylformamide 2.0 mL was added PyBOP((1H-1,2,3-benzotriazol-1-yloxy)(tripyrrolidin-1-yl)phosphonium hexafluorophosphate) 34.0 mg (0.065 mmol) and stirred at 80° C. for overnight. After cooling to room temperature, the reaction mixture was poured into water. The precipitate was collected and washed with water to give the title compound 13.0 mg as a white solid. Yield 60.7%.

Melting point: 234-235° C.
Mass spectrometry: 492
In vitro PI3K-β inhibitory activity: B
In vitro PI3K-γ inhibitory activity: A
H-NMR (500 MHz, DMSO-$d_6$) δ: 2.03 (quint 2H J=6.6 Hz), 3.46 (m 4H), 3.56 (m 4H), 3.96 (s 3H), 3.99 (br d 2H J=8.2 Hz), 4.05 (br d 2H J=8.2 Hz), 4.15 (t 2H J=6.6 Hz), 5.66 (s 1H), 6.98 (d J=8.8 Hz), 7.50 (dd 1H J=7.7 Hz, 4.7 Hz), 7.57 (d 1H J=8.8 Hz), 8.29 (br d 1H J=7.7 Hz), 8.67 (br d 1H J=4.7 Hz), 9.14 (s 1H), 13.76 (s 1H)

In a similar method according to the Example 1-1 to 1-8 above, the compounds in Example 1-9 to 1-210 were synthesized.

TABLE 1

| Ex. No. | Structure | Mol Weight | MS (M + 1) | mp | in vitro |
|---|---|---|---|---|---|
| 1-9 | 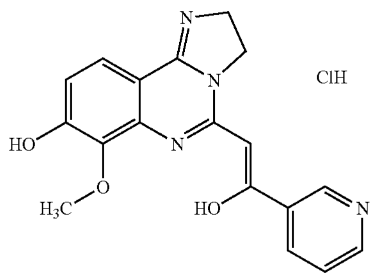 | 372.81 | 337 | 245(dec.) | A |
| 1-10 | 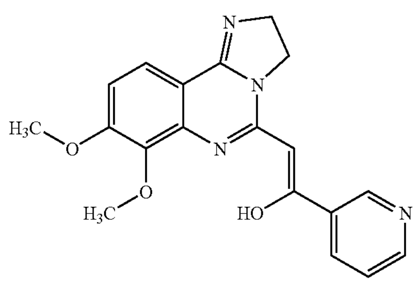 | 350.38 | 351 | 269-270 | A |
| 1-11 | 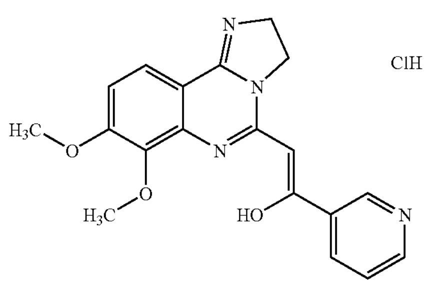 | 386.84 | 351 | 249-250 | A |
| 1-12 | 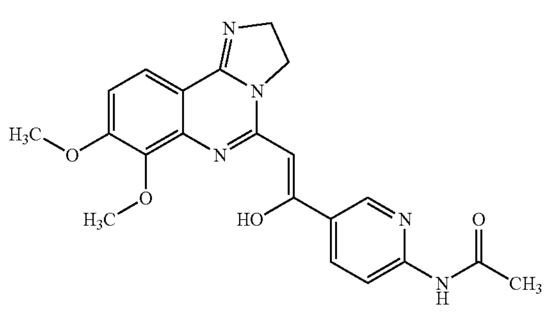 | 407.43 | 408 | 270(dec.) | A |

TABLE 1-continued

| Ex. No. | Structure | Mol Weight | MS (M + 1) | mp | in vitro |
|---|---|---|---|---|---|
| 1-13 | 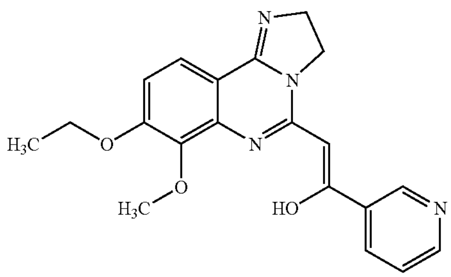 | 364.41 | 365 | 267-268 | A |
| 1-14 | 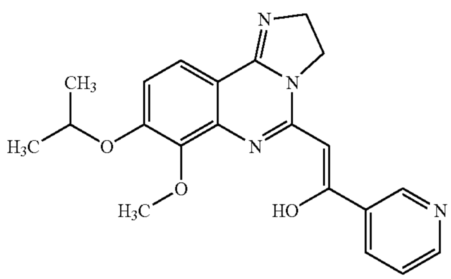 | 378.43 | 379 | 252-253 | A |
| 1-15 | 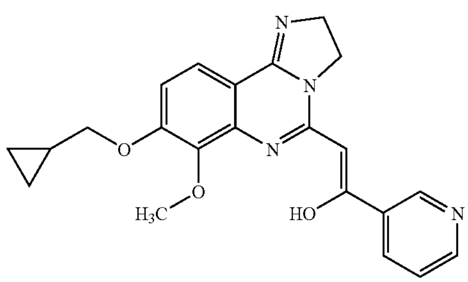 | 390.45 | 391 | 254(dec.) | B |
| 1-16 | 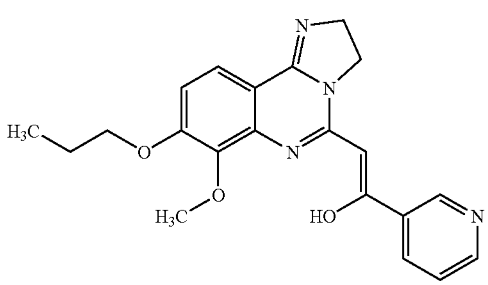 | 380.41 | 381 | 264-265 | A |
| 1-17 | 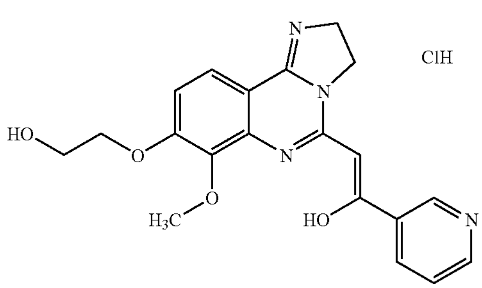 | 416.87 | 381 | 215(dec.) | A |

TABLE 1-continued

| Ex. No. | Structure | Mol Weight | MS (M + 1) | mp | in vitro |
|---|---|---|---|---|---|
| 1-18 | 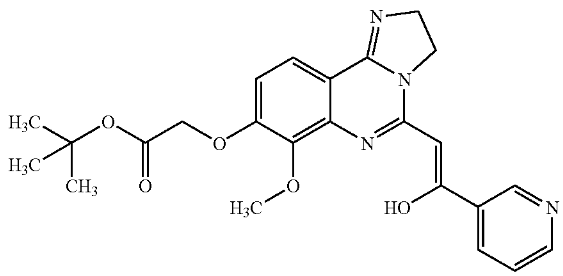 | 450.50 | 451 | 184-186 | B |
| 1-19 | 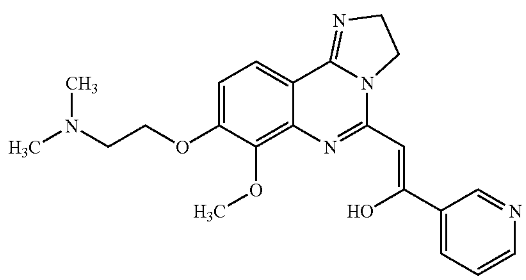 | 407.48 | 408 | 183-184 | B |
| 1-20 | 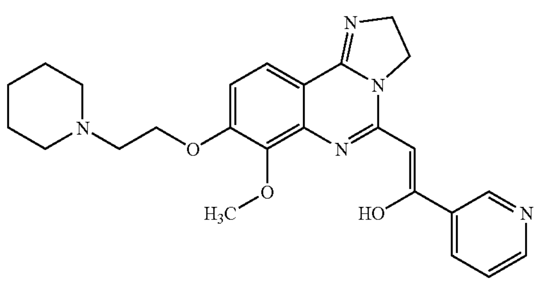 | 447.54 | 448 | 162-163 | B |
| 1-21 | 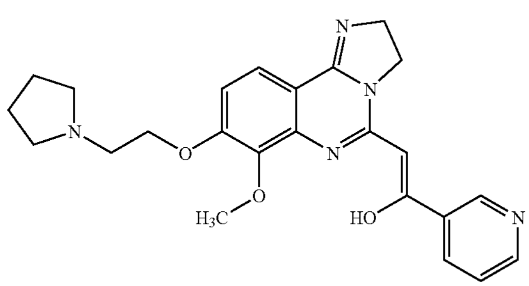 | 433.51 | 434 | 204-205 | A |
| 1-22 | 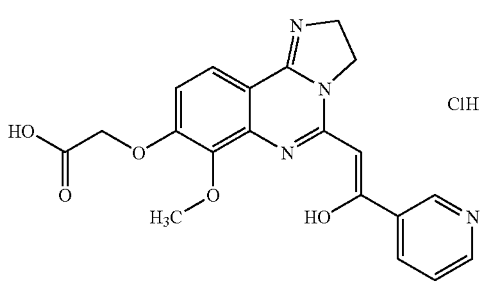 | 430.85 | 395 | 240(dec.) | A |

TABLE 1-continued

| Ex. No. | Structure | Mol Weight | MS (M + 1) | mp | in vitro |
|---|---|---|---|---|---|
| 1-23 | 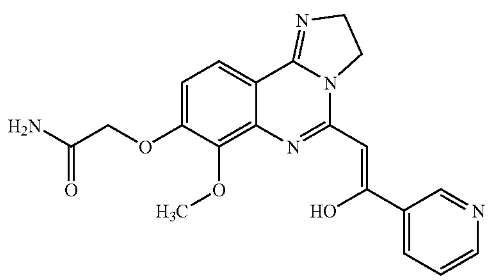 | 393.41 | 394 | 297-298 | A |
| 1-24 | ClH | 429.87 | 394 | 235(dec.) | A |
| 1-25 | ClH | 443.89 | 408 | 240(dec.) | A |
| 1-26 | ClH | 471.95 | 436 | 245(dec.) | A |
| 1-27 | 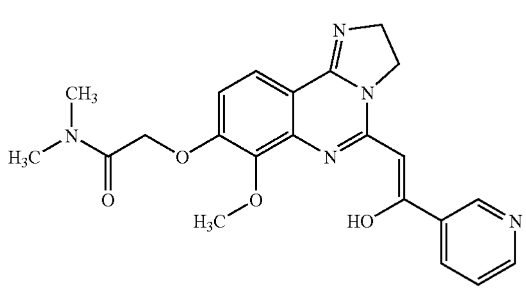 | 421.46 | 422 | 241-242 | A |

| Ex. No. | Structure | Mol Weight | MS (M + 1) | mp | in vitro |
|---|---|---|---|---|---|
| 1-28 | 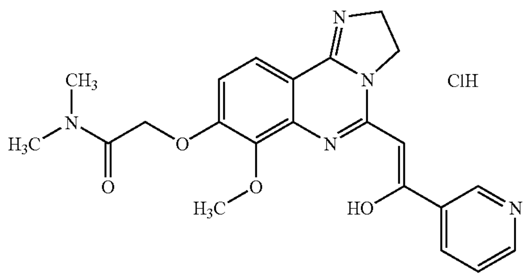 | 457.92 | 422 | 205(dec.) | A |
| 1-29 | 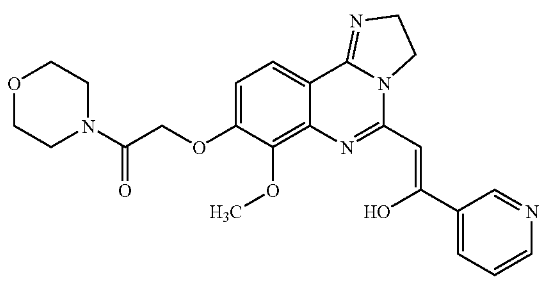 | 463.50 | 464 | 234-235 | A |
| 1-30 | 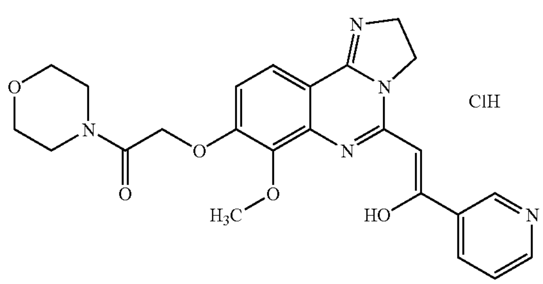 | 499.96 | 464 | 240-241 | A |
| 1-31 | 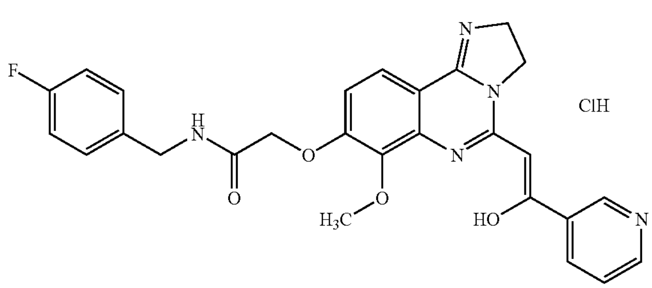 | 537.98 | 502 | 230-231 | B |
| 1-32 | 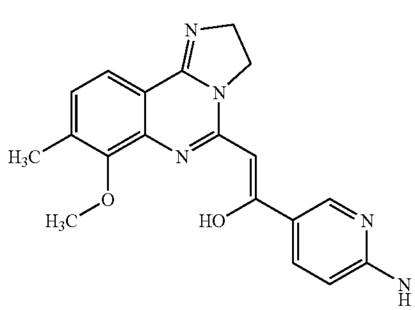 | 391.43 | 392 | >285 | A |

TABLE 1-continued
| Ex. No. | Structure | Mol Weight | MS (M + 1) | mp | in vitro |
|---|---|---|---|---|---|
| 1-33 | 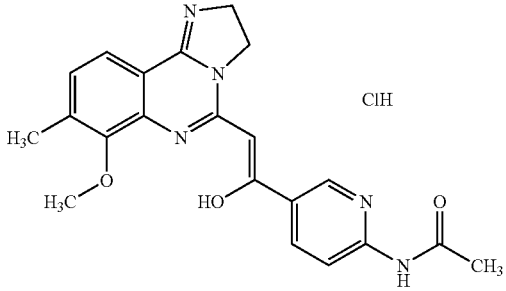 ClH | 427.89 | 392 | 273 | A |
| 1-34 | 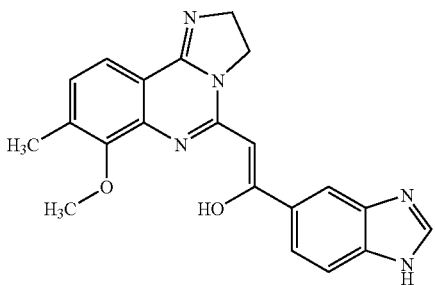 | 373.42 | 374 | >285 | A |
| 1-35 | 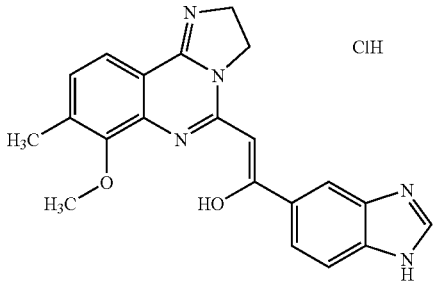 ClH | 409.88 | 374 | 270 | A |
| 1-36 | 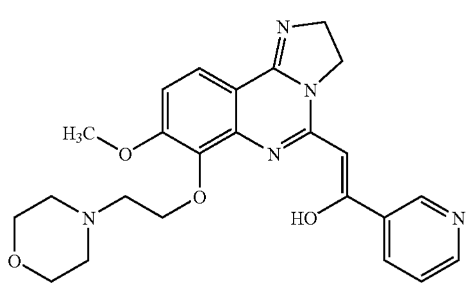 | 449.51 | 450 | 197 | A |
| 1-37 |  ClH | 485.97 | 450 | 215 | A |

TABLE 1-continued
| Ex. No. | Structure | Mol Weight | MS (M + 1) | mp | in vitro |
|---|---|---|---|---|---|
| 1-38 | 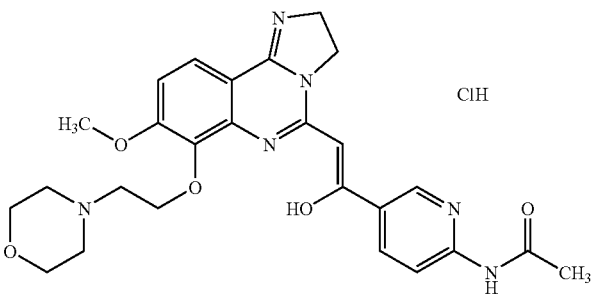 | 543.03 | 507 | 260 | A |
| 1-39 | 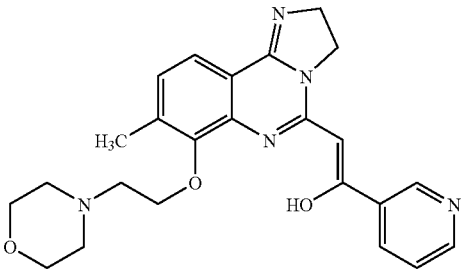 | 433.51 | 434 | 217 | B |
| 1-40 | 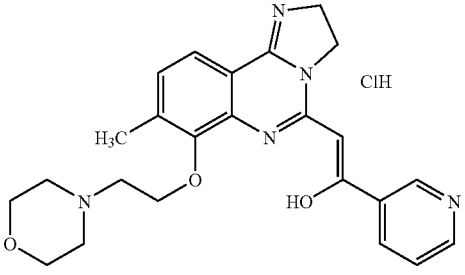 | 469.98 | 434 | 256(dec.) | B |
| 1-41 | 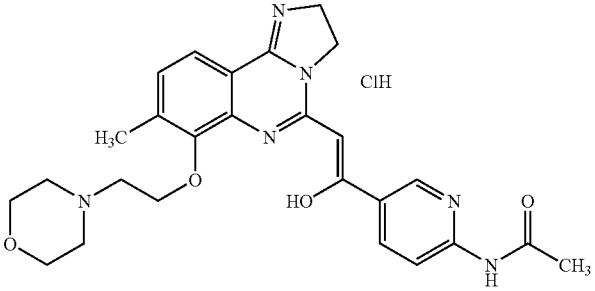 | 527.03 | 491 | 271 | A |
| 1-42 | 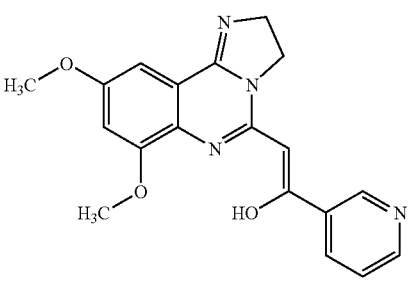 | 350.38 | 351 | 218 | A |

TABLE 1-continued

| Ex. No. | Structure | Mol Weight | MS (M + 1) | mp | in vitro |
|---|---|---|---|---|---|
| 1-43 | 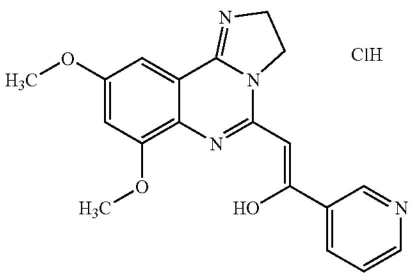 | 386.84 | 351 | 290(dec.) | A |
| 1-44 | 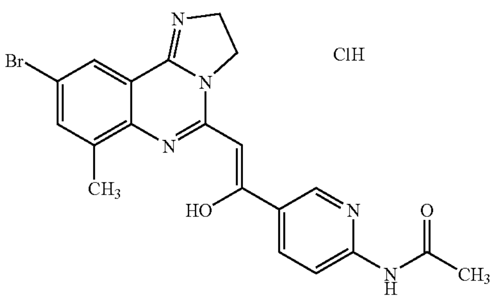 | 476.76 | 442, 440 | >290 | B |
| 1-45 | 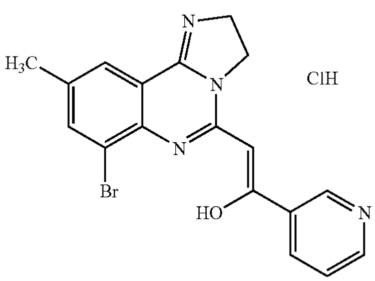 | 419.71 | 385, 383 | >290 | B |
| 1-46 | 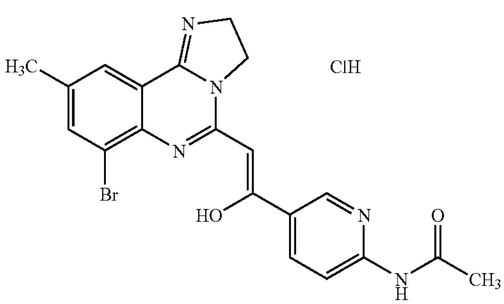 | 476.76 | 442, 440 | >285 | A |
| 1-47 | 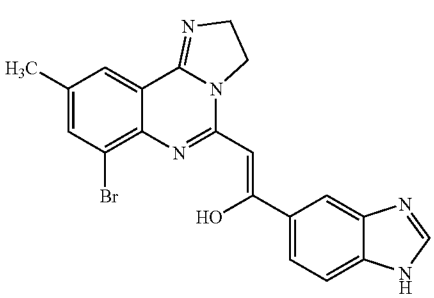 | 422.29 | 424, 422 | >285 | B |

TABLE 1-continued

| Ex. No. | Structure | Mol Weight | MS (M + 1) | mp | in vitro |
|---|---|---|---|---|---|
| 1-48 | 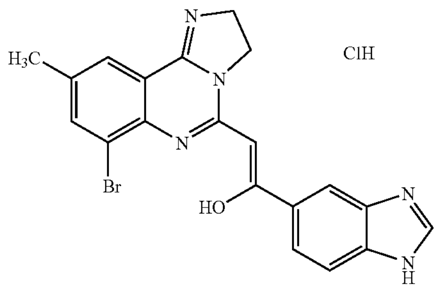 | 458.75 | 424, 422 | >285 | B |
| 1-49 | 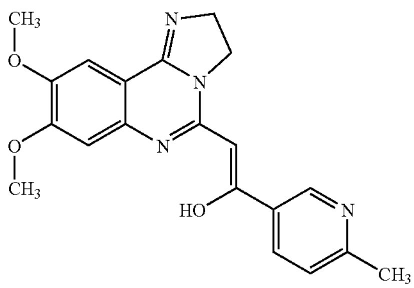 | 364.41 | 365 | 200-204 | A |
| 1-50 | 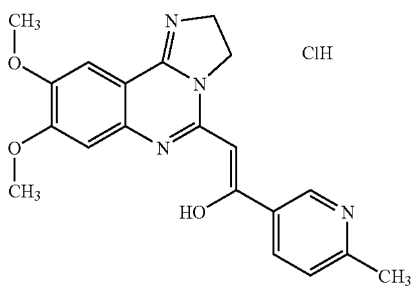 | 400.87 | 365 | 260(dec.) | B |
| 1-51 | 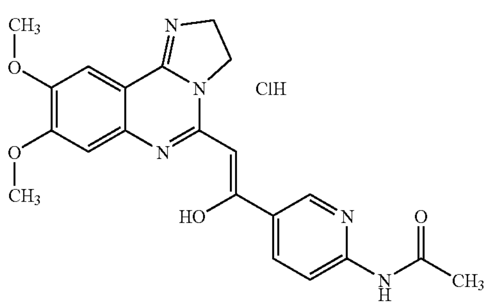 | 443.89 | 408 | 275-280 | B |
| 1-52 | 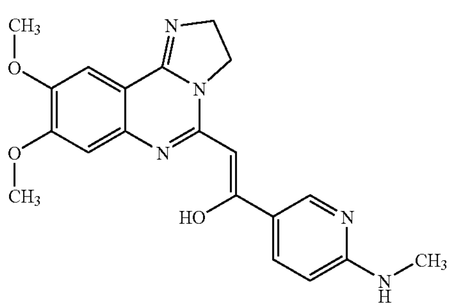 | 379.42 | 380 | 321-325 | B |

TABLE 1-continued

| Ex. No. | Structure | Mol Weight | MS (M + 1) | mp | in vitro |
|---|---|---|---|---|---|
| 1-53 | 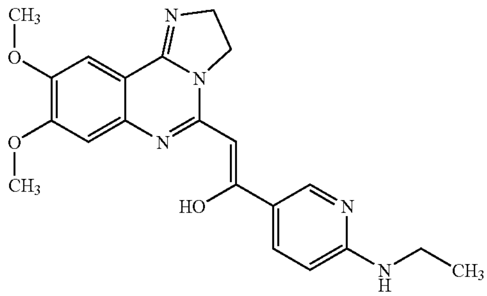 | 393.45 | 394 | 195-198 | B |
| 1-54 | 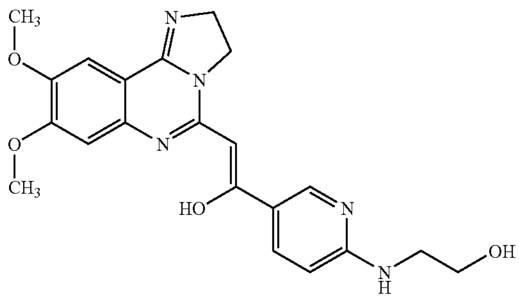 | 409.45 | 410 | 207 | B |
| 1-55 | 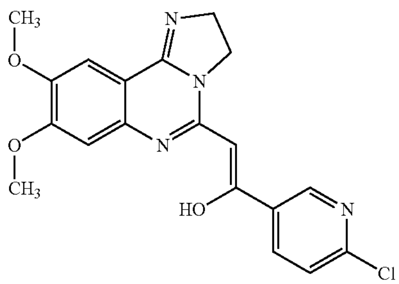 | 384.83 | 385 | 283 | B |
| 1-56 | 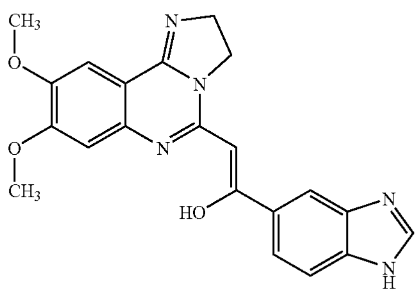 | 389.42 | 390 | 212-215 | A |
| 1-57 | 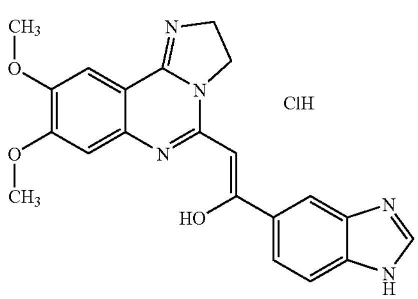 | 425.88 | 390 | 240(dec.) | A |

TABLE 1-continued

| Ex. No. | Structure | Mol Weight | MS (M + 1) | mp | in vitro |
|---|---|---|---|---|---|
| 1-58 | 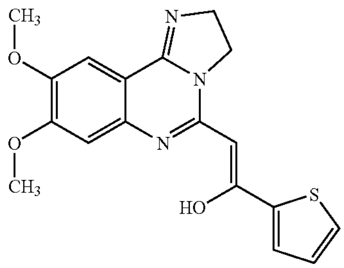 | 355.42 | 356 | 250 | B |
| 1-59 | ClH | 391.88 | 356 | 266-268 | B |
| 1-60 | 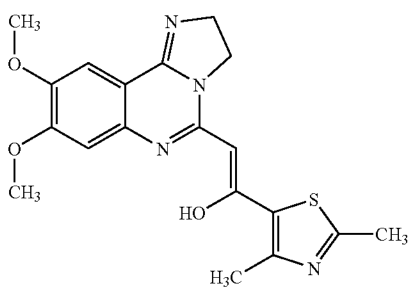 | 384.46 | 385 | 292 | A |
| 1-61 | ClH | 420.92 | 385 | 268-271 | A |
| 1-62 | 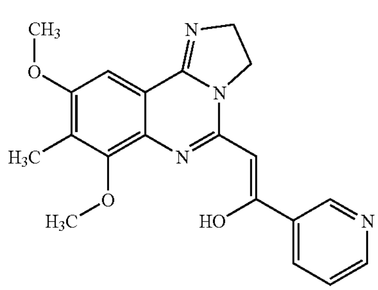 | 364.41 | 365 | 278 | A |

TABLE 1-continued

| Ex. No. | Structure | Mol Weight | MS (M + 1) | mp | in vitro |
|---|---|---|---|---|---|
| 1-63 | 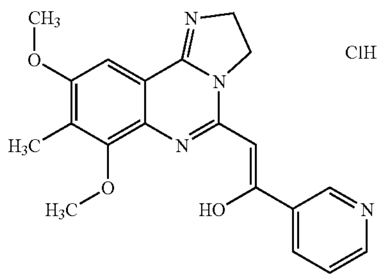 | 400.87 | 365 | 285 | A |
| 1-64 | 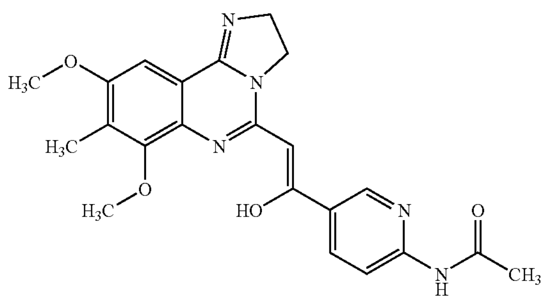 | 421.46 | 422 | >285 | A |
| 1-65 | 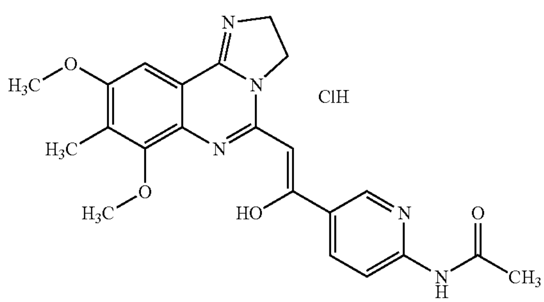 | 457.92 | 422 | >285 | A |
| 1-66 | 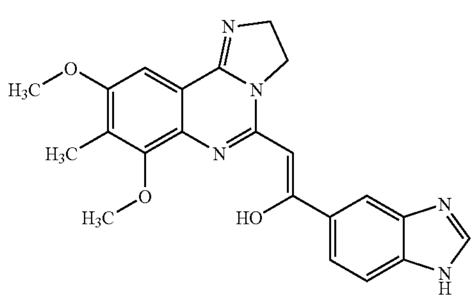 | 403.44 | 404 | 280 | B |
| 1-67 | 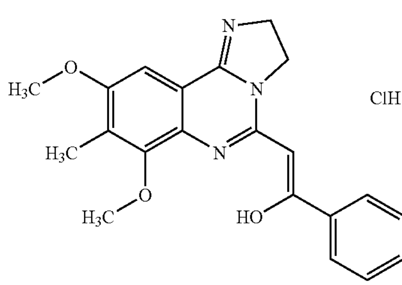 | 439.91 | 404 | >285 | B |

TABLE 1-continued

| Ex. No. | Structure | Mol Weight | MS (M + 1) | mp | in vitro |
|---|---|---|---|---|---|
| 1-68 | 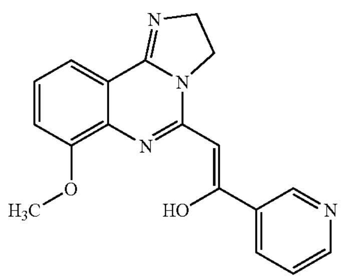 | 320.35 | 321 | 275 | A |
| 1-69 | 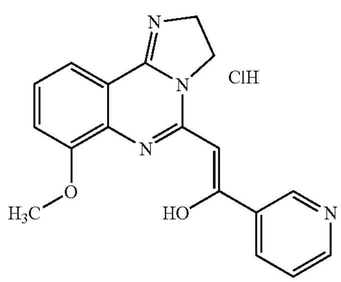 | 356.81 | 321 | 285 | A |
| 1-70 | 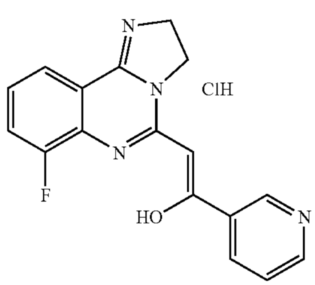 | 308.32 | 309 | 218 | A |
| 1-71 | 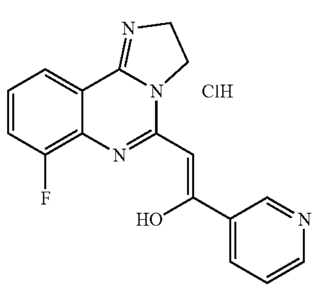 | 344.78 | 309 | 303 | B |
| 1-72 | 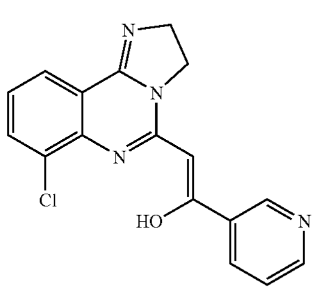 | 324.77 | 325 | 210(dec.) | B |

TABLE 1-continued

| Ex. No. | Structure | Mol Weight | MS (M + 1) | mp | in vitro |
|---|---|---|---|---|---|
| 1-73 | 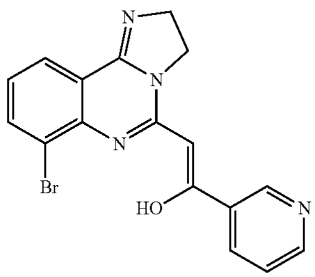 | 369.22 | 371, 369 | 120(dec.) | B |
| 1-74 | 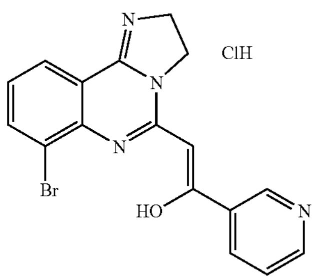 | 405.68 | 371, 369 | 246 | B |
| 1-75 | 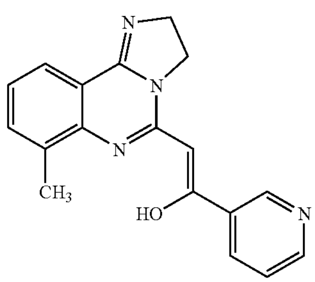 | 304.35 | 305 | 248 | B |
| 1-76 | 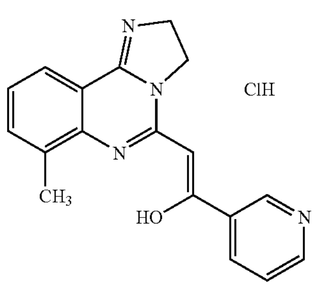 | 340.82 | 305 | >290 | B |
| 1-77 | 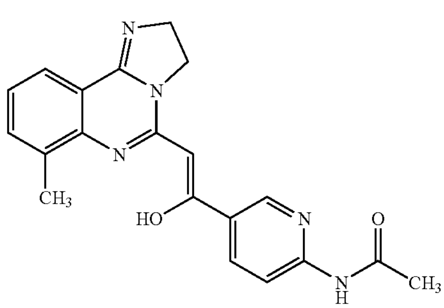 | 361.41 | 362 | >285 | A |

TABLE 1-continued
| Ex. No. | Structure | Mol Weight | MS (M + 1) | mp | in vitro |
|---|---|---|---|---|---|
| 1-78 | 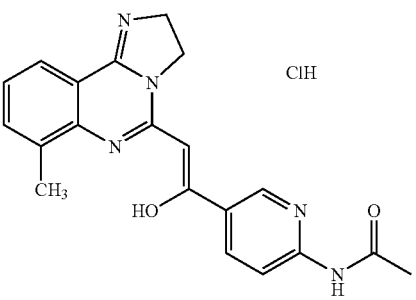 | 397.87 | 362 | >285 | A |
| 1-79 | 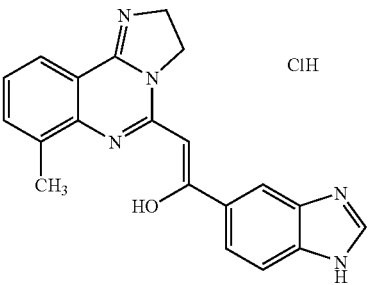 | 379.85 | 344 | >285 | A |
| 1-80 | 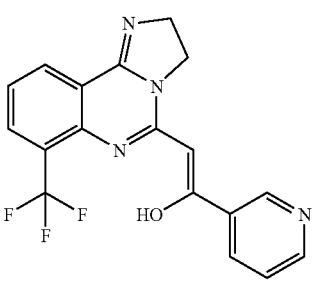 | 358.33 | 359 | 275 | B |
| 1-81 | 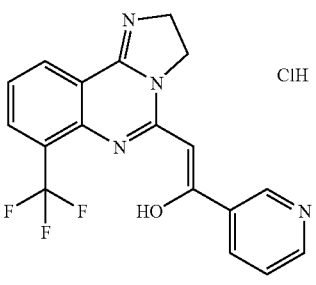 | 394.79 | 359 | >290 | B |
| 1-82 | 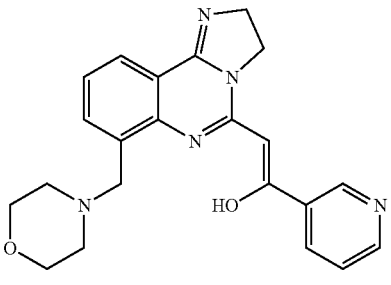 | 389.46 | 390 | 198-202 (dec.) | B |

TABLE 1-continued
| Ex. No. | Structure | Mol Weight | MS (M + 1) | mp | in vitro |
|---|---|---|---|---|---|
| 1-83 | 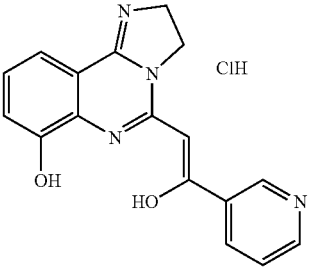 | 342.79 | 307 | >250 | B |
| 1-84 | 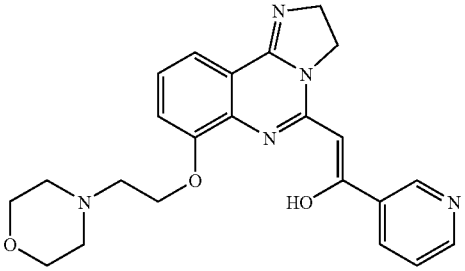 | 419.49 | 420 | 195-196 | B |
| 1-85 | 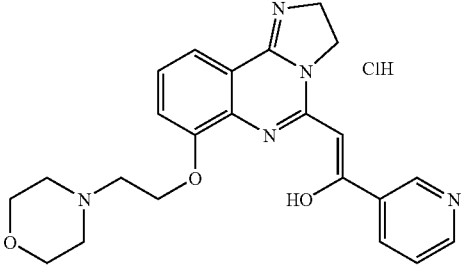 | 455.95 | 420 | 261-262 | B |
| 1-86 | 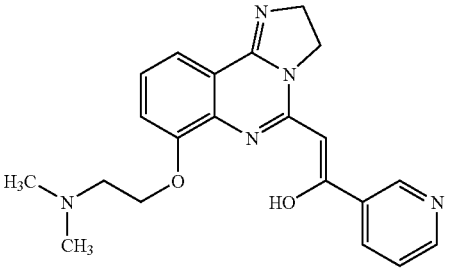 | 377.45 | 378 | 186-187 | B |
| 1-87 | 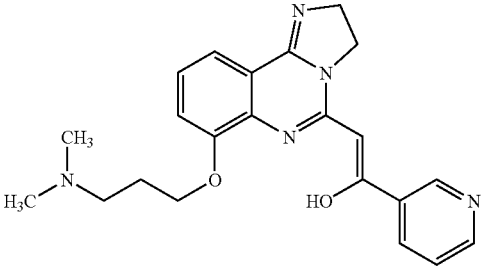 | 391.48 | 392 | 235(dec.) | B |

TABLE 1-continued

| Ex. No. | Structure | Mol Weight | MS (M + 1) | mp | in vitro |
|---|---|---|---|---|---|
| 1-88 | 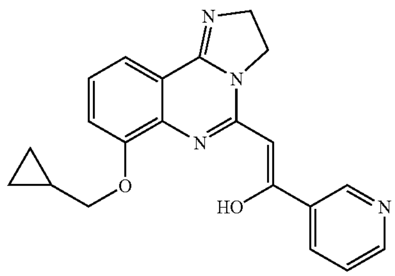 | 360.42 | 361 | 203(dec.). | B |
| 1-89 | ClH | 396.88 | 361 | >300 | B |
| 1-90 | 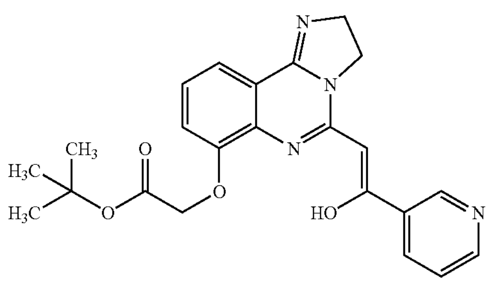 | 420.47 | 421 | 222-223 | A |
| 1-91 | 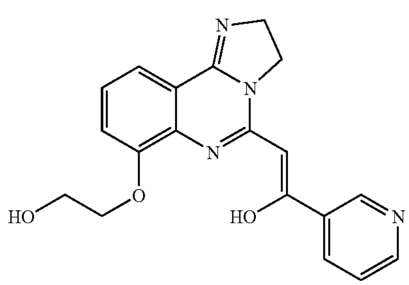 | 350.38 | 351 | 211-212 | B |
| 1-92 | 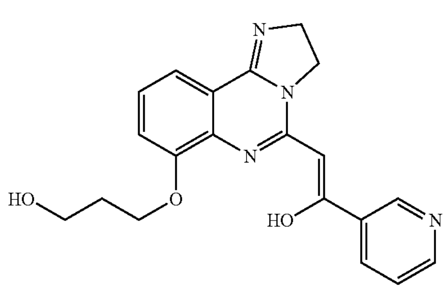 | 364.41 | 365 | 203-205 | A |

TABLE 1-continued

| Ex. No. | Structure | Mol Weight | MS (M + 1) | mp | in vitro |
|---|---|---|---|---|---|
| 1-93 | 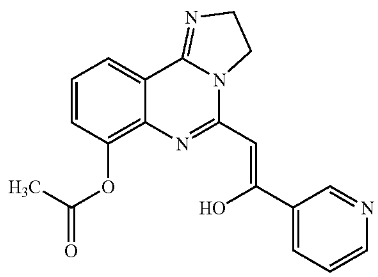 | 348.36 | 349 | 225-226 | B |
| 1-94 | 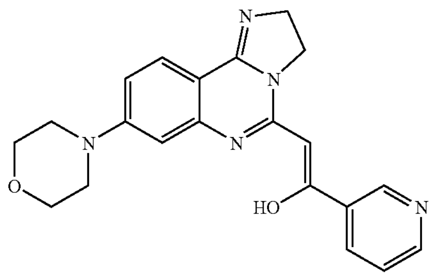 | 375.43 | 376 | 282 | B |
| 1-95 | ClH | 411.89 | 376 | >300 | B |
| 1-96 | 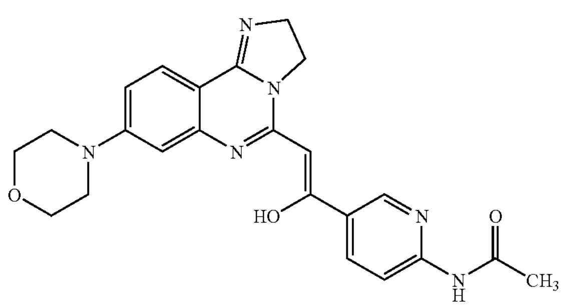 | 432.49 | 433 | 269(dec.) | A |
| 1-97 | ClH | 468.95 | 433 | 246 | A |

TABLE 1-continued

| Ex. No. | Structure | Mol Weight | MS (M + 1) | mp | in vitro |
|---|---|---|---|---|---|
| 1-98 | 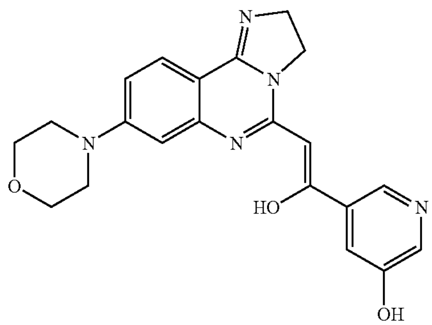 | 391.43 | 392 | 337(dec.) | A |
| 1-99 | ClH | 427.89 | 392 | 312(dec.) | A |
| 1-100 | 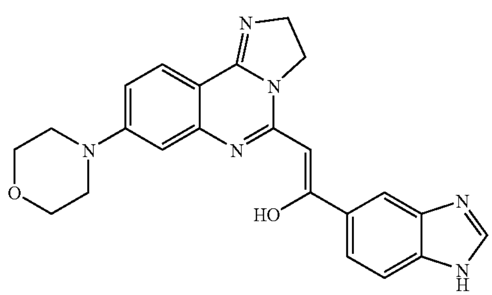 | 414.47 | 415 | 232 | A |
| 1-101 | ClH | 450.93 | 415 | 286(dec.) | A |
| 1-102 | ClH | 482.97 | 447 | 238(dec.) | B |

TABLE 1-continued

| Ex. No. | Structure | Mol Weight | MS (M + 1) | mp | in vitro |
|---|---|---|---|---|---|
| 1-103 | 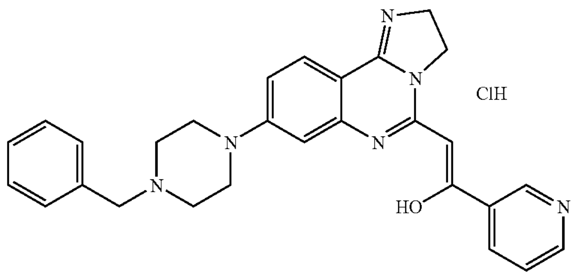 | 501.04 | 466 | 257 | B |
| 1-104 | 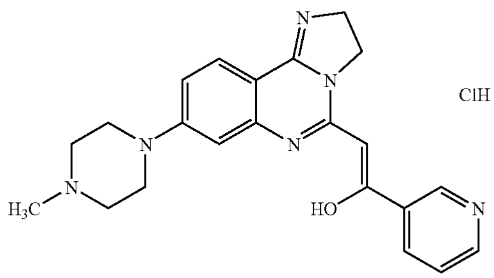 | 424.94 | 389 | 288 | B |
| 1-105 | 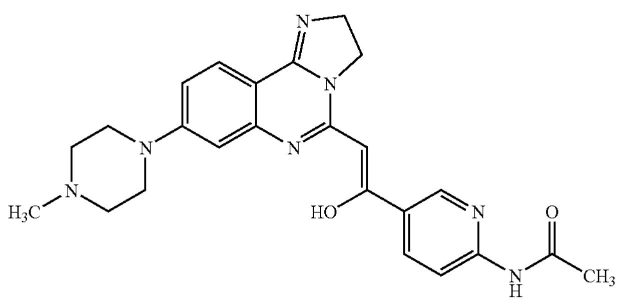 | 445.53 | 446 | 292(dec.) | B |
| 1-106 | 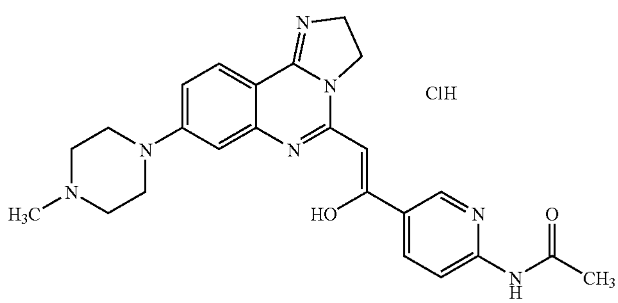 | 481.99 | 446 | 280(dec.) | B |
| 1-107 | 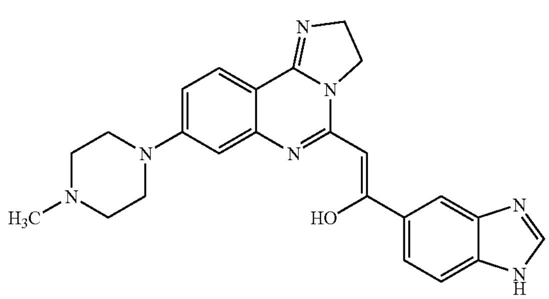 | 427.51 | 428 | 207 | A |

TABLE 1-continued

| Ex. No. | Structure | Mol Weight | MS (M + 1) | mp | in vitro |
|---|---|---|---|---|---|
| 1-108 | 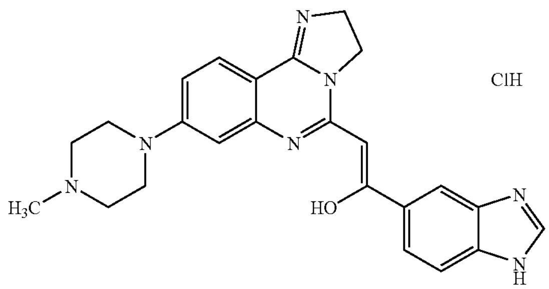 | 463.97 | 428 | >300 | B |
| 1-109 | 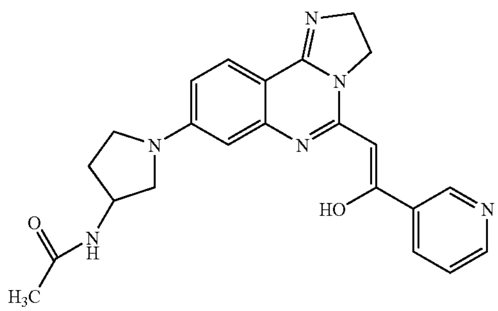 | 416.49 | 416 | | A |
| 1-110 | 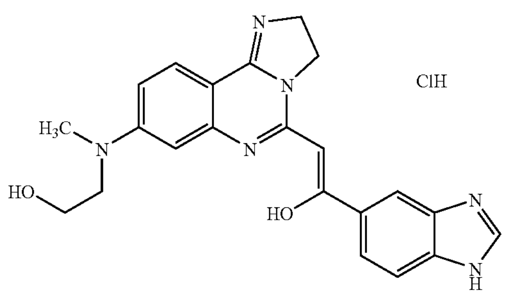 | 438.92 | 240 | 231(dec.) | B |
| 1-111 | 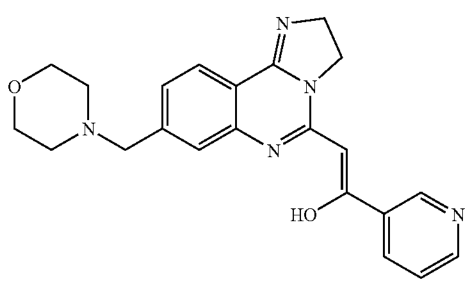 | 389.46 | 390 | 204 | B |
| 1-112 | 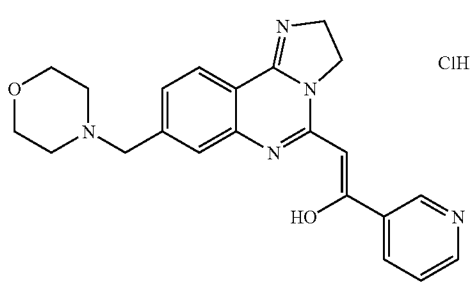 | 425.92 | 390 | 242 | B |

TABLE 1-continued

| Ex. No. | Structure | Mol Weight | MS (M + 1) | mp | in vitro |
|---|---|---|---|---|---|
| 1-113 | 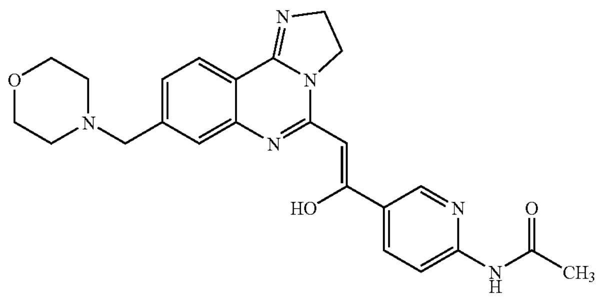 | 446.51 | 447 | 245 | B |
| 1-114 | ClH | 482.97 | 447 | 260 | B |
| 1-115 | 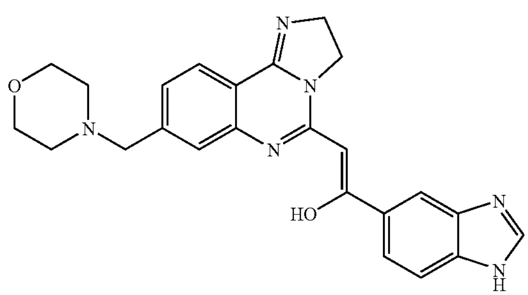 | 428.50 | 429 | 219 | B |
| 1-116 | 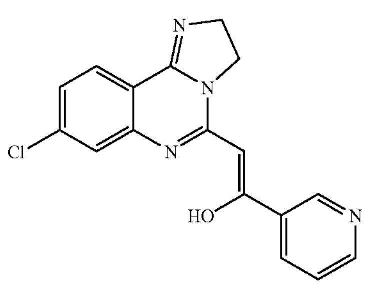 | 324.77 | 325 | 226 | B |
| 1-117 | ClH | 361.23 | 326 | 280(dec.) | B |

TABLE 1-continued

| Ex. No. | Structure | Mol Weight | MS (M + 1) | mp | in vitro |
|---|---|---|---|---|---|
| 1-118 | 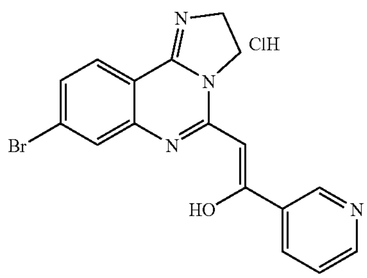 | 405.68 | 371, 369 | 233 | B |
| 1-119 | 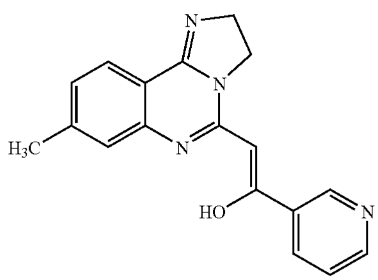 | 304.35 | 305 | 224 | B |
| 1-120 | 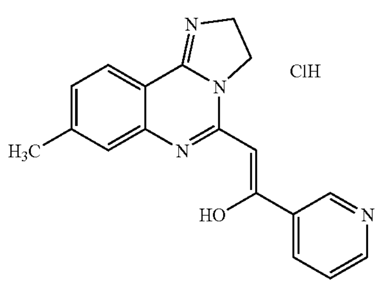 | 340.82 | 305 | >330 | B |
| 1-121 | 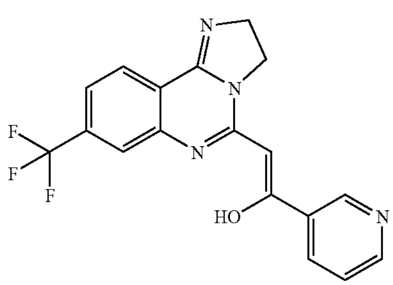 | 358.33 | 359 | 264 | C |
| 1-122 | 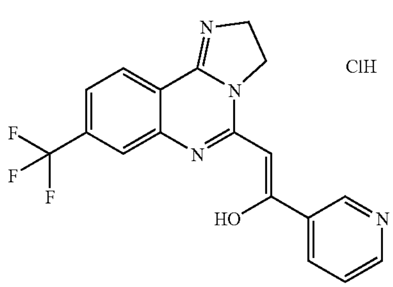 | 394.79 | 359 | 321 | B |

TABLE 1-continued
| Ex. No. | Structure | Mol Weight | MS (M + 1) | mp | in vitro |
|---|---|---|---|---|---|
| 1-123 | 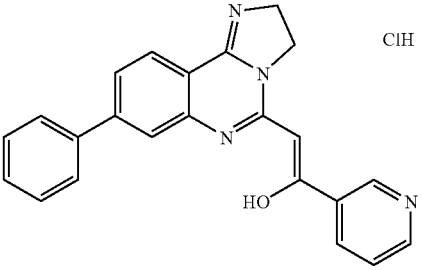 ClH | 402.89 | 367 | >300 | B |
| 1-124 | 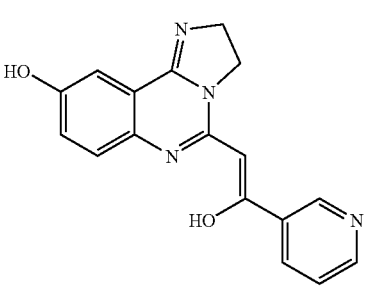 | 306.33 | 307 | 302-303 | B |
| 1-125 | 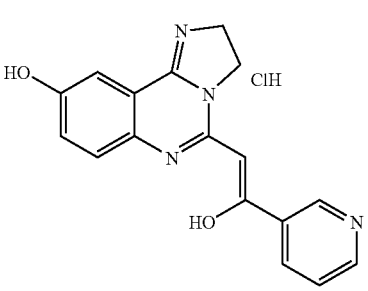 ClH | 342.79 | 307 | >300 | A |
| 1-126 | 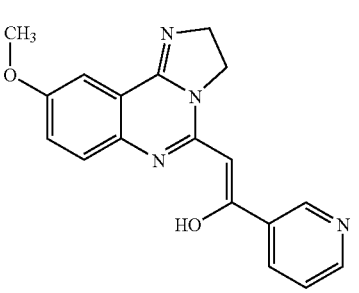 | 320.35 | 321 | 199 | B |
| 1-127 | 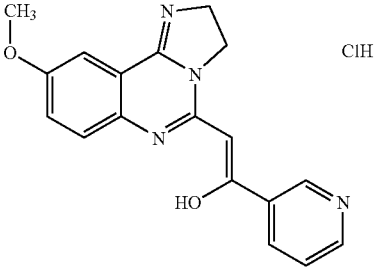 ClH | 356.81 | 321 | >300 | B |

TABLE 1-continued
| Ex. No. | Structure | Mol Weight | MS (M + 1) | mp | in vitro |
|---|---|---|---|---|---|
| 1-128 | 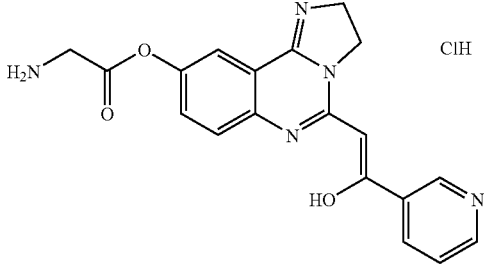 | 399.84 | 364 | >300 | A |
| 1-129 | 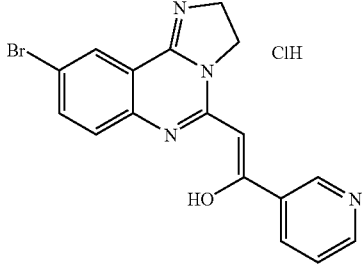 | 405.68 | 371, 369 | >330 | B |
| 1-130 | 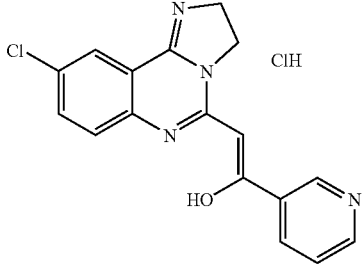 | 361.23 | 326 | >330 | B |
| 1-131 | 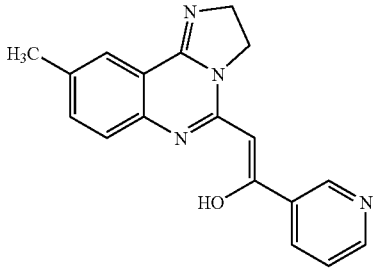 | 304.35 | 305 | 212 | B |
| 1-132 | 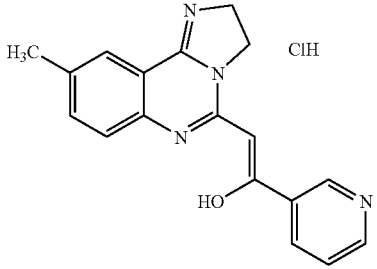 | 340.82 | 305 | >290 | B |

TABLE 1-continued

| Ex. No. | Structure | Mol Weight | MS (M + 1) | mp | in vitro |
|---|---|---|---|---|---|
| 1-133 | 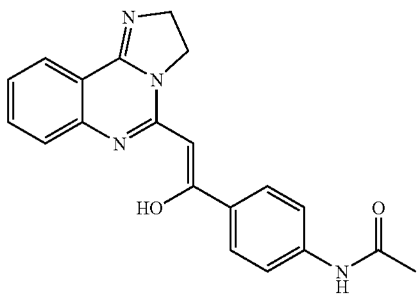 | 346.39 | 347 | >300 | B |
| 1-134 | 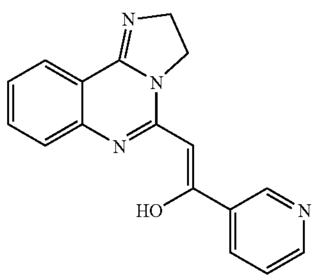 | 290.33 | 291 | 202 | B |
| 1-135 | 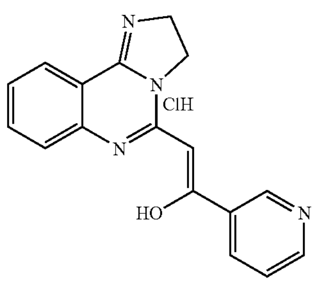 | 326.79 | 291 | 260(dec.) | B |
| 1-136 | 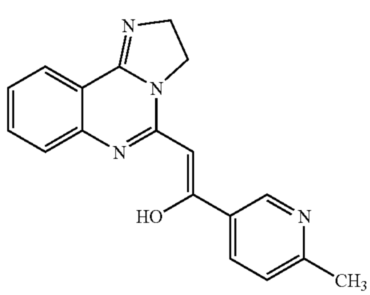 | 304.35 | 305 | 217-219 | B |
| 1-137 | 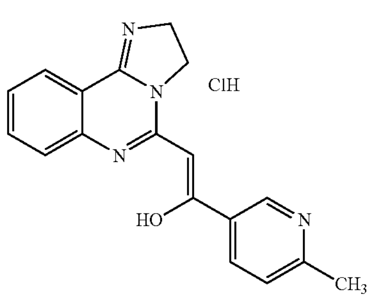 | 340.82 | 305 | >300 | B |

TABLE 1-continued

| Ex. No. | Structure | Mol Weight | MS (M + 1) | mp | in vitro |
|---|---|---|---|---|---|
| 1-138 | 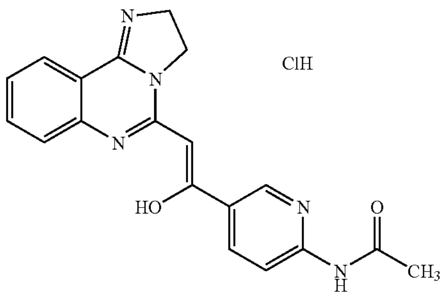 | 383.84 | 348 | 327 | A |
| 1-139 | 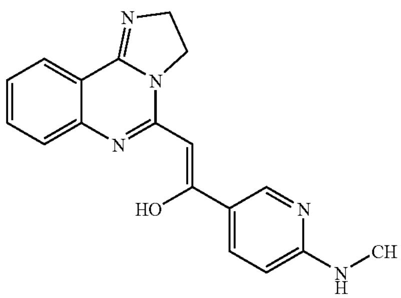 | 319.37 | 320 | 232-237 | A |
| 1-140 | 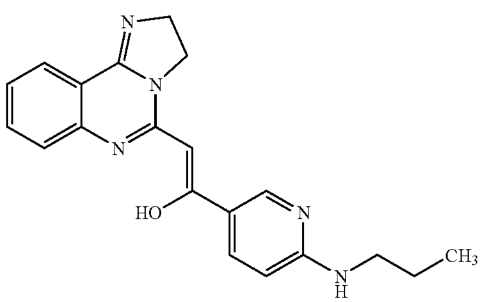 | 347.42 | 348 | 197 | B |
| 1-141 | 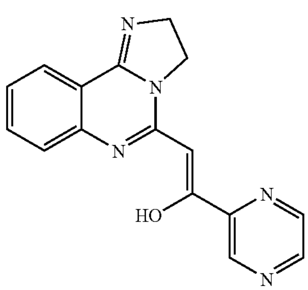 | 291.31 | 292 | 233-235 | B |
| 1-142 | 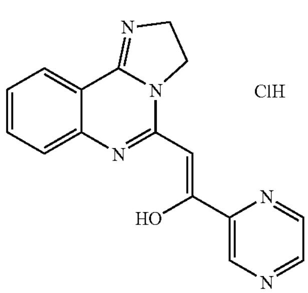 | 327.78 | 292 | 217-222 | B |

TABLE 1-continued

| Ex. No. | Structure | Mol Weight | MS (M + 1) | mp | in vitro |
|---|---|---|---|---|---|
| 1-143 | 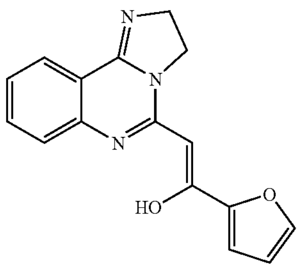 | 279.30 | 280 | 192 | B |
| 1-144 | 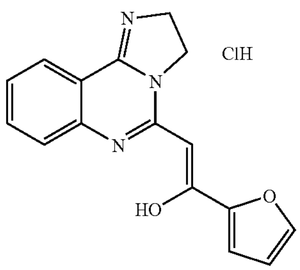 | 315.76 | 280 | >300 | B |
| 1-145 | 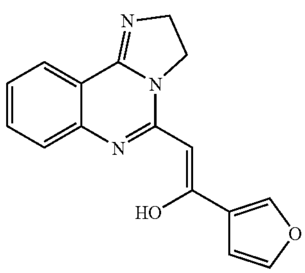 | 279.30 | 280 | 155-156 | B |
| 1-146 | 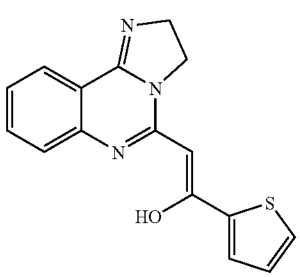 | 295.37 | 296 | 193 | A |
| 1-147 | 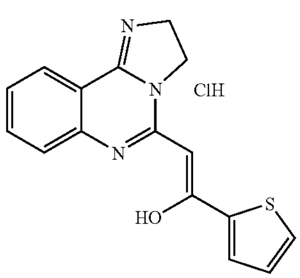 | 331.83 | 296 | >300 | A |

TABLE 1-continued

| Ex. No. | Structure | Mol Weight | MS (M + 1) | mp | in vitro |
|---|---|---|---|---|---|
| 1-148 | 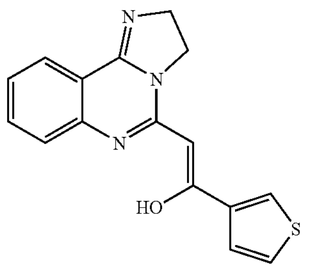 | 295.37 | 296 | 182-183 | B |
| 1-149 | 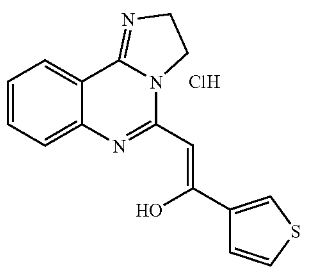 | 331.83 | 296 | >300 | A |
| 1-150 | 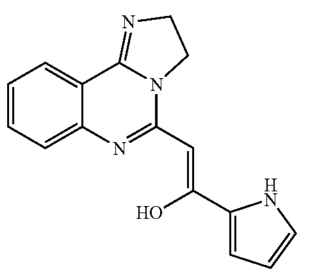 | 278.32 | 279 | 247 | B |
| 1-151 | 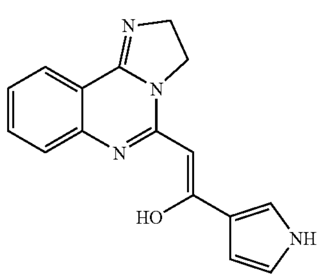 | 278.32 | 279 | 247-249 | A |
| 1-152 | 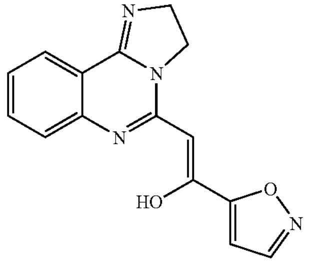 | 280.29 | 281 | 148 | B |

TABLE 1-continued

| Ex. No. | Structure | Mol Weight | MS (M + 1) | mp | in vitro |
|---|---|---|---|---|---|
| 1-153 | 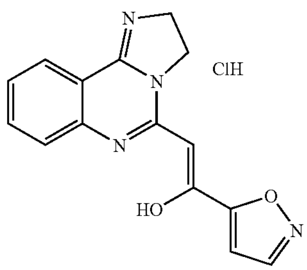 | 316.75 | 281 | 245(dec.) | B |
| 1-154 | 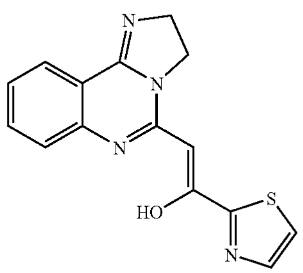 | 296.35 | 297 | 208-210 | A |
| 1-155 | 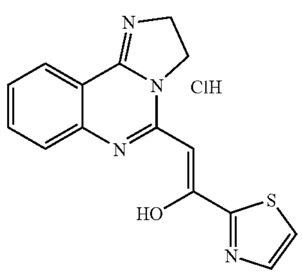 | 332.81 | 297 | >300 | B |
| 1-156 | 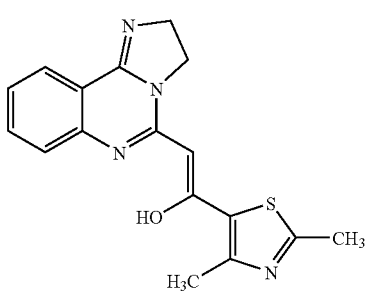 | 324.41 | 325 | 222 | A |
| 1-157 | 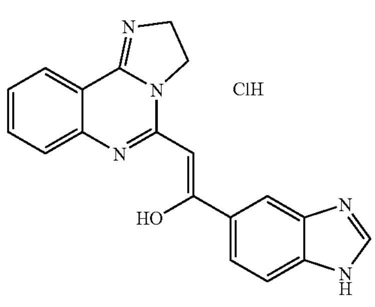 | 365.83 | 330 | >300 | B |

TABLE 1-continued

| Ex. No. | Structure | Mol Weight | MS (M + 1) | mp | in vitro |
|---|---|---|---|---|---|
| 1-158 | 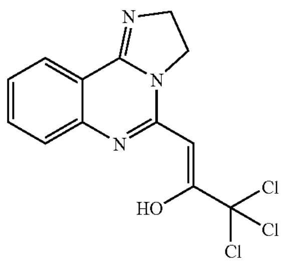 | 330.60 | 330 | 190(dec.) | B |
| 1-159 | 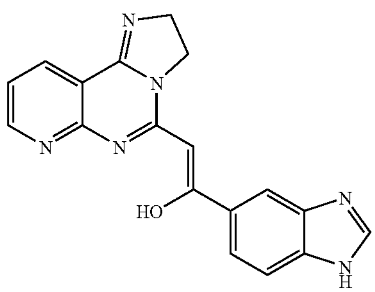 | 330.35 | 331 | >300 | A |
| 1-160 | 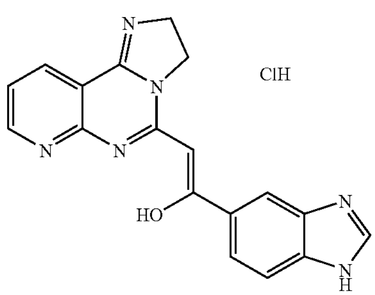 | 366.81 | 331 | 247(dec.) | B |
| 1-161 | 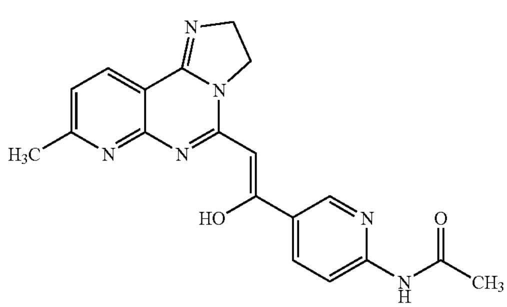 | 362.39 | 363 | >300 | B |
| 1-162 | 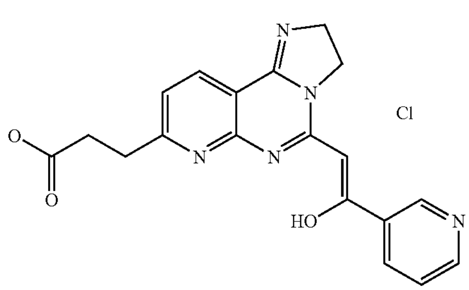 | 399.84 | 400 | >300 | B |

TABLE 1-continued

| Ex. No. | Structure | Mol Weight | MS (M + 1) | mp | in vitro |
|---|---|---|---|---|---|
| 1-163 | 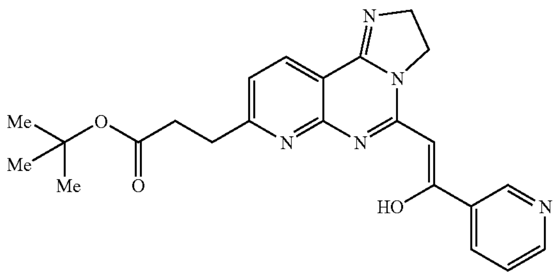 | 419.49 | 420 | 200 | B |
| 1-164 | 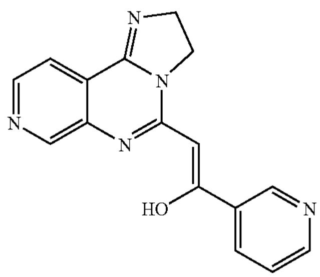 | 291.31 | 292 | 230 | B |
| 1-165 | 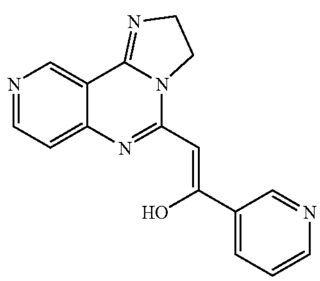 | 291.31 | 292 | 250 | B |
| 1-166 | 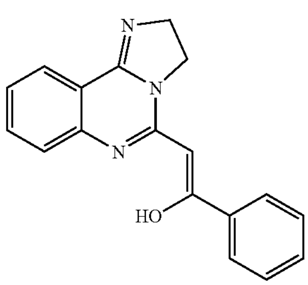 | 289.34 | 290 | 130-139 | C |
| 1-167 | 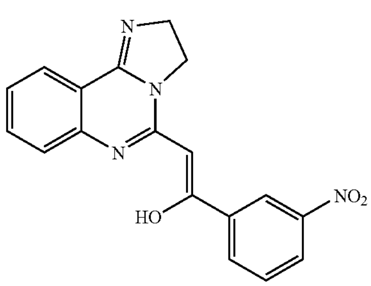 | 334.34 | 335 | 276 | D |

TABLE 1-continued

| Ex. No. | Structure | Mol Weight | MS (M + 1) | mp | in vitro |
|---|---|---|---|---|---|
| 1-168 | 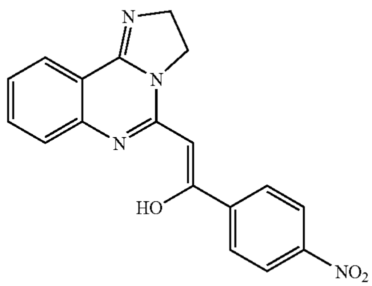 | 334.34 | 335 | 240-248 | D |
| 1-169 | 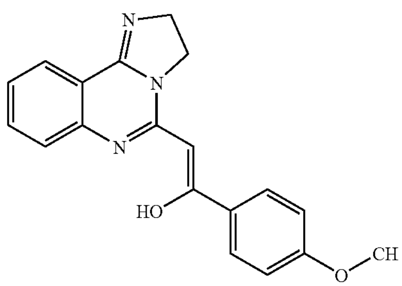 | 319.37 | 320 | 212-214 | D |
| 1-170 | 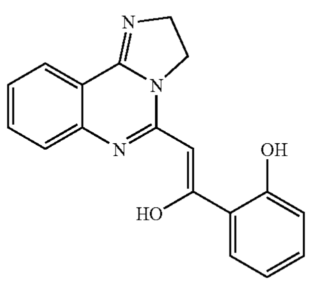 | 305.34 | 306 | 252-256 | D |
| 1-171 | 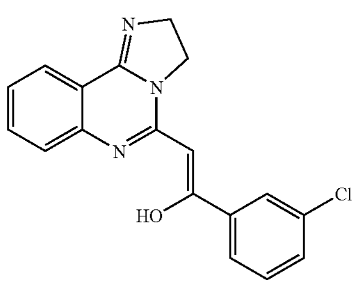 | 323.78 | 324 | 224-227 | D |
| 1-172 | 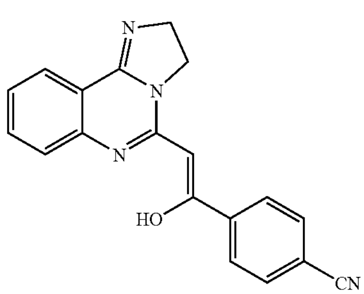 | 314.35 | 315 | 260-264 | D |

TABLE 1-continued
| Ex. No. | Structure | Mol Weight | MS (M + 1) | mp | in vitro |
|---|---|---|---|---|---|
| 1-173 | 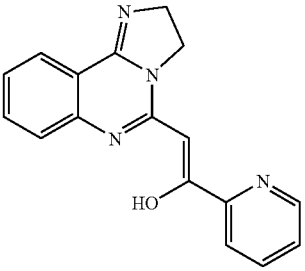 | 290.33 | 291 | 195 | C |
| 1-174 | 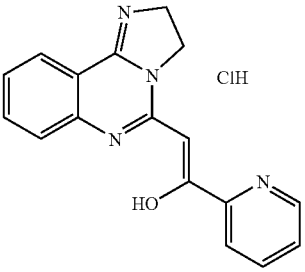 | 326.79 | 291 | 235-240 | C |
| 1-175 | 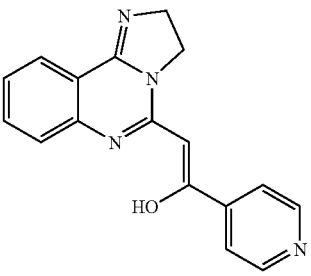 | 290.33 | 291 | 204-205 | B |
| 1-176 | 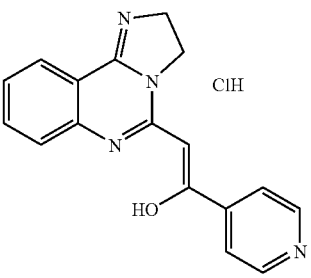 | 326.79 | 291 | 235(dec.) | B |
| 1-177 | 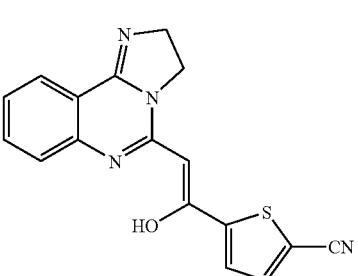 | 320.38 | 321 | 256 | C |

TABLE 1-continued

| Ex. No. | Structure | Mol Weight | MS (M + 1) | mp | in vitro |
|---|---|---|---|---|---|
| 1-178 | 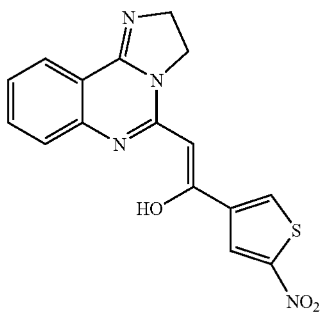 | 340.36 | 341 | 255-258 | D |
| 1-179 | 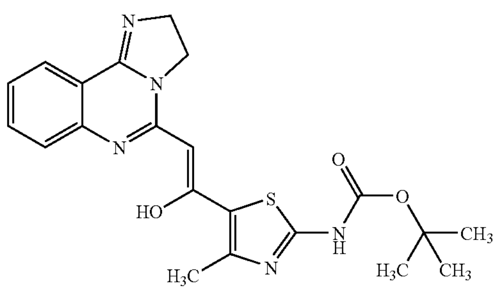 | 425.51 | 426 | >300 | D |
| 1-180 | 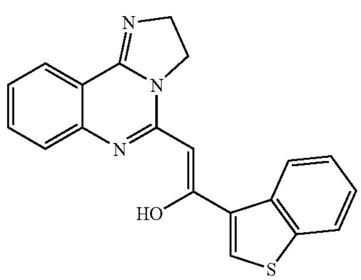 | 345.43 | 346 | 220-225 | D |
| 1-181 | 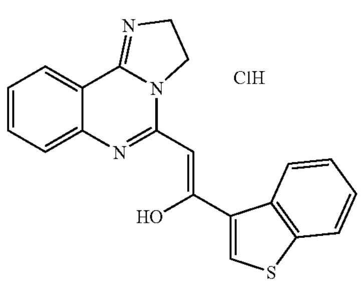 | 381.89 | 346 | >300 | D |
| 1-182 | 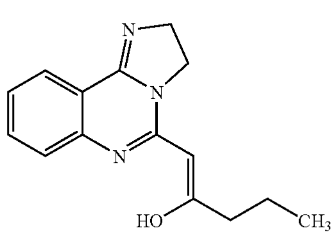 | 255.32 | 256 | 113 | D |

| Ex. No. | Structure | Mol Weight | MS (M + 1) | mp | in vitro |
|---|---|---|---|---|---|
| 1-183 | 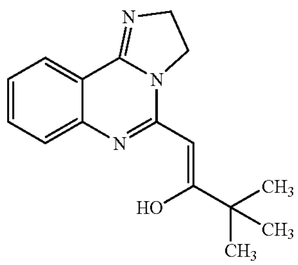 | 269.35 | 270 | 134-138 | C |
| 1-184 | 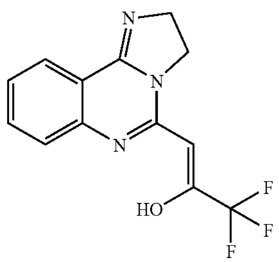 | 281.24 | 282 | 240 | C |
| 1-185 | 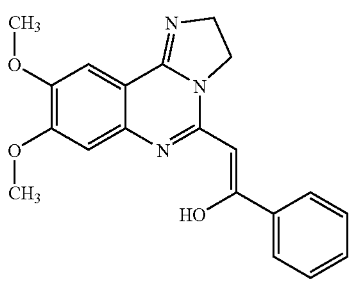 | 349.39 | 350 | 249-252 | C |
| 1-186 | 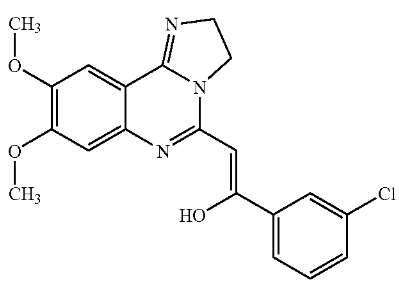 | 383.84 | 384 | 257-259 | D |
| 1-187 | 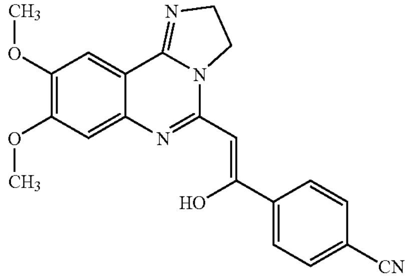 | 374.40 | 375 | 307-308 | D |

TABLE 1-continued

| Ex. No. | Structure | Mol Weight | MS (M + 1) | mp | in vitro |
|---|---|---|---|---|---|
| 1-188 | 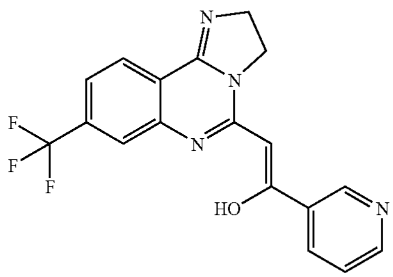 | 358.33 | 359 | 264 | C |
| 1-189 | 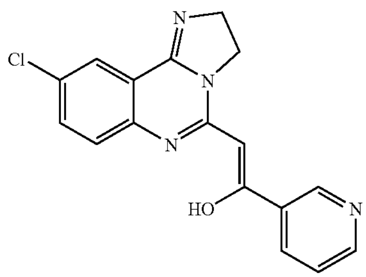 | 324.77 | 325 | 260 | C |
| 1-190 | 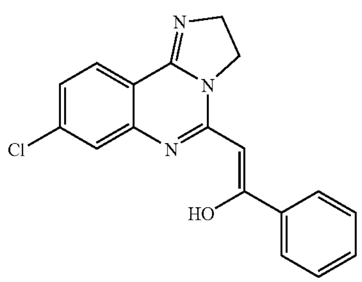 | 323.78 | 324 | 186-188 | C |
| 1-191 | 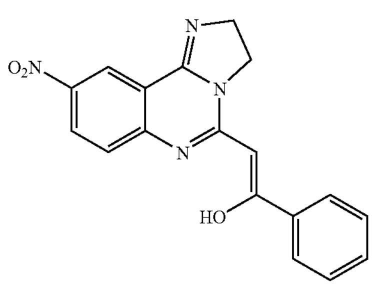 | 334.34 | 335 | 259-262 | D |
| 1-192 | 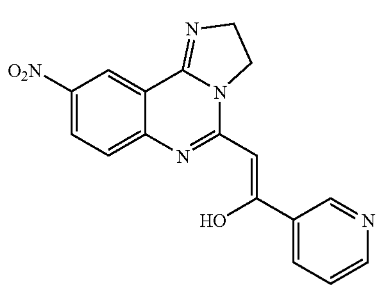 | 335.32 | 336 | 306 | C |

| Ex. No. | Structure | Mol Weight | MS (M + 1) | mp | in vitro |
|---|---|---|---|---|---|
| 1-193 | 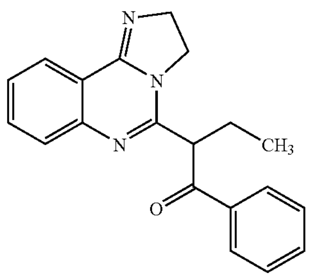 | 317.39 | 318 | 156-160 | D |
| 1-194 | 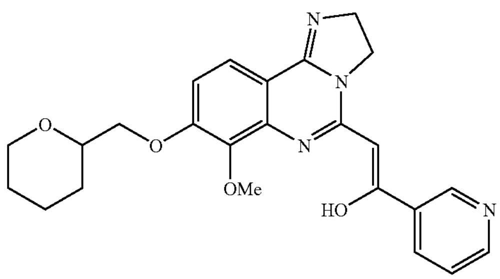 | 434.50 | 435 | 233-234 | A |
| 1-195 | 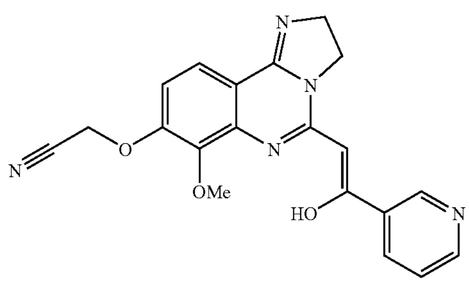 | 375.39 | 376 | 284-285 | A |
| 1-196 | 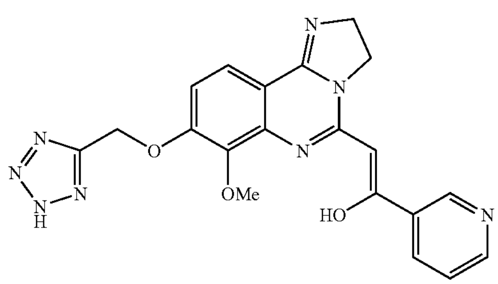 | 418.42 | 419 | 229-231 | A |
| 1-197 | 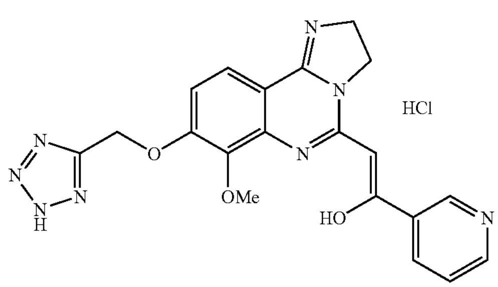 | 454.88 | 419 | 217-218 | A |

TABLE 1-continued

| Ex. No. | Structure | Mol Weight | MS (M + 1) | mp | in vitro |
|---|---|---|---|---|---|
| 1-198 | 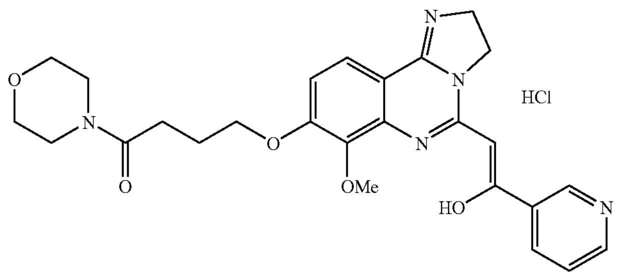 | 528.01 | 492 | 215-216 | A |
| 1-199 | 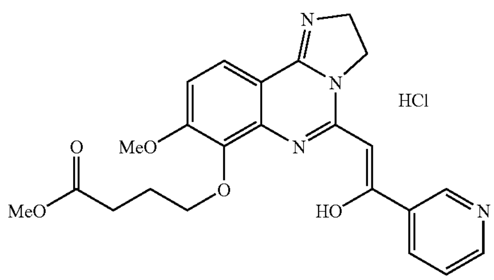 | 436.47 | 437 | 178-179 | A |
| 1-200 | 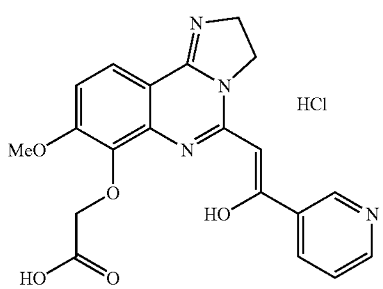 | 430.85 | 395 | 286(dec.) | B |
| 1-201 | 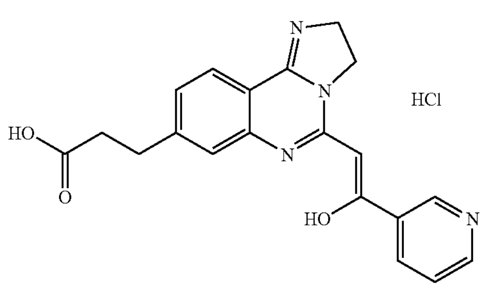 | 398.85 | 363 | 273(dec.) | A |
| 1-202 | 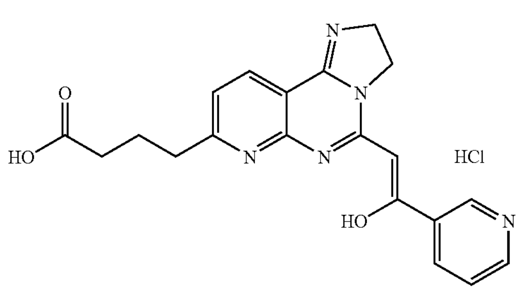 | 413.87 | 378 | 285(dec.) | B |

TABLE 1-continued

| Ex. No. | Structure | Mol Weight | MS (M + 1) | mp | in vitro |
|---|---|---|---|---|---|
| 1-203 | 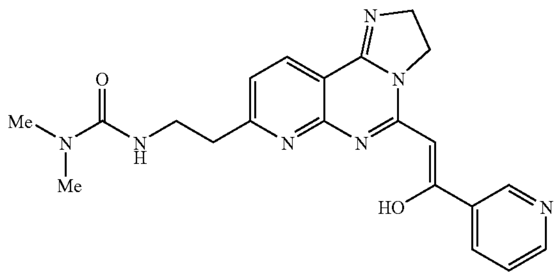 | 405.46 | 406 | 228 | B |
| 1-204 | 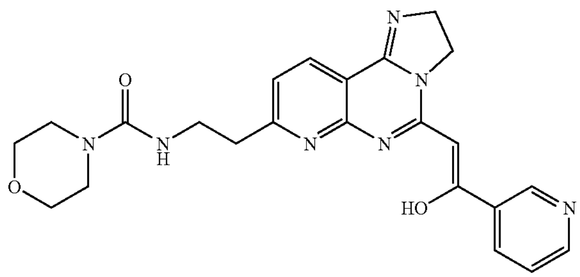 | 447.50 | 448 | 262 | C |
| 1-205 | 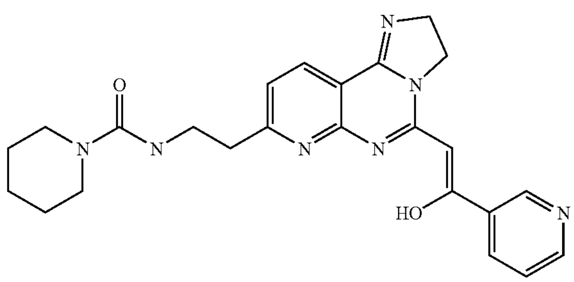 | 445.53 | 446 | 246 | B |
| 1-206 | 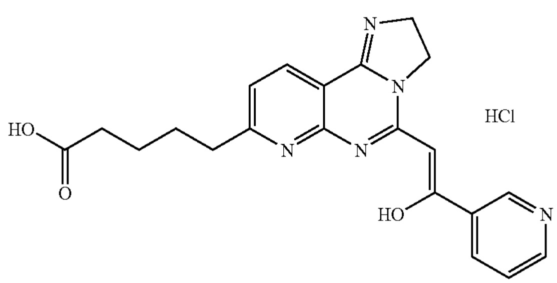 | 427.89 | 392 | 267 | A |
| 1-207 | 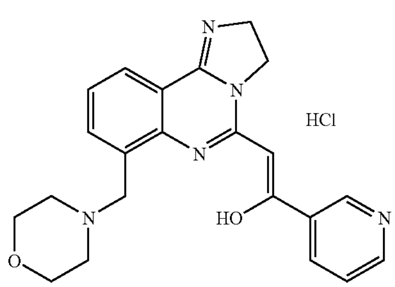 | 425.92 | 390 | 259(dec.) | B |

TABLE 1-continued

| Ex. No. | Structure | Mol Weight | MS (M + 1) | mp | in vitro |
|---|---|---|---|---|---|
| 1-208 | 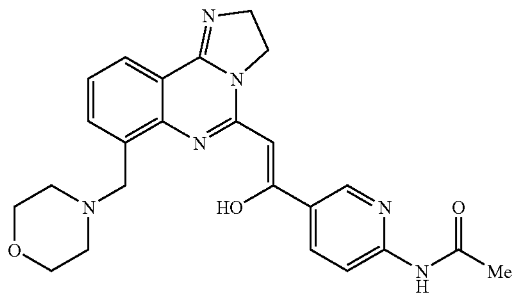 | 446.51 | 447 | 253(dec.) | B |
| 1-209 | 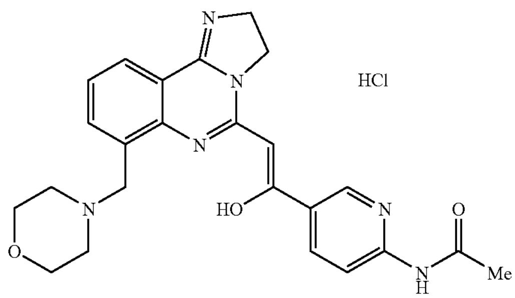 | 482.97 | 447 | >260 | B |
| 1-210 | 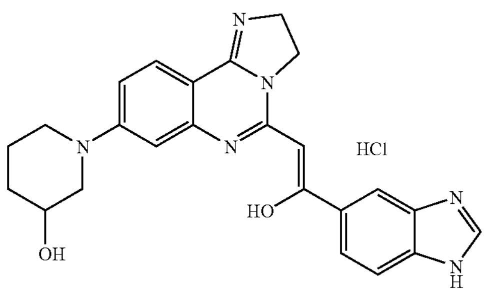 | 464.96 | 429 | >300 | A |

Example 2-1

N-(2,3-Dihydroimidazo[1,2-c]quinazolin-5-yl)nicotinamide (1) 2-(4,5-Dihydro-1H-imidazol-2-yl)aniline 2-Aminobenzonitrile (9.00 g, 76.2 mmol) was added at 0° C. to ethylenediamine (25.5 ml, 381 mmol) in small portions with stirring. After phosphorus pentasulfide (200 mg, 0.900 mmol) was added, the mixture was stirred at 100° C. overnight. After cooling to 0° C., the reaction was diluted with water. The resulting white precipitate was collected by filtration, washed with water and diethyl ether, and dried under reduced pressure to give 2-(4,5-dihydro-1H-imidazol-2-yl)aniline (10.0 g, 81% yield).

(2) 2,3-Dihydroimidazo[1,2-c]quinazolin-5-ylamine hydrobromide

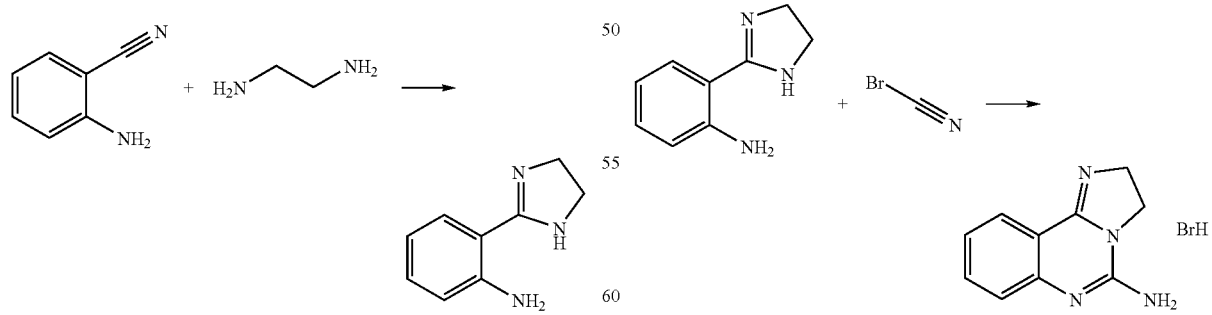

To a suspension of 2-(4,5-dihydro-1H-imidazol-2-yl)aniline (5.00 g, 31.0 mmol) in 85% methanol (60 ml) at 0° C. was added cyanogen bromide (3.61 g, 34.1 mmol) by portions. This mixture was stirred at room temperature overnight. After the mixture was concentrated under reduced pressure, the resulting precipitate was collected by filtration. This pale green solid was washed with water, methanol and diethyl ether successively, and dried under reduced pressure to give 2,3-dihydroimidazo[1,2-c]quinazolin-5-ylamine hydrobromide (4.94 g, 60% yield).

(3) N-(2,3-Dihydroimidazo[1,2-c]quinazolin-5-yl)nicotinamide

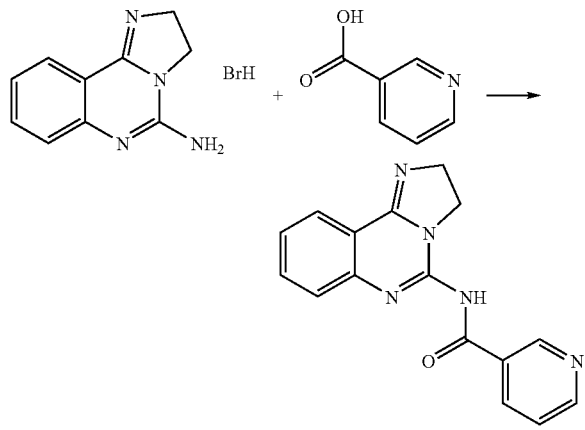

To a suspension of 2,3-dihydroimidazo[1,2-c]quinazolin-5-ylamine hydrobromide (500 mg, 1.87 mmol) and nicotinic acid (346 mg, 2.81 mmol) in N,N -dimethylformamide (25 ml) at room temperature was added benzotriazole-1-yl-oxy-tris-pyrrolidino -phosphonium hexafluorophosphate (1.46 g, 2.81 mmol) followed by N,N-diisopropylethylamine (1.30 ml, 7.49 mmol). The mixture was heated at 80° C. for 4 hours. After cooling to room temperature, the mixture was quenched with aqueous saturated NaHCO₃ solution. The resulting precipitate was collected by filtration, washed with water and diethyl ether, and dried under reduced pressure to give N-(2, 3-dihydroimidazo[1,2-c]quinazolin-5-yl)nicotinamide (450 mg, 83% yield).

Melting point: 238-239° C. (decomposition)
Mass spectrometry: 292
In vitro PI3K-β inhibitory activity: B
In vitro PI3K-γ inhibitory activity: A
¹H-NMR (300 MHz, DMSO-d₆): δ 4.00-4.11 (2H, m), 4.11-4.21 (2H, m), 7.29 (1H, ddd, J=3.0, 5.3, 7.9 Hz), 7.52 (1H, dd, J=4.9, 7.9 Hz), 7.57-7.66 (2H, m), 7.89 (1H, d, J=7.9 Hz), 8.42-8.48 (1H, m), 8-73 (1H, dd, J=1.9, 4.9 Hz), 9.32 (1H, d, J=1.1 Hz), 12.36 (1H, s).

Example 2-2

N-(2,3-Dihydroimidazo[1,2-c]quinazolin-5-yl)nicotinamide hydrochloride

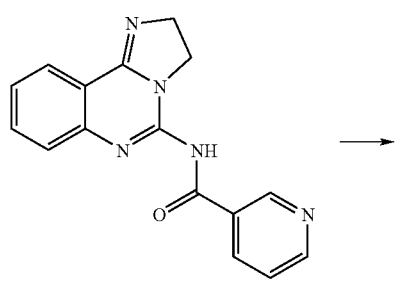

→

-continued

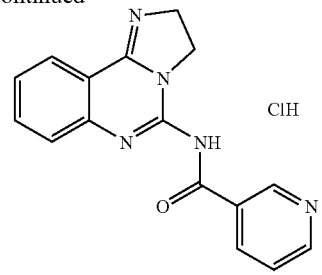

To a suspension of N-(2,3-dihydroimidazo[1,2-c]quinazolin-5-yl)nicotinamide (150 mg, 0.515 mmol) in tetrahydrofuran (4 ml) at 0° C. was added a 4N solution of hydrochloric acid in 1,4-dioxane (2 ml, 8 mmol). The mixture was stirred at room temperature for 1 h, and concentrated under reduced pressure. The resulting residue was triturated with diethyl ether. The resulting precipitate was collected by filtration, washed with ethyl ether, and dried under reduced pressure to give N-(2,3-dihydroimidazo[1,2-c]quinazolin-5-yl)nicotinamide hydrochloride (192 mg, quantitative).

Melting point: 289° C. (decomposition)
Mass spectrometry: 292
In vitro PI3K-β inhibitory activity: B
In vitro PI3K-γ inhibitory activity: A
¹H-NMR (300 MHz, DMSO-d₆): δ 4.18-4.30 (2H, m), 4.54-4.65 (2H, m), 7.56-7.65 (1H, m), 7.88 (1H, dd, J=4.9, 7.9 Hz), 7.97-8.10 (2H, m), 8.64 (1H, d, J=7.9 Hz), 8.80 (1H, d, J=7.9 Hz), 8.95 (1H, dd, J=1.5, 5.3 Hz), 9.43 (1H, d, J=1.1 Hz), 12.7-13.3 (1H, br).

Example 2-3

6-(Acetamido)-N-[8-(morpholin-4-yl)-2,3-dihydroimidazo[1,2-c]quinazolin-5-yl]nicotinamide (1) 4-(Morpholin-4-yl)-2-nitrobenzonitrile

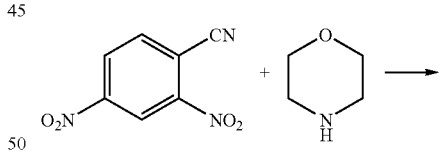

A mixture of 2,4-dinitrobenzonitrile 4.20 g (21.75 mmol) and morpholine 5.7 mL (66.0 mmol) in N,N-dimethylformamide 20 mL was stirred at room temperature for 20 hours. The reaction mixture was poured into water. The precipitate was collected and washed with water to give the title compound 4.20 g as orange solid. Yield 74.5%.

(2) 2-Amino-4-(morpholin-4-yl)benzonitrile

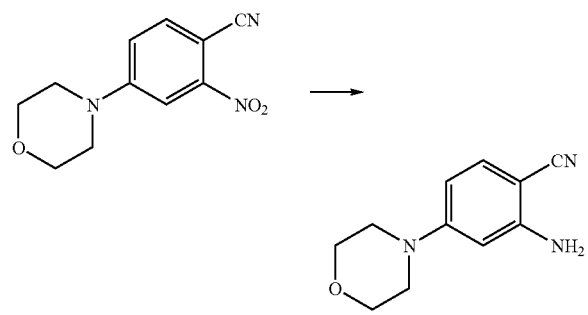

To a cooled mixture of tin(II) chloride dihydrate 12.8 g (56.7 mmol) in conc. HCl mL with ice bath was added 4-(morpholin-4-yl)-2-nitrobenzonitrile 4.20 g (16.09 mmol) and stirred at room temperature for 2 hours. The reaction mixture was poured into diluted NaOH solution and extracted into ethyl acetate. The organic layer was washed with water and brine, dried over MgSO₄ and the solvent was evaporated. The crude product was washed with diethyl ether to give the title compound 3.13 g as off-white solid. Yield 95.0%.

(3) [2-(4,5-dihydro-1H-imidazol-2-yl)-5-(morpholin-4-yl)phenyl]amine

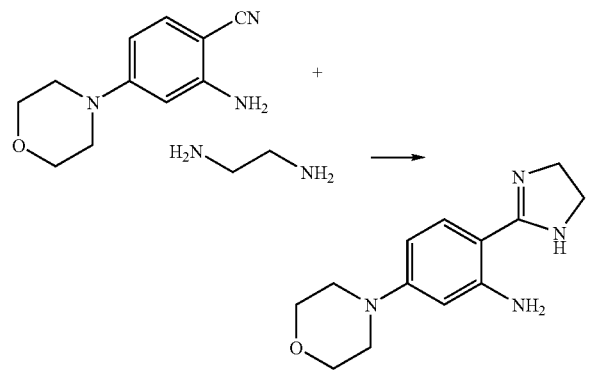

To a solution of 2-amino-4-(morpholin-4-yl)benzonitrile 3.65 g (18.0 mmol) in ethylenediamine 20mL was added phosphorus pentasulfide 4.00 mg (0.018 mmol) and stirred at 140° C. for 16 hours. After cooling to room temperature, the solvent was evaporated. The residue was washed with water and diethyl ether to give the title compound 3.70 g as off-white solid. Yield 83.5%.

(4) 8-(Morpholin-4-yl)-2,3-dihydroimidazo[1,2-c]quinazolin-5-amine hydrobromide

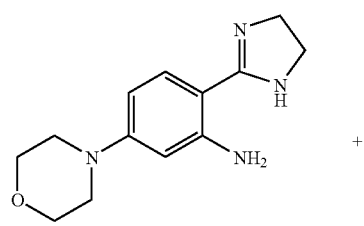

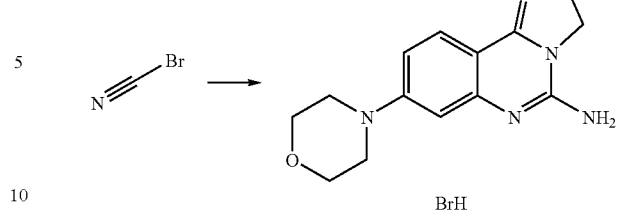

To a suspension of [2-(4,5-dihydro-1H-imidazol-2-yl)-5-(morpholin-4-yl)phenyl]amine 3.60 g (14.6 mmol) in 2-propanol 20 mL was added cyanogen bromide 2.32 g (21.9 mmol) portionwise at 0° C. and stirred at 100° C. for 2 hours. After cooling to room temperature, the precipitate was collected and washed with diethyl ether to give the title compound 1.20 g as yellow solid. Yield 77.5%.

(5) 6-(Acetamido)nicotinic acid

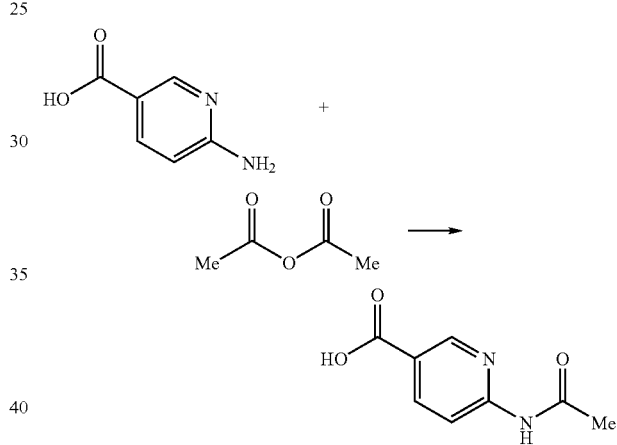

A mixture of 6-aminonicotinic acid 5.00 g (36.5 mmol) and acetic anhydride 3.80mL (40.2 mmol) in pyridine 30 mL was stirred at 140° C. for 24 hours. To the reaction mixture was added ethyl acetate and acidified with diluted HCl solution to pH 2. The organic layer was washed with water and brine, dried over MgSO₄, filtrated and the solvent was evaporated. The residue was washed with diisopropyl ether to give the title compound 1.70 g as off-white solid. Yield 26%.

(6) 6-(Acetamido)-N-[8-(morpholin-4-yl)-2,3-dihydroimidazo[1,2-c]quinazolin-5-yl]nicotinamide

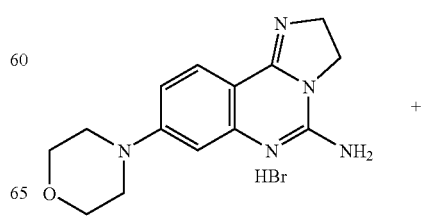

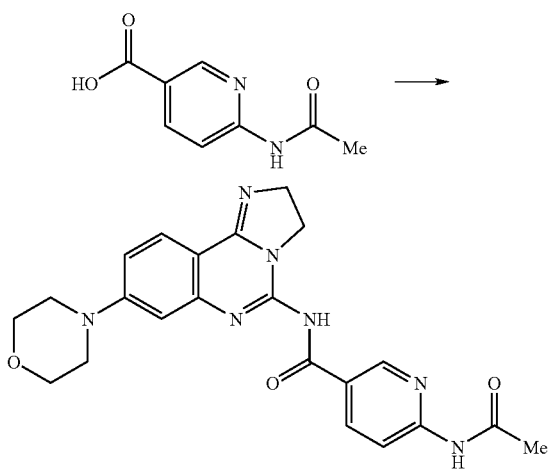

To a mixture of 8-(morpholin-4-yl)-2,3-dihydroimidazo[1,2-c]quinazolin-5-amine hydrobromide 105.7 mg (0.30 mmol), 6-(acetamido)nicotinic acid 81.1 mg (0.45 mmol) and N,N-diisopropylethylamine 0.26 mL (1.50 mmol) in N,N-dimethylformamide 2 mL was added PyBOP((1H-1,2,3-benzotriazol-1-yloxy)(tripyrrolidin-1-yl)phosphonium hexafluorophosphate) 234.2 mg (0.45 mmol) and stirred at 90° C. for 16 hours. After cooling to room temperature, saturated NaHCO₃ solution was added. The precipitate was collected and washed with water, methanol, and diethyl ether to give the title compound 41.1 mg as yellow solid. Yield 31.6%.

Melting point: 228° C.

Mass spectrometry: 434

In vitro PI3K-β inhibitory activity: C

In vitro PI3K-γ inhibitory activity: A

H-NMR (500 MHz, DMSO-d₆) δ: 3.22-3.30 (m 4H), 3.74 (s 3H), 3.86 (m 2H), 3.97 (m 2H), 6.77 (br s 1H), 7.60 (m 1H), 8.07 (m 1H), 8.32 (m 1H), 8.95 (br s 1H), 10.60 (s 1H)

Example 2-4

6-(Acetamido)-N-[8-(morpholin-4-yl)-2,3-dihydroimidazo[1,2-c]quinazolin-5-yl]nicotinamide hydrochloride

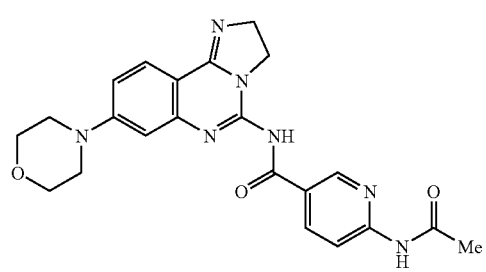

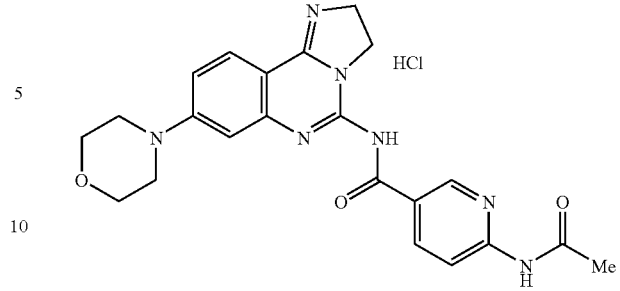

To a mixture of 6-(acetamido)-N-[8-(morpholin-4-yl)-2,3-dihydroimidazo[1,2-c]-quinazolin-5-yl]nicotinamide (Example 2-3) 20.0 mg (0.046 mmol) in 1,4-dioxane 1.5 mL was added 4N HCl in 1,4-dioxane 0.5 mL and stirred at room temperature for 40 minutes. The precipitate was collected and washed with diethyl ether to give the title compound 17.0 mg as yellow solid. Yield 78%.

Melting point: 237° C.

Mass spectrometry: 434

In vitro PI3K-β inhibitory activity: B

In vitro PI3K-γ inhibitory activity: A

H-NMR (500 MHz, DMSO-d₆) δ: 3.41-3.76 (m 7H), 3.86 (m 2H), 4.10 (m 2H), 7.20 (m 1H), 7.39 (m 1H), 8.19 (in 1H), 8.45 (m 1H), 9.09 (br s 1H), 10.86 (s 1H)

Example 2-5

N-(8-Hydroxy-2,3-dihydroimidazo[1,2-c]quinazolin-5-yl)nicotinamide

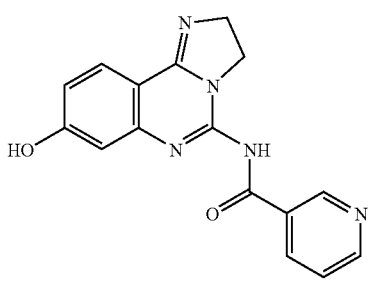

A suspension of N-(8-methoxy-2,3-dihydroimidazo[1,2-c]quinazolin-5-yl)nicotinamide (example 2-22) 3.50 g (10.9 mmol) and sodium sulfide 4.25 g (54.5 mmol) in 1-methyl-2-pyrrolidinone 10 mL was heated to 160° C. for 4 hours (LC-MS indicated complete consumption of the starting material). The mixture was cooled to room temperature and volatile side products were evaporated. The mixture was partitioned between chloroform and 0.5N NaOH solution. The aqueous layer was neutralized and the formed precipitate was collected to give the title compound 2.34 g as off-white solid. Yield 69.9%.

Melting point: 289° C.

Mass spectrometry: 308

In vitro PI3K-β inhibitory activity: C

In vitro PI3K-γ inhibitory activity: B

H-NMR (500 MHz, DMSO-d₆) δ: 4.01 (m 2H), 4.15 (m 2H), 6.75 (dd 1H J=8 Hz, 2 Hz), 6.91 (s 1H), 7.52 (dd 1H J=8

Hz, 5 Hz), 7.75 (d 1H J=8 Hz), 8.44 (d 1H J=8 Hz), 8.73 (dd 1H J=5 Hz, 2 Hz), 9.31 (s 1H), 10.61 (br s 1H), 12.24 (br s 1H)

Example 2-6

N-{8-[2-(1-pyrrolyl)ethoxy]-2,3-dihydroimidazo[1,2-c]quinazolin-5-yl}nicotinamide

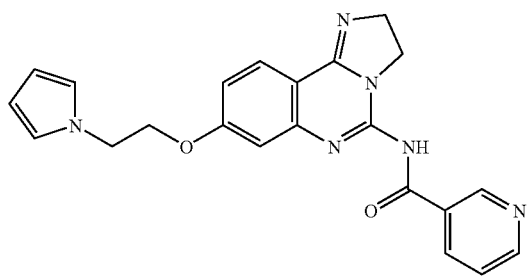

The suspension of N-(8-Hydroxy-2,3-dihydroimidazo[1,2-c]quinazolin-5-yl)nicotinamide (example 2-1) 70.0 mg (0.23 mmol), N-(2-bromoethyl)pyrrole 47.6 mg (0.27 mmol) and potassium carbonate 126 mg (0.91 mmol) in N,N-dimethylformamide 5 mL was heated in a sealed tube to 120° C. for 3 hours. The reaction mixture was concentrated and partitioned between dichloromethane and water. The organic layer was washed with 0.1N NaOH solution and brine, dried over $Na_2SO_4$ and the solvent was evaporated to give the title compound 49.0 mg as off-white solid. Yield 54%.

Melting point: 209° C.
Mass spectrometry: 401
In vitro PI3K-β inhibitory activity: B
In vitro PI3K-γ inhibitory activity: B
H-NMR (500 MHz, DMSO-$d_6$) δ: 4.00 (m 2H), 4.12 (m 2H), 4.30 (s 4H), 6.00 (m 2H), 6.84 (m 2H), 6.85 (dd 1H J=6 Hz, 2 Hz), 7.27 (d 1H J=2 Hz), 7.52 (dd 1H J=6 Hz), 7.76 (d 1H J=8 Hz), 8.44 (dd 1H J=8 Hz, 2 Hz), 8.72 (dd 0.1H J=5 Hz, 2 Hz), 9.31 (s 1H), 12.32 (s 1H)

In a similar method according to the Example 2-1 to 2-6 above, the compounds in Example 2-7 to 2-368 were synthesized.

TABLE 2

| Ex. No. | Structure | MW | MASS | mp/° C. | in vitro PI3K-gamma |
|---|---|---|---|---|---|
| 2-7 | 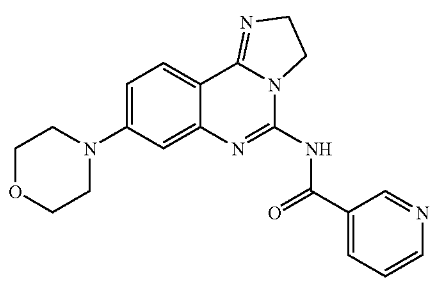 | 376.42 | 377 | 243 | B |
| 2-8 | 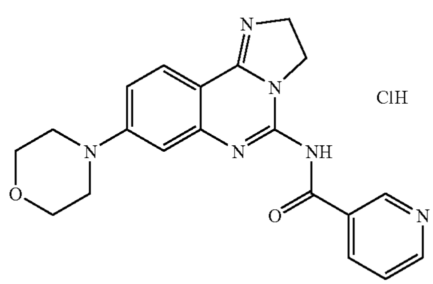 | 412.88 | 377 | 283 | A |
| 2-9 | 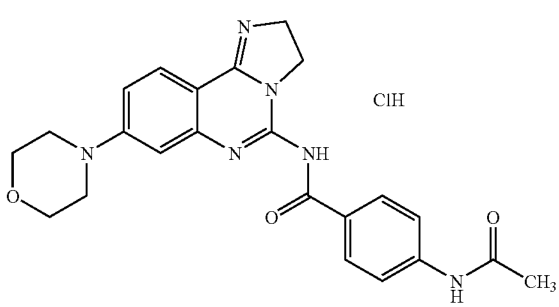 | 468.95 | 433 | 249 | B |

TABLE 2-continued

| Ex. No. | Structure | MW | MASS | mp/° C. | in vitro PI3K-gamma |
|---|---|---|---|---|---|
| 2-10 | 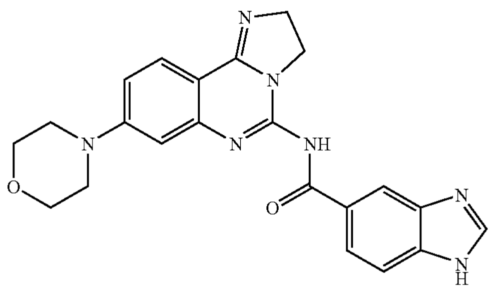 | 415.46 | 416 | 250 (dec.) | B |
| 2-11 | ClH | 451.92 | 416 | 294 (dec.) | A |
| 2-12 | 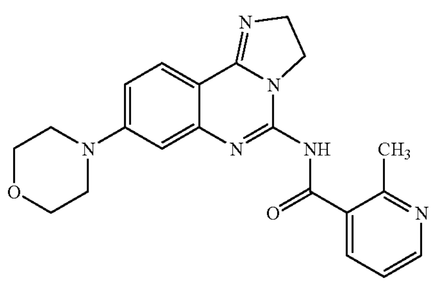 | 390.45 | 391 | 199 (dec.) | B |
| 2-13 | 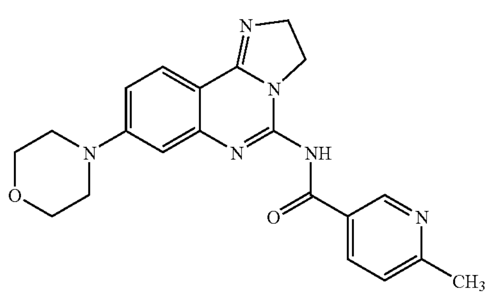 | 390.45 | 391 | 209 | A |
| 2-14 | ClH | 426.91 | 391 | 267 (dec.) | A |

TABLE 2-continued

| Ex. No. | Structure | MW | MASS | mp/° C. | in vitro PI3K-gamma |
|---|---|---|---|---|---|
| 2-15 | 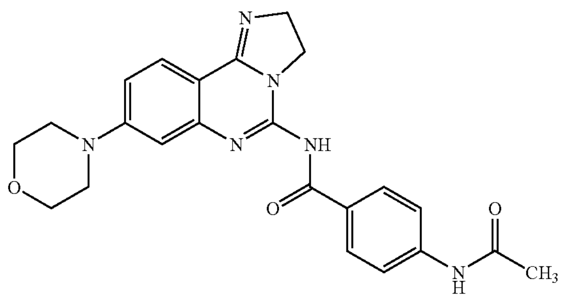 | 432.49 | 433 | 227 | B |
| 2-16 | 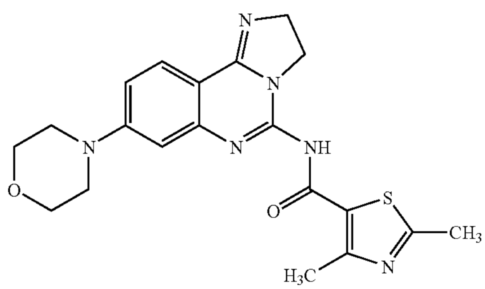 | 410.50 | 411 | 233 (dec.) | B |
| 2-17 | 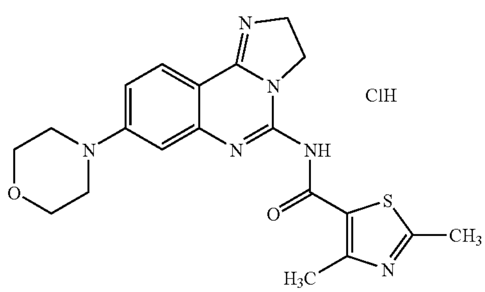 | 446.96 | 411 | 255 (dec.) | A |
| 2-18 | 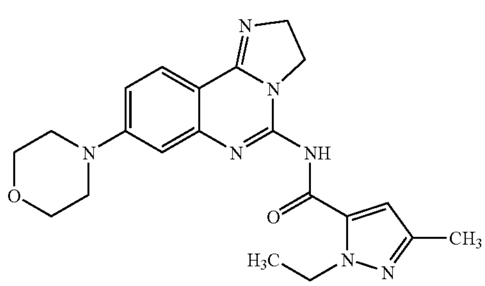 | 407.48 | 408 | 232 | B |
| 2-19 | 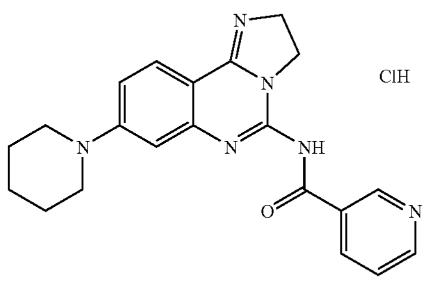 | 410.91 | 376 | >300 | B |

TABLE 2-continued

| Ex. No. | Structure | MW | MASS | mp/° C. | in vitro PI3K-gamma |
|---|---|---|---|---|---|
| 2-20 | 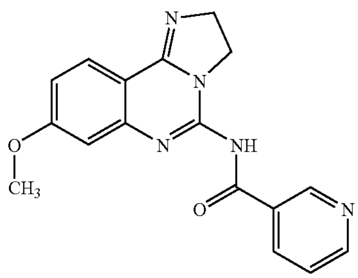 | 321.34 | 322 | 281 (dec.) | B |
| 2-21 | 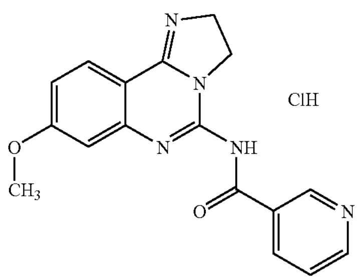 | 357.80 | 322 | 292 (dec.) | B |
| 2-22 | 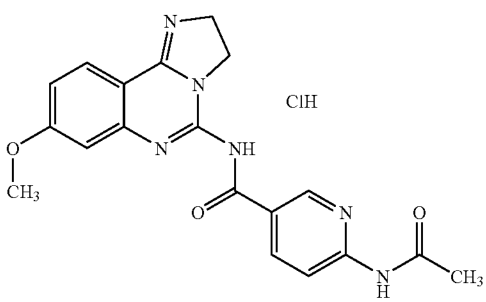 | 414.85 | 379 | 198-205 (dec.) | B |
| 2-23 | 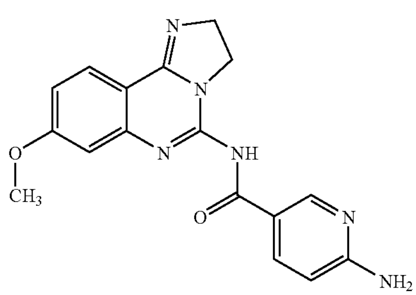 | 336.36 | 337 | 279-282 | A |
| 2-24 | 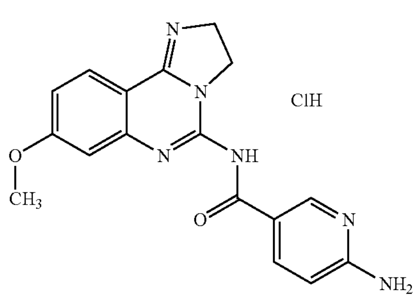 | 372.82 | 337 | 273 (dec.) | A |

TABLE 2-continued

| Ex. No. | Structure | MW | MASS | mp/° C. | in vitro PI3K-gamma |
|---|---|---|---|---|---|
| 2-25 | 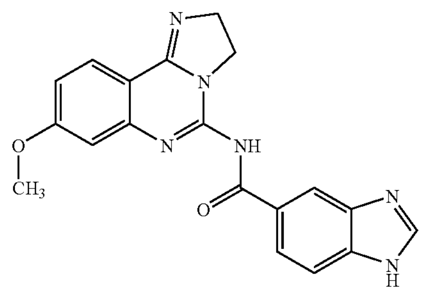 | 360.38 | 361 | 186 | A |
| 2-26 | ClH | 396.84 | 361 | 233 | A |
| 2-27 | 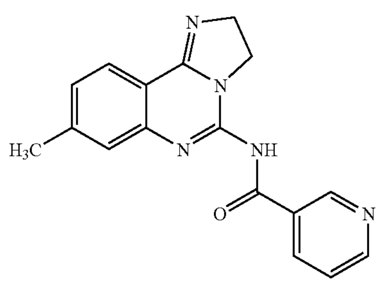 | 305.34 | 306 | 207 | A |
| 2-28 | ClH | 341.80 | 306 | 315 | A |
| 2-29 | 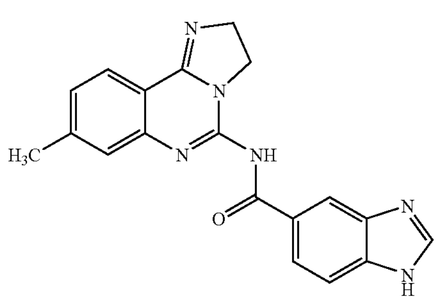 | 344.38 | 345 | 190 | A |

TABLE 2-continued

| Ex. No. | Structure | MW | MASS | mp/° C. | in vitro PI3K-gamma |
|---|---|---|---|---|---|
| 2-30 | 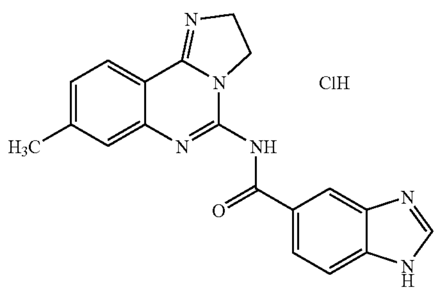 | 380.84 | 345 | 295 | B |
| 2-31 | 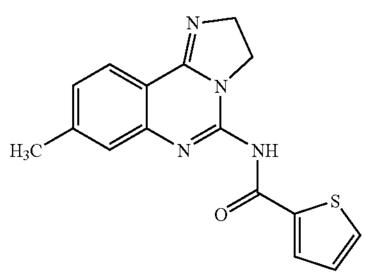 | 310.38 | 311 | 182 | B |
| 2-32 | 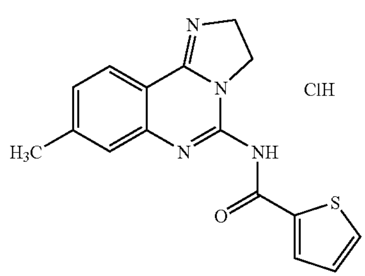 | 346.84 | 311 | 276 | B |
| 2-33 | 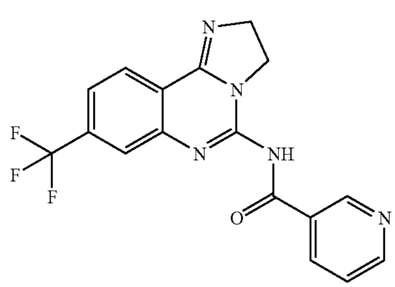 | 359.31 | 360 | 229 | B |
| 2-34 | 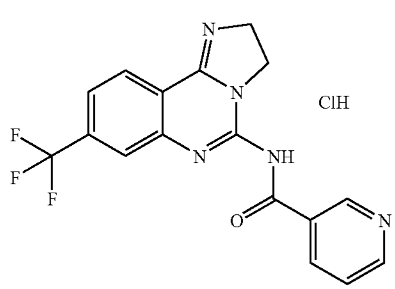 | 395.77 | 360 | 275 | A |

TABLE 2-continued
| Ex. No. | Structure | MW | MASS | mp/° C. | in vitro PI3K-gamma |
|---|---|---|---|---|---|
| 2-35 | 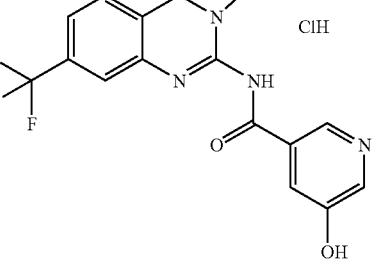 | 411.77 | 375 | 237 (dec.) | A |
| 2-36 | 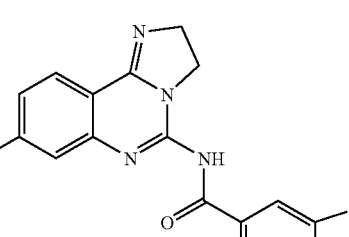 | 398.35 | 399 | >300 | B |
| 2-37 | 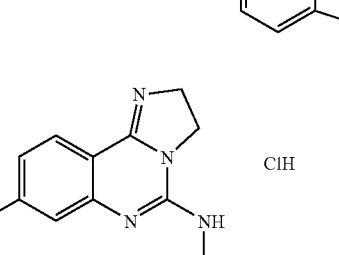 | 434.81 | 399 | 288 | A |
| 2-38 | 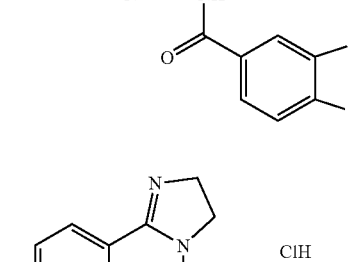 | 362.22 | 327 | 308 | B |
| 2-39 | 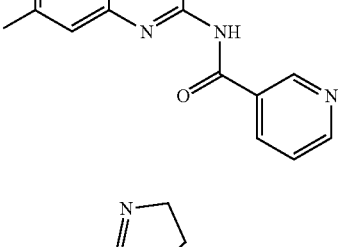 | 364.80 | 366 | 288 | A |

TABLE 2-continued

| Ex. No. | Structure | MW | MASS | mp/° C. | in vitro PI3K-gamma |
|---|---|---|---|---|---|
| 2-40 | 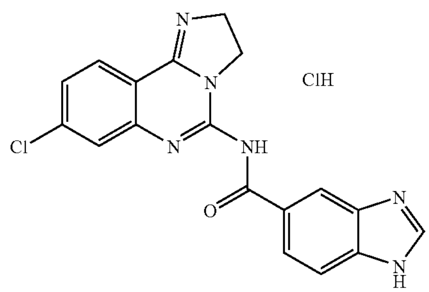 | 401.26 | 366 | 270 | A |
| 2-41 | 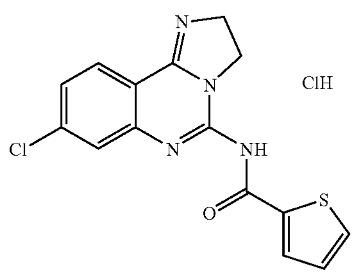 | 367.26 | 332 | 328 | B |
| 2-42 | 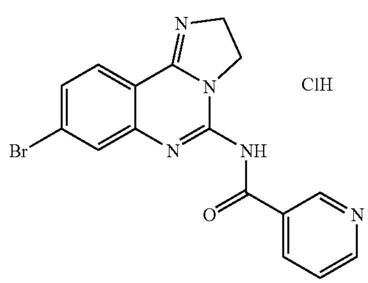 | 406.67 | 372, 370 | 243 | A |
| 2-43 | 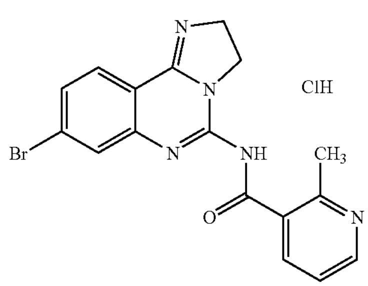 | 420.70 | 386. 384 | 252 (dec.) | B |
| 2-44 | 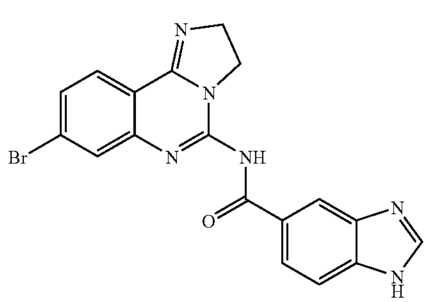 | 409.25 | 411. 409 | 262 | B |

TABLE 2-continued

| Ex. No. | Structure | MW | MASS | mp/° C. | in vitro PI3K-gamma |
|---|---|---|---|---|---|
| 2-45 | 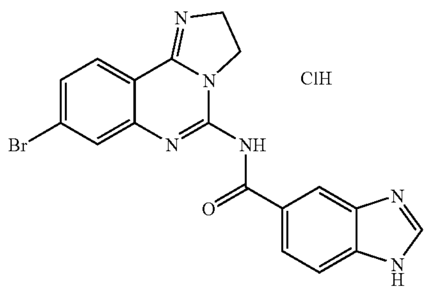 | 445.71 | 411. 409 | 278 | A |
| 2-46 | 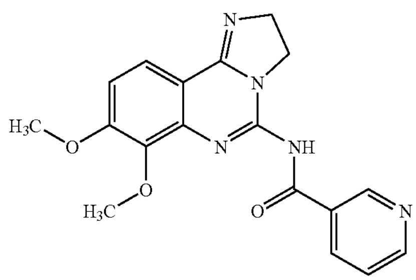 | 351.37 | 352 | 259-260 | A |
| 2-47 | 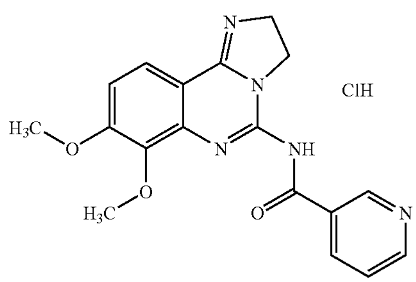 | 387.83 | 352 | 257-257 | A |
| 2-48 | 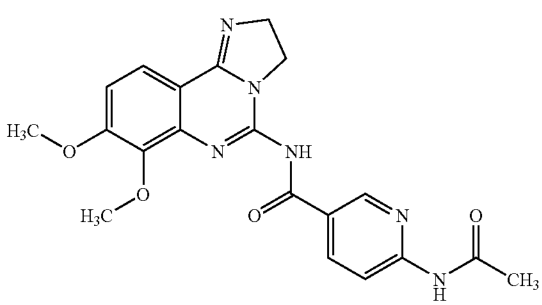 | 408.42 | 409 | 306-307 | A |
| 2-49 | 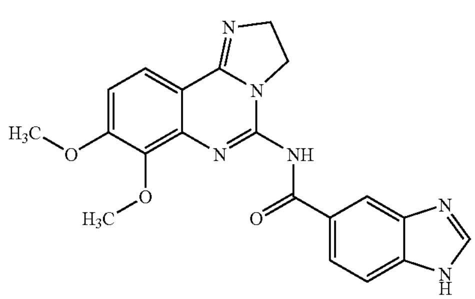 | 390.40 | 391 | 289 (dec.) | A |

TABLE 2-continued
| Ex. No. | Structure | MW | MASS | mp/° C. | in vitro PI3K-gamma |
|---|---|---|---|---|---|
| 2-50 | 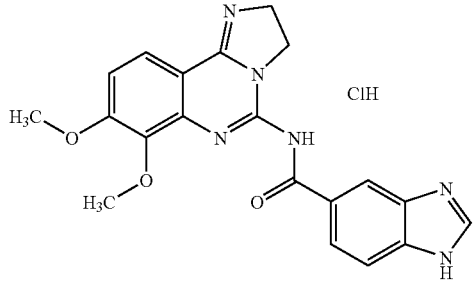 | 426.87 | 391 | 278 (dec.) | A |
| 2-51 | 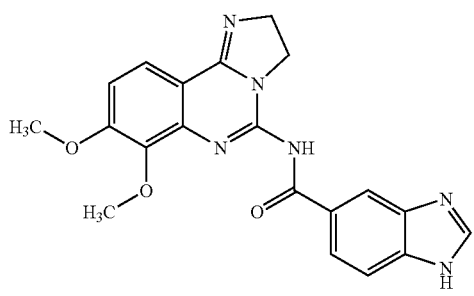 | 391.39 | 392 | 233 (dec.) | A |
| 2-52 | 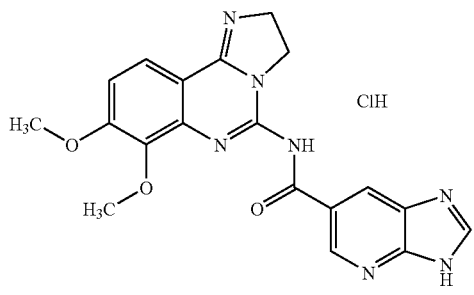 | 427.85 | 392 | 210 (dec.) | A |
| 2-53 | 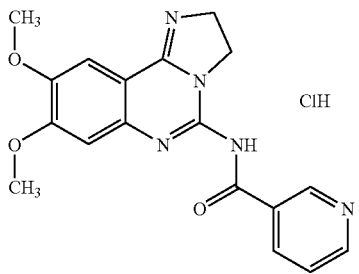 | 387.83 | 352 | 246 | B |
| 2-54 | 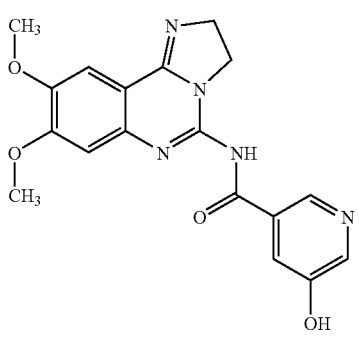 | 367.37 | 367 | 287 (dec.) | A |

TABLE 2-continued
| Ex. No. | Structure | MW | MASS | mp/° C. | in vitro PI3K-gamma |
|---|---|---|---|---|---|
| 2-55 | 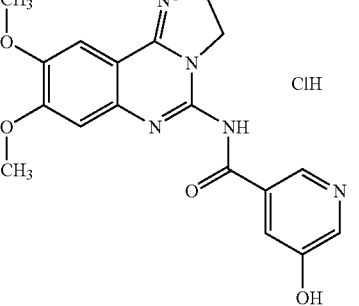 | 403.83 | 367 | 260 (dec.) | A |
| 2-56 | 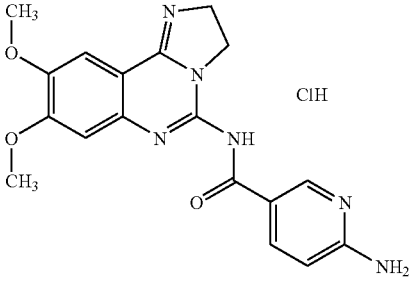 | 402.84 | 367 | 256 | B |
| 2-57 | 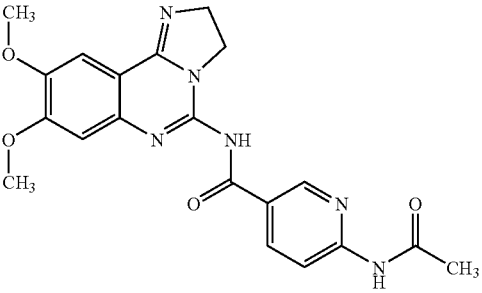 | 408.42 | 409 | 224 | B |
| 2-58 | 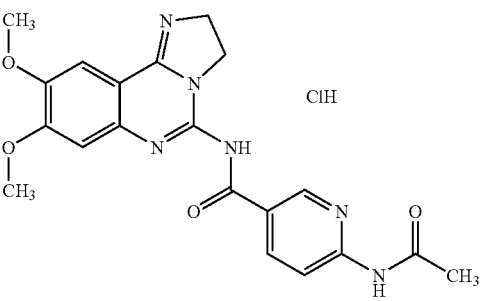 | 444.88 | 409 | 279 | B |
| 2-59 | 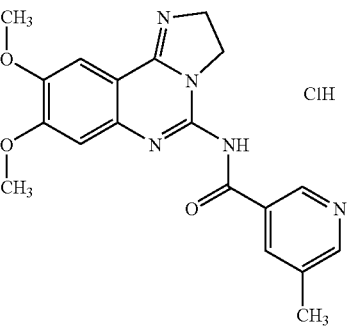 | 401.86 | 366 | 257 (dec.) | B |

TABLE 2-continued

| Ex. No. | Structure | MW | MASS | mp/° C. | in vitro PI3K-gamma |
|---|---|---|---|---|---|
| 2-60 | 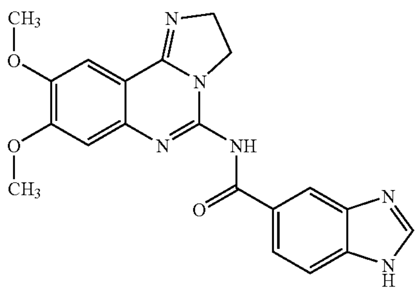 | 390.40 | 391 | 246 | A |
| 2-61 | 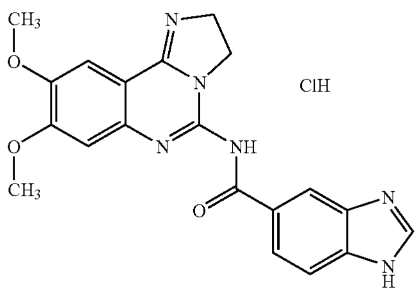 | 426.87 | 391 | 276 | A |
| 2-62 | 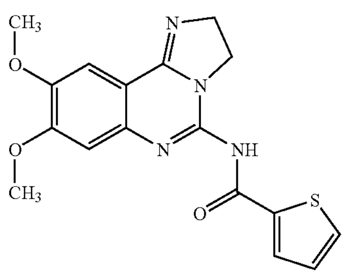 | 356.41 | 357 | 248 | B |
| 2-63 | 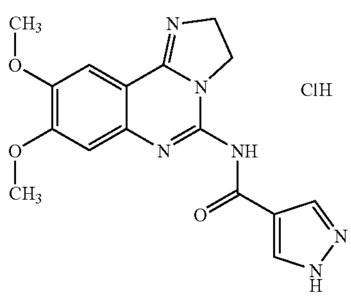 | 376.81 | 340 | 270 (dec.) | B |
| 2-64 | 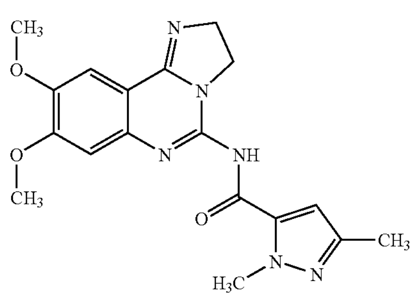 | 368.40 | 368 | 236-237 | B |

TABLE 2-continued

| Ex. No. | Structure | MW | MASS | mp/° C. | in vitro PI3K-gamma |
|---|---|---|---|---|---|
| 2-65 | 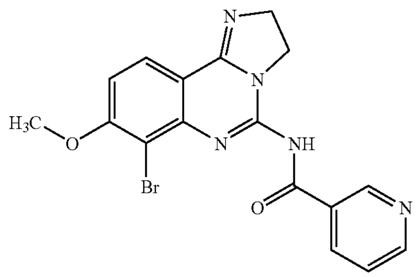 | 400.24 | 402, 400 | 264 | A |
| 2-66 | 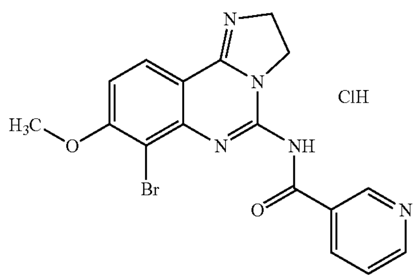 | 436.70 | 402, 400 | 298 | A |
| 2-67 | 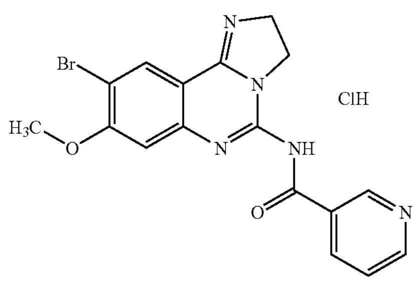 | 436.70 | 402, 400 | 289 (dec.) | B |
| 2-68 | 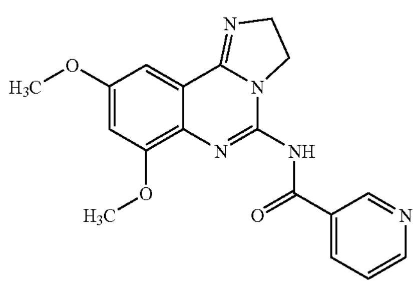 | 351.37 | 352 | 228 (dec.) | A |
| 2-69 | 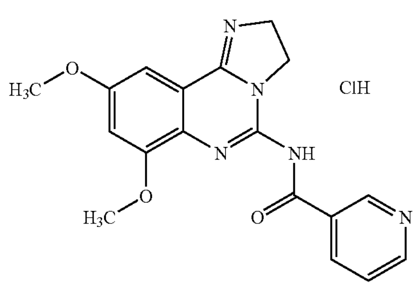 | 387.83 | 352 | 275 (dec.) | B |

TABLE 2-continued

| Ex. No. | Structure | MW | MASS | mp/° C. | in vitro PI3K-gamma |
|---|---|---|---|---|---|
| 2-70 | 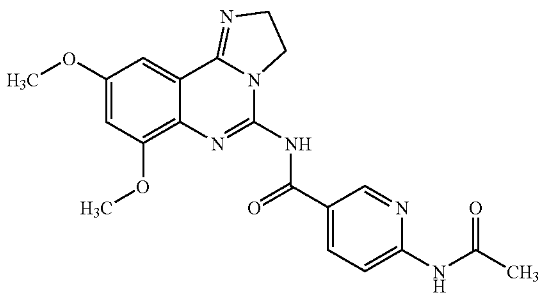 | 408.42 | 408 | 286 (dec.) | B |
| 2-71 | ClH | 444.88 | 408 | 270 (dec.) | B |
| 2-72 | 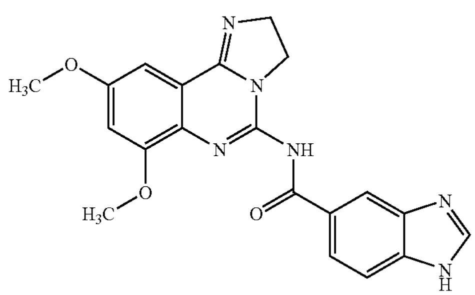 | 390.40 | 391 | 210 (dec.) | A |
| 2-73 | ClH | 426.87 | 391 | 289 (dec.) | A |
| 2-74 | ClH | 420.70 | 386, 384 | 220 | A |

TABLE 2-continued

| Ex. No. | Structure | MW | MASS | mp/° C. | in vitro PI3K-gamma |
|---|---|---|---|---|---|
| 2-75 | 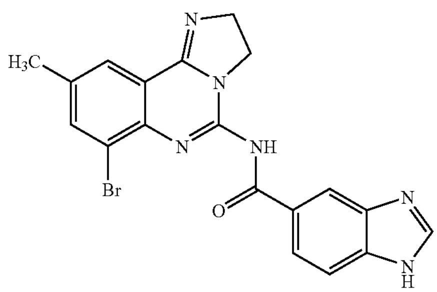 | 423.28 | 425, 423 | >290 | B |
| 2-76 | 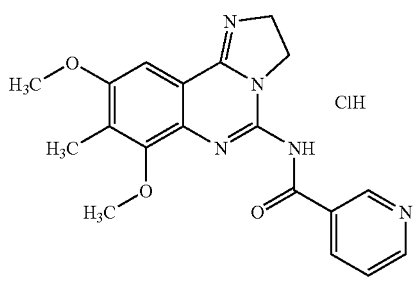 | 401.86 | 366 | 235 (dec.) | B |
| 2-77 | 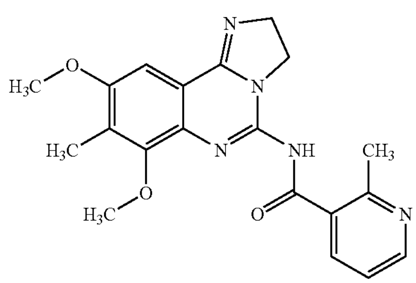 | 379.42 | 379 | 210 (dec.) | A |
| 2-78 | 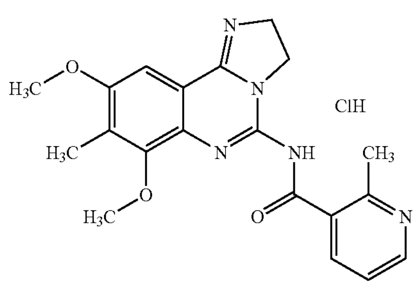 | 415.88 | 379 | 230 (dec.) | A |
| 2-79 | 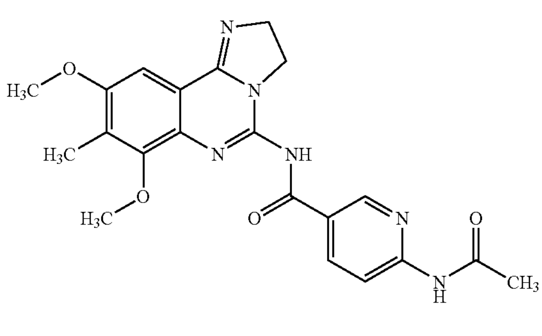 | 422.45 | 422 | >310 | B |

TABLE 2-continued

| Ex. No. | Structure | MW | MASS | mp/° C. | in vitro PI3K-gamma |
|---|---|---|---|---|---|
| 2-80 | 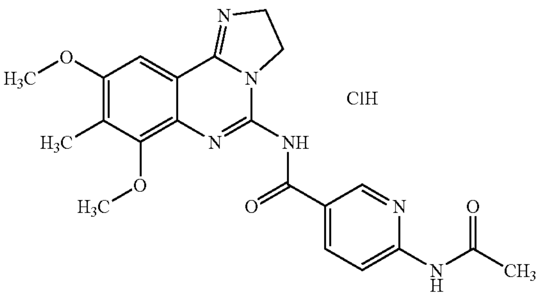 | 458.91 | 422 | 305 (dec.) | A |
| 2-81 | 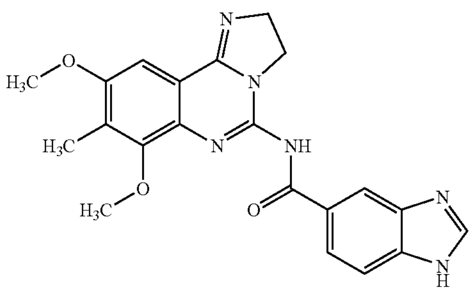 | 404.43 | 405 | 202 | B |
| 2-82 | 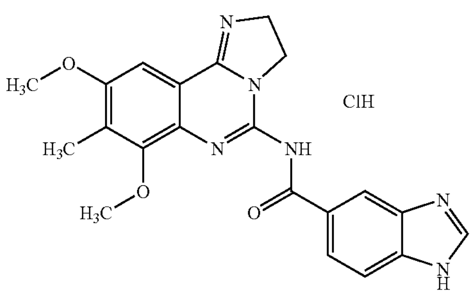 | 440.89 | 405 | 280 (dec.) | B |
| 2-83 | 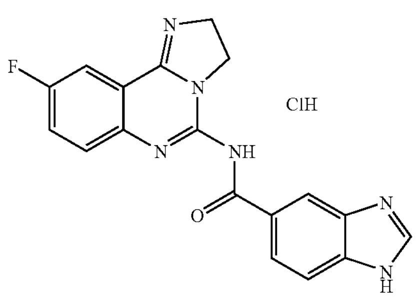 | 384.80 | 349 | >300 | B |
| 2-84 | 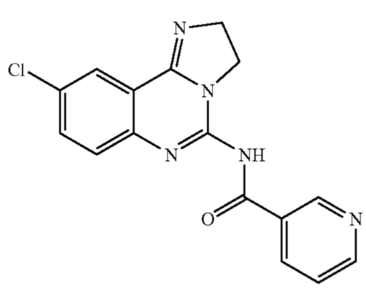 | 325.76 | 326 | 210 | B |

TABLE 2-continued

| Ex. No. | Structure | MW | MASS | mp/° C. | in vitro PI3K-gamma |
|---|---|---|---|---|---|
| 2-85 | 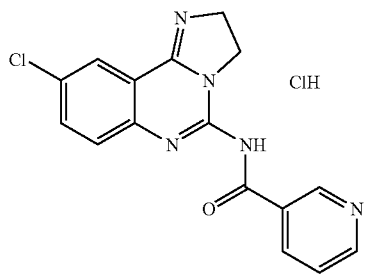 | 362.22 | 327 | 309 | B |
| 2-86 | 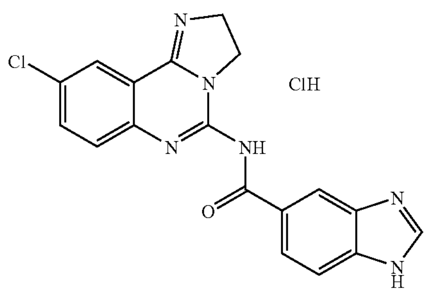 | 401.26 | 366 | 305 (dec.) | B |
| 2-87 | 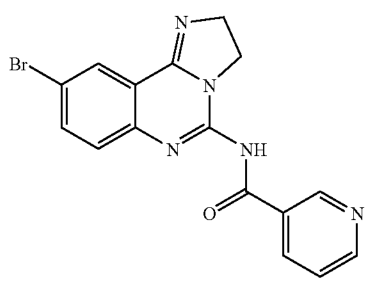 | 370.21 | 372 | 228 | B |
| 2-88 | 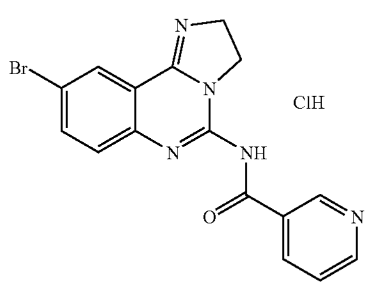 | 406.67 | 372, 370 | 316 | B |
| 2-89 | 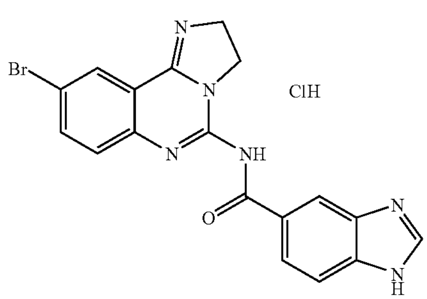 | 455.71 | 411, 409 | 288 | B |

TABLE 2-continued

| Ex. No. | Structure | MW | MASS | mp/° C. | in vitro PI3K-gamma |
|---|---|---|---|---|---|
| 2-90 | 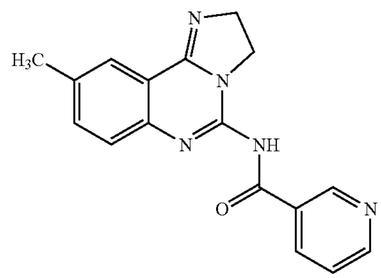 | 305.34 | 306 | 210 | A |
| 2-91 | 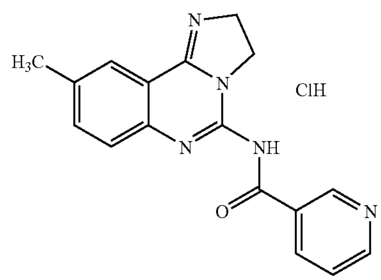 | 341.80 | 306 | >290 | B |
| 2-92 | 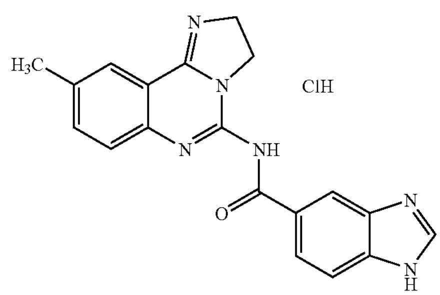 | 380.84 | 345 | >290 | A |
| 2-93 | 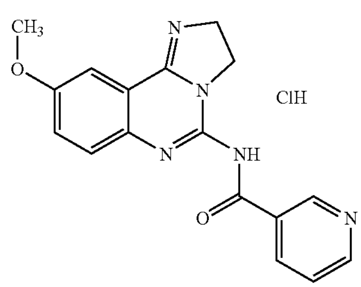 | 357.80 | 322 | >300 | B |
| 2-94 | 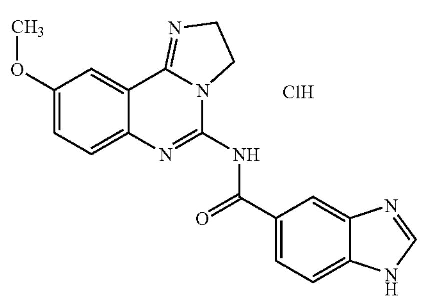 | 396.84 | 361 | 288 | A |

TABLE 2-continued

| Ex. No. | Structure | MW | MASS | mp/° C. | in vitro PI3K-gamma |
|---|---|---|---|---|---|
| 2-95 | 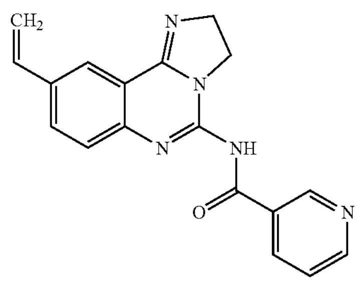 | 317.35 | 318 | 196-198 | B |
| 2-96 | 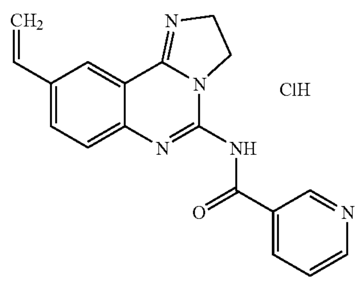 | 353.81 | 318 | 275-277 | B |
| 2-97 | 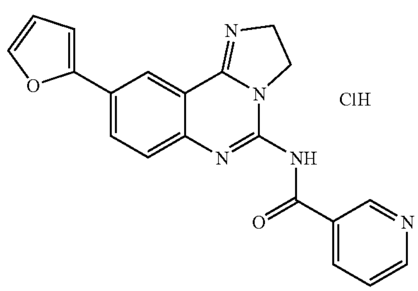 | 393.84 | 358 | 298-299 | B |
| 2-98 | 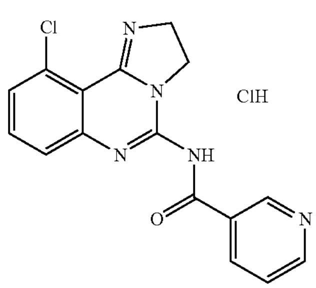 | 362.22 | 327 | 249 | B |
| 2-99 | 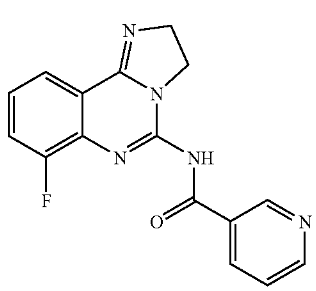 | 309.31 | 310 | 243 | B |

TABLE 2-continued
| Ex. No. | Structure | MW | MASS | mp/° C. | in vitro PI3K-gamma |
|---|---|---|---|---|---|
| 2-100 | 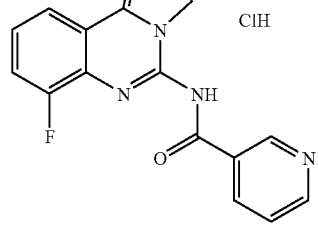 | 345.77 | 310 | 288 | A |
| 2-101 | 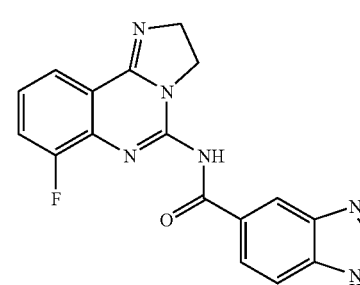 | 348.34 | 349 | >300 | A |
| 2-102 | 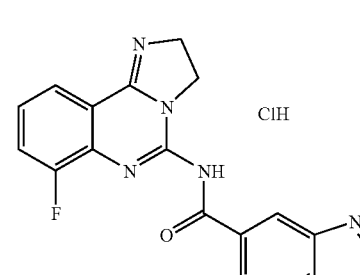 | 384.80 | 349 | >300 | A |
| 2-103 | 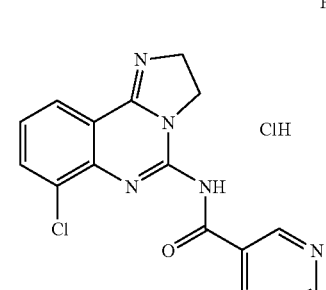 | 362.22 | 326 | >280 | B |
| 2-104 | 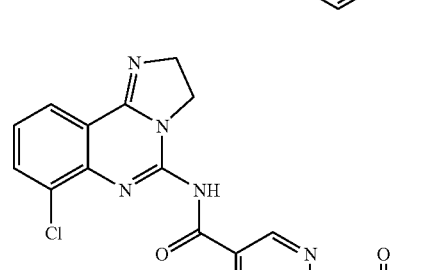 | 382.81 | 383 | >280 | B |

TABLE 2-continued
| Ex. No. | Structure | MW | MASS | mp/° C. | in vitro PI3K-gamma |
|---|---|---|---|---|---|
| 2-105 | 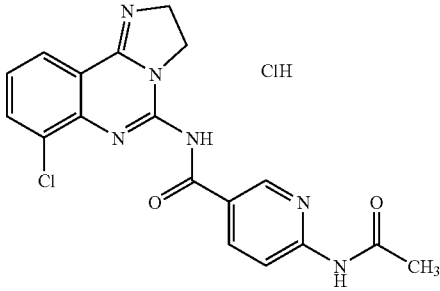 | 419.27 | 383 | >280 | A |
| 2-106 | 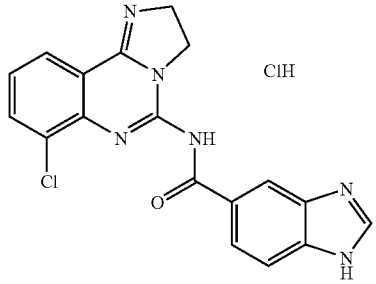 | 401.26 | 365 | >280 | B |
| 2-107 | 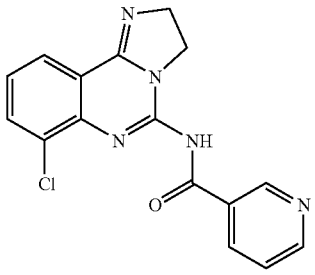 | 305.34 | 306 | 244 | B |
| 2-108 | 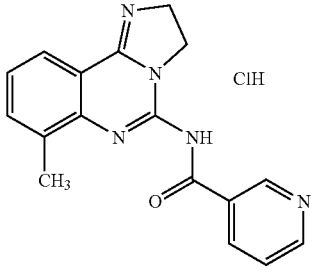 | 341.80 | 306 | >290 | B |
| 2-109 | 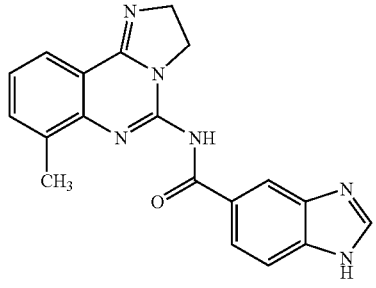 | 344.38 | 345 | >290 | A |

TABLE 2-continued
| Ex. No. | Structure | MW | MASS | mp/° C. | in vitro PI3K-gamma |
|---|---|---|---|---|---|
| 2-110 | 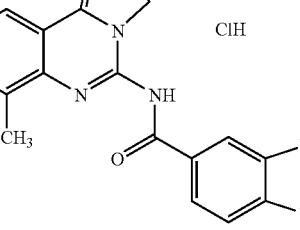 | 380.84 | 345 | >290 | A |
| 2-111 | 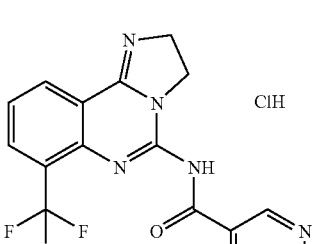 | 395.77 | 360 | 263 | A |
| 2-112 | 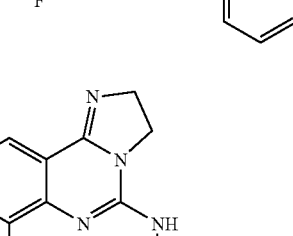 | 398.35 | 399 | 286 | A |
| 2-113 | 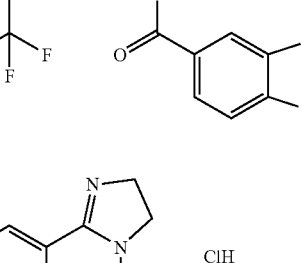 | 434.81 | 399 | 270 | A |
| 2-114 | 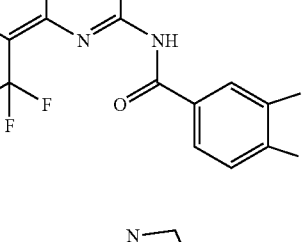 | 321.34 | 322 | 110 | A |

TABLE 2-continued
| Ex. No. | Structure | MW | MASS | mp/° C. | in vitro PI3K-gamma |
|---|---|---|---|---|---|
| 2-115 | 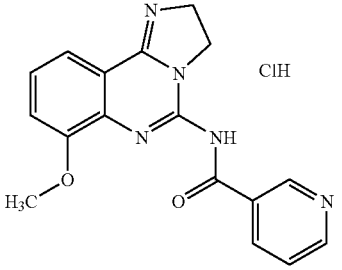 | 357.80 | 322 | 237 (dec.) | A |
| 2-116 | 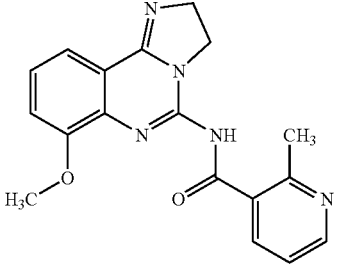 | 335.37 | 335 | 204-205 | B |
| 2-117 | 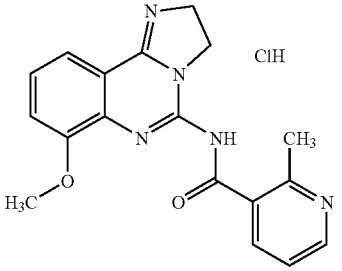 | 371.83 | 335 | 251 (dec.) | A |
| 2-118 | 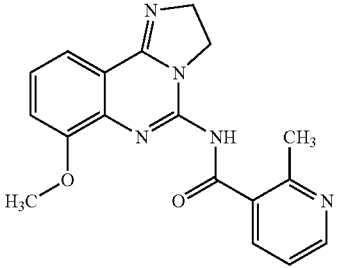 | 355.79 | 355 | 185 (dec) | A |
| 2-119 | 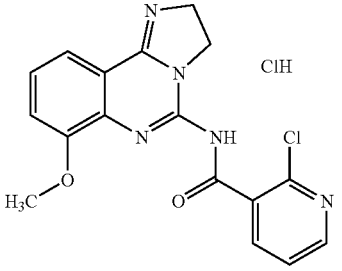 | 392.25 | 355 | 266 (dec.) | A |

TABLE 2-continued
| Ex. No. | Structure | MW | MASS | mp/° C. | in vitro PI3K-gamma |
|---|---|---|---|---|---|
| 2-120 | 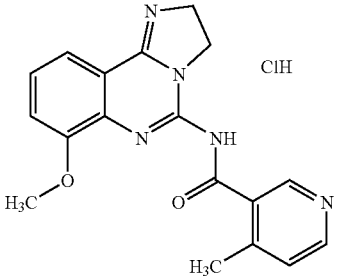 | 371.83 | 335 | 220 (dec.) | A |
| 2-121 | 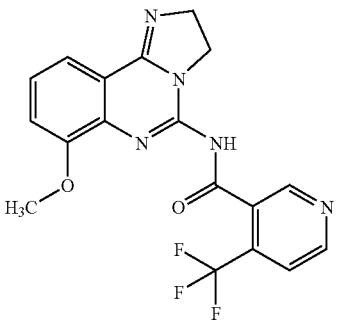 | 389.34 | 389 | 144-145 | B |
| 2-122 | 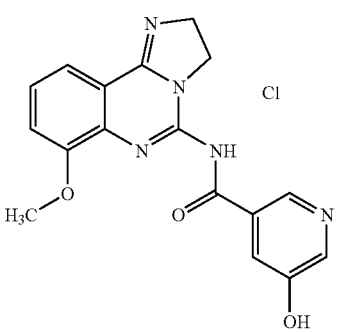 | 373.80 | 338 | 285 (dec.) | A |
| 2-123 | 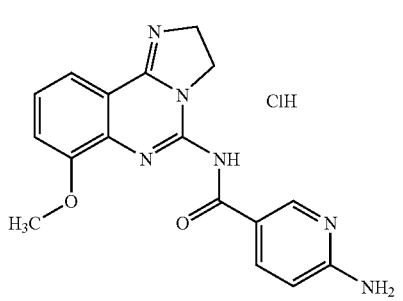 | 372.82 | 337 | 296 | A |
| 2-124 | 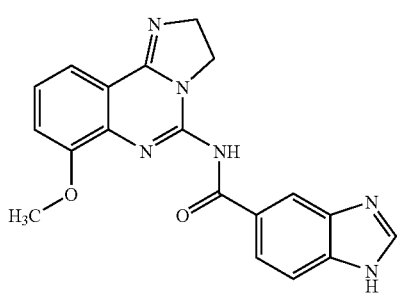 | 360.38 | 361 | 287 | A |

TABLE 2-continued
| Ex. No. | Structure | MW | MASS | mp/° C. | in vitro PI3K-gamma |
|---|---|---|---|---|---|
| 2-125 | 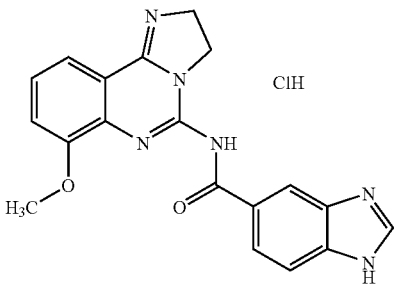 | 396.84 | 361 | 238 | A |
| 2-126 | 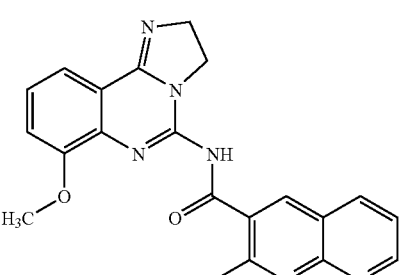 | 386.42 | 386 | 183-184 | A |
| 2-127 | 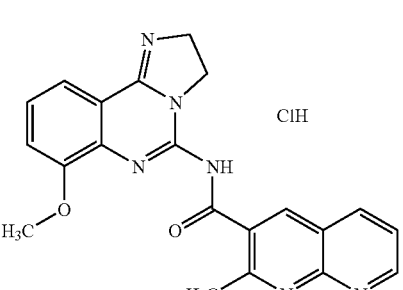 | 422.88 | 386 | 225 (dec.) | A |
| 2-128 | 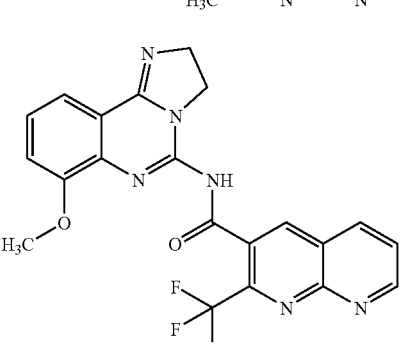 | 440.39 | 440 | 214 (dec.) | A |
| 2-129 | 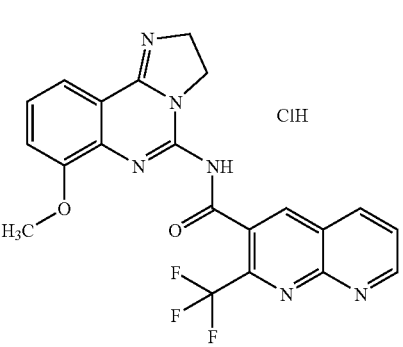 | 476.85 | 440 | 226 (dec.) | A |

TABLE 2-continued

| Ex. No. | Structure | MW | MASS | mp/° C. | in vitro PI3K-gamma |
|---|---|---|---|---|---|
| 2-130 | 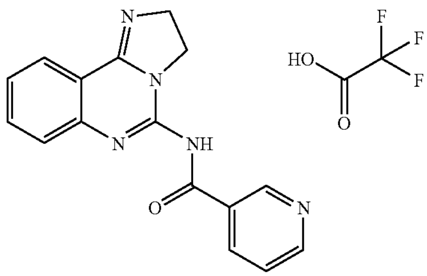 | 405.34 | 292 | 237-239 | A |
| 2-131 | 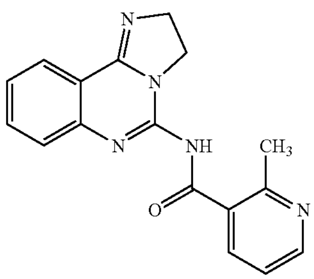 | 305.34 | 306 | 193-194 | B |
| 2-132 | 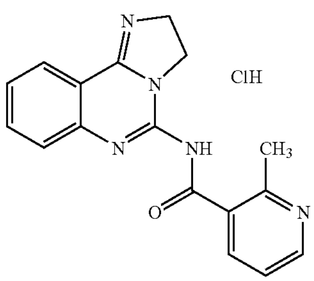 | 341.80 | 306 | 277 (dec.) | B |
| 2-133 | 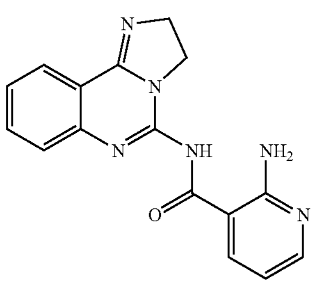 | 306.33 | 306 | 215 (dec.) | B |
| 2-134 | 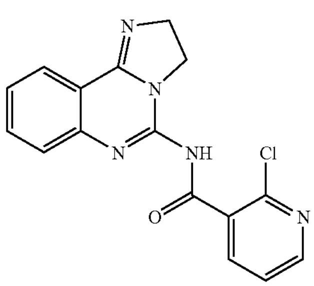 | 325.76 | 326 | 198-199 | A |

TABLE 2-continued
| Ex. No. | Structure | MW | MASS | mp/° C. | in vitro PI3K-gamma |
|---|---|---|---|---|---|
| 2-135 | 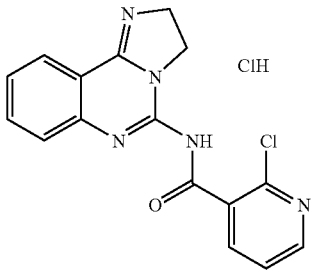 | 362.22 | 326 | 340 (dec:) | B |
| 2-136 | 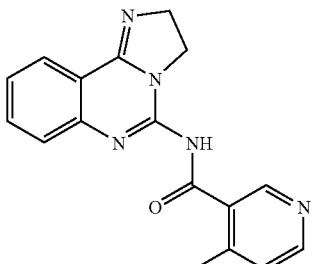 | 305.34 | 305 | 194-195 | B |
| 2-137 | 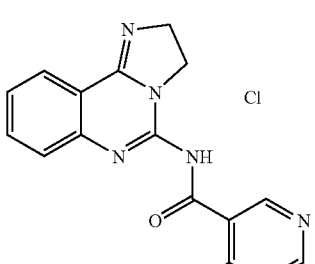 | 341.80 | 305 | 291 (dec.) | B |
| 2-138 | 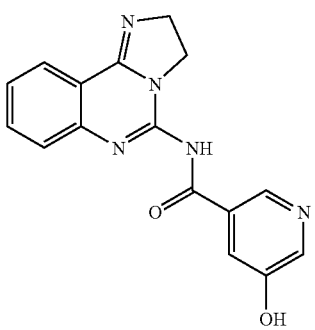 | 307.31 | 307 | 273 (dec.) | A |
| 2-139 | 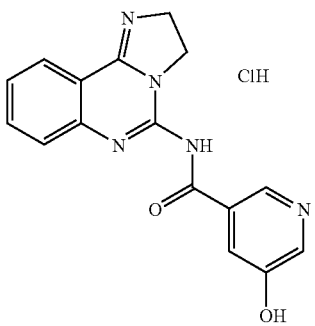 | 343.78 | 307 | 296-297 | A |

TABLE 2-continued

| Ex. No. | Structure | MW | MASS | mp/° C. | in vitro PI3K-gamma |
|---|---|---|---|---|---|
| 2-140 | 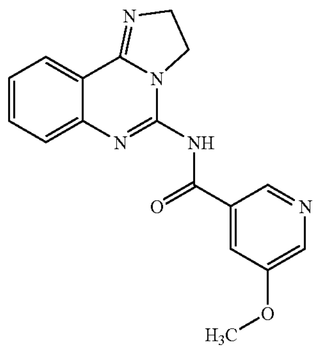 | 321.34 | 321 | 219 (dec.) | B |
| 2-141 | (ClH) | 357.80 | 321 | 272 (dec.) | B |
| 2-142 | 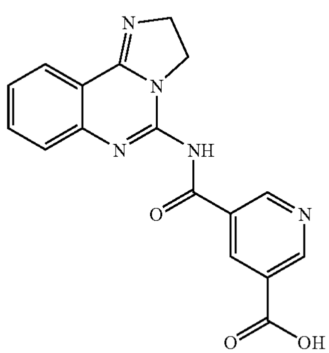 | 335.32 | 336 | 358-359 | B |
| 2-143 | 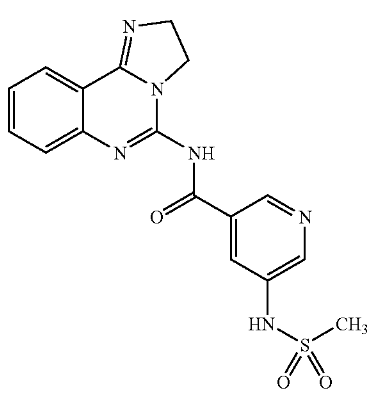 | 384.42 | 385 | 265-269 | A |

TABLE 2-continued

| Ex. No. | Structure | MW | MASS | mp/° C. | in vitro PI3K-gamma |
|---|---|---|---|---|---|
| 2-144 | 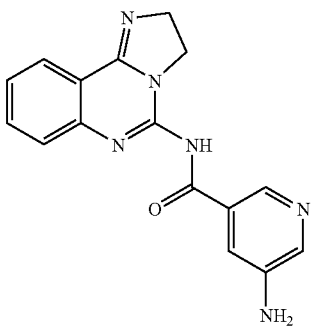 | 306.33 | 307 | 263-266 | A |
| 2-145 | 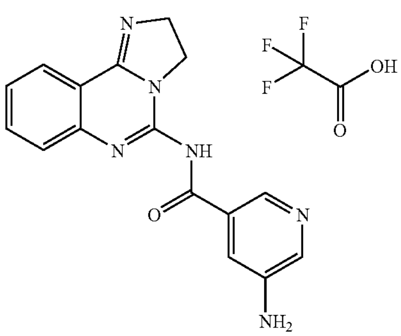 | 420.35 | 307 | 229 (dec.) | B |
| 2-146 | 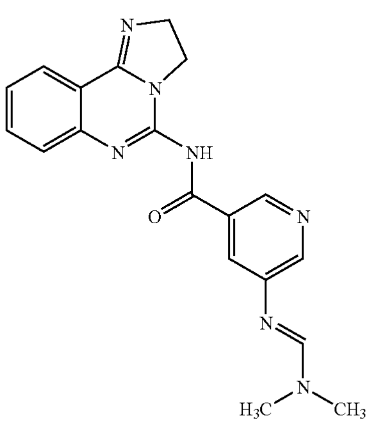 | 361.41 | 362 | 219 (dec.) | B |
| 2-147 | 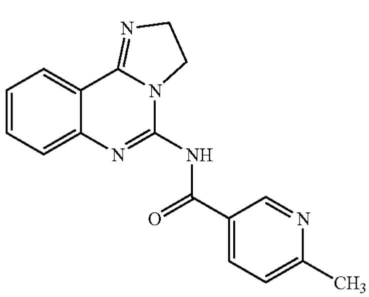 | 305.34 | 306 | 195-196 | A |

TABLE 2-continued
| Ex. No. | Structure | MW | MASS | mp/° C. | in vitro PI3K-gamma |
|---|---|---|---|---|---|
| 2-148 | 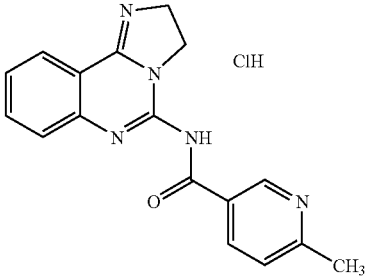 | 341.80 | 306 | 310 (dec.) | A |
| 2-149 | 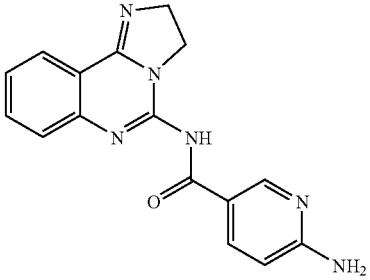 | 306.33 | 307 | >300 | A |
| 2-150 | 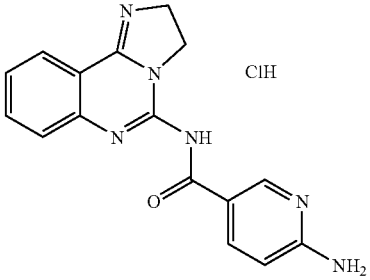 | 342.79 | 307 | 290 (dec.) | A |
| 2-151 | 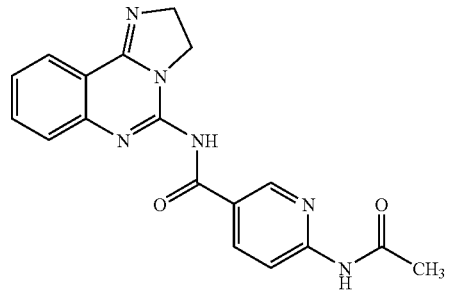 | 348.37 | 349 | 320 (dec.) | A |
| 2-152 | 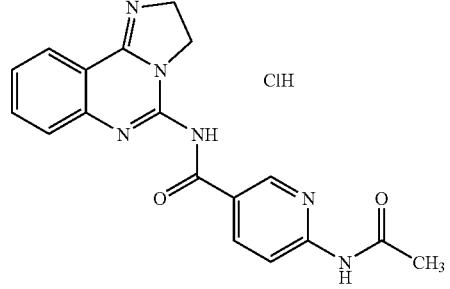 | 384.83 | 349 | 312 (dec.) | A |

TABLE 2-continued

| Ex. No. | Structure | MW | MASS | mp/° C. | in vitro PI3K-gamma |
|---|---|---|---|---|---|
| 2-153 | 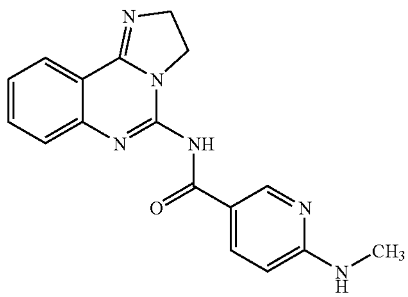 | 320.36 | 320 | 196-197 | B |
| 2-154 | ClH | 356.82 | 320 | 300 (dec.) | B |
| 2-155 | ClH | 362.22 | 326 | 324 (dec.) | B |
| 2-156 | ClH | 376.25 | 340 | 287 (dec.) | B |
| 2-157 | 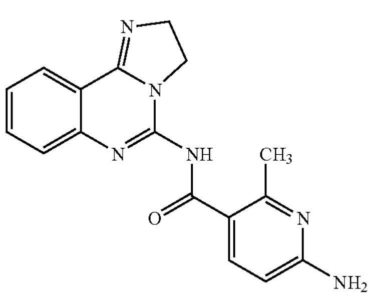 | 320.36 | 321 | 146-148 | B |

TABLE 2-continued
| Ex. No. | Structure | MW | MASS | mp/° C. | in vitro PI3K-gamma |
|---|---|---|---|---|---|
| 2-158 | 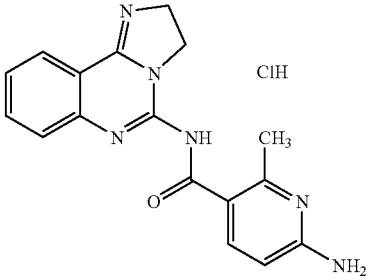 | 356.82 | 321 | 289 (dec.) | B |
| 2-159 | 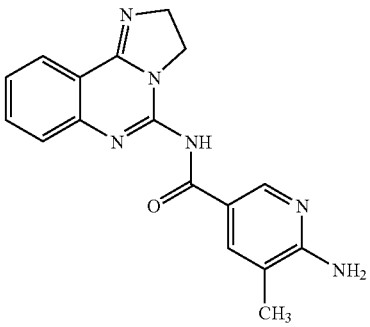 | 320.36 | 320 | 246-247 | B |
| 2-160 | 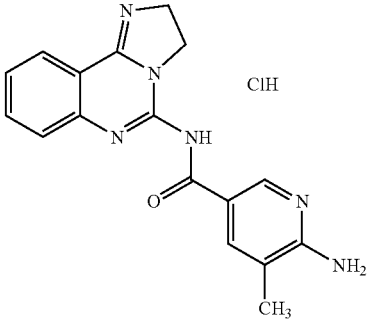 | 356.82 | 320 | 311 (dec.) | B |
| 2-161 | 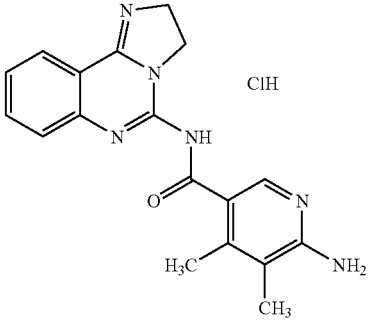 | 370.84 | 334 | 298 (dec.) | B |
| 2-162 | 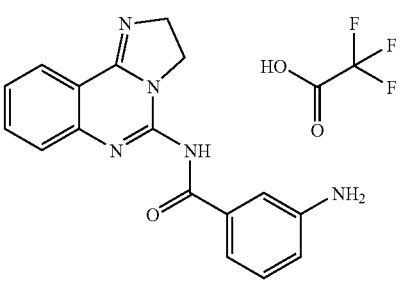 | 419.37 | 306 | 191 (dec.) | B |

TABLE 2-continued

| Ex. No. | Structure | MW | MASS | mp/° C. | in vitro PI3K-gamma |
|---|---|---|---|---|---|
| 2-163 | 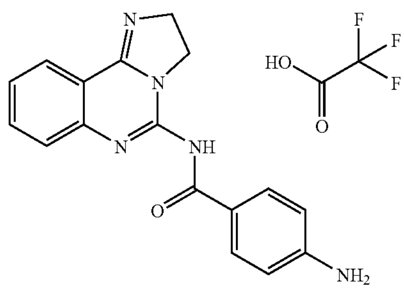 | 419.37 | 306 | 232 (dec.) | B |
| 2-164 | 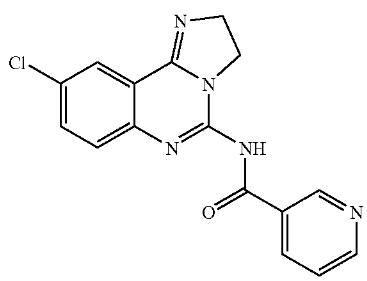 | 461.40 | 348 | 247 (dec.) | A |
| 2-165 | 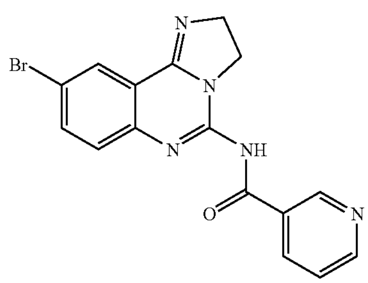 | 328.76 | 292 | 291 (dec.) | B |
| 2-166 | 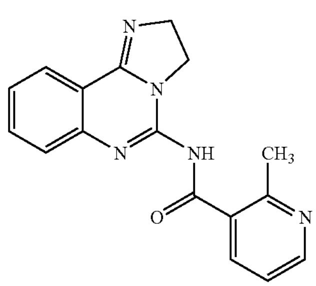 | 444.38 | 331 | 221 (dec.) | A |
| 2-167 | 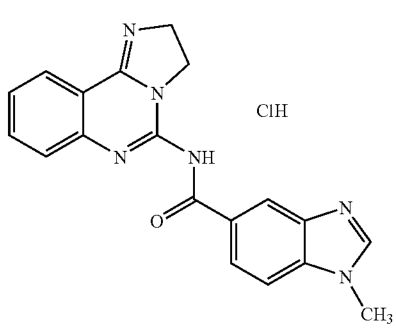 | 380.84 | 345 | 333 (dec.) | B |

TABLE 2-continued

| Ex. No. | Structure | MW | MASS | mp/° C. | in vitro PI3K-gamma |
|---|---|---|---|---|---|
| 2-168 | 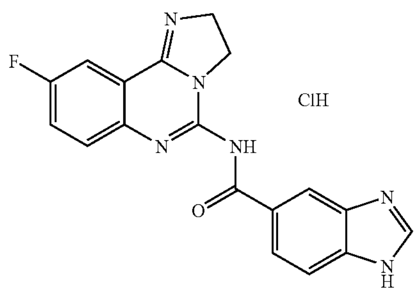 | 329.36 | 330 | 160 (dec.) | B |
| 2-169 | 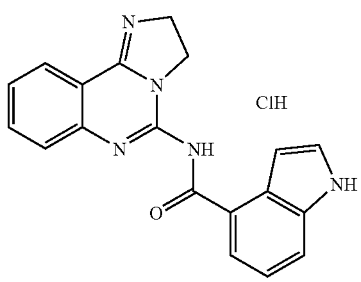 | 365.83 | 330 | 295 (dec.) | B |
| 2-170 | 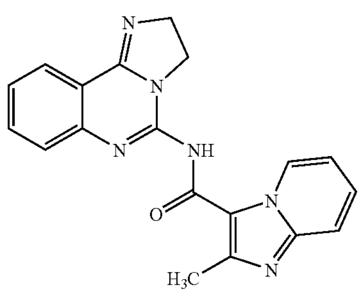 | 344.38 | 345 | 277-279 | B |
| 2-171 | 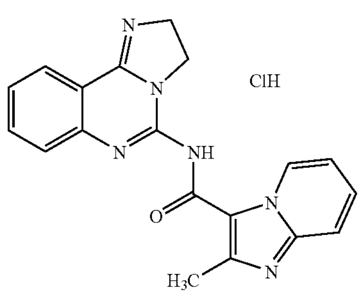 | 380.84 | 345 | 328 (dec.). | B |
| 2-172 | 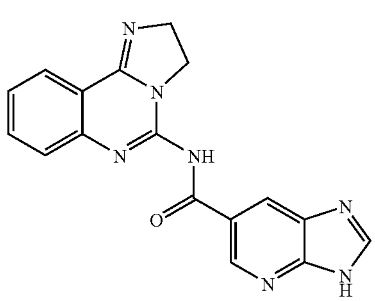 | 331.34 | 332 | >300 | A |

TABLE 2-continued

| Ex. No. | Structure | MW | MASS | mp/° C. | in vitro PI3K-gamma |
|---|---|---|---|---|---|
| 2-173 | 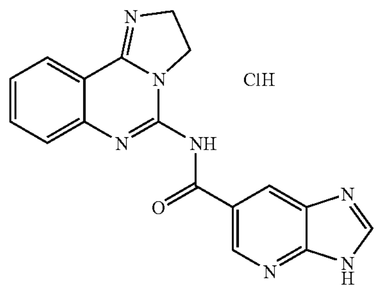 | 367.80 | 332 | 287 (dec.) | A |
| 2-174 | 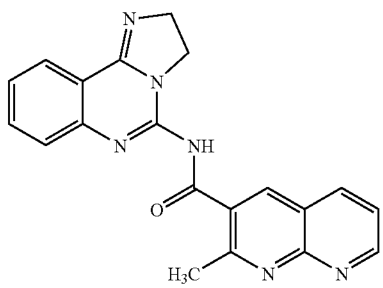 | 356.39 | 356 | 296 (dec.) | B |
| 2-175 | 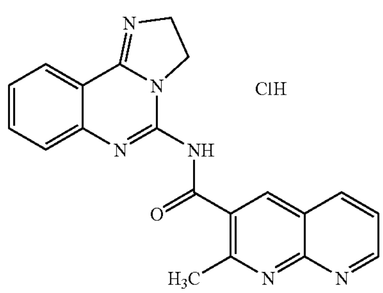 | 392.85 | 356 | 270 (dec.) | B |
| 2-176 | 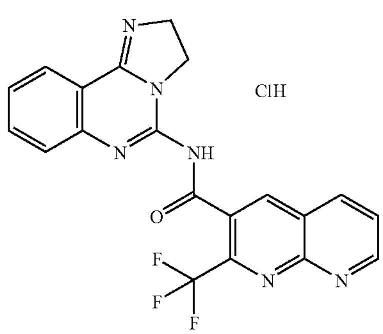 | 446.82 | 410 | 248-249 | B |
| 2-177 | 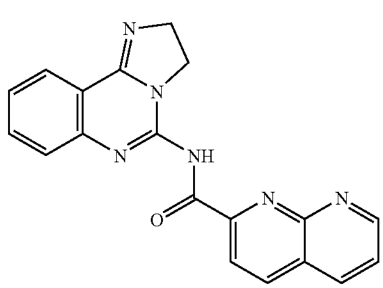 | 342.36 | 342 | 275 (dec.) | B |

TABLE 2-continued

| Ex. No. | Structure | MW | MASS | mp/° C. | in vitro PI3K-gamma |
|---|---|---|---|---|---|
| 2-178 | 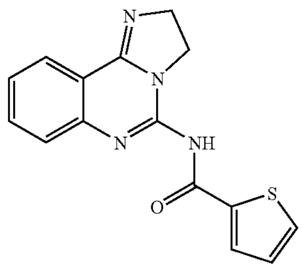 | 296.35 | 297 | 187-188 | B |
| 2-179 | ClH | 332.81 | 297 | 310 (dec.) | A |
| 2-180 | 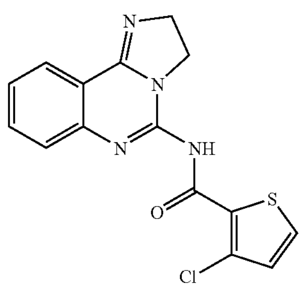 | 330.80 | 330 | 198-199 | B |
| 2-181 | ClH | 367.26 | 330 | 298 (dec) | B |
| 2-182 | ClH | 346.84 | 310 | >250 | B |

TABLE 2-continued

| Ex. No. | Structure | MW | MASS | mp/° C. | in vitro PI3K-gamma |
|---|---|---|---|---|---|
| 2-183 | 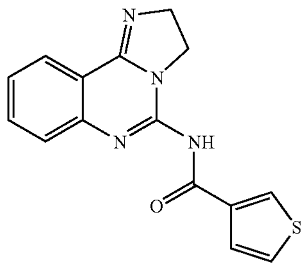 | 296.35 | 297 | 167 (dec.) | B |
| 2-184 | 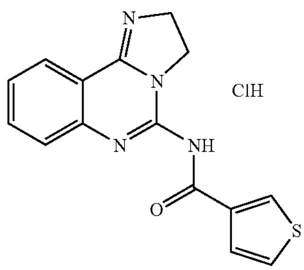 | 332.81 | 297 | 297 (dec.) | B |
| 2-185 | 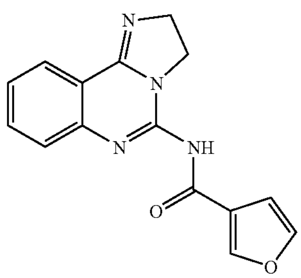 | 280.29 | 280 | 217-218 | B |
| 2-186 | 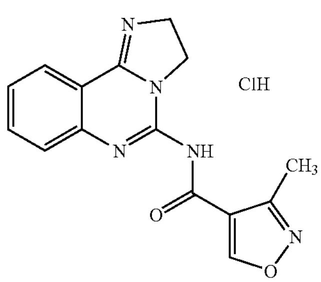 | 331.76 | 295 | 285 (dec.) | B |
| 2-187 | 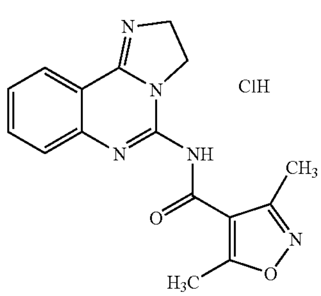 | 345.79 | 309 | 280-281 | B |

TABLE 2-continued

| Ex. No. | Structure | MW | MASS | mp/° C. | in vitro PI3K-gamma |
|---|---|---|---|---|---|
| 2-188 | 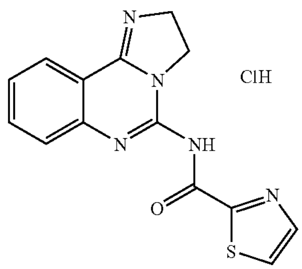 | 333.80 | 298 | 306 (dec.) | B |
| 2-189 | 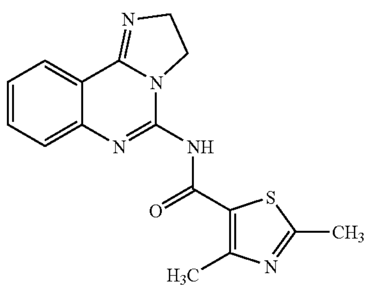 | 325.39 | 326 | 243 (dec.) | B |
| 2-190 | 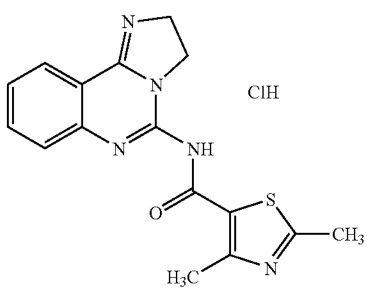 | 361.86 | 326 | 289-290 | A |
| 2-191 | 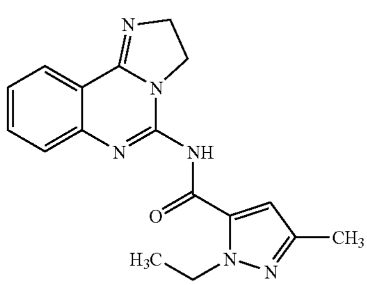 | 322.37 | 322 | 207-208 | B |
| 2-192 | 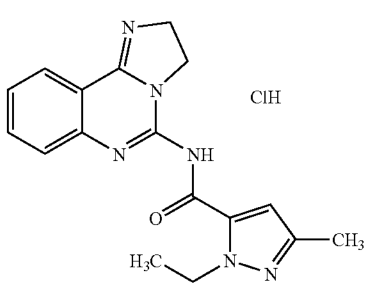 | 358.83 | 322 | 271-272 | B |

TABLE 2-continued

| Ex. No. | Structure | MW | MASS | mp/° C. | in vitro PI3K-gamma |
|---|---|---|---|---|---|
| 2-193 | 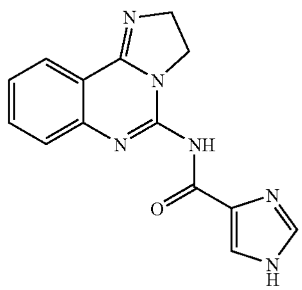 | 280.29 | 281 | 265 (dec.) | B |
| 2-194 | ClH | 316.75 | 281 | 309-310 | B |
| 2-195 | ClH | 343.78 | 308 | 270-274 (dec) | B |
| 2-196 | ClH | 436.90 | 401 | 239 | B |
| 2-197 | 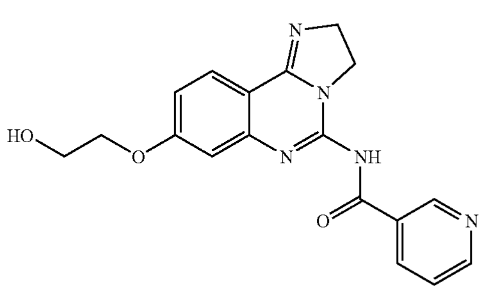 | 351.37 | 352 | 210-215 (dec.) | B |

TABLE 2-continued
| Ex. No. | Structure | MW | MASS | mp/° C. | in vitro PI3K-gamma |
|---|---|---|---|---|---|
| 2-198 | 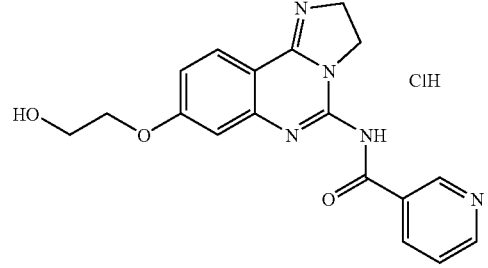 | 387.83 | 352 | 249 (dec.) | B |
| 2-199 | 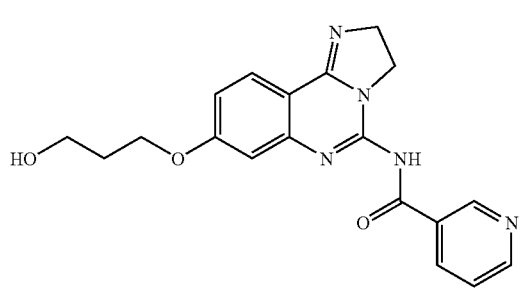 | 365.39 | 366 | 127 | A |
| 2-200 | 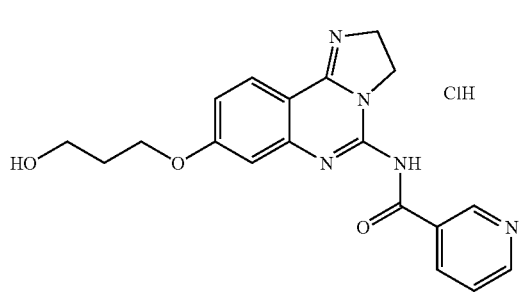 | 401.86 | 366 | 243 (dec.) | B |
| 2-201 | 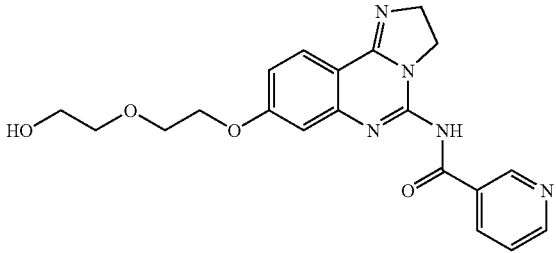 | 395.42 | 396 | 181 | B |
| 2-202 | 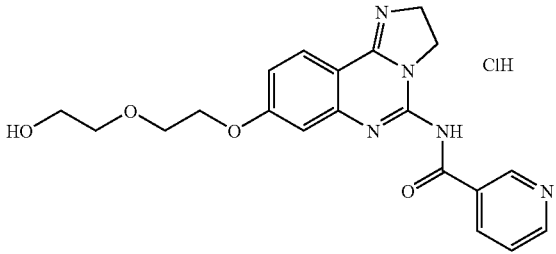 | 431.88 | 396 | 229 (dec.) | B |

TABLE 2-continued

| Ex. No. | Structure | MW | MASS | mp/° C. | in vitro PI3K-gamma |
|---|---|---|---|---|---|
| 2-203 | 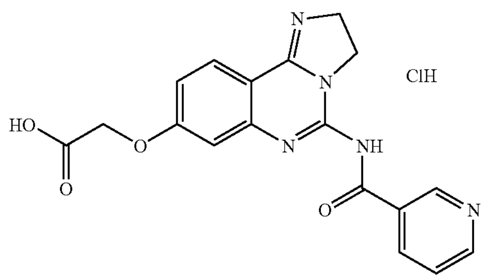 | 401.81 | 366 | 231 (dec.) | B |
| 2-204 | 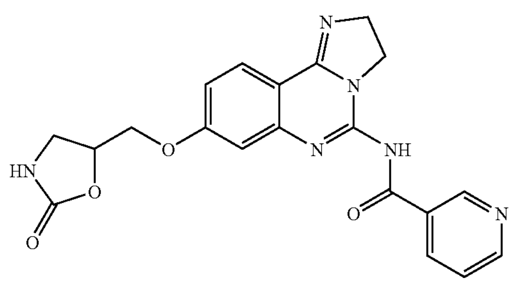 | 406.40 | 407 | 265-269 (dec.) | B |
| 2-205 | 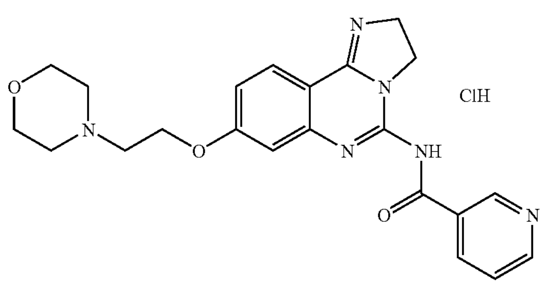 | 456.94 | 421 | 243-247 (dec.) | B |
| 2-206 | 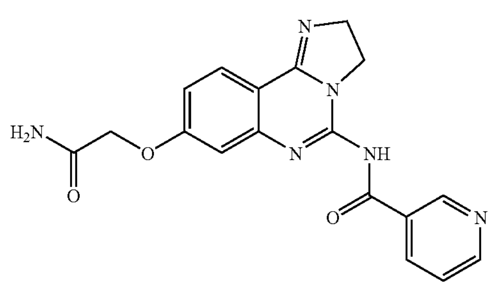 | 364.37 | 365 | 296 | B |
| 2-207 | 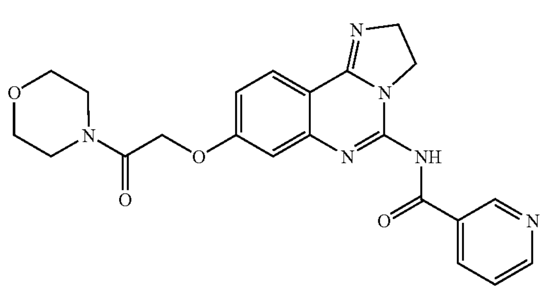 | 434.46 | 435 | 232-236 (dec.) | B |

TABLE 2-continued

| Ex. No. | Structure | MW | MASS | mp/° C. | in vitro PI3K-gamma |
|---|---|---|---|---|---|
| 2-208 | 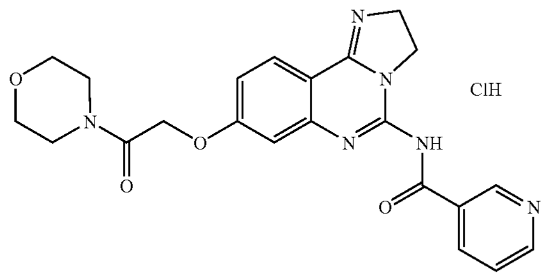 | 470.92 | 435 | 227 | B |
| 2-209 | 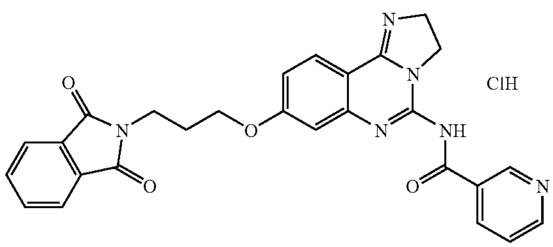 | 530.98 | 495 | 247 | A |
| 2-210 | 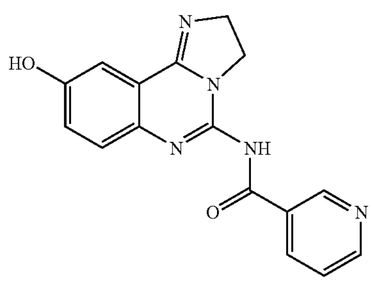 | 307.31 | 308 | >300 | B |
| 2-211 | 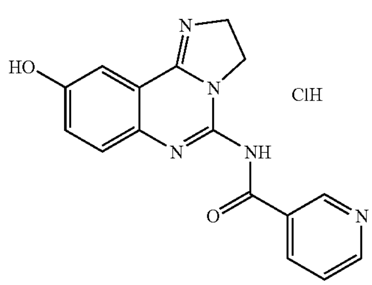 | 343.78 | 308 | >300 | A |
| 2-212 | 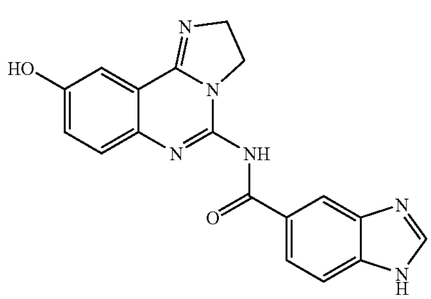 | 346.35 | 347 | 296 (dec.) | B |

TABLE 2-continued

| Ex. No. | Structure | MW | MASS | mp/° C. | in vitro PI3K-gamma |
|---|---|---|---|---|---|
| 2-213 | 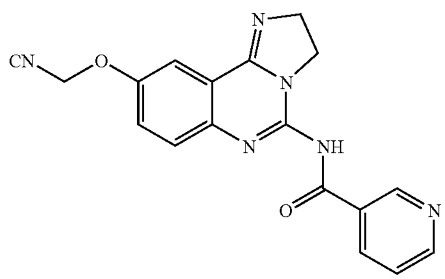 | 346.35 | 347 | 209 | B |
| 2-214 | 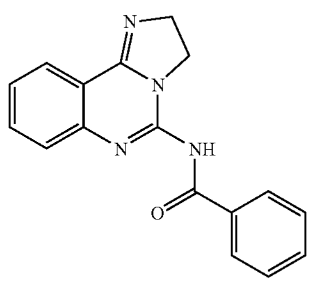 | 290.33 | 291 | 201-203 (dec.) | C |
| 2-215 | 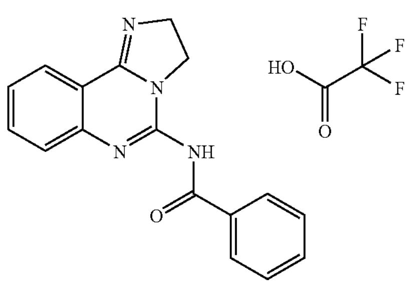 | 404.35 | 291 | 238-242 | B |
| 2-216 | 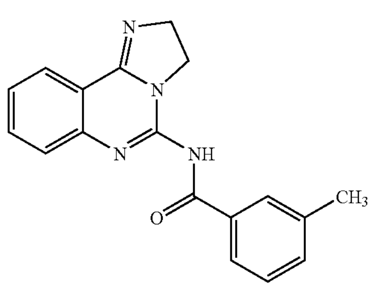 | 304.35 | 305 | 201-203 | D |
| 2-217 | 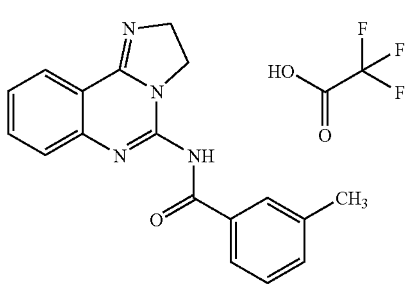 | 418.38 | 305 | 239-241 | B |

TABLE 2-continued

| Ex. No. | Structure | MW | MASS | mp/° C. | in vitro PI3K-gamma |
|---|---|---|---|---|---|
| 2-218 | 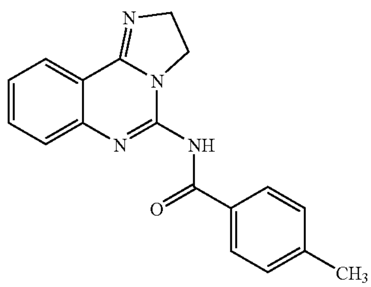 | 304.35 | 305 | 185-186 | D |
| 2-219 | 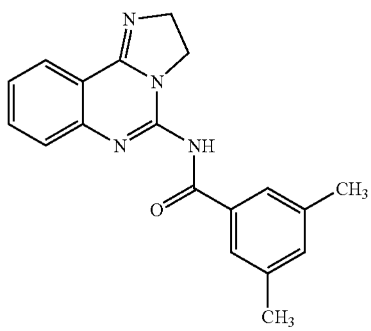 | 318.38 | 319 | 246-248 | D |
| 2-220 | 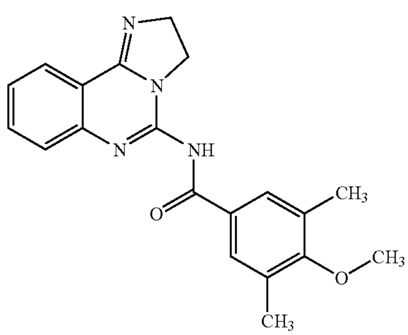 | 348.41 | 349 | 216-218 | D |
| 2-221 | 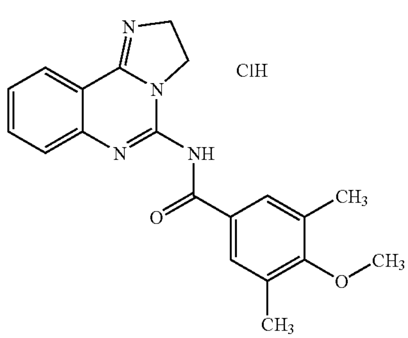 | 384.87 | 349 | 288 (dec.) | D |

TABLE 2-continued

| Ex. No. | Structure | MW | MASS | mp/° C. | in vitro PI3K-gamma |
|---|---|---|---|---|---|
| 2-222 | 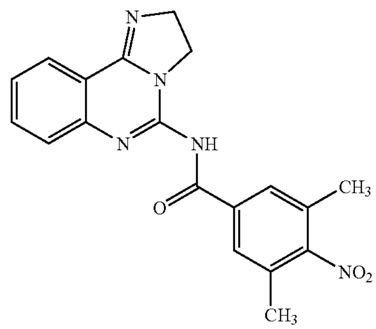 | 363.38 | 364 | 277 (dec.) | D |
| 2-223 | 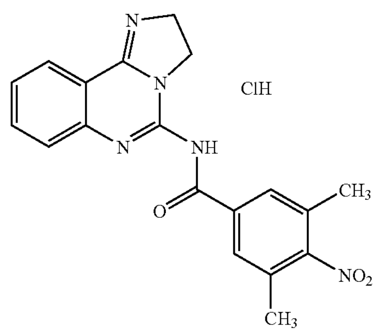 | 399.84 | 364 | 313 (dec.) | D |
| 2-224 | 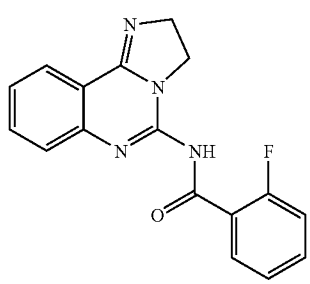 | 308.32 | 309 | 202-204 | C |
| 2-225 | 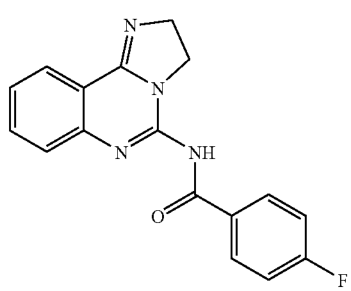 | 308.32 | 309 | 210-212 | D |
| 2-226 | 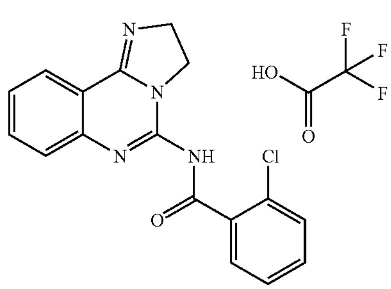 | 438.80 | 325 | 221-224 | D |

TABLE 2-continued

| Ex. No. | Structure | MW | MASS | mp/° C. | in vitro PI3K-gamma |
|---|---|---|---|---|---|
| 2-227 | 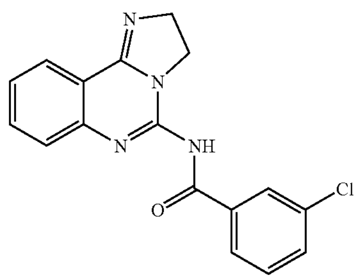 | 324.77 | 325 | 196-197 | D |
| 2-228 | 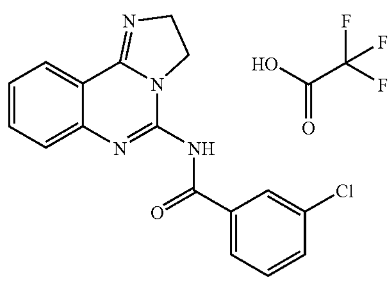 | 438.80 | 325 | 233-235 | C |
| 2-229 | 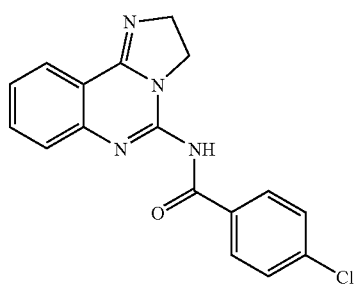 | 324.77 | 325 | 226-228 | D |
| 2-230 | 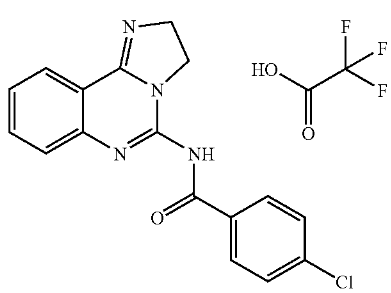 | 438.80 | 325 | 243-245 | D |
| 2-231 | 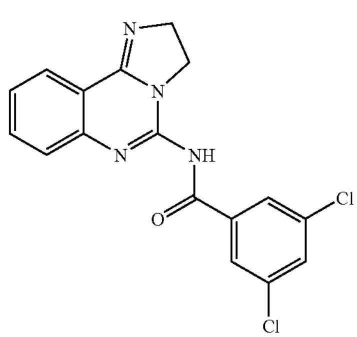 | 359.22 | 358 | 268-269 | D |

TABLE 2-continued

| Ex. No. | Structure | MW | MASS | mp/° C. | in vitro PI3K-gamma |
|---|---|---|---|---|---|
| 2-232 | 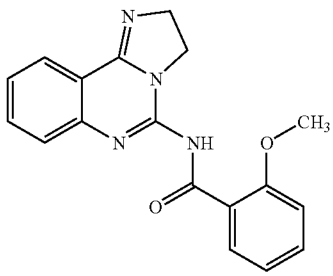 | 320.35 | 321 | 185-187 | D |
| 2-233 | 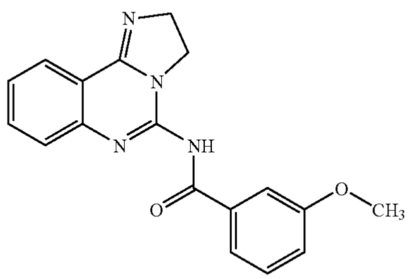 | 320.35 | 321 | 202-204 | D |
| 2-234 | 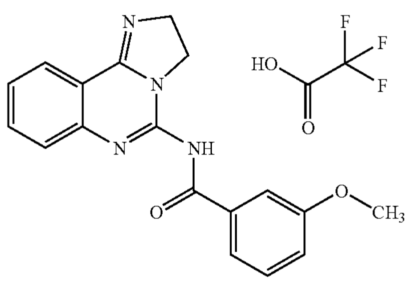 | 434.38 | 321 | 209-211 | C |
| 2-235 | 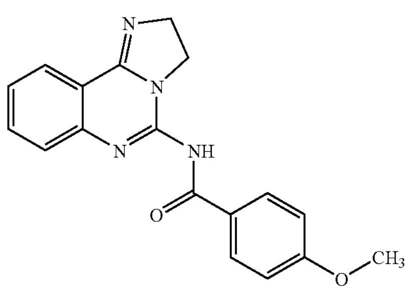 | 320.35 | 321 | 300 (dec.) | D |
| 2-236 | 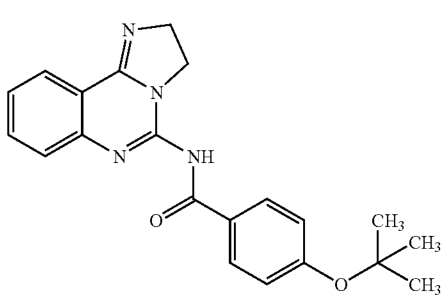 | 362.44 | 363 | >410 | D |

TABLE 2-continued

| Ex. No. | Structure | MW | MASS | mp/° C. | in vitro PI3K-gamma |
|---|---|---|---|---|---|
| 2-237 | 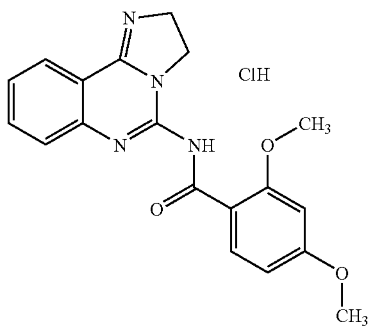 | 386.84 | 351 | 259 (dec.) | D |
| 2-238 | 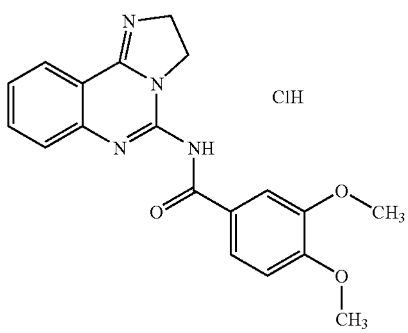 | 386.84 | 351 | 274 (dec.) | B |
| 2-239 | 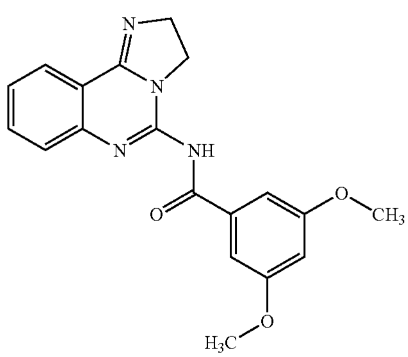 | 350.38 | 351 | 330 (dec.) | D |
| 2-240 | 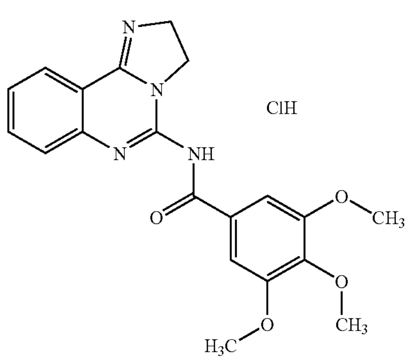 | 416.87 | 381 | 291 (dec.) | D |

TABLE 2-continued

| Ex. No. | Structure | MW | MASS | mp/° C. | in vitro PI3K-gamma |
|---|---|---|---|---|---|
| 2-241 | 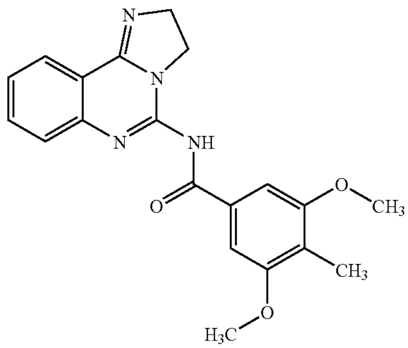 | 364.41 | 365 | 248 (dec.) | D |
| 2-242 | ClH | 400.87 | 365 | 321 (dec.) | D |
| 2-243 | 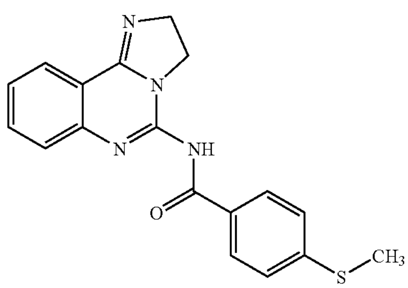 | 336.42 | 337 | 169-170 | D |
| 2-244 | ClH | 372.88 | 337 | 292 (dec.) | D |

TABLE 2-continued
| Ex. No. | Structure | MW | MASS | mp/° C. | in vitro PI3K-gamma |
|---|---|---|---|---|---|
| 2-245 | 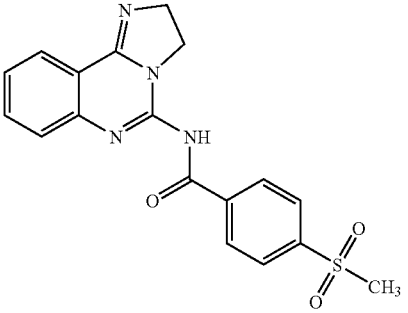 | 368.42 | 369 | 278 (dec.) | D |
| 2-246 | 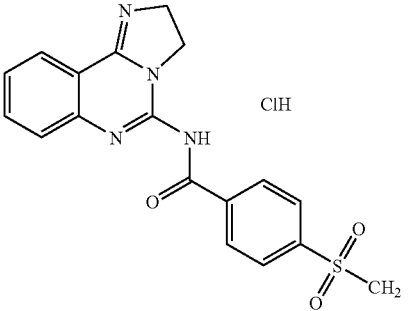 | 404.88 | 369 | 320 (dec.) | D |
| 2-247 | 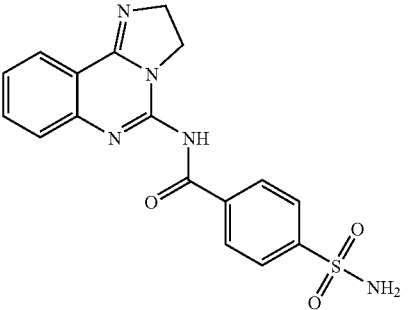 | 369.40 | 370 | 278 (dec.) | C |
| 2-248 | 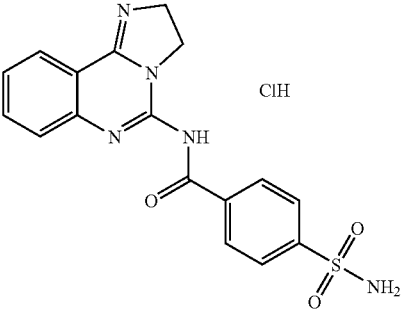 | 405.87 | 370 | 308 (dec.) | C |

TABLE 2-continued

| Ex. No. | Structure | MW | MASS | mp/° C. | in vitro PI3K-gamma |
|---|---|---|---|---|---|
| 2-249 | 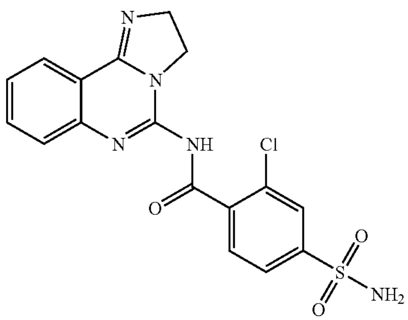 | 403.85 | 403 | 240 (dec.) | D |
| 2-250 | 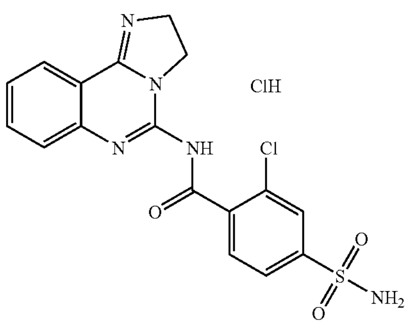 | 440.31 | 403 | 300 (dec.) | D |
| 2-251 | 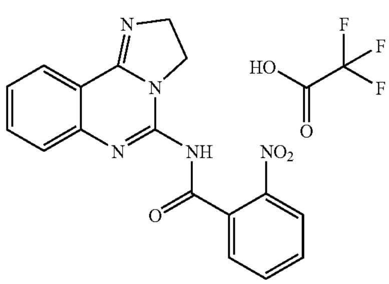 | 449.35 | 336 | 198-200 | D |
| 2-252 | 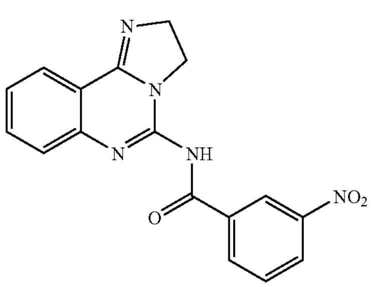 | 335.32 | 334 | 265-267 | D |
| 2-253 | 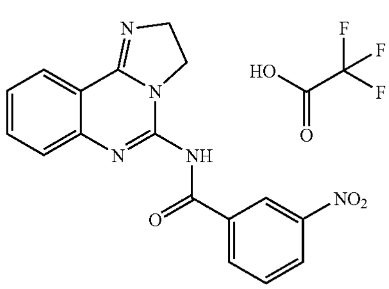 | 449.35 | 336 | 238-239 | D |

TABLE 2-continued

| Ex. No. | Structure | MW | MASS | mp/° C. | in vitro PI3K-gamma |
|---|---|---|---|---|---|
| 2-254 | 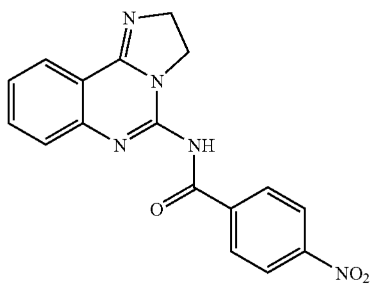 | 335.32 | 334 | 279-281 | D |
| 2-255 | 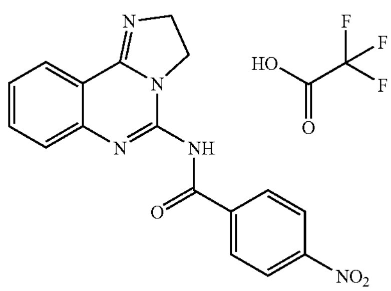 | 449.35 | 336 | 265 (dec.) | D |
| 2-256 | 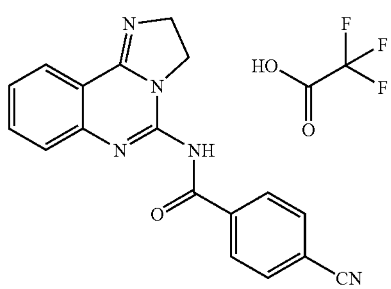 | 429.36 | 316 | 248-250 | D |
| 2-257 | 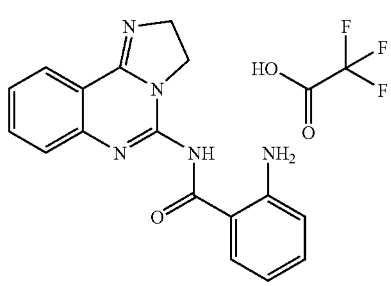 | 419.37 | 306 | 175 (dec.) | D |
| 2-258 | 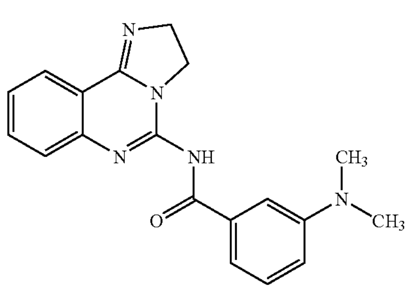 | 333.40 | 334 | 188-190 | D |

TABLE 2-continued
| Ex. No. | Structure | MW | MASS | mp/° C. | in vitro PI3K-gamma |
|---|---|---|---|---|---|
| 2-259 | 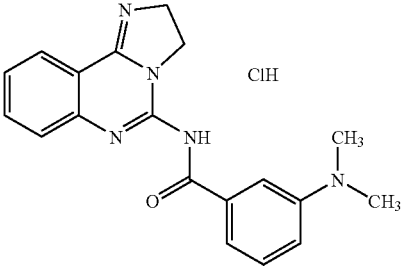 | 369.86 | 334 | 266 (dec.) | D |
| 2-260 | 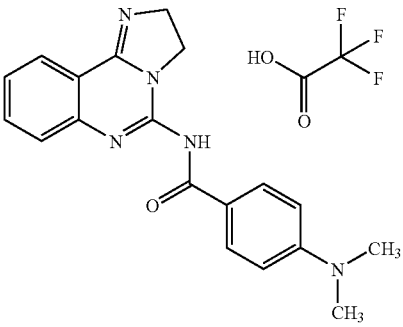 | 447.42 | 334 | 240 (dec.) | D |
| 2-261 | 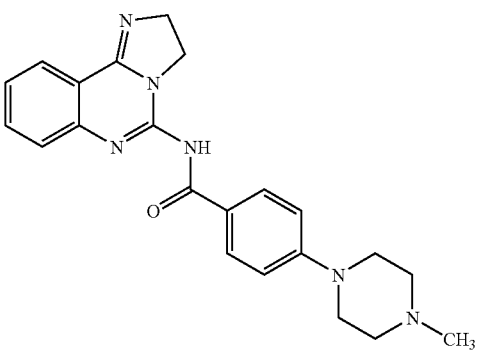 | 388.48 | 389 | 218-222 | D |
| 2-262 | 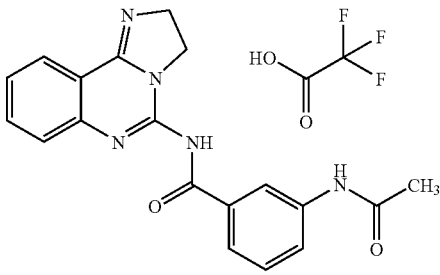 | 461.40 | 348 | 253 (dec.) | D |

TABLE 2-continued

| Ex. No. | Structure | MW | MASS | mp/° C. | in vitro PI3K-gamma |
|---|---|---|---|---|---|
| 2-263 | 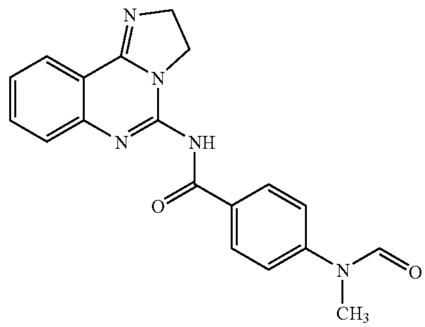 | 347.38 | 348 | 208-210 | D |
| 2-264 | ClH | 383.84 | 348 | 304 (dec.) | D |
| 2-265 | 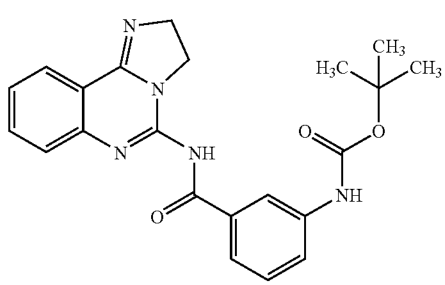 | 405.46 | 406 | 280 (dec.) | D |
| 2-266 | 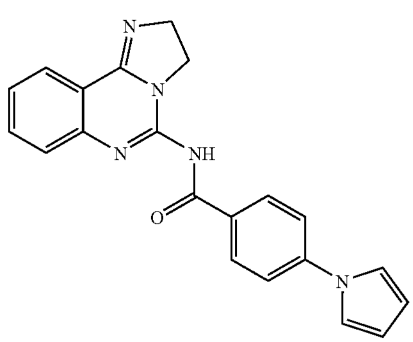 | 355.40 | 356 | 218-220 | D |

TABLE 2-continued

| Ex. No. | Structure | MW | MASS | mp/° C. | in vitro PI3K-gamma |
|---|---|---|---|---|---|
| 2-267 | (structure with ClH) | 391.86 | 356 | 309 (dec.) | D |
| 2-268 | (structure) | 356.39 | 357 | 267 (dec.) | D |
| 2-269 | (structure with ClH) | 392.85 | 357 | 324 (dec.) | D |
| 2-270 | (structure) | 356.39 | 357 | 209-211 | D |

TABLE 2-continued

| Ex. No. | Structure | MW | MASS | mp/° C. | in vitro PI3K-gamma |
|---|---|---|---|---|---|
| 2-271 | 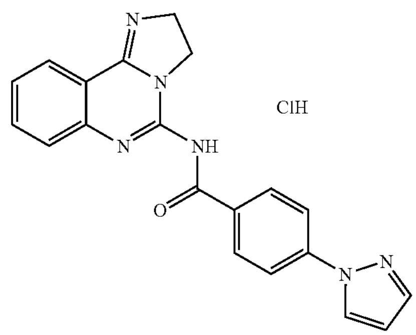 | 392.85 | 357 | 319 (dec.) | D |
| 2-272 | 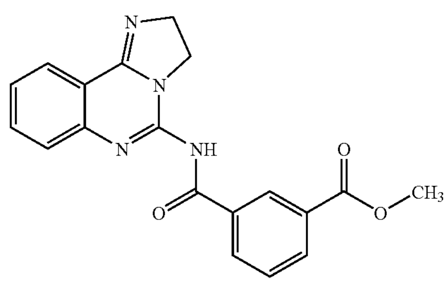 | 348.36 | 349 | 224-226 | D |
| 2-273 | 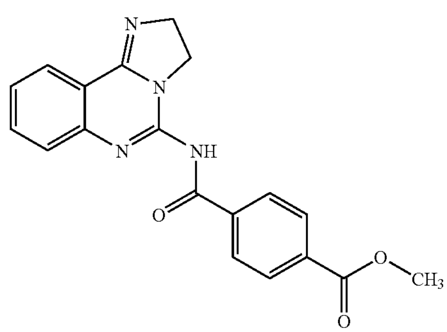 | 348.36 | 349 | 253-255 | D |
| 2-274 | 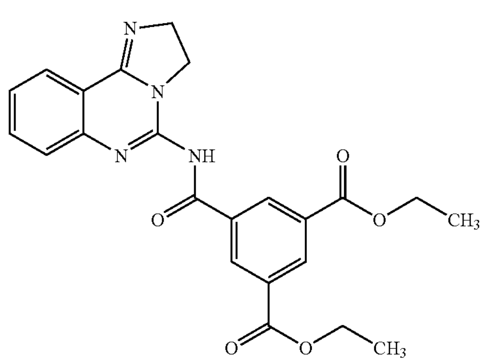 | 434.46 | 435 | 289 (dec.) | D |

TABLE 2-continued

| Ex. No. | Structure | MW | MASS | mp/° C. | in vitro PI3K-gamma |
|---|---|---|---|---|---|
| 2-275 | 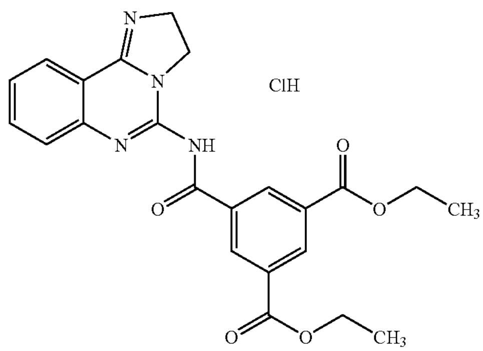 | 470.92 | 435 | 282 | D |
| 2-276 | 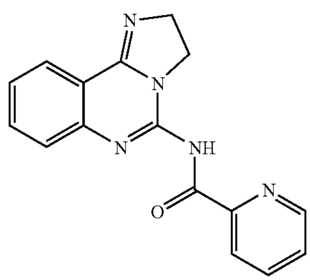 | 291.31 | 292 | 204-205 | C |
| 2-277 | 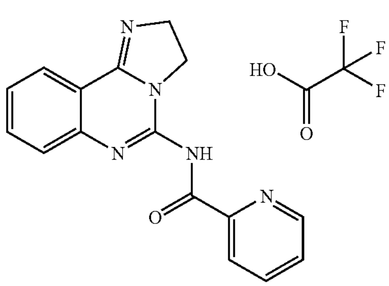 | 405.34 | 292 | 206 (dec.) | C |
| 2-278 | 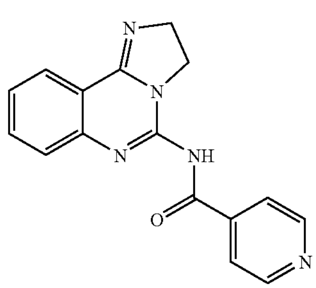 | 291.31 | 292 | 224-225 | C |
| 2-279 | 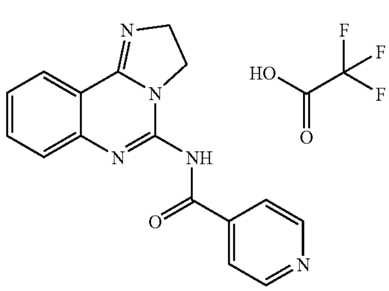 | 405.34 | 292 | 2310 (dec.) | C |

TABLE 2-continued

| Ex. No. | Structure | MW | MASS | mp/° C. | in vitro PI3K-gamma |
|---|---|---|---|---|---|
| 2-280 | 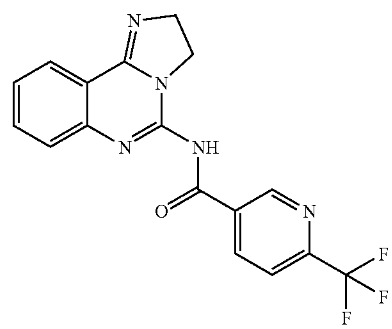 | 359.31 | 360 | 219-220 | D |
| 2-281 | ClH | 395.77 | 360 | >250 | C |
| 2-282 | 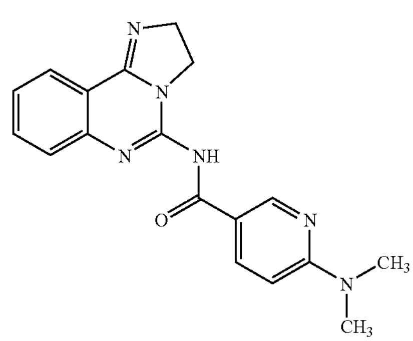 | 334.38 | 335 | 249 (dec.) | D |
| 2-283 | ClH | 370.84 | 335 | 311 (dec.) | C |

TABLE 2-continued
| Ex. No. | Structure | MW | MASS | mp/° C. | in vitro PI3K-gamma |
|---|---|---|---|---|---|
| 2-284 | 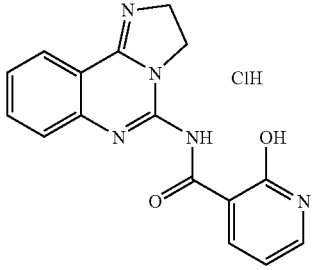 | 343.78 | 308 | 346 (dec.) | D |
| 2-285 | 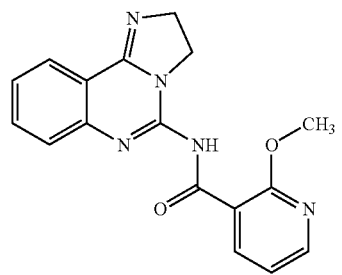 | 321.34 | 322 | 198-199 | C |
| 2-286 | 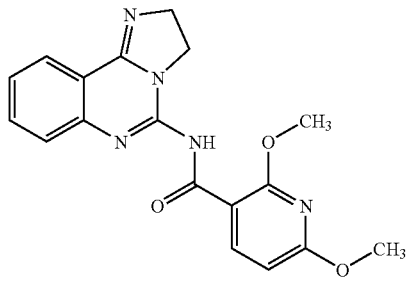 | 351.37 | 352 | 244-245 | D |
| 2-287 | 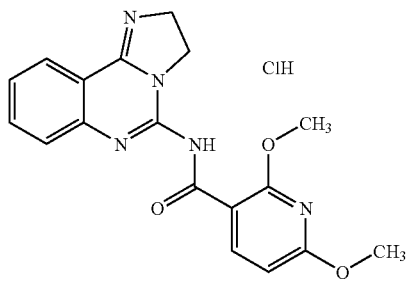 | 387.83 | 352 | 210 (dec.) | C |
| 2-288 | 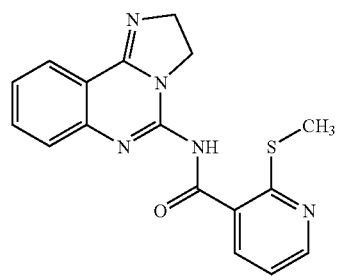 | 337.41 | 338 | 233-234 | D |

TABLE 2-continued
| Ex. No. | Structure | MW | MASS | mp/° C. | in vitro PI3K-gamma |
|---|---|---|---|---|---|
| 2-289 | 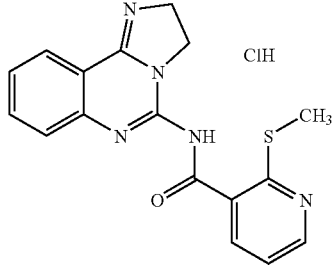 | 373.87 | 338 | 298-299 | C |
| 2-290 | 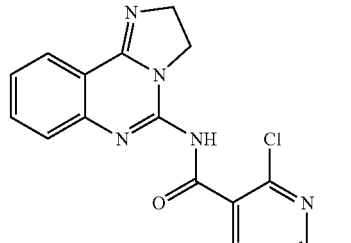 | 339.79 | 340 | 213-214 | B |
| 2-291 | 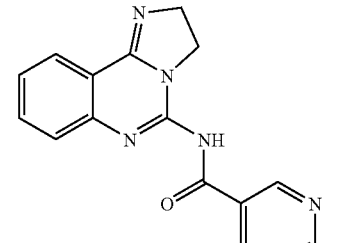 | 325.76 | 326 | 246-247 | B |
| 2-292 | 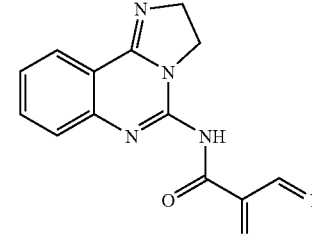 | 292.30 | 293 | 267-268 | C |
| 2-293 | 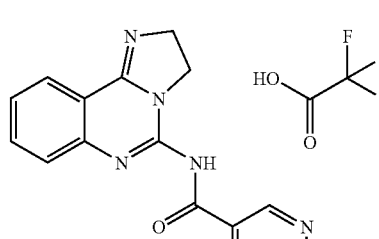 | 406.33 | 293 | 234 (dec.) | C |

TABLE 2-continued

| Ex. No. | Structure | MW | MASS | mp/° C. | in vitro PI3K-gamma |
|---|---|---|---|---|---|
| 2-294 | 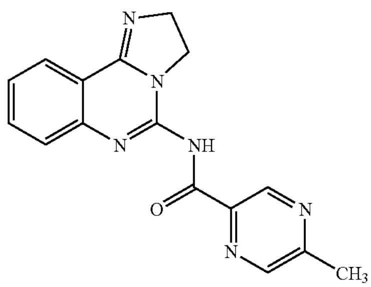 | 306.33 | 307 | 257 (dec.) | C |
| 2-295 | 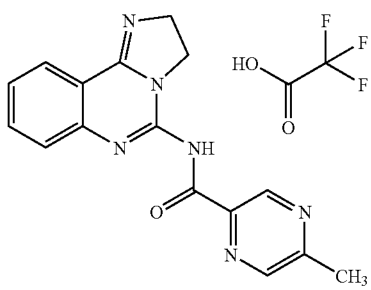 | 420.35 | 307 | 231 (dec.) | C |
| 2-296 | 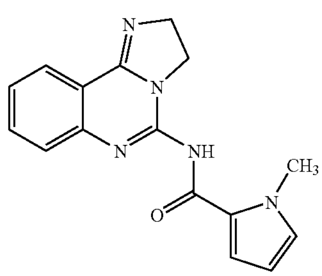 | 293.33 | 294 | 128-129 | C |
| 2-297 | 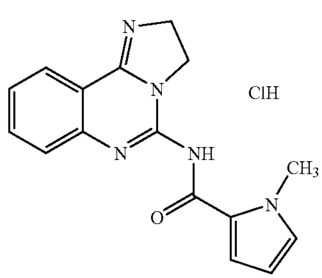 | 329.79 | 294 | 264 (dec.) | C |
| 2-298 | 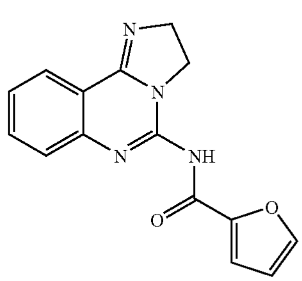 | 280.29 | 281 | 350 (dec.) | C |

TABLE 2-continued
| Ex. No. | Structure | MW | MASS | mp/° C. | in vitro PI3K-gamma |
|---|---|---|---|---|---|
| 2-299 | 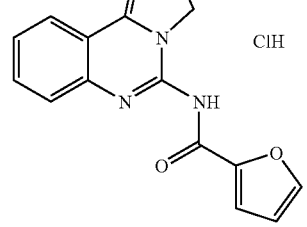 | 316.75 | 281 | 311 (dec.) | C |
| 2-300 | 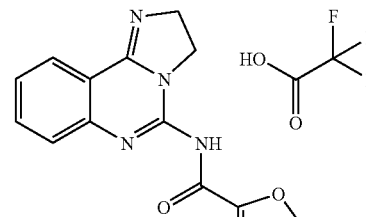 | 394.31 | 281 | 230-232 | B |
| 2-301 | 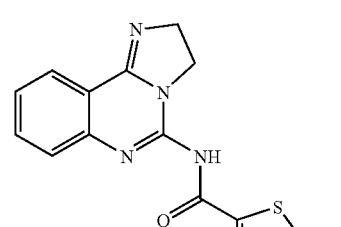 | 330.80 | 331 | 198 (dec.) | D |
| 2-302 | 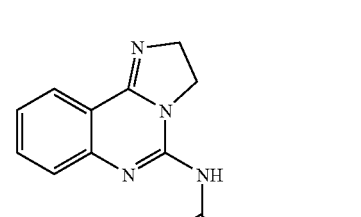 | 310.38 | 311 | 192-193 | C |
| 2-303 | 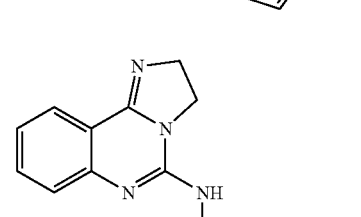 | 341.35 | 342 | 286-287 | D |

TABLE 2-continued

| Ex. No. | Structure | MW | MASS | mp/° C. | in vitro PI3K-gamma |
|---|---|---|---|---|---|
| 2-304 | 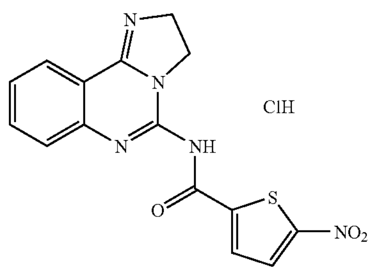 | 377.81 | 342 | 300 (dec.) | D |
| 2-305 | 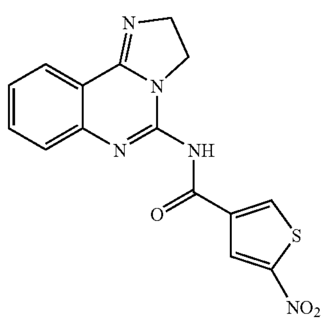 | 341.35 | 342 | 269-270 | D |
| 2-306 | 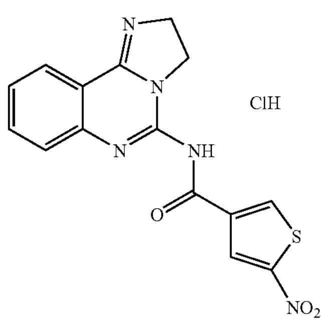 | 377.81 | 342 | 296 (dec.). | D |
| 2-307 | 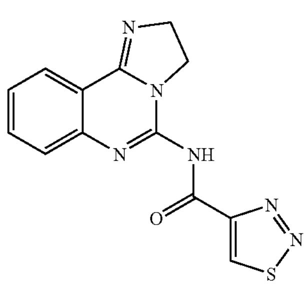 | 298.33 | 299 | 219 (dec.) | C |
| 2-308 | 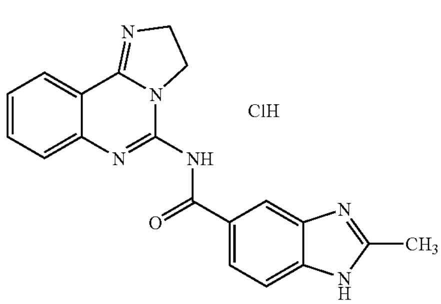 | 380.84 | 345 | 344 (dec.) | B |

TABLE 2-continued

| Ex. No. | Structure | MW | MASS | mp/° C. | in vitro PI3K-gamma |
|---|---|---|---|---|---|
| 2-309 | 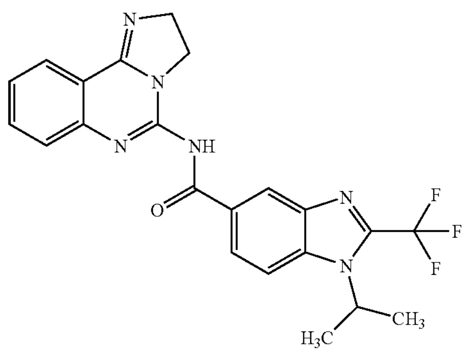 | 440.43 | 441 | 250-253 | D |
| 2-310 | 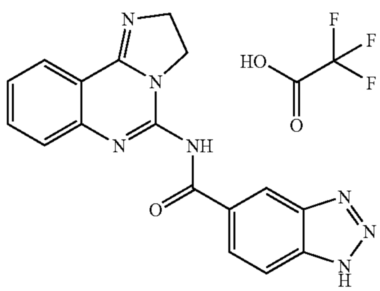 | 445.36 | 332 | 252 (dec.) | B |
| 2-311 | 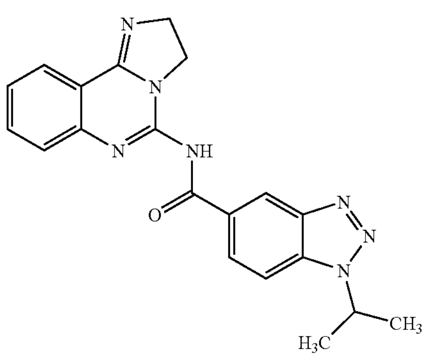 | 373.42 | 374 | 202-203 | D |
| 2-312 | 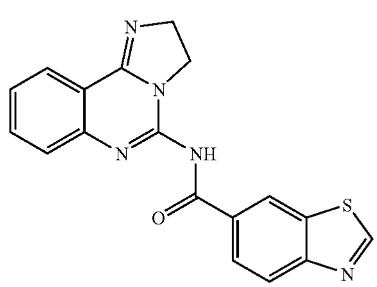 | 347.40 | 348 | 303-305 | D |
| 2-313 | 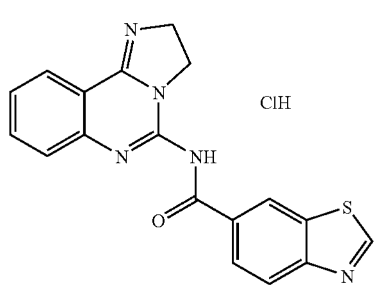 | 383.86 | 348 | 314 (dec.) | C |

TABLE 2-continued

| Ex. No. | Structure | MW | MASS | mp/° C. | in vitro PI3K-gamma |
|---|---|---|---|---|---|
| 2-314 | 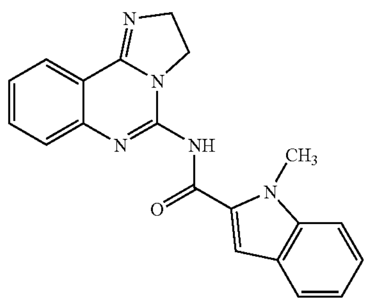 | 343.39 | 344 | 259-260 | D |
| 2-315 | 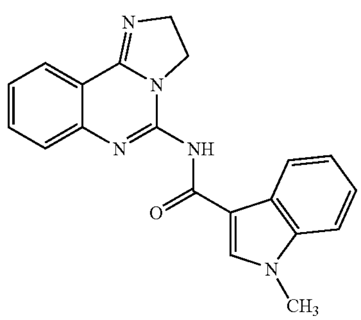 | 343.39 | 344 | 288-289 | D |
| 2-316 | 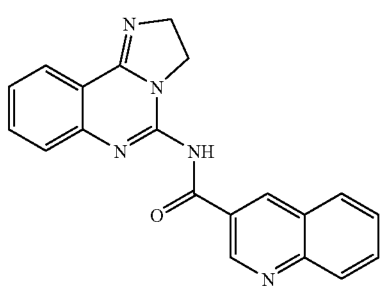 | 341.38 | 342 | 263-264 | D |
| 2-317 | 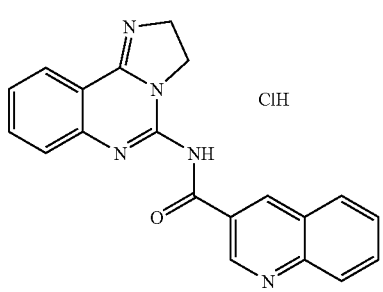 | 377.84 | 342 | 319 (dec.) | B |
| 2-318 | 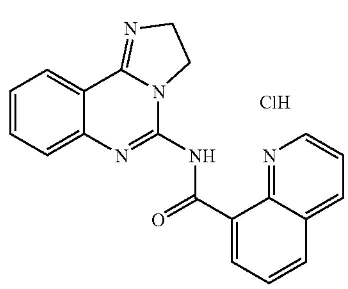 | 377.84 | 342 | 316 (dec.) | D |

TABLE 2-continued

| Ex. No. | Structure | MW | MASS | mp/° C. | in vitro PI3K-gamma |
|---|---|---|---|---|---|
| 2-319 | 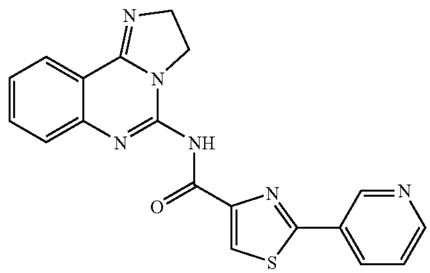 | 374.43 | 375 | 260-261 | D |
| 2-320 | ClH | 410.89 | 375 | 310 (dec.) | D |
| 2-321 | 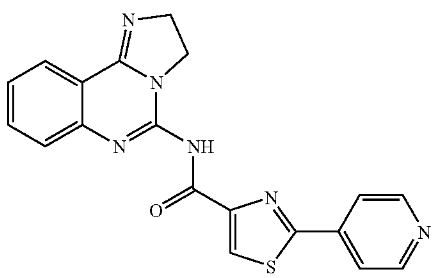 | 374.43 | 375 | 281 (dec.) | D |
| 2-322 | ClH | 410.89 | 375 | 335 (dec.) | D |
| 2-323 | 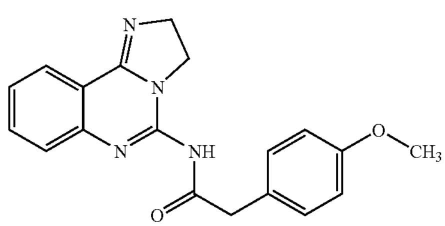 | 334.38 | 335 | 167-168 | D |
| 2-324 | 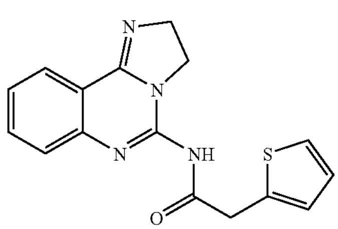 | 310.38 | 311 | 122-123 | D |

TABLE 2-continued

| Ex. No. | Structure | MW | MASS | mp/° C. | in vitro PI3K-gamma |
|---|---|---|---|---|---|
| 2-325 | 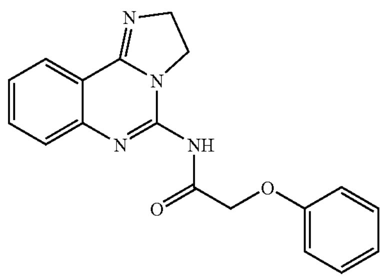 | 320.35 | 321 | 149-150 | D |
| 2-326 | 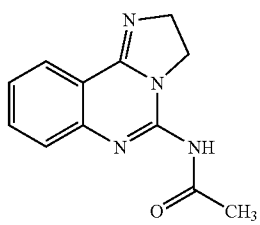 | 228.26 | 229 | 189 | D |
| 2-327 | 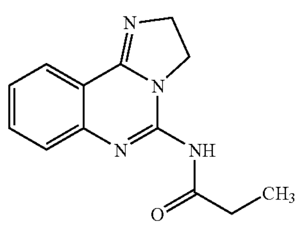 | 242.28 | 243 | amorphous | D |
| 2-328 | 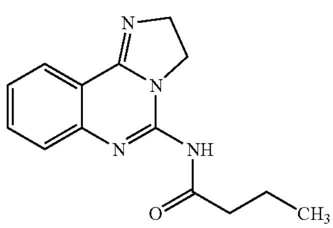 | 256.31 | 257 | 121-122 | D |
| 2-329 | 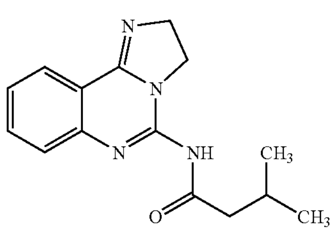 | 270.34 | 271 | 154 (dec.) | D |
| 2-330 | 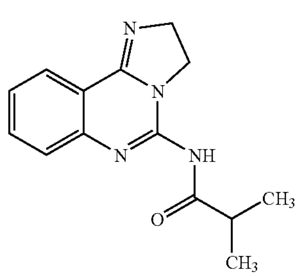 | 256.31 | 257 | 104-105 | D |

TABLE 2-continued

| Ex. No. | Structure | MW | MASS | mp/° C. | in vitro PI3K-gamma |
|---|---|---|---|---|---|
| 2-331 | 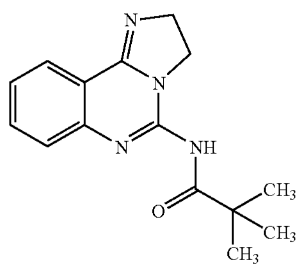 | 270.34 | 271 | 135-136 | D |
| 2-332 | 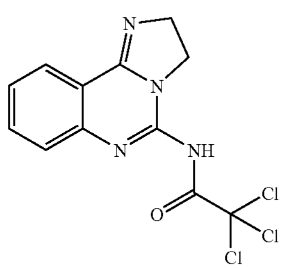 | 331.59 | 331 | 194 (dec.) | C |
| 2-333 | 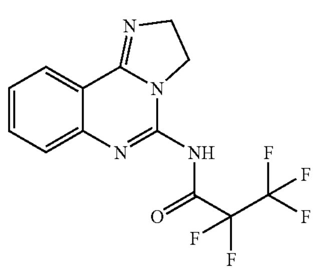 | 332.23 | 333 | 210-211 | D |
| 2-334 | 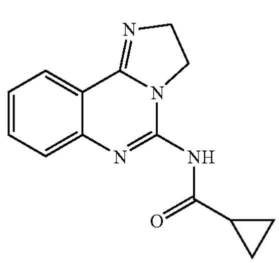 | 254.29 | 255 | 164-165 | D |
| 2-335 | 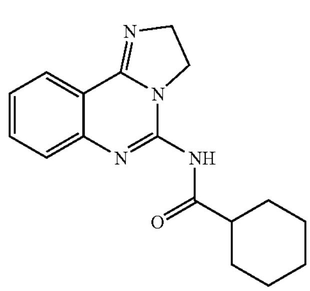 | 296.38 | 297 | 170-172 | D |

TABLE 2-continued

| Ex. No. | Structure | MW | MASS | mp/° C. | in vitro PI3K-gamma |
|---|---|---|---|---|---|
| 2-336 | 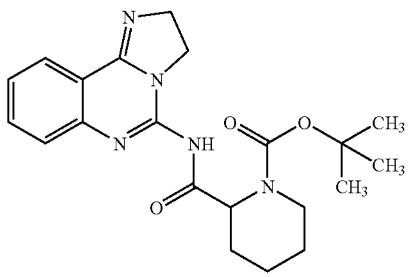 | 397.48 | 398 | amorphous | D |
| 2-337 | 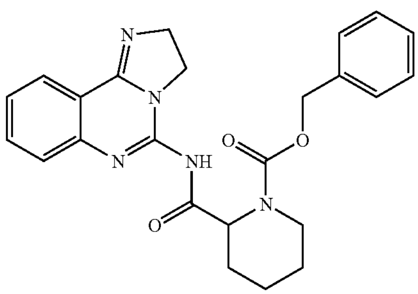 | 431.50 | 432 | 119-120 | D |
| 2-338 | 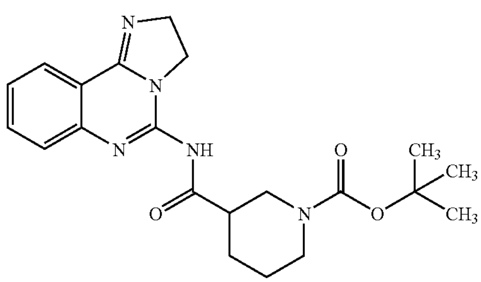 | 397.48 | 398 | 147-148 | D |
| 2-339 | 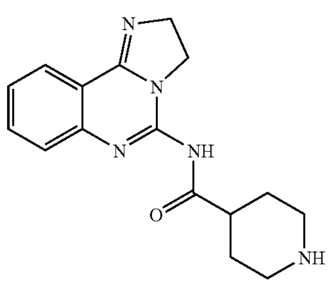 | 297.36 | 298 | 179-180 | D |
| 2-340 | 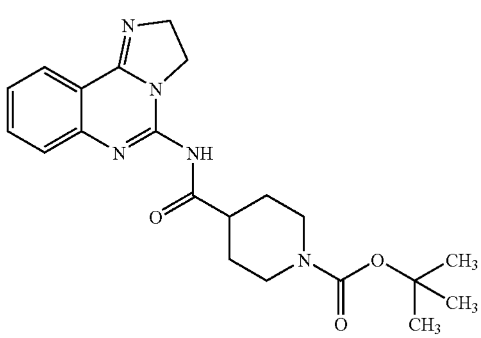 | 397.48 | 398 | amorphous | D |

TABLE 2-continued

| Ex. No. | Structure | MW | MASS | mp/° C. | in vitro PI3K-gamma |
|---|---|---|---|---|---|
| 2-341 | 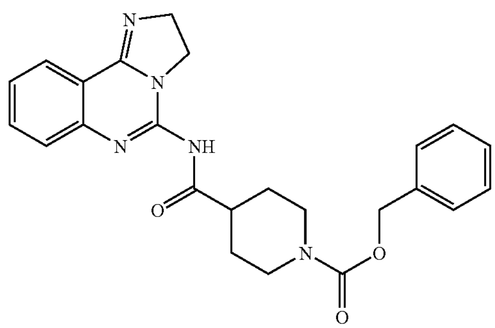 | 431.50 | 432 | 111-112 | D |
| 2-342 | 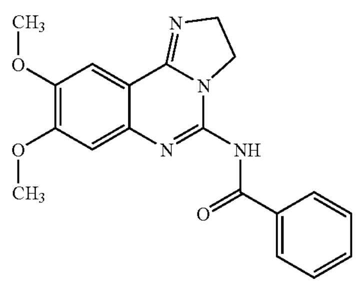 | 350.38 | 351 | amorphous | C |
| 2-343 | 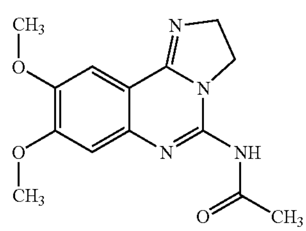 | 288.31 | 289 | 240-241 | D |
| 2-344 | 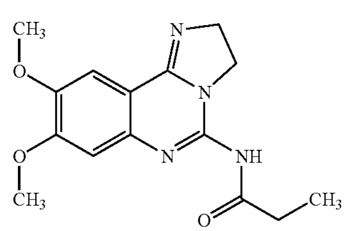 | 302.34 | 303 | 224-225 | D |
| 2-345 | 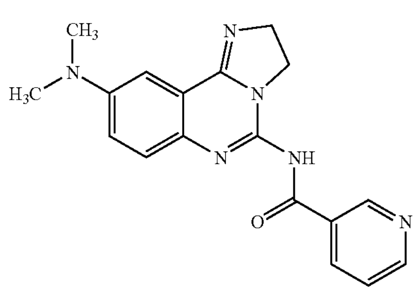 | 334.38 | 335 | 269 | C |

TABLE 2-continued
| Ex. No. | Structure | MW | MASS | mp/° C. | in vitro PI3K-gamma |
|---|---|---|---|---|---|
| 2-346 | 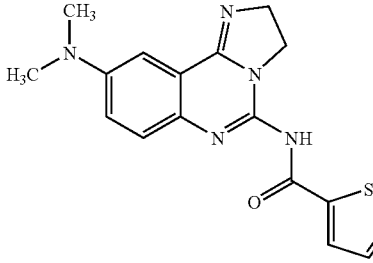 | 339.42 | 340 | 272 | D |
| 2-347 | 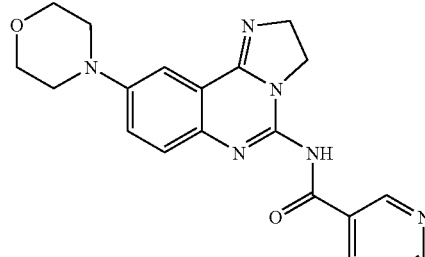 | 376.42 | 377 | 244 | D |
| 2-348 | 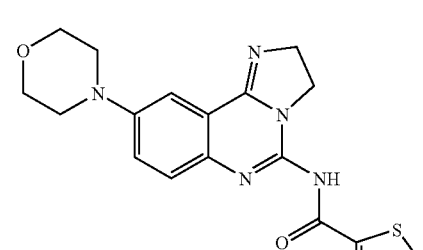 | 381.46 | 382 | 124 | D |
| 2-349 | 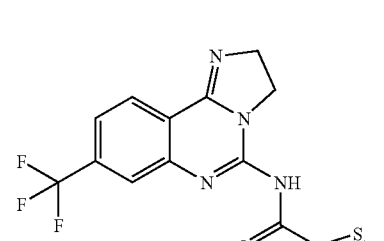 | 364.35 | 365 | 226 | B |
| 2-350 | 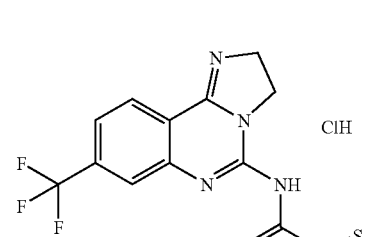 | 400.81 | 365 | 292 | C |

TABLE 2-continued

| Ex. No. | Structure | MW | MASS | mp/° C. | in vitro PI3K-gamma |
|---|---|---|---|---|---|
| 2-351 | 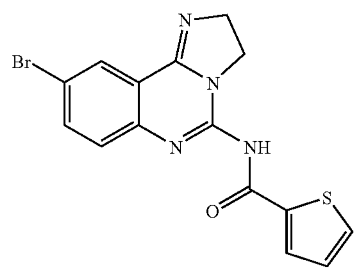 | 375.25 | 376 | 232 | D |
| 2-352 | 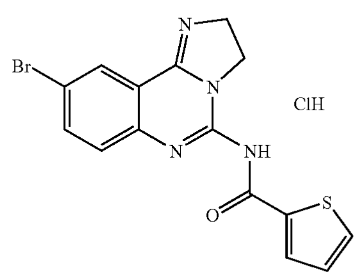 | 411.71 | 376 | 275 | C |
| 2-353 | 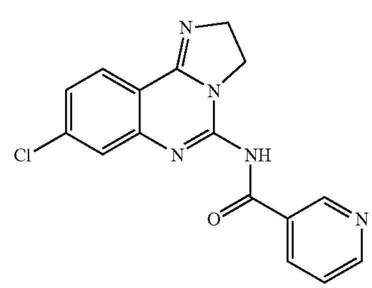 | 325.76 | 326 | 254 | B |
| 2-354 | 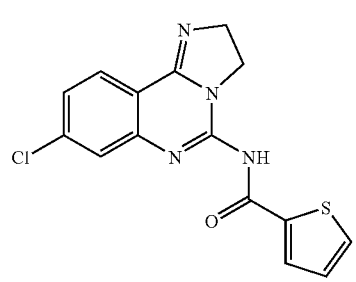 | 330.80 | 331 | 228 | C |
| 2-355 | 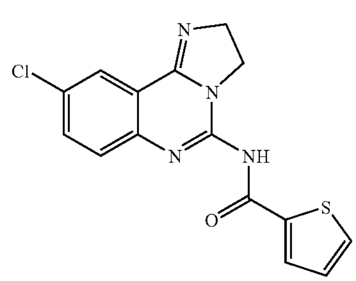 | 330.80 | 331 | 174 | C |

TABLE 2-continued

| Ex. No. | Structure | MW | MASS | mp/° C. | in vitro PI3K-gamma |
|---|---|---|---|---|---|
| 2-356 | 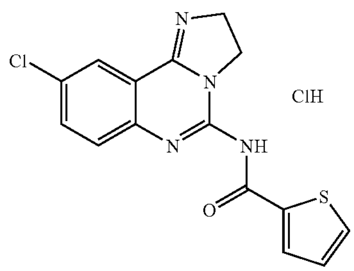 | 367.26 | 331 | 276 | B |
| 2-357 | 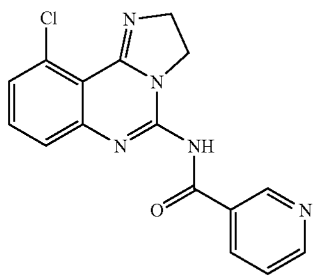 | 325.76 | 326 | 243 | C |
| 2-358 | 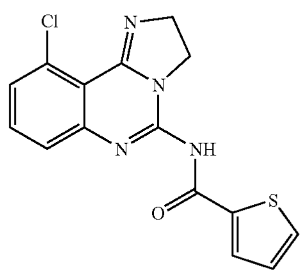 | 330.80 | 331 | 233 | D |
| 2-359 | 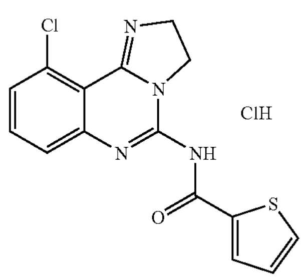 | 367.26 | 331 | 227 | C |
| 2-360 | 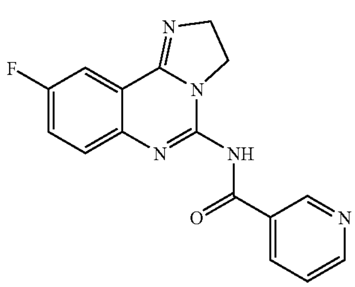 | 309.31 | 310 | 242 | C |

TABLE 2-continued

| Ex. No. | Structure | MW | MASS | mp/° C. | in vitro PI3K-gamma |
|---|---|---|---|---|---|
| 2-361 | 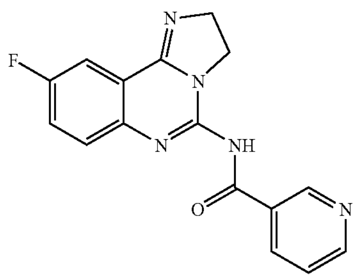 | 314.34 | 214 | 315 | C |
| 2-362 | 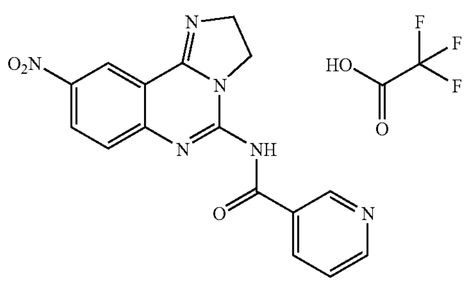 | 450.34 | 336 | 224 | C |
| 2-363 | 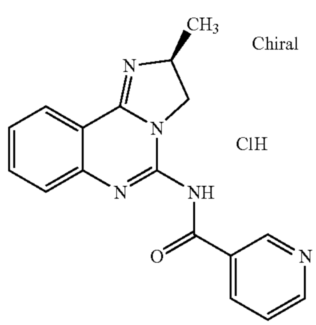 | 341.80 | 306 | 204 (dec.) | D |
| 2-364 | 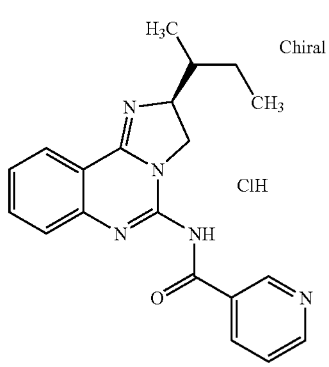 | 383.88 | 348 | 230-240 | D |

TABLE 2-continued

| Ex. No. | Structure | MW | MASS | mp/° C. | in vitro PI3K-gamma |
|---|---|---|---|---|---|
| 2-365 | 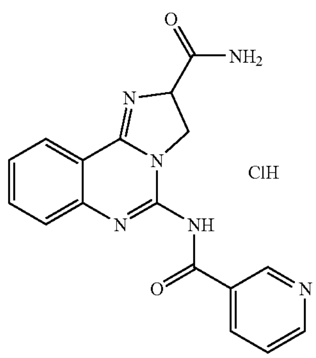 | 370.80 | 335 | 274 (dec.) | D |
| 2-366 | 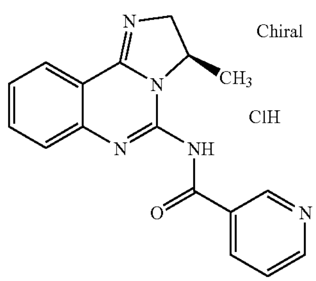 | 341.80 | 306 | 270 (dec.) | D |
| 2-367 | 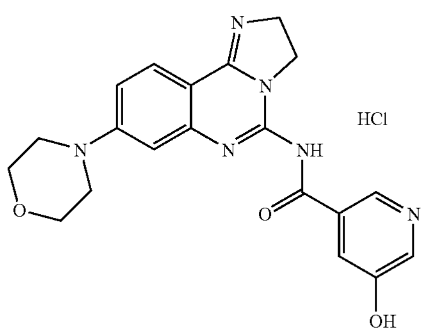 | 428.88 | 398 | 273-274 | A |
| 2-368 | 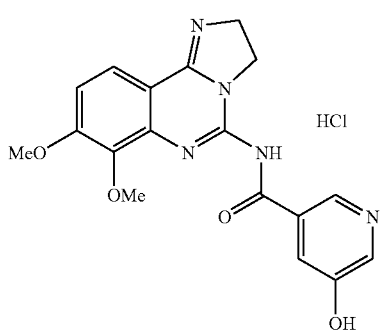 | 403.83 | 368 | 240 (dec.) | A |

Example 3-1

(Z)-2-Imidazo[1,2-c]quinazolin-5-yl-1-(2-thienyl)ethenol

(1) 2-(1H-Imidazol-2-yl)aniline

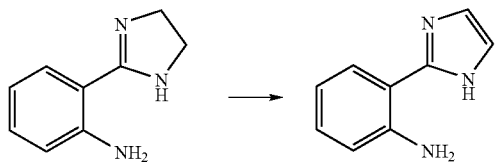

A mixture of 2-(4,5-dihydro-1H-imidazol-2-yl)aniline hydrobromide (50.0 mg, 0.207 mmol) and manganese dioxide (170 mg, 1.96 mmol) in N,N'-dimethylpropylenurea (2.0 mL) was heated at 150. (bath temp.). After 1 hour, the reaction mixture was cooled to room temperature, poured into a solution of hydroxylamine hydrochloride (0.5 g) in water (50 mL), and the resulting mixture was extracted with ethyl acetate. The separated organic layer was washed with brine, dried over magnesium sulfate, filtered, concentrated under reduced pressure. The crude residue was triturated with isopropylether, and the precipitate was removed by filtration. The filtrate was concentrated under reduced pressure, and the residue was purified by preparative thin layer chromatography (silica-gel, ethyl acetate as the eluent) to give 2-(1H-imidazol-2-yl)aniline (20 mg, 61% yield).

(2) Ethyl 3-oxo-3-(2-thienyl)propanoate

To a suspension of 2-thiophenecarboxylic acid (6.48 g, 50.57 mmol) in tetrahydrofurane (100 ml) at 5. was added 1,1'-Carbonyldiimidazole (8.61 g, 53.09 mmol) by portions. The mixture was allowed to warm to room temperature, and the stirring was continued for 1 hour. The reaction mixture was added into a suspension mixture of magnesium chloride (4.86 g, 51.07 mmol) and potassium 3-ethoxy-3-oxopropanoate (12.91 g, 75.85 mmol) in tetrahydrofurane (50 ml). After being stirred at 50. for 2 hours and at room temperature overnight, the reaction mixture was poured into water, and then extracted with ethyl acetate. The extract was washed with brine, dried over magnesium sulfate, filtered, and concentrated under reduced pressure. The residue was purified by column chromatography on silica-gel (ethyl acetate/ hexane, 15/85) to give ethyl 3-oxo-3-(2-thienyl)propanoate (7.83 g, 78% yield) as a yellow oil.

(3) (Z)-2-imidazo[1,2-c]quinazolin-5-yl-1-(2-thienyl)ethenol

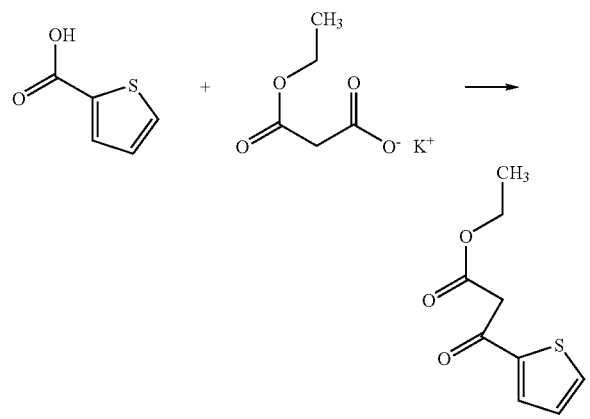

A mixture of 2-(1H-imidazol-2-yl)aniline (60.0 mg, 0.38 mmol), ethyl3-oxo-3-(2-thienyl)propanoate (74.7 mg, 0.38 mmol) and p-tolenesulfonicacid monohydrate (36.1 mg, 0.19 mmol) in toluene (30 ml) was heated at reflux for 2 hours. After cooling to room temperature, the reaction mixture was poured into aqueous saturate NaHCO$_3$ solution, and the resulting mixture was extracted with ethyl acetate. The extract was washed with brine, dried over magnesium sulfate, filtered, and concentrated under reduced pressure. The residue was purified by column chromatography on silica-gel (ethyl acetate/ hexane, 2/3-1/1) to give (Z)-2-imidazo[1,2-c]quinazolin-5-yl-1-(2-thienyl)ethenol (37.0 mg, 33% yield) as a yellow powder.

Melting point: 128° C.

Mass spectrometry: 294

In vitro PI3K-β inhibitory activity:

In vitro PI3K-γ inhibitory activity: D $^1$H-NMR (300 MHz, CDCl$_3$): δ 6.11 (1H, s), 7.16 (1H, dd, J=3.8, 4.9 Hz), 7.34-7.41 (2H, m), 7.53-7.60 (3H, m), 7.64 (1H, d, J=1.7 Hz), 7.73 (1H, dd, J=1.1, 3.8 Hz), 8.34 (1H, dd, J=0.9, 7.8 Hz), 14.70 (1H, bs).

Example 3-2

(Z)-2-imidazo[1,2-c]quinazolin-5-yl-1-(2-thienyl)ethenol hydrochloride

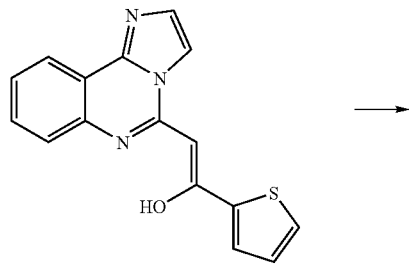

To a solution of (Z)-2-imidazo[1,2-c]quinazolin-5-yl-1-(2-thienyl)ethenol (0.06 g, 0.07 mmol) in chloroform (1.0 ml) was added a 4N solution of HCl in 1,4-dioxane (0.5 ml). The mixture was diluted with ethyl ether, and the resulting precipitate was collected by filtration, washed with ethyl ether, and dried under reduced pressure to give (2)-2-imidazo[1,2-c]quinazolin-5-yl-1-(2-thienyl)ethenol hydrochloride (0.07 g, quantitative) as a yellow solid.

Melting point: 263° C. (decomposition)

Mass spectrometry: 294

In vitro PI3K-β inhibitory activity:

In vitro PI3K-γ inhibitory activity: D $^1$H-NMR (300 MHz, DMSO-d$_6$): δ 6.79 (1H, s), 7.28 (1H, dd, J=3.8, 4.9 Hz), 7.45 (1H, t, J=7.0 Hz), 7.66-7.77 (2H, m), 7.82 (1H, d, 1.7), 7.91 (1H, dd, J=1.1, 5.0 Hz), 8.17 (1H, dd, J=1.1, 3.8 Hz), 8.30 (1H, dd, J=1.0, 8.0 Hz), 8.62 (1H, d, J=1.7 Hz), 14.36 (1H, br).

Example 4-1

N-Imidazo[1,2-c]quinazolin-5-ylnicotinamide (1) Imidazo[1,2-]quinazolin-5-amine

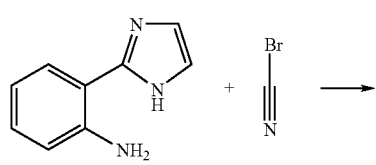

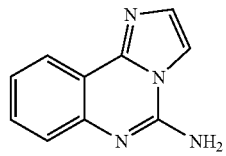

To a solution of 2-(1H-1indazol-2-yl)aniline (0.06 g, 0.38 mmol) in methanol (3 ml) was added cyanogen bromide (0.05 g, 0.45 mmol). The resulting mixture was stirred at room temperature overnight. The reaction mixture was poured into water, and the resulting precipitate was collected by filtration, washed with acetone, and dried under reduced pressure to give imidazo[1,2-c]quinazolin-5-amine hydrobromide (0.06 g, 61% yield) as a white solid.

(2) N-Imidazo[1,2-c]quinazolin-5-ylnicotinamide

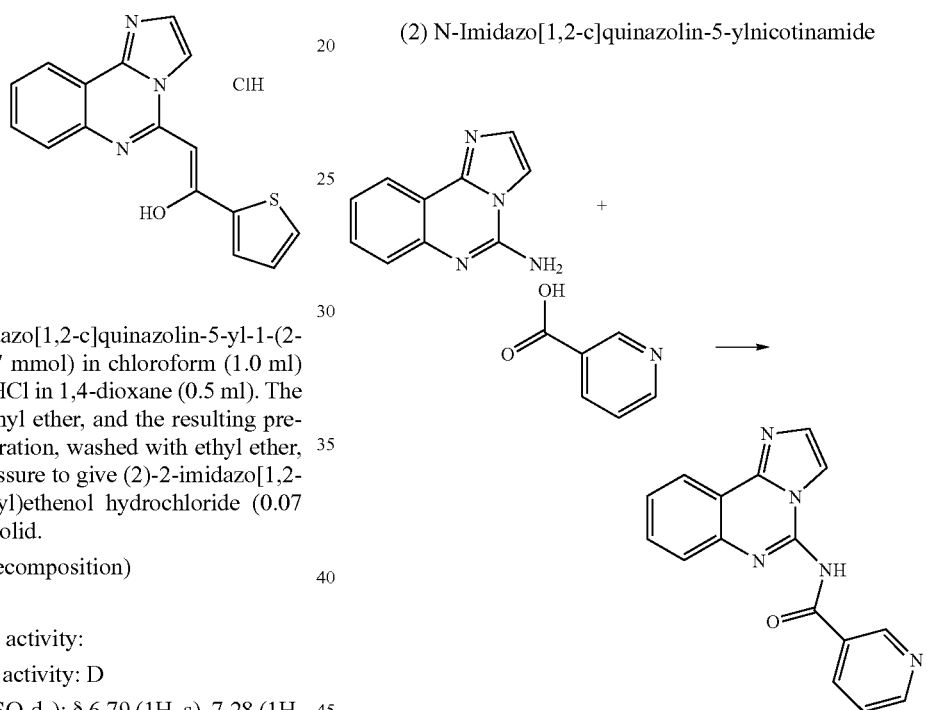

To a mixture of imidazo[1,2-c]quinazolin-5-amine hydrobromide (93 mg, 0.35 mmol) and nicotinic acid (124 mg, 1.01 mmol) and DMF (2.5 ml) at room temperature was added benzotriazole-1-yl-oxy-tris-pyrrolidino-phosphonium hexafluorophosphate (525 mg, 1.01 mmol) followed by N,N-diisopropylethyl amine (0.264 ml, 1.51 mmol), and the mixture was stirred at 80. for 6 hours. After cooling to room temperature, the reaction mixture was poured into aqueous saturated NaHCO$_3$ solution. The resulting precipitate was collected by filtration, washed with acetone, and dried under reduced pressure to give N-imidazo[1,2-c]quinazolin-5-ylnicotinamide (40 mg, 39% yield) as a white solid.

Melting point: 223-224° C. (decomposition)

Mass spectrometry: 290

In vitro PI3K-β inhibitory activity:

In vitro PI3K-γ inhibitory activity: C $^1$H-NMR (300 MHz, DMSO-d$_6$): δ 7.53-7.62 (3H, m), 7.70 (1H, t, J=7.34 Hz), 8.00 (1H, d, J=8.10 Hz), 8.30 (1H, d, J=7.91 Hz), 8.44 (1H, s), 8.63 (1H, d, J=7.72 Hz), 8.81 (1H, dd, J=1.5, 4.7 Hz), 9.49 (1H, s), 13.49 (1H, br).

Example 4-2

N-Imidazo[1,2-c]quinazolin-5-ylnicotinamide hydrochloride

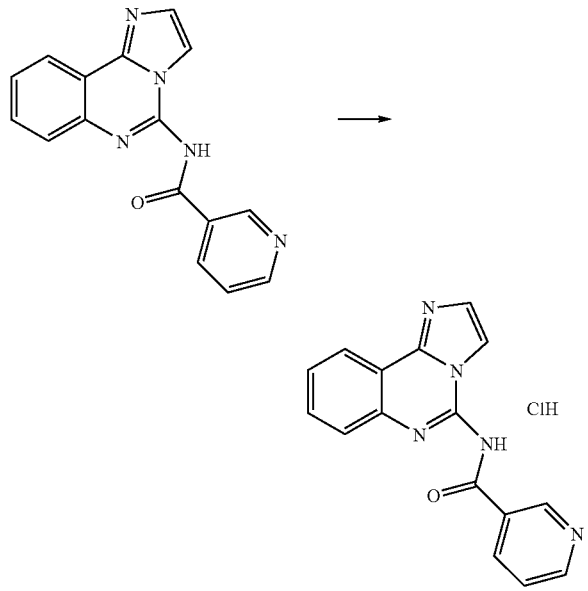

To a solution of N-imidazo[1,2-c]quinazolin-5-ylnicotinamide (40 mg, 0.14 mmol) in methanol (20 ml) was added a 4N solution of HCl in 1,4dioxane (0.5 ml). The mixture was concentrated under reduced pressure. The resulting solid was collected by filtration, washed with tetrahydrofurane and dried under reduced pressure to give N-imidazo[1,2-c]quinazolin-5-ylnicotinamide hydrochloride (40 mg, 89% yield) as a white solid.

Melting point: 228° C. (decomposition)
Mass spectrometry: 290
In vitro PI3K-β inhibitory activity:
In vitro PI3K-γ inhibitory activity: C
$^1$H-NMR (300 MHz, DMSO-d$_6$): δ 7.60 (2H, br), 7.65 (1H, t, J=7.5 Hz), 7.82 (1H, dd, J=7.3, 8.1 Hz), 7.92 (1H, s), 8.02 (1H, dd, J=5.5, 7.9 Hz), 8.54 (1H, d, J=8.3 Hz), 8.73 (1H, s), 9.02 (1H, dd, J=1.3, 5.3 Hz), 9.07 (1H, d, J=7.53 Hz), 9.67 (1H, s).

REFERENCES

[1] Wymann M P, Sozzani S, Altruda F, Mantovani A, Hirsch E: Lipids on the move: phosphoinositide 3-kinases in leukocyte function. Immunol. Today 2000; 6: 260-264.
[2] Stein R C, Waterfield M D: PI3-kinase inhibition: a target for drug development? Mol. Med. Today. 2000; 6: 347-357.
[3] Sean A. Weaver, Stephen G. Ward: Phosphoinositide 3-kinases in the gut: a link between inflammation and cancer? Trends in Molecular Medicine 2001; 7:455-462.
[4] Vanhaesebroeck B, Leevers S J, Panayotou G., Waterfield M D: Phosphoinositide 3-kinases: a conserved family of signal transducers. Trends Biochem. Sci. 1997; 22: 267-272.
[5] Fruman D A, Meyers R E, Cantley L C: Phosphoinositide kinases. Annu. Rev. Biochem. 1998; 67: 481-507
[6] Wymann M P, Pirola L: Structure and function of phosphoinositide 3-kinases. Biochim Biophys. Acta 1998; 1436: 127-150.
[7] Sotsios Y, Ward S G: Phosphoinositide 3-kinase: a key biochemical signal for cell migration in response to chemokines. Immunol. Rev. 2000; 177: 217-235.
[8] Toker A, Cantley L C: Signalling through the lipid products of phosphoinositide-3-OH kinase. Nature 1997; 387: 678-676.
[9] Stephens L R, Jackson T R, Hawkins P T: Agonist-stimulated synthesis of phosphatidylinositol(3,4,5)-trisphosphate: a new intracellular signalling system? Biochim. Biophys. Acta. 1993; 1179: 27-75.
[10] Stephens L R, Eguinoa A, Erdjumentbromage H, Lui M, Cooke F, Coadwell J, Smrcka A S, Thelen M, Cadwallader K, Tempst P, Hawkins PT: The G beta gamma sensitivity of a PI3K is dependent upon a tightly associated adaptor, p101. Cell 1997; 89: 105-114.
[11] Stoyanov B, Volinia S, Hanck T, Rubio I, Loubtchenkov M, Malek D, Stoyanova S, Van-Haesebroeck B, Dhand R, Nurnberg B, Gierschik P, Seedorf K, Hsuan J J, Waterfield M D, Wetzker R: Cloning and characterization of a G protein-activated human phosphoinositide-3 kinase. Science 1995; 269: 690-693.
[12] Krugmann S, Hawkins P T, Pryer N, Brasehnann S: Characterizing the interactions between the two subunits of the p101/p110gamma phosphoinositide 3-kinase and their role in the activation of this enzyme by G beta gamma subunits. J. Biol. Chem. 1999; 274: 17152-17158.
[13] Sasaki T, Suzuki A, Sasaki J, Penninger J M: Phosphoinositide 3-kinases in immunity: lessons from knockout mice. J. Biochem. 2002; 131: 495-501.
[14] Sasaki T, Irie-Sasaki J, Jones R G, Oliveira-dos-Santos A J, Stanford W L, Bolon B, Wakeham A, Itie A, Bouchard D, Kozieradzki, Joza N, Mak T W, Ohashi P S, Suzuki A, Penninger J M: Function of PI3Kγ in thymocyte development, T cell activation, and neutrophil migration. Science 2000; 287: 1040-1046.
[15] Li Z, Jiang H, Xie W, Zhang Z, Smrcka A V, Wu D: Roles of PLC-beta2 and -beta3 and PI3Kγ in chemoattractant-mediated signal transduction. Science 2000; 287: 1046-1049.
[16] Hirsch E, Katanaev V L, Garlanda C, Azzolino O, Pirola L, Silengo L, Sozzani S, Mantovani A, Altruda F, Wymann M P: Central role for G protein-coupled phosphoinositide 3-kinase γ in inflammation. Science 2000; 287: 1049-1053.
[17] Michael A. Crackower, Gravin Y. Oudit, Ivona Kozieradzki, Renu Sarao et al: Regulation of myocardial contractility and cell size by distinct PI3K-PTEN signaling pathways. Cell. 2002; 110: 737-749.
[18] Emilio Hirsch, Ornella Bosco et al: Resistance to thromboembolism in PI3Kγ-deficient mice. The FASEB Journal. 2001; 15: 2019-2021.
[19] Ui M, Okada T, Hazeki K, Hazeki O: Wortmannin as a unique probe for an intracellular signalling protein, phosphoinositide 3-kinase. Trends Biochem. Sci. 1995; 20: 303-307.
[20] Vlahos C J, Matter W F, Hui K Y, Brown R F: A specific inhibitor of phosphatidylinositol 3-kinase, 2-(4-morpholino)-8-phenyl-4H-1-benzopyran-4-one (LY294002). J. Biol. Chem. 1994; 269: 5241-5248.

The invention claimed is:

1. A method for treating or controlling asthma, atopic dermatitis, rhinitis, allergic diseases, chronic obstructive pulmonary disease (COPD), septic shock, joint diseases, an autoimmune pathology, rheumatoid arthritis, Grave's disease, diabetes, cancer, myocardial contractility disorders, or thromboembolism in a human or animal, the method comprising administering to the human or animal an effective amount of a compound of formula (I)

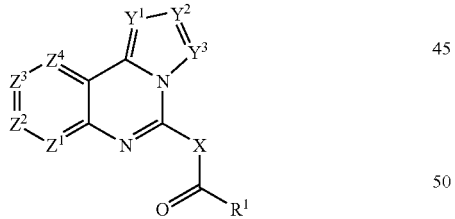

wherein
X represents $CR^5R^6$ or NH;
$Y^1$ represents $CR^3$ or N;
Chemical bond between $Y^2$—$Y^3$ represents a single bond or double bond, with the proviso that when the $Y^2$—$Y^3$ represents a double bond, $Y^2$ and $Y^3$ independently represent $CR^4$ or N, and
when $Y^2$—$Y^3$ represents a single bond, $Y^2$ and $Y^3$ independently represent $CR^3R^4$ or $NR^4$;
$Z^1$, $Z^2$, $Z^3$ and $Z^4$ independently represent CH, $CR^2$ or N;
$R^I$ represents
  $C_{1-6}$ alkyl optionally substituted by mono-, di- or trihalogen, phenyl, methoxyphenyl, phenoxy, or thienyl,
  $C_{1-6}$ alkoxy optionally substituted by mono-, di- or trihalogen, phenyl, methoxyphenyl, phenoxy, or thienyl
or
  one of the following carbocyclic and heterocyclic rings selected from the group consisting of cyclopropyl, cyclohexyl, piperidinyl, piperazinyl, pyrrolyl, pyrazolyl, furyl, thienyl, thiazolyl, isothiazolyl, oxazolyl, isoxazolyl, imidazolyl, isoimidazolyl, pyrazolyl, 1,2,3-thiadiazolyl, 1,2,4-thiadiazolyl, 1,2,5-thiadiazolyl, 1,3,4-thiadiazolyl, 1,2,3-oxadiazolyl, 1,2,4-oxadiazolyl, 1,2,5-oxadiazolyl, 1,3,4-oxadiazolyl, 1,2,3-triazole, 1,2,4-triazole, 1,2,5-triazole, 1,3,4-triazole, phenyl, pyridyl, pyrazinyl, pyrimidinyl, pyridazinyl, 1-benzothiophenyl, benzothiazolyl, benzimidazolyl, 3H-imidazo[4,5-b]pyridinyl, benzotriazolyl, indolyl, indazolyl, imidazo[1,2-a]pyridinyl, quinolinyl, and 1,8- naphthyridinyl,
wherein
said carbocyclic and heterocyclic rings optionally substituted with 1 to 3 substituents selected from the group consisting of hydroxy, halogen, nitro, cyano, carboxy, amino, N—($C_{1-6}$alkyl)amino, N,N-di($C_{1-6}$alkyl)amino, N—($C_{1-6}$acyl)amino, N—($C_{1-6}$alkoxycarbonyl)amino, N-(formyl)-N—($C_{1-6}$alkyl)amino, N[N,N-di($C_{1-6}$alkyl)amino methylene]amino, N[N,N-di($C_{1-6}$alkyl)amino ($C_{1-6}$alkylene)methylene]amino, N—[N,N-di($C_{1-6}$alkyl)amino $C_{2-6}$alkylenyl]amino, $C_{1-6}$alkylthio, $C_{1-6}$alkylanesulfonyl, sulfamoyl, $C_{1-6}$alkoxy, $C_{1-6}$alkoxycarbonyl, pyrrolyl, imidazolyl, pyrazolyl, pyrrolidinyl, pyridyl, phenyl $C_{1-6}$alkoxycarbonyl,
thiazolyl optionally substituted by pyridyl, piperazinyl optionally substituted by $C_{1-6}$ alkyl or $C_{1-6}$alkoxy and $C_{1-6}$alkyl optionally substituted by mono-, di- or trihalogen;

$R^2$ represents hydroxy, halogen, nitro, cyano, carboxy, amino, N—($C_{1-6}$alkyl)amino, N-(hydroxy $C_{1-6}$alkyl)amino, N,N-di($C_{1-6}$alkyl)amino, N-(hydroxy $C_{1-6}$alkyl)-N- ($C_{1-6}$alkyl)amino, $C_{2-6}$alkenyl, $C_{1-6}$alkoxycarbonyl, aminocaronyl, $C_{1-6}$acyloxy, aminoC$_{1-6}$ acyloxy, furyl, morpholino, phenyl, piperidino, aryl,
pyrrolidinyl optionally substituted by $C_{1-6}$acylamino,
piperidino optionally substituted by hydroxy, $C_{1-6}$ alkyl, carboxy, aminocarbonyl, N—($C_{1-6}$ alkyl)aminocarbonyl, or N,N-di($C_{1-6}$ alkyl)aminocarbonyl,
piperazinyl optionally substituted by
$C_{1-6}$alkyl,
$C_{1-6}$ alkyl optionally substituted by cyano, mono-, di- or tri-halogen, hydroxy, amino, N—($C_{1-6}$ alkyl)amino, N-(hydroxy $C_{1-6}$alkyl)amino, N,N-di($C_{1-6}$alkyl)amino, $C_{3-6}$ cycloalkyl, tetrazolyl, tetrahydropyranyl, morpholino, phthalimidyl, 2-oxo-1,3oxazolidinyl, phenyl, —C(O)—$R^{201}$, pypyrrolidinyl optionally substituted by $C_{1-6}$acylamino,
piperidino optionally substituted by hydroxy, $C_{1-6}$ alkyl, carboxy, aminocarbonyl, N—($C_{1-6}$alkyl)aminocarbonyl, or N, N-di($C_{1-6}$alkyl)aminocarbonyl, or piperazinyl optionally substituted by $C_{1-6}$ alkyl,
wherein
$R^{201}$ represents hydroxy, amino, N—($C_{1-6}$alkyl)amino, N,N-di($C_{1-6}$alkyl)amino, N-(halobenzyl)amino, $C_{1-6}$alkyl, $C_{1-6}$ alkoxy, tetrazolyl, tetrahydropyranyl, morpholino,
pyrrolidinyl optionally substituted by $C_{1-6}$acylamino, piperidino optionally substituted by
hydroxy, $C_{1-6}$ alkyl, carboxy, aminocarbonyl, N—($C_{1-6}$ alkyl)aminocarbonyl, or N,N-di($C_{1-6}$alkyl)aminocarbonyl,
or
piperazinyl optionally substituted by $C_{1-6}$ alkyl, $C_{1-6}$ alkoxy optionally substituted by cyano, mono-, di- or tri- halogen, hydroxy, $C_{1-6}$alkoxy, hydroxy $C_{1-6}$ alkoxy, amino, N—($C_{1-6}$alkyl)amino, N,N-di($C_{1-6}$alkyl)amino, pyrrolyl, tetrazolyl, tetrahydropyranyl, morpholino, phthalimidyl, 2-oxo-1,3oxazolidinyl, phenyl, —C(O)—$R^{201}$,
pyrrolidinyl optionally substituted by $C_{1-6}$acylamino, piperidino optionally substituted by hydroxy, $C_{1-6}$ alkyl, carboxy, aminocarbonyl, N—(C1-6-alkyl)aminocarbonyl, or N,N-di(C 1-6alkyl)aminocarbonyl,
or
piperazinyl optionally substituted by $C_{1-6}$ alkyl,
wherein
$R^{201}$ represents hydroxy, amino, N—($C_{1-6}$alkyl)amino, N,N-di($C_{1-6}$alkyl)amino, N-(halobenzyl)amino, $C_{1-6}$ alkyl, $C_{1-6}$ alkoxy, amino $C_{2-6}$ alkylenyl, tetrazolyl, tetrahydropyranyl, morpholino, pyrrolidinyl optionally substituted by $C_{1-6}$acylamino, piperidino optionally substituted by hydroxy, $C_{1-6}$ alkyl, carboxy, aminocarbonyl, N—($C_{1-6}$alkyl)aminocarbonyl, or N,N-di($C_{1-6}$alkyl)aminocarbonyl,
or
piperazinyl optionally substituted by $C_{1-6}$alkyl;
$R^3$ represents hydrogen, halogen, $C_{1-6}$ alkyl optionally substituted by aminocarbonyl, aryl$C_{1-6}$ alkoxy, or mono-, di- or tri-halogen;
$R^4$ represents hydrogen or $C_{1-6}$ alkyl;
$R^5$ represents hydrogen or $C_{1-6}$ alkyl; and
$R^6$ represents hydrogen, halogen or $C_{1-6}$ alkyl,
a tautomeric or stereoisomeric form, or a physiologically acceptable salt thereof.

2. The method of claim 1, wherein
X represents $CR^5R^6$ or NH;
$Y^1$ represents N;
$Y^2$ and $Y^3$ represent $CR^3R^4$;
Chemical bond between $Y^2$—$Y^3$ represents a single bond.
$Z^4$ represents CH;
$Z^1$, $Z^2$ and $Z^3$ independently represent CH, $CR^2$ or N;
$R^1$ represents
$C_{1-6}$ alkyl optionally substituted by mono-, di- or tri-halogen, phenyl, methoxyphenyl, phenoxy, or thienyl,
$C_{1-6}$ alkoxy optionally substituted by phenyl phenoxy, thienyl or mono-, di- or tri- halogen,
or
one of the following carbocyclic and heterocyclic rings selected from the group consisting of cyclopropyl, cyclopentyl, cyclohexyl, piperidinyl, piperazinyl, pyrrolyl, pyrazolyl, furyl, thienyl, thiazolyl, isothiazolyl, oxazolyl, isoxazolyl, imidazolyl, isoimidazolyl, pyrazolyl, 1,2,3-thiadiazolyl, 1,2,4-thiadiazolyl, 1,2,5-thiadiazolyl, 1,3,4-thiadiazolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,2,5-triazolyl, 1,3,4-triazolyl, phenyl, pyridyl, pyrazinyl, pyrimidinyl, pyridazinyl, 1-benzothiophenyl, benzothiazolyl, benzimidazolyl, 3H-imidazo[4,5-b]pyridinyl, benzotriazolyl, indolyl, indazolyl, imidazo[1,2-a]pyridinyl, quinolinyl, and 1,8-naphthyridinyl,
wherein
said carbocyclic and heterocyclic rings optionally substituted with 1 to 3 substituents selected from the group consisting of hydroxy, halogen, nitro, cyano, carboxy, amino, N—($C_{1-6}$ alkyl)amino, N-(hydroxy $C_{1-6}$ alkyl)amino, N,N-di($C_{1-6}$alkyl)amino, N—($C_{1-6}$ acyl)amino, N—($C_{1-6}$ alkoxycarbonyl)amino, N-(formyl)-N—($C_{1-6}$alkyl)amino, N,N-di($C_{1-6}$alkyl) amino ($C_{2-6}$alkenyl) amino, N—($C_{1-6}$alkane)sulfonyl amino, N[N,N-di($C_{1-6}$ alkyl)amino methylene] amino, $C_{1-6}$alkylthio, $C_{1-6}$ alkanesulfonyl, sulfamoyl, $C_{1-6}$alkoxy, $C_{1-6}$alkoxycarbonyl, pyrrolyl, imidazolyl, pyrazolyl, pyrrolidinyl, pyridyl, phenyl $C_{1-6}$alkoxycarbonyl, thiazolyl optionally substituted by pyridyl, piperazinyl optionally substituted by $C_{1-6}$ alkyl or $C_{1-6}$alkoxy and $C_{1-6}$alkyl optionally substituted by mono-, di- or tri- halogen;
$R^2$ represents halogen, hydroxy, nitro, cyano, amino, N—($C_{1-6}$alkyl)amino, N,N-di($C_{1-6}$alkyl)amino, N-(hydroxy$C_{1-6}$ alkyl)-N—($C_{1-6}$alkyl)amino, ($C_{2-6}$)alkenyl, $C_{1-6}$alkoxycarbonyl, aminocarbonyl, furyl, piperidino, morpholino, phenyl, pyrrolidinyl optionally substituted by N—($C_{1-6}$ acyl)amino, or N—($C_{1-6}$alkyl)carbonylamino, piperidino optionally substituted by hydroxy, piperazinyl optionally substituted by $C_{1-6}$alkyl, phenyl$C_{1-6}$alkyl, $C_{1-6}$alkoxycarbonyl, or aminocarbonyl;
$C_{1-6}$ alkyl optionally substituted by amino, cyano, $C_{1-6}$alkoxycarbonyl, morpholino, or mono-, di- or tri-halogen,
or
$C_{1-6}$ alkoxy optionally substituted by hydroxy, cyano, carboxy, $C_{1-6}$ alkoxy, $C_{1-6}$ acyl, $C_{1-6}$alkoxycarbonyl, amino, N—($C_{1-6}$ alkyl)amino, N—($C_{1-6}$-alkyl)aminocarbonyl, N,N-di($C_{1-6}$ alkyl)amino, N,N-di($C_{1-6}$ alkyl)aminocarbonyl, aminocarbonyl, amino$C_{1-6}$ alkylcarbonyl, N-(halo-benzyl)aminocarbonyl, hydroxy $C_{1-6}$ alkoxy, $C_{3-6}$ cycloalkyl, morpholino, morpholinocarbonyl, pyrrolidinyl, pyrrolyl, piperidino, phthalimidyl, or
piperazinyl optionally substituted by benzyl;
R³ represents hydrogen;
R⁴ represents hydrogen;
R⁵ represents hydrogen; and
R⁶ represents hydrogen.

3. The method of claim 1, wherein
X represents $CR^5R^6$ or NH;
$Y^1$ represents N;
$Y^2$ and $Y^3$ represent $CR^3R^4$;
Chemical bond between $Y^2$—$Y^3$ represents a single bond
$Z^4$ represents CH;
$Z^1$, $Z^2$ and $Z^3$ independently represent N, CH or $CR^2$;
$R^1$ represents cyclopropyl, cyclopentyl, cyclohexyl, 2-furyl, 3-furyl, imidazolyl, pyrimidinyl, pyridazinyl, piperazinyl, 1,2,3-thiadiazolyl, 1,3-benzothiazolyl, quinolyl, 3H-imidazo[4,5-b]pyridinyl, 1H-pyrrol-2-yl optionally substituted by $C_{1-6}$alkyl, 1H-pyrrol-3-yl optionally substituted by $C_{1-6}$alkyl, pyrazolyl optionally substituted by 1 or 2 $C_{1-6}$alkyl, isoxazolyl optionally substituted by 1 or 2 $C_{1-6}$alkyl, 2-thienyl optionally substituted by chloro, nitro, cyano, or $C_{1-6}$ alkyl, 3-thienyl optionally substituted by chloro, nitro, cyano, or $C_{1-6}$ alkyl, piperidinyl optionally substituted by $C_{1-6}$alkoxycarbonyl, or benzyloxycarbonyl, phenyl optionally substituted by 1 to 3 substituents selected from the group consisting of fluoro, chloro, hydroxy, nitro, cyano, carboxy, $C_{1-6}$ alkyl, $C_{1-6}$alkoxy, $C_{1-6}$ alkoxycarbonyl, amino, N—($C_{1-6}$ alkyl)amino, N—($C_{1-6}$ acyl)amino, N—($C_{1-6}$ alkoxycarbonyl)amino, N,N-di($C_{1-6}$alkyl)amino, N-(formyl)-N—$C_{1-6}$ alkyl amino, $C_{1-6}$ alkylthio, $C_{1-6}$alkanesulfonyl, sulfamoyl, pyrrolyl, imidazolyl, pyrazolyl, and piperazinyl optionally substituted by $C_{1-6}$alkyl,
pyridyl optionally substituted by 1 or 2 substituents selected from the group consisting of chloro, hydroxy, carboxy, $C_{1-6}$alkoxy, $C_{1-6}$alkylthio, amino, N—($C_{1-6}$ alkyl)amino, N-(hydroxy$C_{1-6}$alkyl)amino, N,N-di($C_{1-6}$alkyl)amino, N—($C_{1-6}$acyl)amino, N—($C_{1-6}$alkane)sulfonyl amino, N[N,N-di($C_{1-6}$ alkyl)amino methylene]amino, and $C_{1-6}$alkyl optionally substituted by tri halogen,
pyrazinyl optionally substituted by $C_{1-6}$alkyl, 1,3-thiazolyl optionally substituted by 1 or 2 substituents selected from the group consisting of $C_{1-6}$alkyl, pyridyl and N—($C_{1-6}$ alkoxycrbonyl)amino,
indolyl optionally substituted by $C_{1-6}$alkyl,
benzimidazolyl optionally substituted by $C_{1-6}$alkyl or tri-halo $C_{1-6}$alkyl,
1,2,3-benzotriazolyl optionally substituted by $C_{1-6}$alkyl,
1,8-naphthyridinyl optionally substituted by $C_{1-6}$alkyl optionally substituted by tri halogen,
$C_{1-6}$ alkyl optionally substituted by tri- halogen, phenyl, phenoxy, or thienyl,
or
$C_{1-6}$alkoxy optionally substituted by phenyl, phenoxy, or thienyl;
$R^2$ represents fluoro, chloro, bromo, hydroxy, nitro, vinyl, cyano, amino, aminoacetoxy, N—($C_{1-6}$alkyl)amino, N,N-di($C_{1-6}$alkyl)amino, N-(hydroxy$C_{1-6}$alkyl)-N—($C_{1-6}$alkyl)amino, 2-furyl, piperidino, morpholino, phenyl, pyrrolidinyl optionally substituted by acetamido, piperidino optionally substituted by hydroxy, piperazinyl optionally substituted by methyl, benzyl, $C_{1-6}$alkoxycarbonyl, or aminocarbonyl,
$C_{1-6}$alkyl optionally substituted by cyano, tri-fluoro, carboxy, methoxycarbonyl, aminocarbonyl, tert-butoxycarbonyl, tetrahydropyranyl, or morpholino, $C_{1-6}$ alkoxy optionally substituted by hydroxy, cyano, methoxy, methoxycarbonyl, tert-butoxycarbonyl, carboxy, aminoacetyl, dimethylamino, aminocarbonyl, methylaminocarbonyl, dimethylaminocarbonyl, isopropylaminocarbonyl, fluorobenzylaminocarbonyl, cyclopropyl, pyrrolidinyl, piperidino, tetrahydropyranyl, morpholino, morpholinocarbonyl, 2-oxo-1,3-oxazolidin-4-yl, phthalimid-N-yl, or hydroxy $C_{1-6}$ alkyleneoxy,
R³ represents hydrogen;
R⁴ represents hydrogen;
R⁵ represents hydrogen; and
R⁶ represents hydrogen.

4. The method of claim 1, wherein
X represents $CR^5R^6$ or NH;
$Y^1$ represents N;
$Y^2$ and $Y^3$ represent $CR^3R^4$;
Chemical bond between $Y^2$—$Y^3$ represents a single bond
$Z^3$ and $Z^4$ represent CH;
$Z^1$ and $Z^2$ independently represent CH or $CR^2$;
$R^1$ represents cyclopropyl, cyclopentyl, cyclohexyl, 2-furyl, 3-furyl, imidazolyl, 1H-pyrrol-2-yl, 1H-pyrrol-3-yl, pyrimidinyl, pyridazinyl, piperazinyl, 1,2,3-thiadiazolyl, 1,3-benzothiazolyl, quinolyl, 3H-imidazo[4,5-b]pyridinyl,
pyrrolyl optionally substituted by $C_{1-6}$alkyl, pyrazolyl optionally substituted by 1 or 2 $C_{1-6}$alkyl, isoxazolyl optionally substituted by 1 or 2 $C_{1-6}$alkyl, 2-thienyl optionally substituted by chloro, nitro, cyano, or $C_{1-6}$ alkyl, 3-thienyl optionally substituted by chloro, nitro, cyano, or $C_{1-6}$ alkyl,
piperidinyl optionally substituted by $C_{1-6}$alkoxycarbonyl, or benzyloxycarbonyl,
phenyl optionally substituted by 1 to 3 substituents selected from the group consisting of fluoro, chloro, hydroxy, nitro, cyano, carboxy, $C_{1-6}$ alkyl, $C_{1-6}$alkoxy, $C_{1-6}$alkoxycarbonyl, amino, N—($C_{1-6}$ alkyl)amino, N—($C_{1-6}$acyl)amino, N—($C_{1-6}$alkoxycabonyl)amino, N,N-di($C_{1-6}$alkyl)amino, N-(formyl)-N—$C_{1-6}$alkyl amino, $C_{1-6}$ alkylthio, $C_{1-6}$alkanesulfonyl, sulfamoyl, pyrrolyl, imidazolyl, pyrazolyl, and piperazinyl optionally substituted by $C_{1-6}$alkyl,
pyridyl optionally substituted by 1 or 2 substituents selected from the group consisting of chloro, hydroxy, carboxy, $C_{1-6}$alkoxy, $C_{1-6}$alkylthio, amino, N—($C_{1-6}$ alkyl)amino, N-(hydroxy$C_{1-6}$alkyl)amino, N,N-di($C_{1-6}$alkyl)amino, N—($C_{1-6}$acyl)amino, N—($C_{1-6}$alkane)sulfonyl amino, N[N,N-di($C_{1-6}$alkyl)amino methylene]amino, and $C_{1-6}$alkyl optionally substituted by tri halogen,
pyrazinyl optionally substituted by $C_{1-6}$alkyl, 1,3-thiazolyl optionally substituted by
1 or 2 substituents selected from the group consisting of $C_{1-6}$alkyl, pyridyl and N—($C_{1-6}$alkoxycrbonyl)amino, indolyl optionally substituted by $C_{1-6}$alkyl, benzimidazolyl optionally substituted by $C_{1-6}$alkyl or tri-halo $C_{1-6}$alkyl, 1,2,3-benzotriazolyl optionally substituted by $C_{1-6}$alkyl, 1,8-naphthyridinyl optionally substituted by $C_{1-6}$alkyl optionally substituted by tri halogen,
$C_{1-6}$ alkyl optionally substituted by tri- halogen, phenyl, phenoxy, or thienyl,
or
$C_{1-6}$alkoxy substituted by phenyl, phenoxy, or thienyl;

$R^2$ represents fluoro, chloro, bromo, hydroxy, nitro, vinyl, cyano, amino, amino-acetoxy, N-($C_{1-6}$alkyl)amino, N,N-di($C_{1-6}$alkyl)amino, N-(hydroxy$C_{1-6}$alkyl)-N—($C_{1-6}$alkyl)amino, 2-furyl, piperidino, morpholino, phenyl,
pyrrolidinyl optionally substituted by acetamido,
piperidino optionally substituted by hydroxy,
piperazinyl optionally substituted by methyl, benzyl, $C_{1-6}$alkoxycarbonyl, or aminocarbonyl,
$C_{1-6}$ alkyl optionally substituted by cyano tri-fluoro, carboxy, methoxycarbonyl, aminocarbonyl, tert-butoxycarbonyl, tetrahydropyranyl, or morpholino,
or
$C_{1-6}$ alkoxy optionally substituted by hydroxy, cyano, methoxy, methoxycarbonyl, tert-butoxycarbonyl, carboxy, aminoacetyl, dimethylamino, aminocarbonyl, methylaminocarbonyl, dimethylaminocarbonyl, isopropylaminocarbonyl, fluorobenzylaminocarbonyl, cyclopropyl, pyrrolidinyl, piperidino, tetrahydropyranyl, morpholino, morpholinocarbonyl, 2-oxo-1,3-oxazolidin-4-yl, phthalimid-N-yl, or hydroxy $C_{1-6}$ alkyleneoxy;
$R^3$ represents hydrogen;
$R^4$ represents hydrogen;
$R^5$ represents hydrogen; and
$R^6$ represents hydrogen.

5. The method of claim 1, wherein
X represents $CR^5R^6$ or NH;
$Y^1$ represents N;
$Y^2$ and $Y^3$ represent $CR^3R^4$;
Chemical bond between $Y^2$—$Y^3$ represents a single bond
$Z^1$ and $Z^4$ represent CH;
$Z^2$ and $Z^3$ independently represent CH or $CR^2$;
$R^1$ represents cyclopropyl, cyclopentyl, cyclohexyl, 2-furyl, 3-furyl, imidazolyl, 1H-pyrrol-2-yl, 1H-pyrrol-3-yl, pyrimidinyl, piperazinyl, pyridazinyl, 1,2,3-thiadiazolyl, 1,3-benzothiazolyl, quinolyl, 3H-imidazo[4,5-b]pyridinyl,
pyrrolyl optionally substituted by $C_{1-6}$alkyl,
pyrazolyl optionally substituted by 1 or 2 $C_{1-6}$alkyl,
isoxazolyl optionally substituted by 1 or 2 $C_{1-6}$alkyl,
2-thienyl optionally substituted by chloro, nitro, cyano, or $C_{1-6}$ alkyl,
3-thienyl optionally substituted by chloro, nitro, cyano, or $C_{1-6}$ alkyl,
piperidinyl optionally substituted by $C_{1-6}$alkoxycarbonyl, or benzyloxycarbonyl,
phenyl optionally substituted by 1 to 3 substituents selected from the group consisting of fluoro, chloro, hydroxy, nitro, cyano, carboxy, $C_{1-6}$ alkyl, $C_{1-6}$alkoxy, $C_{1-6}$alkoxycarbonyl, amino, N—($C_{1-6}$alkyl)amino, N—($C_{1-6}$acyl)amino, N—($C_{1-6}$alkoxycabonyl)amino, N,N-di($C_{1-6}$alkyl)amino, N-(formyl)-N—$C_{1-6}$alkyl amino, $C_{1-6}$alkylthio, $C_{1-6}$alkanesulfonyl, sulfamoyl, pyrrolyl, imidazolyl, pyrazolyl, and piperazinyl optionally substituted by $C_{1-6}$alkyl,
pyridyl optionally substituted by 1 or 2 substituents selected from the group consisting of chloro, hydroxy, carboxy, $C_{1-6}$alkoxy, $C_{1-6}$alkylthio, amino, N—($C_{1-6}$alkyl)amino, N-(hydroxy$C_{1-6}$alkyl)amino, N,N-di($C_{1-6}$alkyl)amino, N—($C_{1-6}$acyl)amino, N—($C_{1-6}$alkane)sulfonyl amino, N[N,N-di($C_{1-6}$alkyl)amino methylene]amino, $C_{1-6}$alkoxyphenyl$C_{1-6}$alkoxy, and $C_{1-6}$alkyl optionally substituted by tri halogen,
pyrazinyl optionally substituted by $C_{1-6}$alkyl,
1,3-thiazolyl optionally substituted by 1 or 2 substituents selected from the group consisting of $C_{1-6}$alkyl, pyridyl and N—($C_{1-6}$alkoxycrbonyl)amino, indolyl optionally substituted by $C_{1-6}$alkyl,
benzimidazolyl optionally substituted by $C_{1-6}$alkyl or tri-halo $C_{1-6}$alkyl,
1,2,3-benzotriazolyl optionally substituted by $C_{1-6}$alkyl,
1,8-naphthyridinyl optionally substituted by $C_{1-6}$alkyl optionally substituted by tri halogen,
$C_{1-6}$ alkyl optionally substituted by tri-halogen, phenyl, phenoxy, or thienyl,
or
$C_{1-6}$alkoxy substituted by phenyl, phenoxy, or thienyl;
$R^2$ represents fluoro, chloro, bromo, hydroxy, nitro, vinyl, cyano, amino, aminoacetoxy, N—($C_{1-6}$alkyl)amino, N,N-di($C_{1-6}$alkyl)amino, N-(hydroxy$C_{1-6}$alkyl)-N—($C_{1-6}$alkyl)amino, 2-furyl, piperidino, morpholino, phenyl,
pyrrolidinyl optionally substituted by acetamido, piperidino optionally substituted by hydroxy, piperazinyl optionally substituted by methyl, benzyl, $C_{1-6}$alkoxycarbonyl, or aminocarbonyl,
$C_{1-6}$ alkyl optionally substituted by cyano, tri-fluoro, carboxy, methoxycarbonyl,
aminocarbonyl, tert-butoxycarbonyl, tetrahydropyranyl, or morpholino,
or
$C_{1-6}$ alkoxy optionally substituted by hydroxy, cyano, methoxy, methoxycarbonyl, tert-butoxycarbonyl, carboxy, aminoacetyl, dimethylamino, aminocarbonyl, methylaminocarbonyl, dimethylaminocarbonyl, isopropylaminocarbonyl, fluorobenzylaminocarbonyl, cyclopropyl, pyrrolidinyl, piperidino, tetrahydropyranyl, morpholino, morpholinocarbonyl, tetrazolyl, 2-oxo-1,3-oxazolidin-4y1, phthalimid-N-yl, or hydroxy $C_{1-6}$ alkyleneoxy;
$R^3$ represents hydrogen;
$R^4$ represents hydrogen;
$R^5$ represents hydrogen; and
$R^6$ represents hydrogen.

6. The method of claim 1, wherein
X represents $CR^5R^6$ or NH;
$Y^1$ represents N;
$Y^2$ and $Y^3$ represent $CR^3R^4$;
Chemical bond between $Y^2$—$Y^3$ represents a single bond
$Z^3$ and $Z^4$ represent CH;
$Z^1$ and $Z^2$ independently represent CH or $CR^2$;
$R^1$ represents 3H-imidazo[4,5-b]pyridinyl, benzimidazolyl pyridyl optionally substituted by hydroxy, amino, acetamido, methoxybenzyloxy or methylsulfonylamino,
or
1,3-thiazolyl optionally substituted by 1 or 2 methyl;
$R^2$ represents fluoro, chloro, bromo, morpholino, piperazinyl, methylpiperazinyl, methyl, tri-fluoro methyl, or $C_{1-6}$ alkoxy optionally substituted by hydroxy, cyano, carboxy, dimethylaminocarbonyl, tetrahydropyranyl, morpholino, morpholinocarbonyl, tetrazolyl, or phthalimid-N-yl;
$R^3$ represents hydrogen;
$R^4$ represents hydrogen;
$R^5$ represents hydrogen; and
$R^6$ represents hydrogen.

7. The method of claim 1, wherein
X represents $CR^5R^6$ or NH;
$Y^1$ represents N;
$Y^2$ and $Y^3$ represent $CR^3R^4$;
Chemical bond between $Y^2$—$Y^3$ represents a single bond;

$Z^1$, $Z^3$ and $Z^4$ represent CH;
$Z^2$ represents $CR^2$;
$R^1$ represents 3H-imidazo[4,5-b]pyridinyl, benzimidazolyl pyridyl optionally substituted by hydroxy, amino, acetamido, methoxybenzyloxy or methylsulfonylamino, or
1,3-thiazolyl optionally substituted by 1 or 2 methyl,
$R^2$ represents fluoro, chloro, bromo, morpholino, piperazinyl, methylpiperazinyl, methyl, tri-fluoro methyl, $C_{1-6}$ alkoxy optionally substituted by hydroxy, cyano, carboxy, dimethylaminocarbonyl, tetrahydropyranyl, morpholino, morpholinocarbonyl, tetrazolyl, or phthalimid-N-yl;
$R^3$ represents hydrogen;
$R^4$ represents hydrogen;
$R^5$ represents hydrogen; and
$R^6$ represents hydrogen.

8. The method of claim 1, wherein said compound is selected from the group consisting of:
N-(7,8-dimethoxy-2,3-dihydroimidazo[1,2-c]quinazolin-5-yl)nicotinamide;
2-(7,8-dimethoxy-2,3-dihydroimidazo[1,2-c]quinazolin-5-yl)-1-pyridin-3-ylethylenol;
N-(7,8-dimethoxy-2,3-dihydroimidazo[1,2-c]quinazolin-5-yl)-1H-benzimidazole-5-carboxamide;
6-(acetamido)-N-(7,8-dimethoxy-2,3-dihydroimidazo[1,2-c]quinazolin-5-yl)nicotinamide;
N-{5-[2-(7,8-dimethoxy-2,3-dihydroimidazo[1,2-c]quinazolin-5-yl)-1-hydroxyvinyl]pyridin-2-yl}acetamide;
2-({5-[2-hydroxy-2-pyridin-3-ylvinyl]-7-methoxy-2,3-dihydroimidazo[1,2-c]quinazolin-8-yl}oxy)-N,N-dimethylacetamide;
2-[7-methoxy-8-(tetrahydro-2H-pyran-2-ylmethoxy)-2,3-dihydroimidazo[1,2-c]quinazolin-5-yl]-1-pyridin-3-yl-ethylenol;
2-[8-(2-hydroxyethoxy)-7-methoxy-2,3-dihydroimidazo[1,2-c]quinazolin-5-yl]-1-pyridin-3-ylethylenol;
({5-[2-hydroxy-2-pyridin-3-ylvinyl]-7-methoxy-2,3-dihydroimidazo[1,2-c]quinazolin-8-yl}oxy)acetic acid;
4-({5-[2-hydroxy-2-pyridin-3-ylvinyl]-7-methoxy-2,3-dihydroimidazo[1,2-c]quinazolin-8-yl}oxy)butanoic acid;
({5-[2-hydroxy-2-pyridin-3-ylvinyl]-7-methoxy-2,3-dihydroimidazo[1,2-c]quinazolin-8-yl}oxy)acetonitrile;
2-[7-methoxy-8-(2H-tetrazol-5-ylmethoxy)-2,3-dihydroimidazo[1,2-c]quinazolin-5-yl]-1-pyridin-3-ylethylenol;
2-[7-methoxy-8-(4-morpholin-4-yl-4-oxobutoxy)-2,3-dihydroimidazo[1,2-c]quinazolin-5-yl]-1-pyridin-3-ylethylenol;
5-[1-hydroxy-2-(8-morpholin-4-yl-2,3-dihydroimidazo[1,2-c]quinazolin-5-yl)vinyl]pyridin-3-ol;
N-(2,3-dihydroimidazo[1,2-c]quinazolin-5-yl)-5-hydroxynicotinamide;
6-(acetamido)-N-(7,9-dimethoxy-8-methyl-2,3-dihydroimidazo[1,2-c]quinazolin-5-yl)nicotinamide;
N-(8,9-dimethoxy-2,3-dihydroimidazo[1,2-c]quinazolin-5-yl)-5-hydroxynicotinamide;
5-hydroxy-N-(7-methoxy-2,3-dihydroimidazo[1,2-c]quinazolin-5-yl)nicotinamide;
N-(7,8-dimethoxy-2,3-dihydroimidazo[1,2-c]quinazolin-5-yl)-5-[(4-methoxybenzyl)oxy]nicotinamide;
N-(7,8-dimethoxy-2,3-dihydroimidazo[1,2-c]quinazolin-5-yl)-5-hydroxynicotinamide;
5-hydroxy-N-[8-(trifluoromethyl)-2,3-dihydroimidazo[1,2-c]quinazolin-5-yl]nicotinamide;
N-{8-[3-(1,3-dioxo-1,3-dihydro-2H-isoindol-2-yl)propoxy]-2,3-dihydroimidazo[1,2-c]quinazolin-5-yl}nicotinamide;
N-(7-bromo-8-methoxy-2,3-dihydroimidazo[1,2-c]quinazolin-5-yl)nicotinamide;
6-amino-N-(8-methoxy-2,3-dihydroimidazo[1,2-c]quinazolin-5-yl)nicotinamide;
1-(1H-benzimidazol-5-yl)-2-(8,9-dimethoxy-2,3-dihydroimidazo[1,2-c]quinazolin-5-yl)ethylenol;
2-(8,9-dimethoxy-2,3-dihydroimidazo[1,2-c]quinazolin-5-yl)-1-(2,4-dimethyl-1,3-thiazol-5-yl)ethylenol;
N-(9-methoxy-2,3-dihydroimidazo[1,2-c]quinazolin-5-yl)-1H-benzimidazole-5-carboxamide;
N-(8-bromo-2,3-dihydroimidazo[1,2-c]quinazolin-5-yl)nicotinamide;
N-(8-bromo-2,3-dihydroimidazo[1,2-c]quinazolin-5-yl)-1H-benzimidazole-5-carboxamide;
N-(8-methoxy-2,3-dihydroimidazo[1,2-c]quinazolin-5-yl)-1H-benzimidazole-5-carboxamide;
N-(8-methyl-2,3-dihydroimidazo[1,2-c]quinazolin-5-yl)-1H-benzimidazole-5-carboxamide;
N-[8-(trifluoromethyl)-2,3-dihydroimidazo[1,2-c]quinazolin-5-yl]-1H-benzimidazole-5-carboxamide;
N-(7-fluoro-2,3-dihydroimidazo[1,2-c]quinazolin-5-yl)-1H-benzimidazole-5-carboxamide;
N-(7-methoxy-2,3-dihydroimidazo[1,2-c]quinazolin-5-yl)nicotinamide;
N-(8-chloro-2,3-dihydroimidazo[1,2-c]quinazolin-5-yl)-1H-benzimidazole-5-carboxamide;
6-(acetamido)-N-(8-morpholin-4-yl-2,3-dihydroimidazo[1,2-c]quinazolin-5-yl)nicotinamide;
1-(1H-benzimidazol-5-yl)-2-(8-morpholin-4-yl-2,3-dihydroimidazo[1,2-c]quinazolin-5-yl)ethylenol;
N-{5-[1-hydroxy-2-(8-morpholin-4-yl-2,3-dihydroimidazo[1,2-c]quinazolin-5-yl)vinyl]pyridin-2-yl}acetamide;
6-methyl-N-(8-morpholin-4-yl-2,3-dihydroimidazo[1,2-c]quinazolin-5-yl)nicotinamide;
1-(1H-benzimidazol-5-yl)-2[8-(4-methylpiperazin-1-yl)-2,3-dihydroimidazo[1,2-c]quinazolin-5-yl]ethylenol;
N-(2,3-dihydroimidazo[1,2-c]quinazolin-5-yl)-3H-imidazo[4,5-b]pyridine-6-carboxamide;
N-(7,8-dimethoxy-2,3-dihydroimidazo[1,2-c]quinazolin-5-yl)-3H-imidazo[4,5-b]pyridine-6-carboxamide;
N-[7-(trifluoromethyl)-2,3-dihydroimidazo[1,2-c]quinazolin-5-yl]-1H-benzimidazole-5-carboxamide;
N-(7,9-dimethoxy-2,3-dihydroimidazo[1,2-c]quinazolin-5-yl)-1H-benzimidazole-5-carboxamide;
N-{5[2-(7,9-dimethoxy-8-methyl-2,3-dihydroimidazo[1,2-c]quinazolin-5-yl)-1-hydroxyvinyl]pyridin-2-yl}acetamide;
N-{5[2-(7-bromo-9-methyl-2,3-dihydroimidazo[1,2-c]quinazolin-5-yl)-1-hydroxyvinyl]pyridin-2-yl}acetamide; and
2-(8,9-dimethoxy-2,3-dihydroimidazo[1,2-c]quinazolin-5-yl)-1-pyridin-3-ylethylenol.

9. The method of claim 1, wherein the compound is administered for treating or controlling asthma, rhinitis, allergic diseases, or an autoimmune pathology.

10. The method of claim 4, wherein the compound is administered for treating or controlling asthma, rhinitis, allergic diseases, or an autoimmune pathology.

11. The method of claim 6, wherein the compound is administered for treating or controlling asthma, rhinitis, allergic diseases, or an autoimmune pathology.

12. The method of claim 8, wherein the compound is administered for treating or controlling asthma, rhinitis, allergic diseases, or an autoimmune pathology.

13. The method of claim 1, wherein the compound is administered for treating or controlling diabetes, cancer, or myocardial contractility disorders.

14. The method of claim 4, wherein the compound is administered for treating or controlling diabetes, cancer, or myocardial contractility disorders.

15. The method of claim 6, wherein the compound is administered for treating or controlling diabetes, cancer, or myocardial contractility disorders.

16. The method of claim 8, wherein the compound is administered for treating or controlling diabetes, cancer, or myocardial contractility disorders.

* * * * *

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Ile Ser Asp Phe Gly Leu Ser Lys Ala Leu Arg Ala Asp Glu Asn
1               5                   10                  15

Tyr Tyr Lys Ala Gln Thr His Gly Lys Trp Pro Val Lys Trp
            20                  25                  30